US012384765B2

(12) United States Patent
Jørgensen et al.

(10) Patent No.: US 12,384,765 B2
(45) Date of Patent: *Aug. 12, 2025

(54) CATECHOLAMINE PRODRUGS FOR USE IN THE TREATMENT OF PARKINSON'S DISEASE

(71) Applicant: H. Lundbeck A/S, Valby (DK)

(72) Inventors: Morten Jørgensen, Valby (DK); Martin Juhl, Valby (DK); Klaus Gjervig Jensen, Valby (DK); Lisbet Kværnø, Valby (DK)

(73) Assignee: H. Lundbeck A/S, Valby (DK)

( * ) Notice: Subject to any disclaimer, the term of this patent is extended or adjusted under 35 U.S.C. 154(b) by 777 days.

This patent is subject to a terminal disclaimer.

(21) Appl. No.: 17/606,319

(22) PCT Filed: May 19, 2020

(86) PCT No.: PCT/EP2020/063914
§ 371 (c)(1),
(2) Date: Oct. 25, 2021

(87) PCT Pub. No.: WO2020/234274
PCT Pub. Date: Nov. 26, 2020

(65) Prior Publication Data
US 2022/0213071 A1   Jul. 7, 2022

(30) Foreign Application Priority Data
May 21, 2019   (DK) .............................. PA201900608

(51) Int. Cl.
*C07D 405/12*   (2006.01)
(52) U.S. Cl.
CPC ................. *C07D 405/12* (2013.01)
(58) Field of Classification Search
CPC .................................................. C07D 405/12
See application file for complete search history.

(56) References Cited

U.S. PATENT DOCUMENTS

| 3,132,171 | A | 5/1964 | Plaut |
| 4,374,829 | A | 2/1983 | Harris |
| 4,543,256 | A | 9/1985 | Neumeyer |
| 4,565,818 | A | 1/1986 | Nordmann et al. |
| 4,692,453 | A | 9/1987 | Seiler |
| 5,073,547 | A | 12/1991 | Casagrande et al. |
| 5,747,513 | A | 5/1998 | Montanari et al. |
| 5,885,988 | A | 3/1999 | Neumann et al. |
| 5,955,468 | A | 9/1999 | Markstein |
| 6,410,664 | B1 | 6/2002 | Bansleben et al. |
| 8,129,530 | B2 | 3/2012 | Jorgensen et al. |
| 10,729,710 | B2* | 8/2020 | Jensen .................. A61K 31/473 |
| 11,104,697 | B2 | 8/2021 | Juhl et al. |
| 11,110,110 | B2 | 9/2021 | Jensen et al. |
| 11,111,263 | B2* | 9/2021 | Juhl ..................... C07D 405/12 |
| 11,130,775 | B2 | 9/2021 | Jensen et al. |
| 11,168,056 | B2 | 11/2021 | Jacobsen et al. |
| 11,707,476 | B2 | 7/2023 | Jensen et al. |
| 11,827,665 | B2 | 11/2023 | Juhl et al. |
| 11,851,456 | B2* | 12/2023 | Juhl ..................... C07D 405/12 |
| 11,858,954 | B2 | 1/2024 | Jensen et al. |
| 11,866,410 | B2 | 1/2024 | Jacobsen et al. |
| 12,226,428 | B2 | 2/2025 | Jensen et al. |
| 2009/0062324 | A1 | 3/2009 | Jorgensen et al. |
| 2009/0124651 | A1 | 5/2009 | Jorgensen et al. |
| 2012/0077836 | A1 | 3/2012 | Wilkstrom et al. |
| 2017/0335357 | A1 | 11/2017 | Divi et al. |
| 2020/0338102 | A1 | 1/2020 | Balmer et al. |
| 2020/0369615 | A1 | 11/2020 | Jacobsen et al. |
| 2020/0369705 | A1 | 11/2020 | Juhl et al. |
| 2020/0369706 | A1 | 11/2020 | Juhl et al. |
| 2020/0392176 | A1 | 12/2020 | Jensen et al. |
| 2022/0024875 | A1 | 1/2022 | Jacobsen et al. |
| 2022/0024962 | A1 | 1/2022 | Jensen et al. |
| 2022/0185839 | A1 | 6/2022 | Juhl et al. |
| 2022/0194978 | A1 | 6/2022 | Juhl et al. |
| 2022/0213040 | A1 | 7/2022 | Jorgensen et al. |
| 2022/0213136 | A1 | 7/2022 | Jorgensen et al. |
| 2022/0220077 | A1 | 7/2022 | Jorgensen et al. |
| 2022/0257623 | A1 | 8/2022 | Jensen et al. |
| 2024/0018107 | A1 | 1/2024 | Jacobsen et al. |

(Continued)

FOREIGN PATENT DOCUMENTS

| CN | 102746351 | A | 10/2012 |
| CN | 105218606 | A | 1/2016 |

(Continued)

OTHER PUBLICATIONS

PCT/EP2020/063914, Jul. 14, 2020, International Search Report and Written Opinion.
U.S. Appl. No. 17/386,686, filed Jul. 28, 2021, Pending.
U.S. Appl. No. 17/385,166, filed Jul. 26, 2021, Pending.
U.S. Appl. No. 17/391,439, filed Aug. 2, 2021, Pending.
U.S. Appl. No. 17/392,970, filed Aug. 3, 2021, Published, 2022-0024962.
U.S. Appl. No. 17/495,997, filed Oct. 7, 2021, Published, 2022-0024875.
U.S. Appl. No. 17/606,313, filed Oct. 25, 2021, Pending.
U.S. Appl. No. 17/606,332, filed Oct. 25, 2021, Pending.
U.S. Appl. No. 17/606,303, filed Oct. 25, 2021, Pending.

(Continued)

*Primary Examiner* — Brandon J Fetterolf
*Assistant Examiner* — Jerica Katlynn Wilson
(74) *Attorney, Agent, or Firm* — Wolf, Greenfield & Sacks, P.C.

(57) ABSTRACT

The present invention provides compounds of formula (Id) that are prodrugs of catecholamine for use in treatment of neurodegenerative diseases and disorders. The present invention also provides pharmaceutical compositions comprising compounds of the invention and methods of treating neurodegenerative or neuropsychiatric diseases and disorders using the compounds of the invention, in particular Parkinson's disease.

27 Claims, 11 Drawing Sheets

(56) References Cited

U.S. PATENT DOCUMENTS

| | | |
|---|---|---|
| 2024/0025857 A1 | 1/2024 | Jørgensen et al. |
| 2024/0156851 A1 | 5/2024 | Jensen et al. |
| 2024/0190909 A1 | 6/2024 | Jensen et al. |
| 2024/0352055 A1 | 10/2024 | Juhl et al. |

FOREIGN PATENT DOCUMENTS

| | | | |
|---|---|---|---|
| EP | 0 352 815 A1 | 1/1990 | |
| GB | 2 192 394 A | 1/1998 | |
| JP | S60-172975 A | 9/1985 | |
| JP | 2007-532670 A | 11/2007 | |
| JP | 2010-536889 A | 12/2010 | |
| WO | WO 90/12574 A1 | 11/1990 | |
| WO | WO 97/03054 A1 | 1/1997 | |
| WO | WO 98/38155 A1 | 9/1998 | |
| WO | WO 00/47571 A1 | 8/2000 | |
| WO | WO 01/36428 A1 | 5/2001 | |
| WO | WO 01/76602 A1 | 10/2001 | |
| WO | WO 01/78713 A1 | 10/2001 | |
| WO | WO 02/13827 A1 | 2/2002 | |
| WO | WO 02/14279 A1 | 2/2002 | |
| WO | WO 02/100377 A1 | 12/2002 | |
| WO | WO 03/006458 A1 | 1/2003 | |
| WO | WO 03/013532 A1 | 2/2003 | |
| WO | WO 03/074511 A1 | 9/2003 | |
| WO | WO 03/080074 A1 | 10/2003 | |
| WO | WO 2004/052841 A1 | 6/2004 | |
| WO | WO 2005/062894 A2 | 7/2005 | |
| WO | WO 2006/012640 A2 | 2/2006 | |
| WO | WO 2006/056604 A1 | 6/2006 | |
| WO | 2009/026934 A1 | 3/2009 | |
| WO | WO 2009/026935 A1 | 3/2009 | |
| WO | WO 2009/156458 A1 | 12/2009 | |
| WO | 2010/097092 A1 | 9/2010 | |
| WO | WO 2010/097091 A1 | 9/2010 | |
| WO | WO 2013/020979 A1 | 2/2013 | |
| WO | WO 2013/034119 A1 | 3/2013 | |
| WO | WO 2015/067927 A1 | 5/2015 | |
| WO | WO 2016/065019 A1 | 4/2016 | |
| WO | WO 2017/184871 A1 | 10/2017 | |
| WO | 2019/101917 A1 | 5/2019 | |
| WO | WO-2020234271 A1 * | 11/2020 | ............... A61P 25/00 |

OTHER PUBLICATIONS

PCT/EP2018/082361, Feb. 22, 2019, International Search Report and Written Opinion.
PCT/EP2020/063909, Jul. 2, 2020, International Search Report and Written Opinion.
PCT/EP2020/063910, Jul. 14, 2020, International Search Report and Written Opinion.
PCT/EP2020/063913, Jul. 15, 2020, International Search Report and Written Opinion.
PCT/EP2020/063908, Sep. 11, 2020, International Search Report and Written Opinion.
PCT/EP2020/063915, Jul. 13, 2020, International Search Report and Written Opinion.
PCT/EP2020/063918, Aug. 10, 2020, International Search Report and Written Opinion.
PCT/EP2020/063916, Sep. 28, 2020, International Search Report and Written Opinion.
International Search Report and Written Opinion for Application No. PCT/EP2020/063914 mailed Jul. 14, 2020.
U.S. Appl. No. 17/386,686, filed Jul. 28, 2021, Allowed, 2022-0257623.
U.S. Appl. No. 17/385,166, filed Jul. 26, 2021, Allowed, 2022-0185839.
U.S. Appl. No. 17/391,439, filed Aug. 2, 2021, Published, 2022-0194978.
International Search Report and Written Opinion for Application No. PCT/EP2018/082361 mailed Feb. 22, 2019.
International Search Report and Written Opinion for Application No. PCT/EP2020/063909 mailed Jul. 2, 2020.
International Search Report and Written Opinion for Application No. PCT/EP2020/063910 mailed Jul. 14, 2020.
International Search Report and Written Opinion for Application No. PCT/EP2020/063913 mailed Jul. 15, 2020.
International Search Report and Written Opinion for Application No. PCT/EP2020/063908 mailed Sep. 11, 2020.
International Search Report and Written Opinion for Application No. PCT/EP2020/063915 mailed Jul. 13, 2020.
International Search Report and Written Opinion for Application No. PCT/EP2020/063918 mailed Aug. 10, 2020.
International Search Report and Written Opinion for Application No. PCT/EP2020/063916 mailed Sep. 28, 2020.
Ahari et al., A direct stereoselective approach to trans-2,3-disubstituted piperidines: application in the synthesis of 2-Epi-CP-99,994 and (+)-epilupinine. Org Lett. Jun. 19, 2008;10(12):2473-6. doi: 10.1021/ol800722a. Epub May 14, 2008.
Alexander et al., Functional architecture of basal ganglia circuits: neural substrates of parallel processing. Trends Neurosci. Jul. 1990;13(7):266-71.
Atkinson et al., Derivatives of apomorphine and of other N-substituted norapomorphines. J Pharm Sci. Nov. 1976;65(11):1682-5.
Bibbiani et al., Continuous dopaminergic stimulation reduces risk of motor complications in parkinsonian primates. Exp Neurol. Mar. 2005;192(1):73-8.
Billeter et al., 8-Hydroxyflavonoid Glucuronides from Malva Sylvestris. Phytochemistry. 1991; 30(3):987-90.
Brown et al., Structurally constrained hybrid derivatives containing octahydrobenzo[g or f]quinoline moieties for dopamine D2 and D3 receptors: binding characterization at D2/D3 receptors and elucidation of a pharmacophore model. J Med Chem. Dec. 25, 2008;51(24):7806-19. doi: 10.1021/jm8008629.
Campbell et al., Behavioral effects of (−)10,11-methylenedioxy-N-n-propylnoraporphine, an orally effective long-acting agent active at central dopamine receptors, and analogous aporphines. Neuropharmacology. Oct. 1982;21(10):953-61.
Cannon et al., N-Alkyl derivatives of trans-6,7-dihydroxy-1,2,3,4,4a,5,10,10b-octahyrobenzo[g]quinoline A congener of apomorphine lacking the non-oxygenated aromatic ring. J. Heterocyclic Chem. Nov. 1980;17:1633-1636.
Cavero et al., Safety Pharmacology assessment of drugs with biased 5-HT(2B) receptor agonism mediating cardiac valvulopathy. J Pharmacol Toxicol Methods. Mar.-Apr. 2014;69(2):150-61. doi: 10.1016/j.vascn.2013.12.004. Epub Dec. 19, 2013.
Delong, Primate models of movement disorders of basal ganglia origin. Trends Neurosci. Jul. 1990;13(7):281-5.
Di Stefano et al., Antiparkinson prodrugs. Molecules. Jan. 16, 2008;13(1):46-68.
Fan et al., Differential effects of pro-BDNF on sensory neurons after sciatic nerve transection in neonatal rats. Eur J Neurosci. May 2008;27(9):2380-90. doi: 10.1111/j.1460-9568.2008.06215.x. Epub Apr. 22, 2008.
Fan et al., Modifications of the isonipecotic acid fragment of SNS-032: analogs with improved permeability and lower efflux ratio. Bioorg Med Chem Lett. Dec. 1, 2008;18(23):6236-9. doi: 10.1016/j.bmcl.2008.09.099. Epub Oct. 2, 2008. (citation on PubMed).
Fumeaux et al., First synthesis, characterization, and evidence for the presence of hydroxycinnamic acid sulfate and glucuronide conjugates in human biological fluids as a result of coffee consumption. Org Biomol Chem. Nov. 21, 2010;8(22):5199-211. doi: 10.1039/c0ob00137f. Epub Sep. 14, 2010.
Gerfen et al., D1 and D2 dopamine receptor-regulated gene expression of striatonigral and striatopallidal neurons. Science. Dec. 7, 1990;250(4986):1429-32.
Giardina et al., Adrogolide HCl (ABT-431; DAS-431), a prodrug of the dopamine D1 receptor agonist, A-86929: preclinical pharmacology and clinical data. CNS Drug Rev. 2001 Fall;7(3):305-16.
Goswami et al., Intestinal absorption and metabolism of retinoyl beta-glucuronide in humans, and of 15-[14C]-retinoyl beta-glucuronide in rats of different vitamin A status. J Nutr Biochem. Dec. 2003;14(12):703-9.

(56) References Cited

OTHER PUBLICATIONS

Grosset et al., Inhaled dry powder apomorphine (VR040) for 'off' periods in Parkinson's disease: an in-clinic double-blind dose ranging study. Acta Neurol Scand. Sep. 2013;128(3):166-71. doi: 10.1111/ane.12107. Epub Mar. 26, 2013.
Hauser et al., Sublingual apomorphine (APL-130277) for the acute conversion of OFF to ON in Parkinson's disease. Mov Disord. Sep. 2016;31(9):1366-72. Epub Jul. 19, 2016.
Knobloch et al., Keto Esters Derived from 2-(Trimethylsilyl) ethanol: An Orthogonal Protective Group for β-Keto Esters. Synthesis 2008.14 (2008): 2229-2246.
Kotsuki et al., Highly practical, enantiospecific synthesis of the cyclohexyl fragment of the immunosuppressant FK-506. J Org Chem. Aug. 1992;57(18):5036-40.
Liu et al., A novel synthesis and pharmacological evaluation of a potential dopamine D1/D2 agonist: 1-propyl-1,2,3,4,4a,5,10,10a-octahydrobenzo[g]quinoline-6,7-diol. Bioorg Med Chem. Mar. 15, 2008;16(6):3438-44. doi: 10.1016/j.bmc.2007.06.036. Epub Jun. 23, 2007.
Liu et al., Extremely potent orally active benzo[g]quinoline analogue of the dopaminergic prodrug: 1-propyl-trans-2,3,4,4a,5,7,8,9,10,10a-decahydro-1H-benzo-[g]quinolin-6-one [corrected]. J Med Chem. Feb. 23, 2006;49(4):1494-8. Erratum in: J Med Chem. Nov. 16, 2006;49(23):6930.
Loozen et al., An approach to the synthesis of [2] benzopyrano [3, 4?c] pyrroles; alternative dopaminergic molecules. Recueil des Travaux Chimiques des Pays?Bas. 1982;101(9):298-310.
Morissette et al., High-throughput crystallization: polymorphs, salts, co-crystals and solvates of pharmaceutical solids. Adv Drug Deliv Rev. Feb. 23, 2004;56(3):275-300. doi: 10.1016/j.addr.2003.10.020.
Nolen et al., Budesonide-beta-D-glucuronide: a potential prodrug for treatment of ulcerative colitis. J Pharm Sci. Jun. 1995;84(6):677-81.
Poewe et al., Parkinson disease. Nat Rev Dis Primers. Mar. 23, 2017;3:17013.
Rothman et al., Evidence for possible involvement of 5-HT(2B) receptors in the cardiac valvulopathy associated with fenfluramine and other serotonergic medications. Circulation. Dec. 5, 2000;102(23):2836-41.
Sozio et al., Designing prodrugs for the treatment of Parkinson's disease. Expert Opin Drug Discov. May 2012;7(5):385-406. Epub Apr. 12, 2012.
Sprenger et al., Management of motor and non-motor symptoms in Parkinson's disease. CNS Drugs. Apr. 2013;27(4):259-72.
Stain-Texier et al., Intestinal absorption and stability of morphine 6-glucuronide in different physiological compartments of the rat. Drug Metab Dispos. May 1998;26(5):383-7.
Zhang et al., Flavonoid metabolism: the synthesis of phenolic glucuronides and sulfates as candidate metabolites for bioactivity studies of dietary flavonoids. Tetrahedron. 2012; 68:4194-4201.
Banker et al., Modern Pharmaceuticals. Third Edition, Revised and Expanded. Marcel Dekker, Inc., New York, 1996. p. 596.
David et al., Control of catalytic debenzylation and dehalogenation reactions during liquid-phase reduction by $H_2$. Journal of Catalysis. 2006; 237(2): 349-358.
Kummerer, K. Pharmaceuticals in the Environment. Annu. Rev. Environ. Resour. 2010. 35:57-75. doi: 10.1146/annurev-environ-052809-161223.
Levin et al., Cognitive and neuropsychiatric disorders in extrapyramidal diseases. Neurology, Neuropsychiatry, Psychosomatics. 2012;4(2S):22-30. https://doi.org/10.14412/2074-2711-2012-2505.
Mironov, The Guidelines for Preclinical Trials of Medicinal Products. Grif & Co. Moscow, Russia. 2012. 941 pages.
Przedborski et al., Neurodegeneration: What is it and where are we? J Clin Invest. 2003;111(1):3-10. https://doi.org/10.1172/JCI17522.
Sun et al., Oral bioavailability and brain penetration of (-)-stepholidine, a tetrahydroprotoberberine agonist at dopamine D(1) and antagonist at D(2) receptors, in rats. Br J Pharmacol. Nov. 2009;158(5):1302-12. Epub Sep. 25, 2009.
Szajewska, H. Evidence-based medicine and clinical research: both are needed, neither is perfect. Ann Nutr Metab. 2018;72 Suppl 3:13-23. doi: 10.1159/000487375. Epub Apr. 9, 2018. PMID: 29631266.
Ugrumov M.V., Development of preclinical diagnosis and preventive treatment of neurodegenerative diseases. Zh Nevrol Psikhiatr Im S S Korsakova. 2015;115(11):4-14. Russian. doi: 10.17116/jnevro20151151114-14.
Wesserling et al., Will in vitro tests replace animal models in experimental oncology? J Tissue Scie Eng. 2011; 2:102e. doi:10.4172/2157-7552.1000102e.
Wolff, M.E. Burger's Medicinal Chemistry and Drug Discovery. vol. 1, Principles and Practice, Fifth Edition. John Wiley & Sons 1995. pp. 975-977.
Byrn et al., Pharmaceutical Solids: A Strategic Approach to Regulatory Considerations. Pharmaceutical Research. 1995;12(7):945-54.
Caira, Crystalline Polymorphism of Organic Compounds. Design of Organic Solids. Topics in Current Chemistry.1998(198):163-208.
Choi et al., Dopamine Agonists. NIH National Library of Medicine, In: StatPearls [Internet].Treasure Island (FL): StatPearls Publishing;. Jan. 2024. Last updated Jun. 26, 2023, 8 pages.
Clarke, Recent developments in the homogeneous hydrogenation of carboxylic acid esters. Catal. Sci. Technol. Sep. 25, 2012;2:2418-23.
Elger et al., Estrogen sulfamates: a new approach to oral estrogen therapy. Reprod Fertil Dev. 2001;13(4):297-305. doi: 10.1071/rd01029.
Elger et al., Novel oestrogen sulfamates: a new approach to oral hormone therapy. Expert Opin Investig Drugs. Apr. 1998;7(4):575-89. doi: 10.1517/13543784.7.4.575.
Elger et al., Sulfamates of various estrogens are prodrugs with increased systemic and reduced hepatic estrogenicity at oral application. J Steroid Biochem Mol Biol. Dec. 1995;55(3-4):395-403. doi: 10.1016/0960-0760(95)00214-6.
Fernandez et al., Synthesis and biological studies of glycosyl dopamine derivatives as potential antiparkinsonian agents. Carbohydr Res. Aug. 7, 2000;327(4):353-65. doi: 10.1016/s0008-6215(00)00073-2.
Kuznetsova, Qualitative X-ray phase analysis—Methodological guidelines. Irkutsk State University, General Physics Department. 2005;6 pages.
Malmquist et al., The synthesis of tritiated (R)-2-methoxy-N-n-propyl-nor-apomorphine (MNPA). J Label Compd Radiopharm. Sep. 2007;50(13):1211-1214.
Reutov et al., Organic Chemistry: Manual for Chemical Students and Post-Graduates. 1999; 903-904; 905; 1738-1739 (with reference to N. Kornblum, 1963).
Reutov et al., Organic Chemistry: textbook for students of chemical specialties and graduate students.1999. Chapter 27, Section 27.9.1. c., 1999;6 pages.
Yu, Amorphous pharmaceutical solids: preparation, characterization and stabilization. Adv Drug Deliv Rev. May 16, 2001;48(1):27-42. doi: 10.1016/s0169-409x(01)00098-9.
Yujian et al., Prodrug: Design and Clinical Application. Int J Pharm Res. Oct. 2008;5(35): 377-380, 387.
U.S. Appl. No. 16/198,917, filed Nov. 23, 2018, Granted, U.S. Pat. No. 10,729,710.
U.S. Appl. No. 16/872,802, filed May 12, 2020, Granted, U.S. Pat. No. 11,110,110.
U.S. Appl. No. 17/386,686, filed Jul. 28, 2021, Granted, U.S. Pat. No. 11,707,476.
U.S. Appl. No. 18/330,293, filed Jun. 6, 2023, Allowed, 2024-0156851.
U.S. Appl. No. 16/876,843, filed May 18, 2020, Granted, U.S. Pat. No. 11,104,697.
U.S. Appl. No. 17/385,166, filed Jul. 26, 2021, Granted, U.S. Pat. No. 11,827,665.
U.S. Appl. No. 16/876,878, filed May 18, 2020, Granted, U.S. Pat. No. 11,111,263.
U.S. Appl. No. 17/391,439, filed Aug. 2, 2021, Granted, U.S. Pat. No. 11,851,456.
U.S. Appl. No. 18/507,662, filed Nov. 13, 2023, Published, 2024-0352055.

(56) References Cited

OTHER PUBLICATIONS

U.S. Appl. No. 16/876,908, filed May 18, 2020, Granted, U.S. Pat. No. 11,130,775.
U.S. Appl. No. 17/392,970, filed Aug. 3, 2021, Granted, U.S. Pat. No. 11,858,954.
U.S. Appl. No. 18/511,231, filed Nov. 16, 2023, Published, 2024-0190909.
U.S. Appl. No. 16/876,966, filed May 18, 2020, Granted, U.S. Pat. No. 11,168,056.
U.S. Appl. No. 17/495,997, filed Oct. 7, 2021, Granted, U.S. Pat. No. 11,866,410.
U.S. Appl. No. 18/359,136, filed Jul. 26, 2023, Published, 2024-0018107.
U.S. Appl. No. 17/606,313, filed Oct. 25, 2021, Published, 2022-0213136.
U.S. Appl. No. 17/606,332, filed Oct. 25, 2021, Published, 2022-0213040.
U.S. Appl. No. 17/606,303, filed Oct. 25, 2021, Published, 2022-0220077.
U.S. Appl. No. 18/036,596, filed May 11, 2023, Published, 2024-0025857.
Khalafi-Nezhad et al., Efficient and Selective Protection of Alcohols and Phenols with Triisopropylsilyl Chloride/Imidazole Using Microwave Irradiation. Tetrahedron. Apr. 4, 2000; 56(38): 7503-7506. doi.org/10.1016/S0040-4020(00)00638-4.
Murakami et al., Practical, modular, and general synthesis of benzofurans through extended Pummerer annulation/cross-coupling strategy. Angew Chem Int Ed Engl. Jul. 14, 2014;53(29):7510-3. doi: 10.1002/anie.201403288. Epub Jun. 12, 2014.

\* cited by examiner

CATECHOLAMINE PRODRUGS FOR USE IN THE TREATMENT OF PARKINSON'S DISEASE

CROSS REFERENCE TO RELATED APPLICATIONS

This Application is a National Stage filing under 35 U.S.C. 371 of International PCT Application No. PCT/EP2020/063914, filed May 19, 2020, which claims priority to Denmark Application Number PA201900608, filed May 21, 2019. The entire contents of these applications are incorporated herein by reference in their entirety.

FIELD OF THE INVENTION

The present invention provides compounds that are prodrugs of the dopamine agonist (4aR,10aR)-1-Propyl-1,2,3,4,4a,5,10,10a-octahydro-benzo[g]quinoline-6,7-diol and their use in the treatment of Parkinson's disease and/or other conditions for which treatment with a dopamine agonist is therapeutically beneficial such as but not limited to Restless leg syndrome, Huntington's disease and Alzheimer's disease; and also neuropsychiatric diseases and disorders such as but not limited to schizophrenia, attention deficit hyperactivity disorder and drug addiction. The present invention also provides pharmaceutical compositions comprising compounds of the invention.

BACKGROUND OF THE INVENTION

Parkinson's disease (PD) is a common neurodegenerative disorder that becomes increasingly prevalent with age and affects an estimated seven to ten million people worldwide. Parkinson's disease is a multi-faceted disease characterized by both motor and non-motor symptoms. Motor symptoms include resting tremor (shaking), bradykinesia/akinesia (slowness and poverty of movements), muscular rigidity, postural instability and gait dysfunction; whereas non-motor symptoms include neuropsychiatric disorders (e.g. depression, psychotic symptoms, anxiety, apathy, mild-cognitive impairment and dementia) as well as autonomic dysfunctions and sleep disturbances (Poewe et al., Nature Review, (2017) vol 3 article 17013: 1-21).

A key hallmark of Parkinson's disease pathophysiology is the loss of pigmented dopaminergic neurons in the substantia nigra pars compacta that provides dopaminergic innervation to the striatum and other brain areas. Such progressive neurodegeneration leads to the decrease in dopamine striatal levels which ultimately results in a series of changes in the basal ganglia circuitry, ultimately ending up in the occurrence of the four cardinal motor features of Parkinson's disease. The main target of dopamine in the striatum consists of medium spiny GABAergic neurons (MSNs) selectively expressing D1 or D2 receptors pending topographical projections. GABAergic-MSN projecting to the external pallidum, also called striato-pallidal 'indirect pathway' express D2 receptors (MSN-2); whereas GABAergic-MSN projecting to the substantia nigra pars reticulata and internal pallidum, also called striato-nigral 'direct pathway' express D1 receptors (MSN-1). Depletion of dopamine because of neuronal loss results in an imbalanced activity of the two pathways, resulting in a marked reduction of thalamic and cortical output activities and ultimately motor dysfunctions (Gerfen et al, Science (1990) 250: 1429-32; Delong, (1990) Trends in Neuroscience 13: 281-5; Alexander et Crutcher, (1990) Trends in Neuroscience 13: 266-71; and for review Poewe et al., Nature Review (2017) vol. 3 article 17013: 1-21).

The most effective therapeutic strategies available to patients suffering from Parkinson's disease, and aiming at controlling motor symptoms are primarily indirect and direct dopamine agonists. The classic and gold standard treatment regimen includes chronic oral intake of L-3,4-dihydroxy phenylalanine (L-DOPA) which is decarboxylated in the brain to form dopamine. Other approaches consist in the administration of dopamine receptor agonists such as apomorphine which acts both on the D1 and D2 receptors subtypes, or pramipexole, ropinirole and others which are predominantly directed towards D2 receptors subtypes. Optimal motor relief is obtained with use of both L-DOPA and apomorphine due to their activation of both D1 and D2 receptor subtypes and holistic re-equilibrium of the indirect-direct pathways (i.e. while D2 agonists only reverse the indirect pathway dysfunction).

L-DOPA and apomorphine with the structures depicted below are currently the most efficacious PD drugs in clinical use.

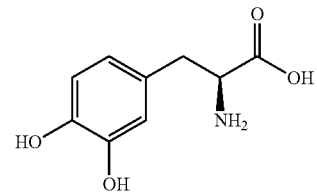

L-DOPA

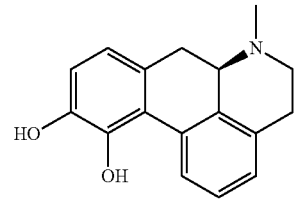

apomorphine

L-DOPA is a prodrug of dopamine and remains the most efficacious drug in the treatment of motor Parkinson's disease. However, after several years of treatment (i.e. honeymoon period), complications arise due the inherent progression of the disease (i.e. sustained loss of dopaminergic neurons) as well as poor pharmacokinetic (PK) profile of L-DOPA. Those complications include 1) dyskinesia which are abnormal involuntary movements occurring during the optimal 'on-time effect' of the drug; and 2) off fluctuations, period during which the L-DOPA positive effect wears off and symptoms re-emerge or worsen (Sprenger and Poewe, CNS Drugs (2013), 27: 259-272).

Direct dopamine receptor agonists are able to activate the dopamine autoreceptors as well as the postsynaptic dopamine receptors located on the medium spiny neurons MSN-1 and MSN-2. Apomorphine belongs to a class of dopamine agonists with a 1,2-dihydroxybenzene (catechol) moiety. When combined with a phenethylamine motif, catecholamines often possess low or no oral bioavailability as is the case for apomorphine. Apomorphine is used clinically in PD therapy albeit with a non-oral delivery (typically intermittent subcutaneous administration or daytime continuous parenteral infusion via a pump). For apomorphine, animal studies have shown that transdermal delivery or implants may provide possible forms of administration. However, when the delivery of apomorphine from implants was studied in monkeys (Bibbiani et al., Chase Experimental Neurology (2005), 192: 73-78) it was found that in most cases the animals had to be treated with the immunosuppressant dexamethasone to prevent local irritation and other complications following the implantation surgery. Alternative delivery strategies for apomorphine therapy in PD such as inhalation and sublingual formulations have been extensively explored (see e.g. Grosset et al., Acta Neurol Scand. (2013), 128:166-171 and Hauser et al., Movement Disorders (2016), Vol. 32 (9): 1367-1372). However, these efforts are yet not in clinical use for the treatment of PD.

An alternative to the non-oral formulations of the catecholamines involves the use of a prodrug masking the free catechol hydroxyl groups to enable oral administration. However, a known problem associated with the development of prodrugs for clinical use is the difficulties associated with predicting conversion to the parent compound in humans.

Various ester prodrugs of catecholamines have been reported in the literature such as enterically coated N-propyl-noraporphine (NPA) and the mono pivaloyl ester of apomorphine for duodenal delivery (see eg. WO 02/100377), and the D1-like agonist adrogolide, a diacetyl prodrug of A-86929 (Giardina and Williams; CNS Drug Reviews (2001), Vol. 7 (3): 305-316). Adrogolide undergoes extensive hepatic first-pass metabolism in man after oral dosing and, as a result, has a low oral bioavailability (app. 4%). In PD patients, intravenous (IV) adrogolide has antiparkinson efficacy comparable to that of L-DOPA (Giardina and Williams; CNS Drug Reviews (2001), Vol. 7 (3): 305-316).

In addition to the ester prodrugs of catecholamines, an alternative prodrug approach involves the masking of the two catechol hydroxyl groups as the corresponding methylenedioxy (MDO) derivative or di-acetalyl derivative. This prodrug principle has been described for example in Campbell et al., Neuropharmacology (1982); 21(10): 953-961 and in U.S. Pat. No. 4,543,256, WO 2009/026934 and WO 2009/026935.

Yet another suggested approach for a catecholamine prodrug is the formation of an enone derivative as suggested in for example WO 2001/078713 and in Liu et al., Bioorganic Med. Chem. (2008), 16: 3438-3444. For further examples of catecholamine prodrugs see for example Sozio et al., Exp. Opin. Drug Disc. (2012); 7(5): 385-406.

The compound (4aR,10aR)-1-Propyl-1,2,3,4,4a,5,10,10a-octahydro-benzo[g]quinoline-6,7-diol depicted as compound (I) below is disclosed in WO 2009/026934. The trans-isomer was disclosed previously in Liu et al., J. Med. Chem. (2006), 49: 1494-1498 and then in Liu et al., Bioorganic Med. Chem. (2008), 16: 3438-3444 including pharmacological data indicating that the compound has a low oral bioavailability in rats. The racemate was disclosed for the first time in Cannon et al., J. Heterocyclic Chem. (1980); 17: 1633-1636.

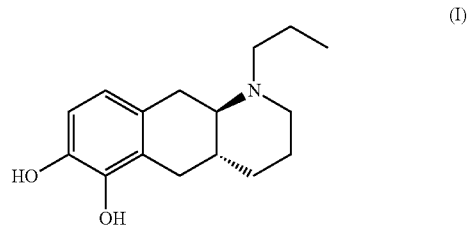 [SMILES: CCCN1CCC[C@@H]2Cc3c(ccc(O)c3O)C[C@H]21]

Compound (I) is a dopamine receptor agonist with mixed D1 and D2 activity. Some prodrug derivatives of compound (I) are known in the art.

Liu et al., J. Med. Chem. (2006), 49: 1494-1498 and Liu et al., Bioorganic Med. Chem. (2008), 16: 3438-3444 disclose the enone derivative of formula (Ia) depicted below which was shown to be converted to the active compound (I) in rats.

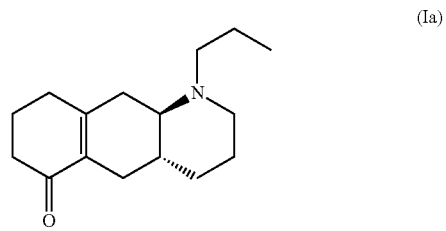 [SMILES: CCCN1CCC[C@@H]2CC3=C(CCCC3=O)C[C@H]21]

WO 2009/026934 and WO 2009/026935 disclose two types of prodrug derivatives of compound (I) including (6aR,10aR)-7-propyl-6,6a,7,8,9,10,10a,11-octahydro-[1,3]dioxolo[4',5':5,6]benzo[1,2-g]quinoline, a methylenedioxy (MDO) derivative with the formula (Ib) below:

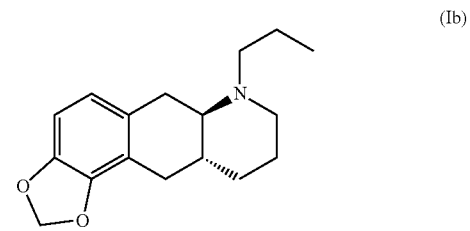 [SMILES: CCCN1CCC[C@@H]2Cc3c(ccc4c3OCO4)C[C@H]21]

The conversion of compound (Ib) to compound (I) in rat and human hepatocytes has been demonstrated in WO 2010/097092. Furthermore, the in vivo pharmacology of the compounds (Ia) and (Ib) as well as the active "parent compound" (I) has been tested in various animal models relevant for Parkinson's Disease (WO 2010/097092). Both compound (I) and compounds (Ia) and (Ib) were found to be effective, indicating that compounds (Ia) and (Ib) are converted in vivo to compound (I). All three compounds were reported to have a duration of action that was longer than observed for L-dopa and apomorphine.

The other prodrug of compound (I) disclosed in WO 2009/026934 and WO 2009/026935 is a conventional ester prodrug of the formula (Ic):

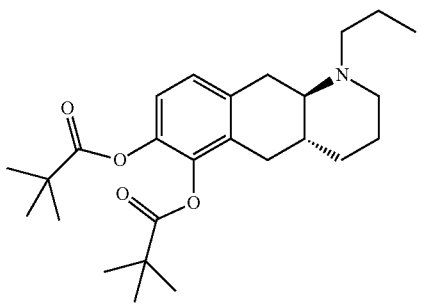

(Ic)

Despite the long-standing interest in the field, there is evidently still an unmet need as regards developing efficient, well-tolerated and orally active drugs for the treatment of PD. A prodrug derivative of a mixed D1/D2 agonist giving a stable PK profile which can provide continuous dopaminergic stimulation may fulfil such unmet needs.

Masking of catechol hydroxy groups of carbidopa derivatives with benzyl or small alkyl for improvement of intestinal absorption has been suggested in WO 2004/052841 but prodrug potential of such compounds was not demonstrated.

SUMMARY OF THE INVENTION

The present invention relates to new compounds which are glucuronide derivatives of compound (I) further derivatised by esterification of the free hydroxyl and carboxylic acid groups in the molecule, or unsaturated glycosyl derivatives, and ester derivatives and ether derivatives of compound (I) for treatment of Parkinson's Disease. More specifically, the invention relates to new prodrug derivatives of the compound (4aR,10aR)-1-Propyl-1,2,3,4,4a,5,10,10a-octahydro-benzo[g]quinoline-6,7-diol (compound (I)). The compounds of the invention have proven particularly useful for oral delivery of compound (I).

Accordingly, the present invention relates to compounds of formula (Id)

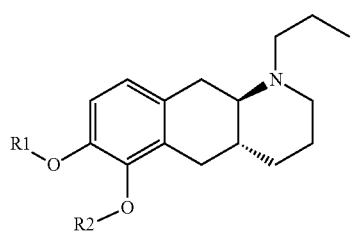

(Id)

wherein
a) R1 is selected from the group consisting of H, $C_1$-$C_6$ alkyl, methyl substituted with $C_3$-$C_6$ cycloalkyl, benzyl and —C(O)$C_1$-$C_6$ alkyl, and R2 is selected from one of the substituents (i) and (ii) below; or
b) R1 is selected from one of the substituents (i) and (ii) below and R2 is selected from the group consisting of H, $C_1$-$C_6$ alkyl, methyl substituted with $C_3$-$C_6$ cycloalkyl, benzyl and —C(O)$C_1$-$C_6$ alkyl; or
c) R1 and R2 are independently selected from substituent (i) and substituent (ii) below; or
d) R1 and R2 are both represented by substituent (i) below; or
e) R1 and R2 are both represented by substituent (ii) below;

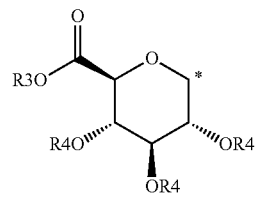

(i)

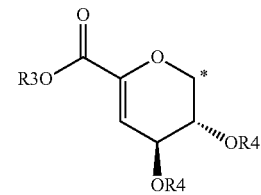

(ii)

and wherein * indicates the attachment point; and
wherein the carbon atom at the attachment point on substituent (i) is in the S-configuration; and wherein R3 is selected from H, $C_1$-$C_6$ alkyl and benzyl; and
wherein R4 is selected from H, —C(O)$C_1$-$C_6$alkyl and —C(O)phenyl;
with the proviso that when both of R3 and R4 in substituent (i) are H, then R1 and R2 cannot both be substituent (i);
and with the proviso that when one of R1 and R2 is substituent (i) wherein both of R3 and R4 in substituent are H, then the other of R1 and R2 cannot be H;
or a pharmaceutically acceptable salt thereof.

One aspect of the invention relates to a pharmaceutical composition comprising a compound according formula (Id) or a pharmaceutically acceptable salt thereof, and one or more pharmaceutically acceptable excipients.

Another aspect of the invention relates to a compound according to formula (Id) for use as a medicament.

Another aspect of the invention relates to a compound according to formula (Id) or a pharmaceutically acceptable salt thereof for use in the treatment of a neurodegenerative disease or disorder such as Parkinson's Disease, Huntington's disease, Restless leg syndrome or Alzheimer's disease; or a neuropsychiatric disease or disorder such as schizophrenia, attention deficit hyperactivity disorder or drug addiction.

Another aspect of the invention relates to a method for the treatment of a neurodegenerative disease or disorder such as Parkinson's Disease, Huntington's disease, Restless leg syndrome or Alzheimer's disease; or a neuropsychiatric disease or disorder such as schizophrenia, attention deficit hyperactivity disorder or drug addiction; which method comprises the administration of a therapeutically effective amount of a compound of formula (Id) or a pharmaceutically acceptable salt thereof, to a patient in need thereof.

Another aspect of the invention relates to the use of a compound according to formula (Id) or a pharmaceutically acceptable salt thereof, for the manufacture of a medicament for the treatment of a neurodegenerative disease or disorder such as Parkinson's disease, Huntington's disease, Restless leg syndrome or Alzheimer's disease; or for the treatment of a neuropsychiatric disease or disorder such as schizophrenia, attention deficit hyperactivity disorder or drug addiction.

Definitions

Attachment Point

In the context of the present invention, it is understood that the carbon atom at the attachment point on substituent (i) is at the anomeric position of (i). Similarly, the carbon atom at the attachment point on substituent (ii) (depicted in embodiment 1) is at the anomeric position of (ii).

Compounds of the Invention

Reference to compounds encompassed by the invention includes the free substance (e.g. the free base or zwitter ion) of compounds of the invention, pharmaceutically acceptable salts of compounds of the invention, such as acid addition salts or base addition salts, and polymorphic and amorphic forms of compounds of the invention and of pharmaceutically acceptable salts thereof. Furthermore, the compounds of the invention and pharmaceutically acceptable salts thereof may potentially exist in unsolvated as well as in solvated forms with pharmaceutically acceptable solvents such as water, ethanol and the like. Both solvated and unsolvated forms are encompassed by the present invention.

Pharmaceutically Acceptable Salts

Pharmaceutically acceptable salts in the present context is intended to indicate non-toxic, i.e. physiologically acceptable salts.

The term "pharmaceutically acceptable salts" include pharmaceutically acceptable acid addition salts which are salts formed with inorganic and/or organic acids on the nitrogen atom in the parent molecule. Said acids may be selected from for example hydrochloric acid, hydrobromic acid, phosphoric acid, nitrous acid, sulphuric acid, benzoic acid, citric acid, gluconic acid, lactic acid, maleic acid, succinic acid, tartaric acid, acetic acid, propionic acid, oxalic acid, malonic acid, fumaric acid, glutamic acid, pyroglutamic acid, salicylic acid, gentisic acid, saccharin, and sulfonic acids such as methanesulfonic acid, ethanesulfonic acid, toluenesulfonic acid, naphthalene-2-sulphonic acid, 2-hydroxy ethanesulphonic acid and benzenesulfonic acid.

The term pharmaceutically acceptable salts also include pharmaceutically acceptable base addition salts which are salts formed with inorganic and/or organic bases on the acidic groups of compounds of formula (Id). Said bases may be selected from for example zinc hydroxide, and alkali metal bases, such as sodium hydroxide, lithium hydroxide, potassium hydroxide, and alkaline earth bases, such as calcium hydroxide and magnesium hydroxide, and organic bases, such as choline, diethylamine, trimethylamine and triethylamine.

Additional examples of useful acids and bases to form pharmaceutically acceptable salts can be found e.g. in Stahl and Wermuth (Eds) "Handbook of Pharmaceutical salts. Properties, selection, and use", Wiley-VCH, 2008.

Prodrug

In the present context, the terms "prodrug" or "prodrug derivative" indicates a compound that, after administration to a living subject, such as a mammal, preferably a human is converted within the body into a pharmacologically active moiety. The conversion preferably takes place within a mammal, such as in a mouse, rat, dog, minipig, rabbit, monkey and/or human. In the present context a "prodrug of the compound (4aR,10aR)-1-Propyl-1,2,3,4,4a,5,10,10a-octahydro-benzo[g]quinoline-6,7-diol" or "a prodrug of the compound of formula (I)" or "a prodrug of compound (I)" is understood to be a compound that, after administration, is converted within the body into the compound (4aR,10aR)-1-Propyl-1,2,3,4,4a,5,10,10a-octahydro-benzo[g]quinoline-6,7-diol. Said administration may be by any conventional route of administration of pharmaceutical compositions known in the art, preferably by oral administration.

In the present context, the terms "parent compound" and "parent molecule" indicate the pharmacologically active moiety obtained upon conversion of a corresponding prodrug. For example, the "parent compound" of one of the compounds (Ia), (Ib), (Ic) or any of the compounds of the invention is understood to be the compound of formula (I).

Substituents

In the present context, a given range may interchangeably be indicated with "-" (dash) or "to", e.g. the term "$C_1$-$C_6$ alkyl" is equivalent to "$C_1$ to $C_6$ alkyl".

The term "alkyl" refers to a linear (i.e. unbranched) or branched saturated hydrocarbon having from one up to 10 carbon atoms, inclusive. Likewise, the term "$C_1$-$C_6$-alkyl" means a straight or branched chain hydrocarbon, unless explicitly state otherwise, containing from 1 to 6 carbon atoms. Examples of such groups include, but are not limited to, methyl, ethyl, 1-propyl, 2-propyl, 1-butyl, 2-butyl, 2-methyl-2-propyl, 2-methyl-1-butyl and n-hexyl. The term "linear $C_1$-$C_6$ alkyl" refers to a linear (i.e. unbranched) saturated hydrocarbon having from one up to six carbon atoms, inclusive. Examples of such groups include, methyl, ethyl, 1-propyl, 1-butyl, n-pentyl and n-hexyl.

The term "carbonyl" represents a —C(O)— group.

The term "C3-C6-cycloalkyl" means a saturated, monovalent, monocyclic hydrocarbon ring which contains 3, 4, 5 or 6 carbon atoms ("C3-C6-cycloalkyl"). Said C3-C6-cycloalkyl group is for example, a monocyclic hydrocarbon ring, e.g. a cyclopropyl, cyclobutyl, cyclopentyl or cyclohexyl group.

The term "alkylcarbonyl" refers to an alkyl group as defined herein attached to the parent molecular moiety through a carbonyl group. Likewise, the term "—C(O)$C_1$-$C_6$-alkyl" refers to an $C_1$-$C_6$-alkyl as defined herein attached to the parent molecular moiety through a carbonyl group.

Pharmacokinetic Definitions and Abbreviations

As used herein, a "PK profile" is an abbreviation of "pharmacokinetic profile". Pharmacokinetic profiles and pharmacokinetic parameters described herein are based on the plasma concentration-time data obtained for the compound of formula (I) after oral dosing of a compound of the invention, using non-compartmental modelling. Abbreviated PK parameters are: $C_{max}$ (maximum concentration); $t_{max}$ (time to $C_{max}$); $t_{1/2}$ (half-life); $AUC_{0-24}$ (area under the curve from time of dosing and until 24 hours after dosing), and "Exposure at 24 h" is the plasma concentration of the compound of formula (I) as measured 24 hours after dosing.

Therapeutically Effective Amount

In the present context, the term "therapeutically effective amount" of a compound means an amount sufficient to alleviate, arrest, partly arrest, remove or delay the clinical manifestations of a given disease and its complications in a therapeutic intervention comprising the administration of said compound. An amount adequate to accomplish this is defined as "therapeutically effective amount". Effective amounts for each purpose will depend e.g. on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician.

In the context of the present invention, a "therapeutically effective amount" of a compound of the invention indicates an amount of said compound of the invention that is able to provide an amount of compound (I) that is sufficient to alleviate, arrest, partly arrest, remove or delay the clinical manifestations of a given disease and its complications when said compound of the invention is administered, preferably by the oral route, to a mammal, preferably a human.

Treatment and Treating

In the present context, "treatment" or "treating" is intended to indicate the management and care of a patient for the purpose of alleviating, arresting, partly arresting, removing or delaying progress of the clinical manifestation of the disease. The patient to be treated is preferably a mammal, in particular a human being.

Conditions for Treatment

The compounds of the present invention are intended for treatment of neurodegenerative diseases and disorders such as Parkinson's disease and/or other conditions for which treatment with a dopamine agonist is therapeutically beneficial.

Therapeutic indications include a variety of central nervous system disorders characterized by motor and/or non-motor disturbances and for which part of the underlying pathophysiology is a dysfunction of the striatal-mediated circuitry. Such functional disturbances can be seen in neurodegenerative diseases such as but not limited to Parkinson's disease (PD), Restless leg syndrome, Huntington's disease, and Alzheimer's disease but also neuropsychiatric diseases such as, but not limited to schizophrenia, attention deficit hyperactivity disorder and drug addiction.

In addition to neurodegenerative diseases and disorders, other conditions in which an increase in dopaminergic turnover may be beneficial are in the improvement of mental functions including various aspects of cognition. It may also have a positive effect in depressed patients, and it may also be used in the treatment of obesity as an anorectic agent and in the treatment of drug addiction. It may improve minimal brain dysfunction (MBD), narcolepsy, attention deficit hyperactivity disorder and potentially the negative, the positive as well as the cognitive symptoms of schizophrenia.

Restless leg syndrome (RLS) and periodic limb movement disorder (PLMD) are alternative indications, which are clinically treated with dopamine agonists. In addition, impotence, erectile dysfunction, SSRI induced sexual dysfunction, ovarian hyperstimulation syndrome (OHSS) and certain pituitary tumors (prolactinoma) are also likely to be improved by treatment with dopamine agonists. Dopamine is involved in regulation of the cardiovascular and renal systems, and accordingly, renal failure and hypertension can be considered alternative indications for the compounds of the invention.

The invention encompasses use of the compounds of the invention for treatment of the diseases and disorders listed above.

Combinations

In one embodiment of the invention, the compounds of formula (Id) are for use as stand-alone treatment as the sole active compound. In another embodiment of the invention, the compounds of formula (Id) may be used in combination with other agents useful in the treatment of a neurodegenerative disease or disorder such as Parkinson's disease. The terms "combined use", "in combination with" and "a combination of" and the like as used herein in the context of the method of the invention comprising the combined administration of therapeutically effective amounts of a compound of formula (Id), and another compound, which compound is useful in the treatment a neurodegenerative disease or disorder, is intended to mean the administration of a compound of formula (Id) simultaneously or sequentially, in any order, together with said other compound.

The two compounds may be administered simultaneously or with a time gap between the administrations of the two compounds. The two compounds may be administered either as part of the same pharmaceutical formulation or composition, or in separate pharmaceutical formulations or compositions. The two compounds may be administered on the same day or on different days. They may be administered by the same route, such for example by oral administration, subcutaneous injection, by transdermal administration, by depot, by intramuscular injection or intravenous injection; or by different routes wherein one compound is for example administered orally or placed by depot and the other compound is for example injected. The two compounds may be administered by the same dosage regime or interval, such as once or twice daily, weekly, or monthly; or by different dosage regimes for example wherein one is administered once daily and the other is administered twice daily or weekly or monthly.

In some instances, the patient to be treated may already be in treatment with one or more other compounds useful in the treatment of a neurodegenerative disease or disorder when treatment with a compound of formula (Id) is initiated. In other instances, the patient may already be in treatment with a compound of formula (Id) when treatment with one or more other compounds useful in the treatment of a neurodegenerative disease or disorder is initiated. In other instances, the treatment with a compound of formula (Id) and treatment with one or more other compounds useful in the treatment of a neurodegenerative disease or disorder is initiated at the same time.

Compounds for Combination Treatment

In the context of the invention, compounds to be used in combination with a compound of formula (Id) may be selected from for example L-DOPA, droxidopa, foliglurax, MAO-B inhibitors such as selegiline or rasagiline, COMT inhibitors such as entacapone or tolcapone, adenosine 2a antagonists such as istradefylline, antiglutamatergic agents such as amantadine or memantine, acetylcholinesterase inhibitors such as rivastigmine, donepezil or galantamine and antipsychotic agents such as quetiapine, clozapine, risperidone, pimavanserin, olanzapine, haloperidol, aripiprazole or brexpiprazole.

In addition to small molecules, compounds for combination could also include emerging biologics approaches in treatments for neurodegenerative diseases or disorders such as for example antibodies targeting alpha-synuclein, Tau or A-beta proteins.

Administration Routes

The pharmaceutical compositions comprising a compound of formula (Id), either as the sole active compound or in combination with another active compound, may be specifically formulated for administration by any suitable route such as the oral, rectal, nasal, buccal, sublingual, pulmonal, transdermal and parenteral (e.g. subcutaneous, intramuscular, and intravenous) route. In the context of the present invention the oral route is the preferred route of administration.

It will be appreciated that the route will depend on the general condition and age of the subject to be treated, the nature of the condition to be treated and the active ingredient.

Pharmaceutical Formulations and Excipients

In the following, the term, "excipient" or "pharmaceutically acceptable excipient" refers to pharmaceutical excipients including, but not limited to, carriers, fillers, diluents, antiadherents, binders, coatings, colours, disintegrants, flavours, glidants, lubricants, preservatives, sorbents, sweeteners, solvents, vehicles and adjuvants.

The present invention also provides a pharmaceutical composition comprising a compound of formula (Id), such as one of the compounds disclosed in the Experimental Section herein. The present invention also provides a process for making a pharmaceutical composition comprising a compound of formula (Id). The pharmaceutical compositions according to the invention may be formulated with pharmaceutically acceptable excipients in accordance with conventional techniques such as those disclosed in Remington, "The Science and Practice of Pharmacy", 22$^{th}$ edition (2013), Edited by Allen, Loyd V., Jr.

The pharmaceutical composition comprising a compound of the present invention is preferably a pharmaceutical composition for oral administration. Pharmaceutical compositions for oral administration include solid oral dosage forms such as tablets, capsules, powders and granules; and liquid oral dosage forms such as solutions, emulsions, suspensions and syrups as well as powders and granules to be dissolved or suspended in an appropriate liquid.

Solid oral dosage forms may be presented as discrete units (e.g. tablets or hard or soft capsules), each containing a predetermined amount of the active ingredient, and preferably one or more suitable excipients. Where appropriate, the solid dosage forms may be prepared with coatings such as enteric coatings or they may be formulated so as to provide modified release of the active ingredient such as delayed or extended release according to methods well known in the art. Where appropriate, the solid dosage form may be a dosage form disintegrating in the saliva, such as for example an orodispersible tablet.

Examples of excipients suitable for solid oral formulation include, but are not limited to, microcrystalline cellulose, corn starch, lactose, mannitol, povidone, croscarmellose sodium, sucrose, cyclodextrin, talcum, gelatin, pectin, magnesium stearate, stearic acid and lower alkyl ethers of cellulose. Similarly, the solid formulation may include excipients for delayed or extended release formulations known in the art, such as glyceryl monostearate or hypromellose. If solid material is used for oral administration, the formulation may for example be prepared by mixing the active ingredient with solid excipients and subsequently compressing the mixture in a conventional tableting machine; or the formulation may for example be placed in a hard capsule e.g. in powder, pellet or mini tablet form. The amount of solid excipient will vary widely but will typically range from about 25 mg to about 1 g per dosage unit.

Liquid oral dosage forms may be presented as for example elixirs, syrups, oral drops or a liquid filled capsule. Liquid oral dosage forms may also be presented as powders for a solution or suspension in an aqueous or non-aqueous liquid. Examples of excipients suitable for liquid oral formulation include, but are not limited to, ethanol, propylene glycol, glycerol, polyethylenglycols, poloxamers, sorbitol, poly-sorbate, mono and di-glycerides, cyclodextrins, coconut oil, palm oil, and water. Liquid oral dosage forms may for example be prepared by dissolving or suspending the active ingredient in an aqueous or non-aqueous liquid, or by incorporating the active ingredient into an oil-in-water or water-in-oil liquid emulsion.

Further excipients may be used in solid and liquid oral formulations, such as colourings, flavourings and preservatives etc.

Pharmaceutical compositions for parenteral administration include sterile aqueous and nonaqueous solutions, dispersions, suspensions or emulsions for injection or infusion, concentrates for injection or infusion as well as sterile powders to be reconstituted in sterile solutions or dispersions for injection or infusion prior to use. Examples of excipients suitable for parenteral formulation include, but are not limited to, water, coconut oil, palm oil and solutions of cyclodextrins. Aqueous formulations should be suitably buffered if necessary and rendered isotonic with sufficient saline or glucose.

Other types of pharmaceutical compositions include suppositories, inhalants, creams, gels, dermal patches, implants and formulations for buccal or sublingual administration.

It is requisite that the excipients used for any pharmaceutical formulation comply with the intended route of administration and are compatible with the active ingredients.

Doses

In one embodiment, the compound of the present invention is administered in an amount from about 0.0001 mg/kg body weight to about 5 mg/kg body weight per day. In particular, daily dosages may be in the range of 0.001 mg/kg body weight to about 2 mg/kg body weight per day. The exact dosages will depend upon the frequency and mode of administration, the sex, the age, the weight, and the general condition of the subject to be treated, the nature and the severity of the condition to be treated, any concomitant diseases to be treated, the desired effect of the treatment and other factors known to those skilled in the art.

A typical oral dosage for adults will be in the range of 0.01-100 mg/day of a compound of the present invention, such as 0.05-50 mg/day, such as 0.1-10 mg/day or 0.1-5 mg/day. Conveniently, the compounds of the invention are administered in a unit dosage form containing said compounds in an amount of about 0.01 to 50 mg, such as 0.05 mg, 0.1 mg, 0.2 mg, 0.5 mg, 1 mg, 5 mg, 10 mg, 15 mg, 20 mg or up to 50 mg of a compound of the present invention.

Solid arrows: conversion demonstrated in vitro and in vivo. Dotted arrows: conversion demonstrate in vitro. Streaky arrows: conversion demonstrated in vivo. Open arrows: conversion not demonstrated. The illustrations have been divided into FIGS. 1a-1e to provide a better overview. R is selected from methyl, ethyl and benzyl.

Figure 1A:
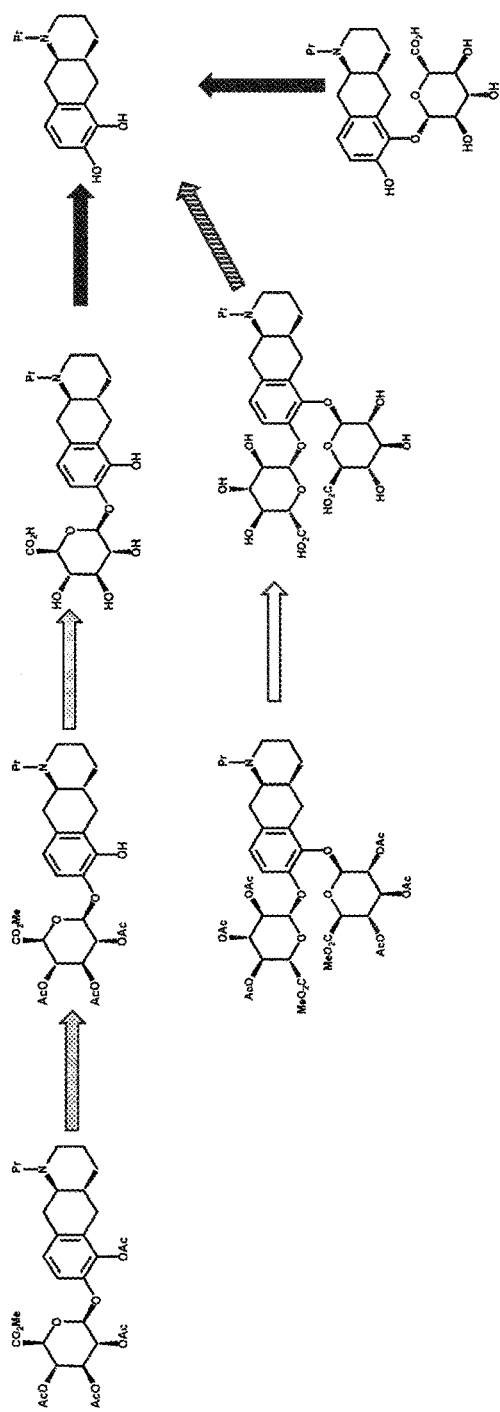
FIG. 1: graphic illustration of conversion of compounds to the invention to compound (Id).
Figure 1B:
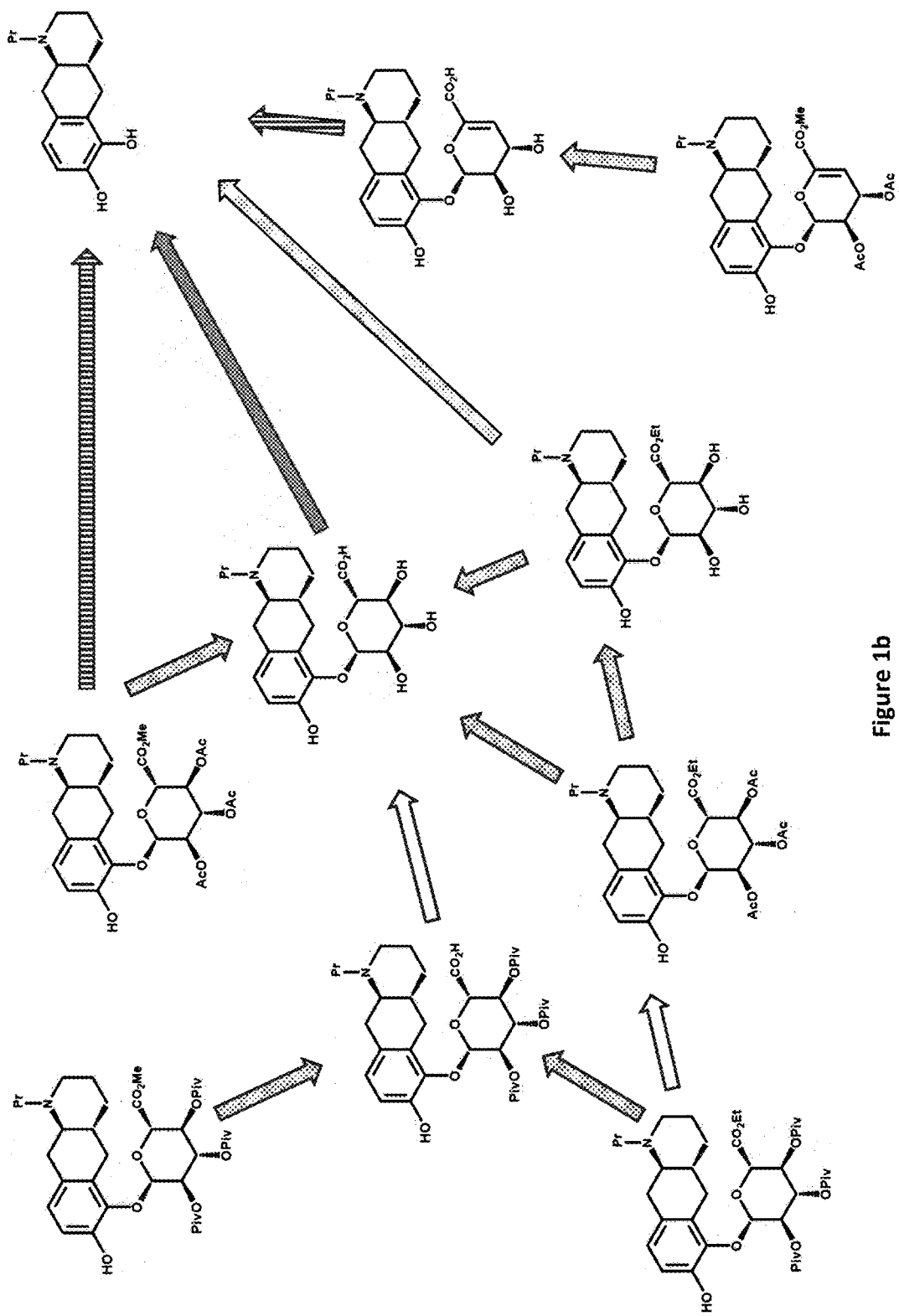
Figure 1C:
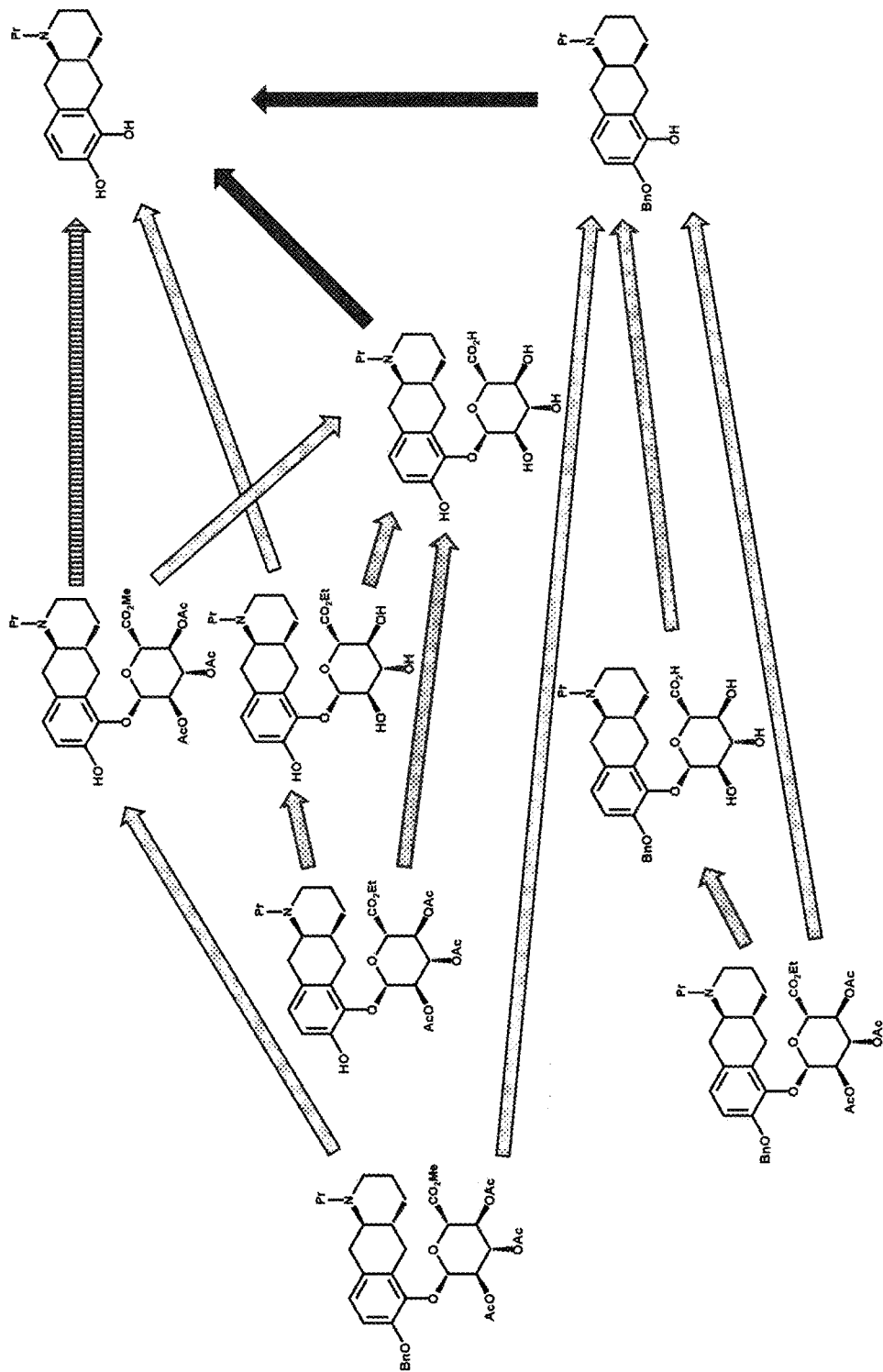
Figure 1D:
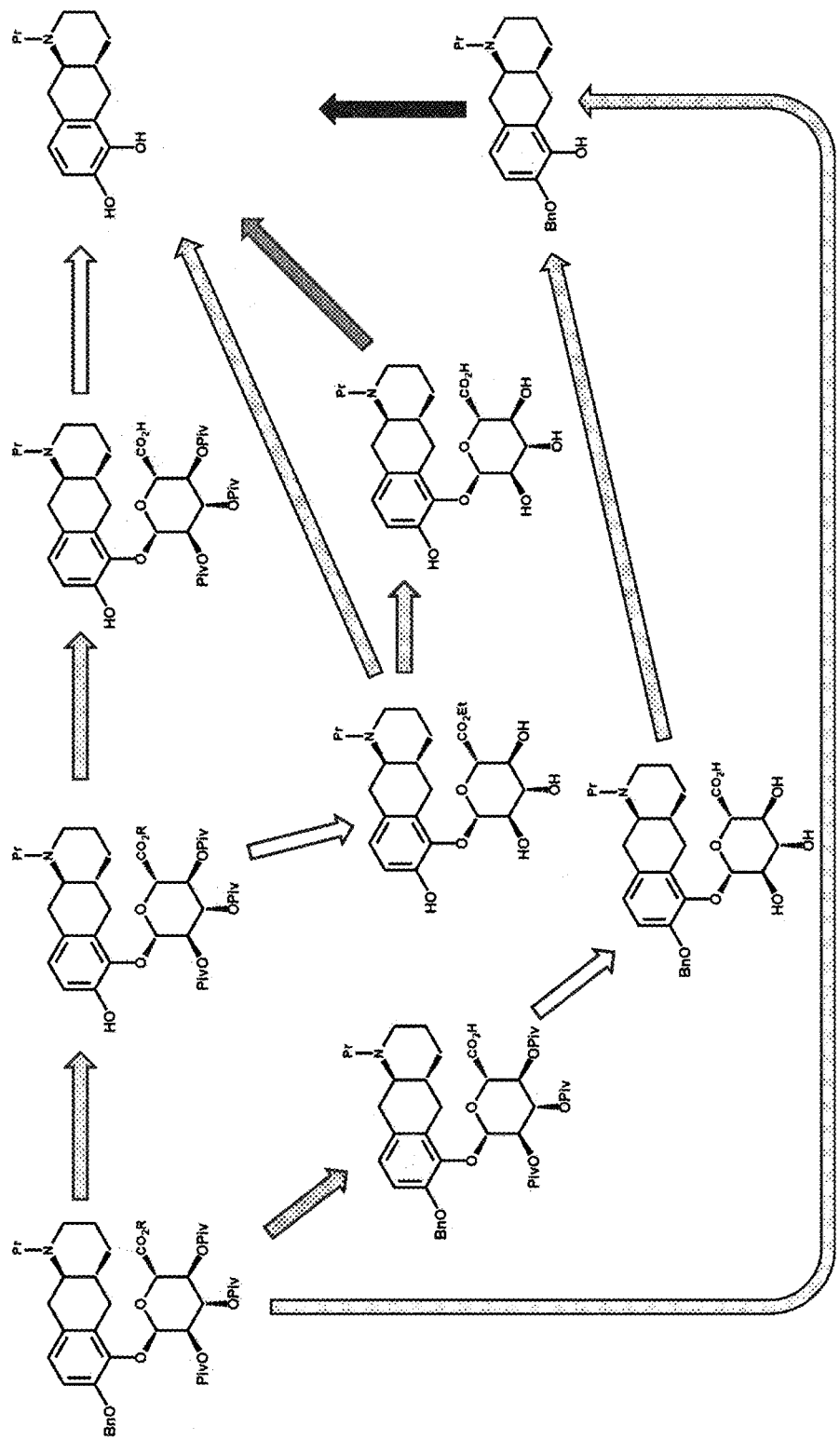
Figure 1E:
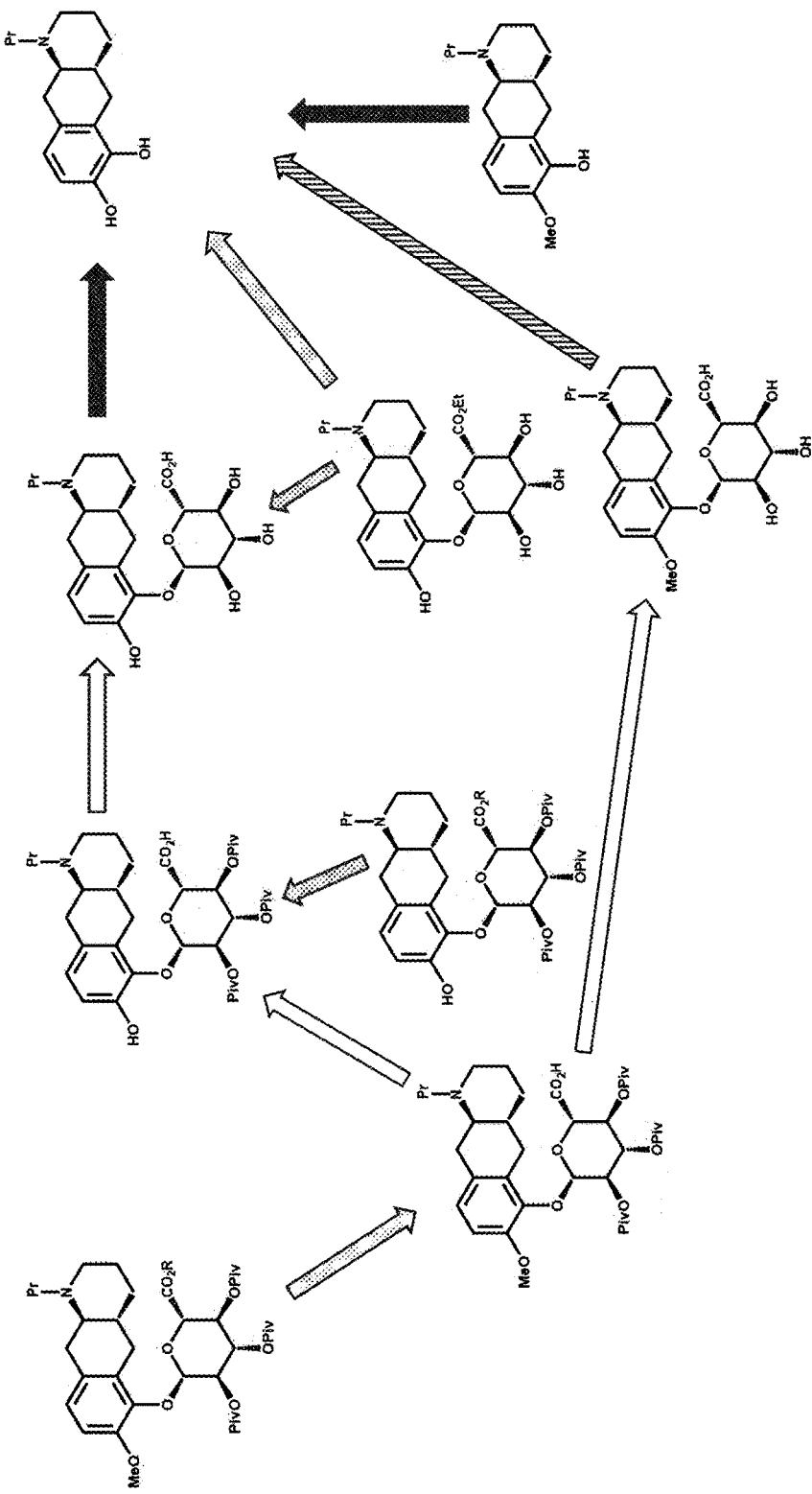
Figure 2A:
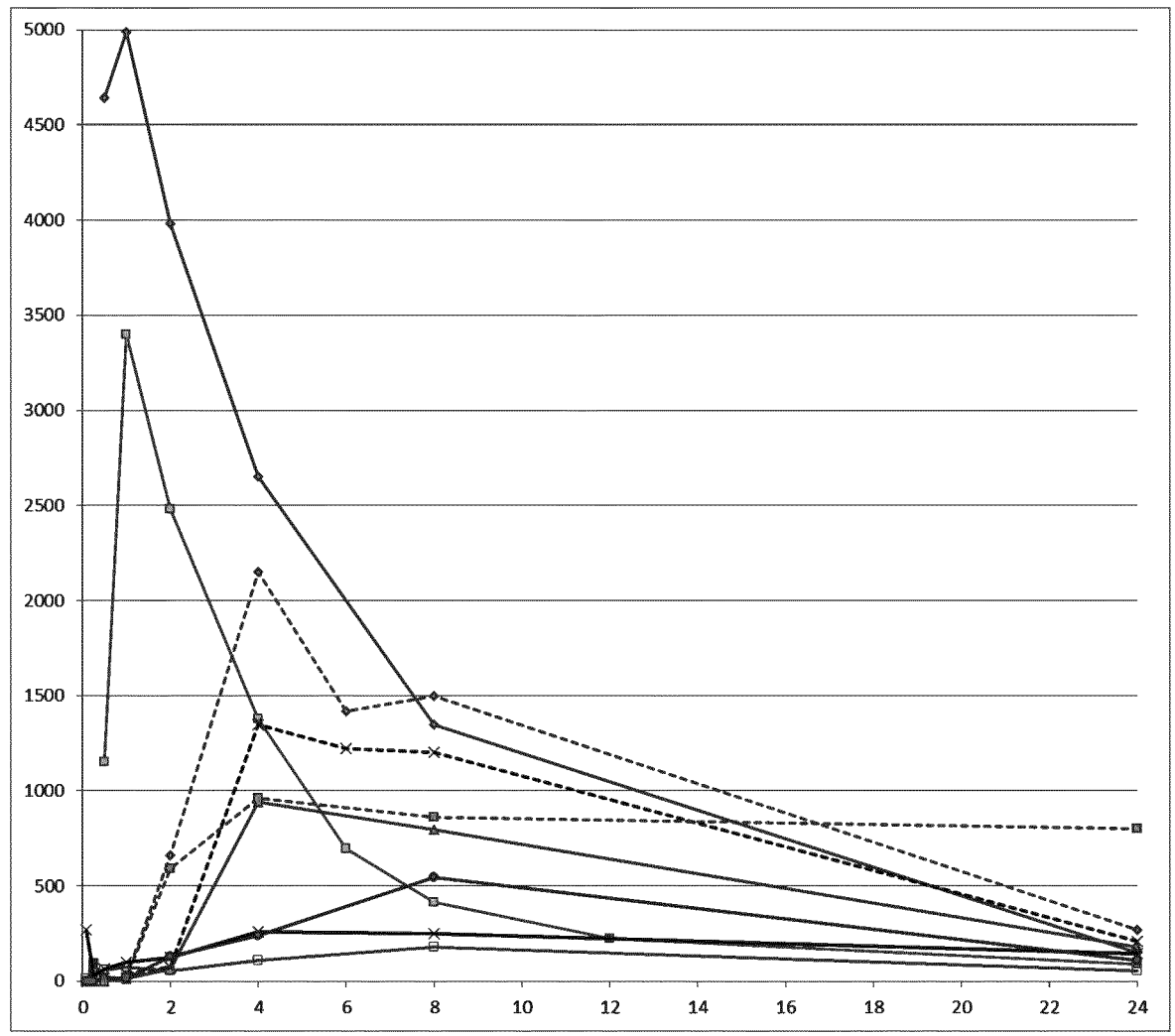
Figure 2B:
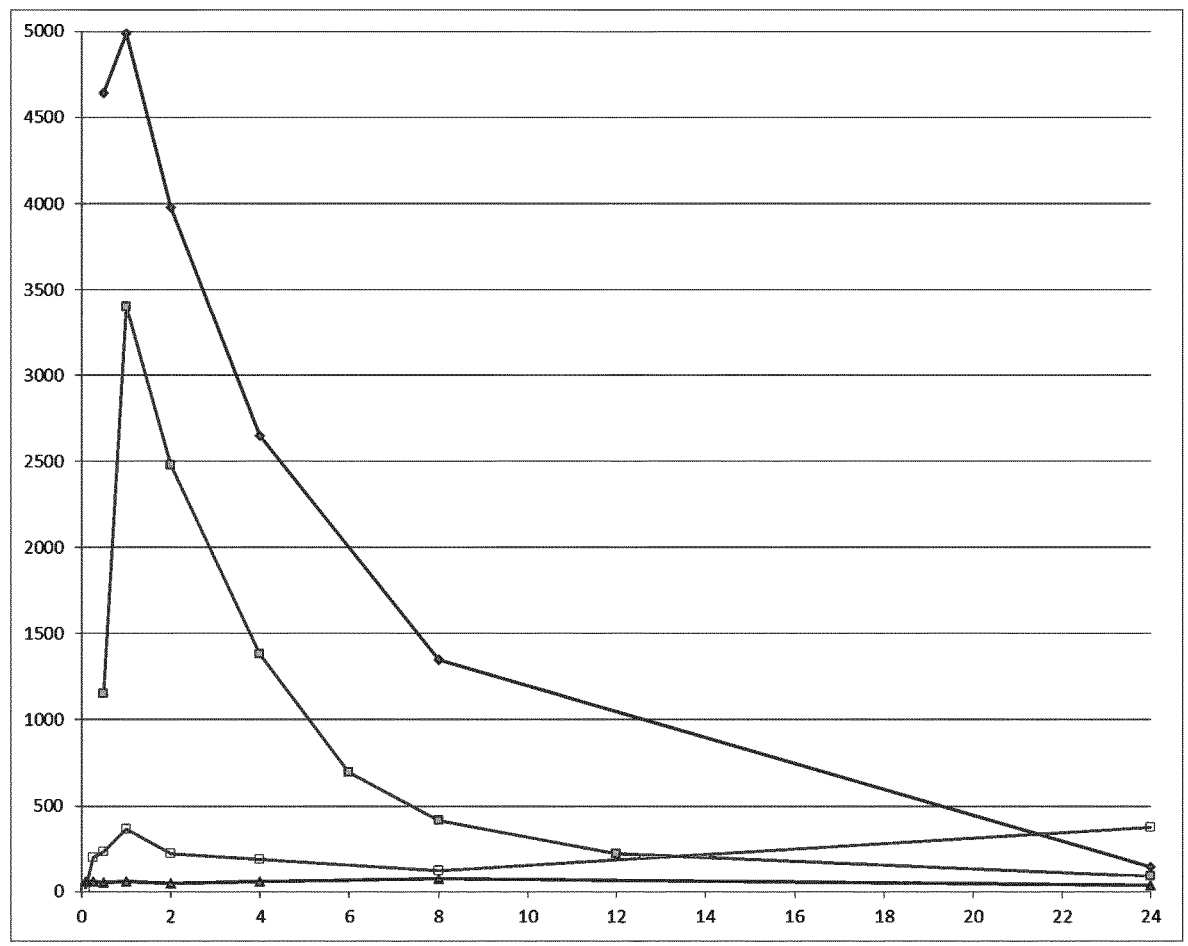

FIG. 2: PK profiles in Wistar rats obtained after oral dosing according to Example 3. Profiles are based on mean plasma concentrations from 3 subjects for each compound.

X-axis: time (hours); Y-axis: plasma concentration of Compound (I) (pg/mL).

2a: profiles obtained after dosing of the following compounds ■: compound (Ia); ♦: compound (Ib); ♦-with dotted lines: compound (Id-ib); X-with dotted lines: compound (Id); n-with dotted lines: compound (Id-iab); ▲: compound (9); ●: compound (15); X: compound (27); and □compound (2);

2b: profiles obtained after dosing of the following compounds ■: compound (Ia); ♦: compound (Ib); ♦: A2; □: A7.

Figure 3:
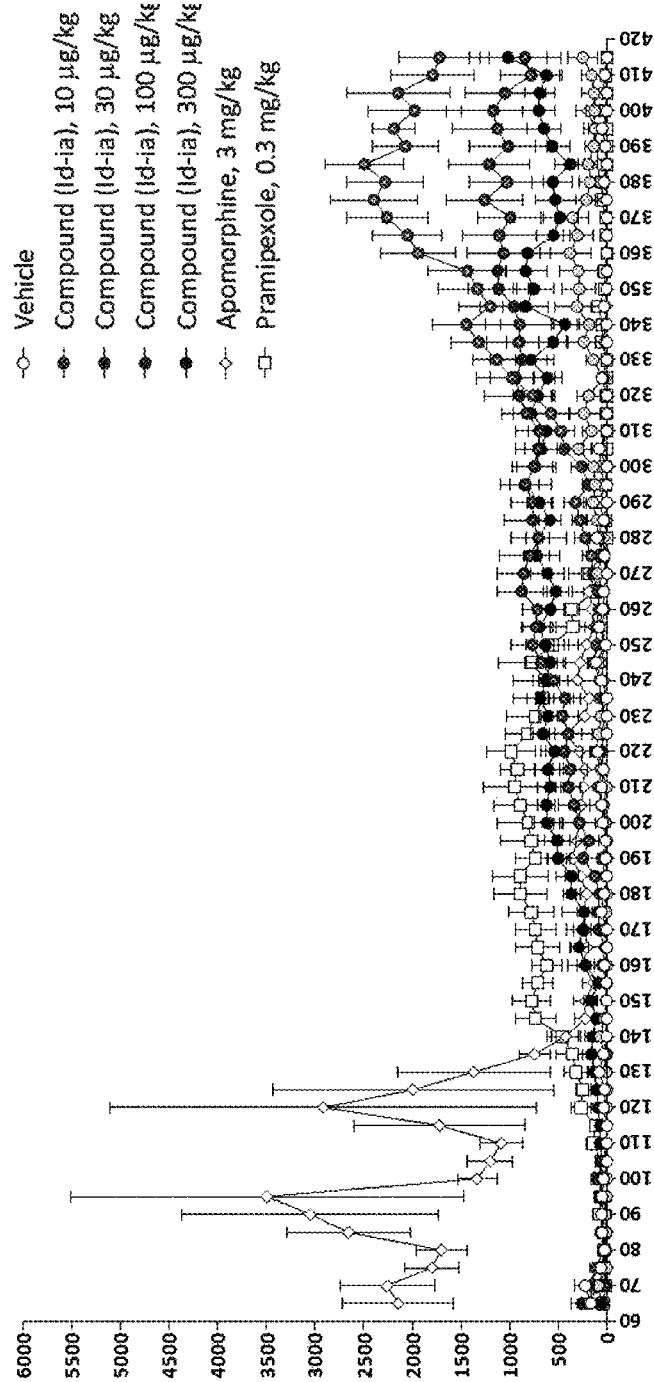
Figure 4:
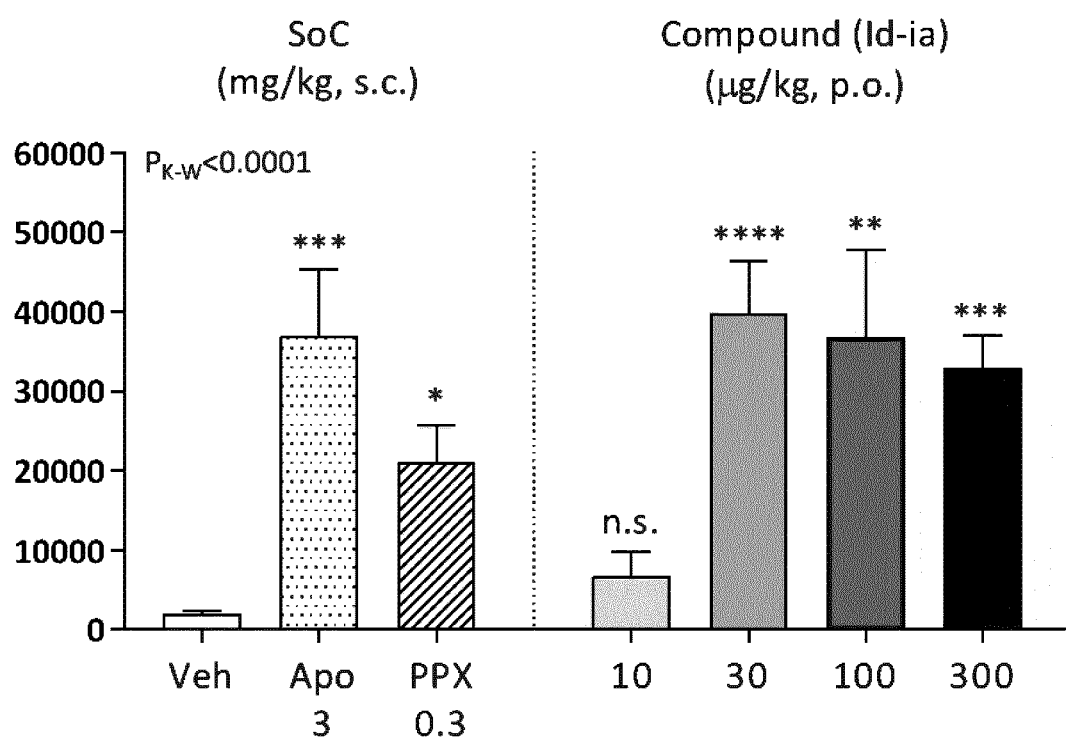

FIGS. 3 and 4: Locomotor activity time-course (FIG. 3) and total distance travelled (FIG. 4) following treatment with vehicle (H$_2$O, p.o.), or compound (Id-ia) (10, 30, 100 or 300 µg/kg, p.o.) and compared to standard-of-care (SoC) treatments: apomorphine (APO, 3 mg/kg, s.c.), pramipexole (PPX, 0.3 mg/kg, s.c.). Animals were dosed at t=60 minutes after a 60-minute habituation period in test chambers, and activity was monitored for 350 minutes thereafter. Data was evaluated by use of a Kruskal-Wallis test with Dunn's Multiple Comparisons test, resulting in an overall P-value of <0.0001.

FIG. 3: X-axis: time (min); Y-axis: Distance travelled (cm)±SEM/5-minute-bins FIG. 4: Y-axis: Total distance travelled (cm)±SEM. Significance levels for post-hoc comparisons (relative to the vehicle group) are indicated: *<0.05, <0.01, *<0.001, ****<0.0001.

Figure 5:
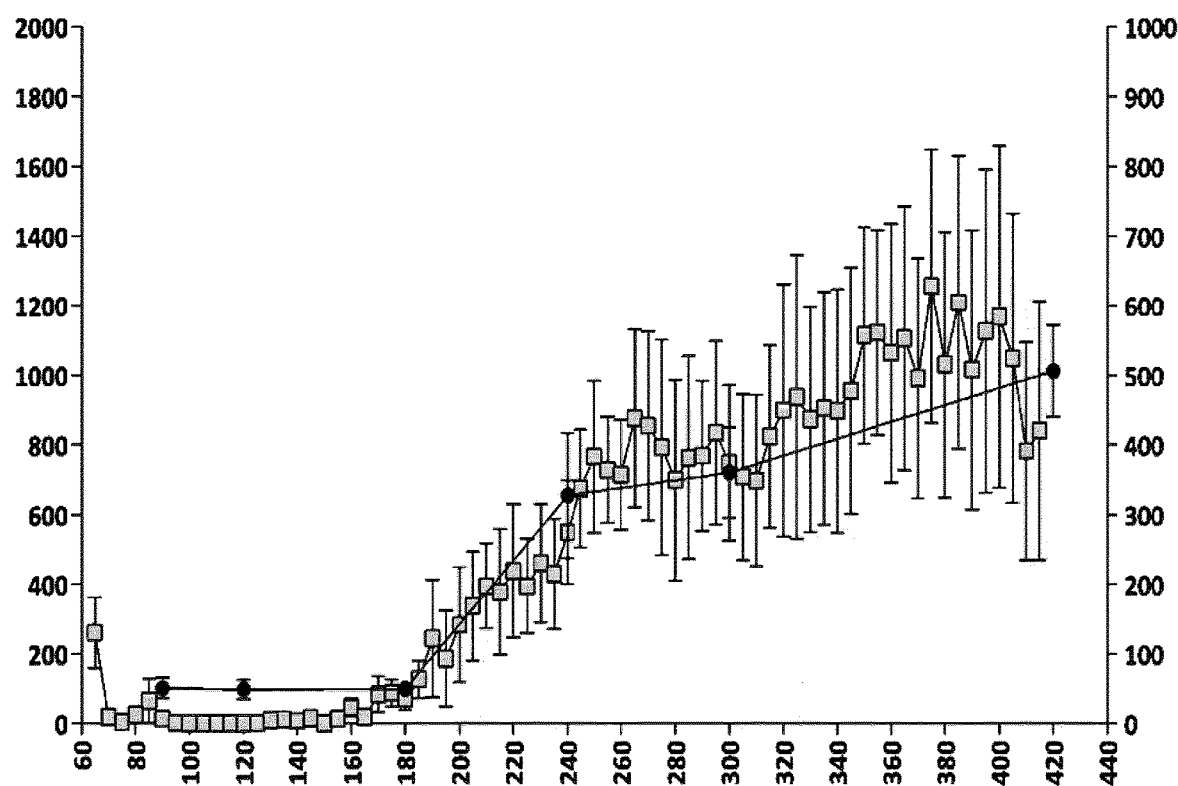
Figure 6:
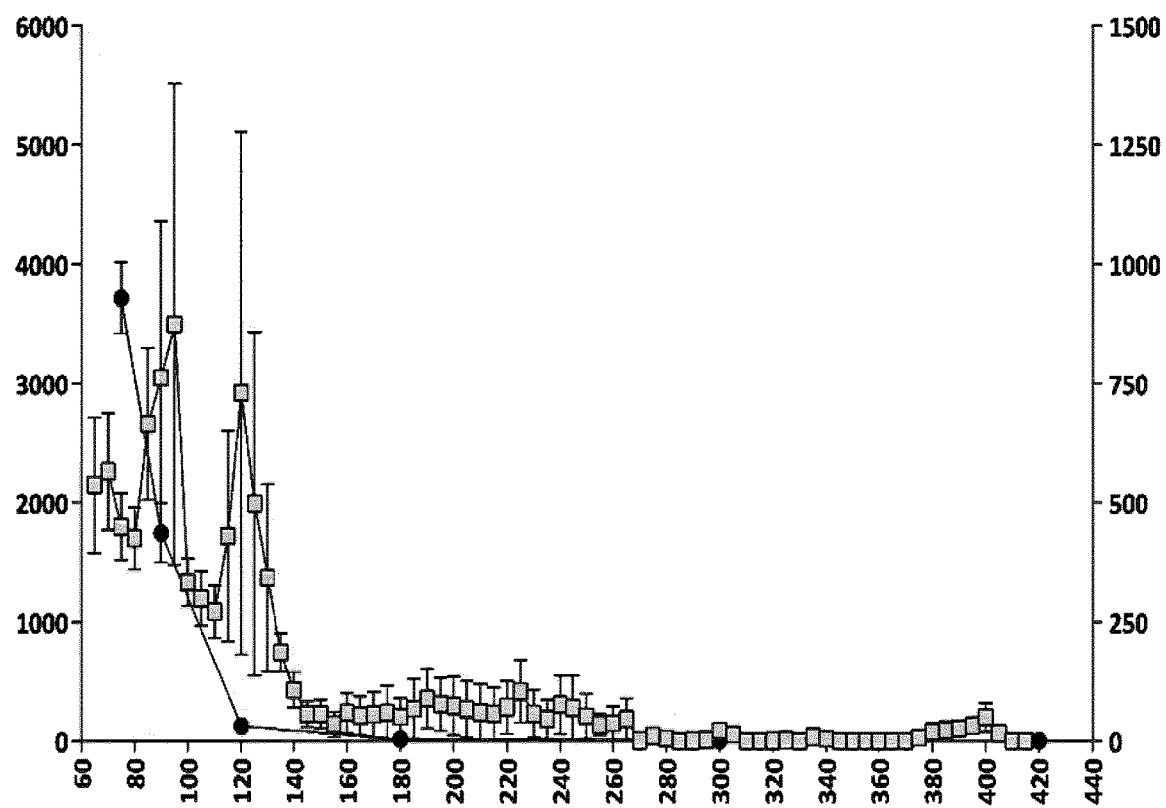

FIGS. 5 and 6: Relationships between plasma concentrations of compound (Id-ia) and compound (I) and hyperactivity induced by compound (Id-ia) (100 µg/kg, p.o.) (FIG. 5) and the corresponding relationship between plasma apomorphine concentrations and hyperactivity induced by apomorphine (3 mg/kg, s.c.) (FIG. 6).

X-axis time (min); Y-axis left: Distance travelled (cm) ±SEM/5-minute-bins; Y-axis right (FIG. 5): plasma concentration of compound (I) (pg/mL); Y axis right (FIG. 6): plasma concentration of apomorphine (ng/mL).

□: Distance travelled (cm) ● plasma concentration.

DETAILED DESCRIPTION OF THE INVENTION

The inventors have identified new compounds which are glucuronide derivatives further derivatised by esterification of the free hydroxyl and carboxylic acid groups, unsaturated glycosyl derivatives, and ester derivatives and ether derivatives of compound (I). These compounds are prodrugs of (4aR,10aR)-1-Propyl-1,2,3,4,4a,5,10,10a-octahydro-benzo[g]quinoline-6,7-diol [compound (I)] which is a dual D1/D2 agonist (see for example WO 2009/026934).

The inventors have observed that compound (I) is conjugated in rat and human hepatocytes to the glucuronide derivatives (Id-ia) and (Id-ib) with the formula showed below:

The conjugates have shown to be converted to compound (I) by conjugation and de-conjugation in the body.

Glucuronide derivatives are commonly known to be unstable in the intestine. The derivatives are formed as highly polar and soluble metabolites to facilitate the elimination of compounds from the body and are consequently easily excreted. For example, in bile duct cannulated rats, glucuronide conjugates are often found in bile while their de-conjugate (i.e. the parent compound) is found in faeces. The back-conversion of glucuronide conjugates in the intestine to the parent compound which is then sometimes subsequently reabsorbed, is known as part of the enterohepatic re-circulation process. As mentioned earlier, oral dosing of phenethyl catecholamines, such as apomorphine, has generally proven unsuccessful due to low bioavailability. Likewise, compound (I) suffers from low oral bioavailability (Liu et al., Bioorganic Med. Chem. (2008), 16: 3438-3444). With this in mind and considering the instability of glucuronide conjugates in the gastrointestinal tract, it would not be expected that oral dosing of glucuronide conjugates of compound (I) can be used to achieve sufficient plasma exposure of the compound.

The principle of applying glucuronide derivatives as prodrugs for oral delivery has been explored for retinoic acid (Goswami et al., J. Nutritional Biochem. (2003) 14: 703-709) and for morphine (Stain-Texier et al., Drug Metab. and Disposition (1998) 26 (5): 383-387). Both studies showed very low exposure levels of the parent compounds after oral dosing of the derivatives. Another study suggests the use of budenoside-R-D-glucuronide as a prodrug for local delivery of budenoside to the large intestine for treatment of Ulcerative Colitis based on poor absorption of the prodrug itself from the intestinal system (Nolen et al., J. Pharm Sci. (1995), 84 (6): 677-681).

Nevertheless, it has been observed that oral dosing of the glucuronide conjugates (Id-ia), (Id-ib) and (Id-iab) with the formula below

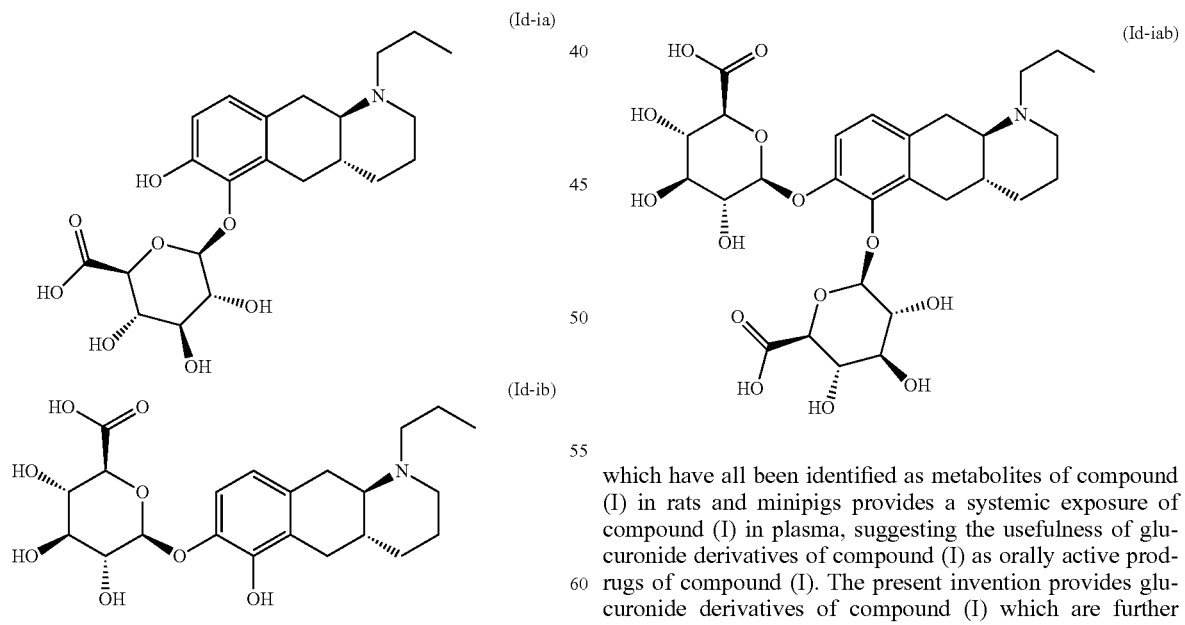

which have all been identified as metabolites of compound (I) in rats and minipigs provides a systemic exposure of compound (I) in plasma, suggesting the usefulness of glucuronide derivatives of compound (I) as orally active prodrugs of compound (I). The present invention provides glucuronide derivatives of compound (I) which are further derivatised by esterification of the free hydroxyl and carboxylic acid groups in the molecule. Unsaturated glycosyl derivatives (exemplified by compound (9)) are also encompassed by the scope of the invention. The scope of the invention also encompasses ester derivatives and ether derivatives of compound (I).

The plasma concentration profiles of compound (I) resulting from oral dosing of compounds (Ia), (Ib), (Id-ia), (Id-ib) and (Id-iab) and exemplified compounds of the invention to Wistar rats according to Example 3 are shown in FIG. 2. For all the compounds, the doses were corrected by molecular weight to equal a dose of 300 µg/kg of compound (Ib) corresponding to 287 µg/kg of compound (I). It has been found that oral dosing of compounds (Ia) and (Ib) to Wistar rats results in early and high peak plasma concentrations of compound (I). Such high peak concentrations are in humans likely to be associated with dopaminergic side effects such as for example nausea, vomiting and light headedness. In contrast, for the compounds of the invention a slower absorption rate was observed accompanied by a sustained exposure of compound (I) in plasma avoiding rapid peak plasma concentrations. Additionally, the plasma exposure of compound (I) in Wistar rats is maintained throughout 24 hours although the obtained AUC of compound (I) is generally lower than the AUC obtained after dosing of compounds (Ia) and (Ib). However, since the peak concentrations of compound (I) which are expected to drive the side effects are lower, higher doses may be administered of the compounds of the invention to potentially achieve higher overall plasma concentrations of compound (I) compared to what is achievable from dosing compounds (Ia) and (Ib). When investigating PK properties of compound (Ic), the inventors found that the plasma concentrations of compound (I) were extremely low, leaving compound (Ic) unsuitable as a prodrug of compound (I) for oral administration and confirming that the oral bioavailability of the compounds of the invention is highly unpredictable. PK parameters for the PK studies in Wistar rats are listed in Table 4 and PK profiles are depicted in FIG. 2. All the compounds evaluated in vivo showed conversion to compound (I).

Bioconversion of the compounds of the invention to the compound of formula (I) has also been assessed by incubation in human plasma and/or human hepatocytes as described in Example 1. For the parent compound (I) itself a short half-life in the plasma assay was observed, which likely explains why appearance of compound (I) was in some instances difficult to detect or only detected in very small amounts as compound (I) may have been metabolised at the same time as it was formed. For compound (15), compound (2) and compound (9) all showed conversion in vivo while no appearance of compound (I) could be detected in vitro. For some of the compounds no direct appearance of compound (I) was observed in the in vitro study, but the diagrams of FIG. 1 make it reasonable to believe that these compounds are converted to compound (I). For example, compound (11) which is an acetylated glucuronide derivative is converted to compound (Id-ia) which is converted to compound (I). Another example is 12 which is an acetylated bis-glucuronide derivative. For this compound no vitro conversion could be demonstrated (the compound has not been tested in vivo). However, when looking at the diagrams in FIG. 1 as a whole, it is reasonable to believe that 12 is converted to compound (1) via compound (Id-iab). In general, when looking at the diagrams as a whole, it is plausible that the esterificated glucuronide derivatives in general are converted to compound (I) either directly or via the respective glucuronide derivatives ((Id-ia), (Id-ib) or (Id-iab).

For compounds of the invention, conversion was evaluated either in vitro or both in vivo and in vitro c.f. table 1 below and in FIG. 1.

TABLE 1

Observed metabolites in in vitro and in vivo

| Compound ID | Incubation in human plasma | Incubation in human hepatocytes | In vivo PK study after oral dosing (rats) |
|---|---|---|---|
| | | Observed metabolite | |
| (Id-ia) | Compound (I) | Compound (I) | Compound (I) |
| (Id-ib) | Compound (I) | Compound (I) | Compound (I) |
| (Id-iab) | Compound (I) | Compound (I) | Compound (I) |
| Compound (27) | Compound (Id-ib) | nd | Compound (I) |
| I2 | nd | nd | nt |
| A3 | compound (27) | nd | nt |
| Compound (9) | nd | nd | nt |
| Compound (6) | nd | nd | nt |
| Compound (12) | Compounds (I) and (Id-ia) | nd | nt |
| Compound (3) | Compound (9) | nd | nt |
| Compound (26) | Compound (6) | nd | nt |
| Compound (2) | Compound (Id-ia) | nd | Compound (I) |
| Compound (14) | Compound (6) | nd | nt |
| Compound (11) | Compound (Id-ia) and Compound (12) | nd | nt |
| A2 | Compound (I) | Compound (I) | Compound (I) |
| Compound (4) | Compound A2 | nd | nt |
| Compound (1) | Compound A2, compound (2) | Compound A2, Compound (4) | nt |
| Compound (10) | Compound A2, Compound (4) | Compound A2, Compound (4) | nt |
| Compound (24) | nd | nd | nt |
| Compound (25) | Compound A2, Compound (24) | Compound A2, Compound (24) | nt |
| Compound (13) | nd | Compound (14) | nt |
| Compound (5) | Compound (24) | Compound (24) | nt |
| A7 | nd | Compound (I) | Compound (I) |
| Compound (15) | nd | nd | nt |
| Compound (21) | nd | nd | nt |
| Compound (22) | Compound (21) | Compound (21) | nt |
| Compound (23) | nd | nd | nt |
| Compound (20) | Compound (21) | Compound (21) | nt | nt: not tested
nd: not detected

Thus, in conclusion, the compounds of the invention are useful as orally active prodrugs of compound (I) and has been observed in rats to provide a PK profile avoiding the peak $C_{max}$ observed for the known prodrugs (Ia) and (Ib) and providing a significantly higher AUC of compound (I) than compound (Ic).

Compound (Id-ia) has further been explored in the rat locomotor activity assay according to Example 4. The assay demonstrated a dopaminergic effect obtained after oral administration of compound (Id-ia) c.f. FIGS. 3, 4 and 5. The fact that compound (Id-ia) possess no in vitro dopaminergic activity (data not shown), further indicates that the effect of compound (Id-ia) in the rat locomotor activity assay is obtained by conversion of compound (Id-ia) to compound (I).

Finally, an important issue associated with the prior art compound (Ib) is that this compound is an agonist of the 5-HT2B receptor. Since 5-HT2B receptor agonists have been linked to pathogenesis of valvular heart disease (VHD) after long term exposure, such compounds are not suitable for use in the treatment of chronical diseases (Rothman et al., Circulation (2000), 102: 2836-2841; and Cavero and Guillon, J. Pharmacol. Toxicol. Methods (2014), 69: 150-161). Thus, a further advantage of the compounds of the invention is that these are not 5-HT2B agonists c.f. example 2 and Table 3.

The compounds of the invention are useful in the treatment of neurodegenerative diseases and disorders such as Parkinson's disease and/or other conditions for which treatment with a dopamine agonist is therapeutically beneficial. The compounds, being suitable for oral administration have the potential of providing a new treatment paradigm in Parkinson's Disease.

In one embodiment of the invention, the compounds are for use as stand-alone treatment of a neurodegenerative disease or disorder. In another embodiment of the invention, the compounds are to be used in combination with other agents for treatment of PD such as a compound selected from the group consisting of L-DOPA, droxidopa, foliglurax, a MAO-B inhibitor such as selegiline or rasagiline, a COMT inhibitor such as entacapone or tolcapone, an adenosine 2a antagonist such as istradefylline, an antiglutamatergic agent such as amantadine or memantine, an acetylcholinesterase inhibitor such as rivastigmine, donepezil or galantamine, an antipsychotic agent such as quetiapine, clozapine, risperidone, pimavanserin, olanzapine, haloperidol, aripiprazole or brexpiprazole; or in combination with an antibody targeting alpha-synuclein, Tau or A-beta protein.

Embodiments of the Invention

In the following, embodiments of the invention are disclosed. The first embodiment is denoted E1, the second embodiment is denoted E2 and so forth:

E1. A compound according to formula (Id)

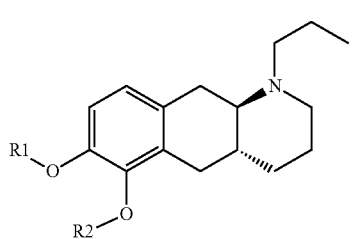

wherein
a) R1 is selected from the group consisting of H, $C_1$-$C_6$ alkyl, methyl substituted with $C_2$-$C_6$ cycloalkyl, benzyl and —C(O)$C_1$-$C_6$ alkyl, and R2 is selected from one of the substituents (i) and (ii) below; or
b) R1 is selected from one of the substituents (i) and (ii) below and R2 is selected from the group consisting of H, $C_1$-$C_6$ alkyl, methyl substituted with $C_2$-$C_6$ cycloalkyl, benzyl and —C(O)$C_1$-$C_6$ alkyl; or
c) R1 and R2 are independently selected from substituent (i) and substituent (ii) below; or
d) R1 and R2 are both represented by substituent (i) below; or
e) R1 and R2 are both represented by substituent (ii) below;

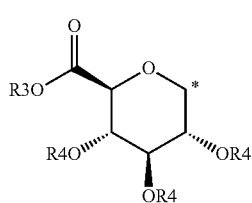

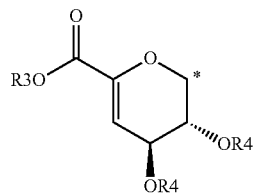

and wherein * indicates the attachment point; and wherein the carbon atom at the attachment point on substituent (i) is in the S-configuration; and wherein R3 is selected from H, $C_1$-$C_6$ alkyl and benzyl; and wherein R4 is selected from H, —C(O)$C_1$-$C_6$alkyl and —C(O)phenyl;

with the proviso that when both of R3 and R4 in substituent (i) are H, then R1 and R2 cannot both be substituent (i);

and with the proviso that when one of R1 and R2 is substituent (i) wherein both of R3 and R4 in substituent are H, then the other of R1 and R2 cannot be H;

or a pharmaceutically acceptable salt thereof.

E2. A compound according to formula (Id)

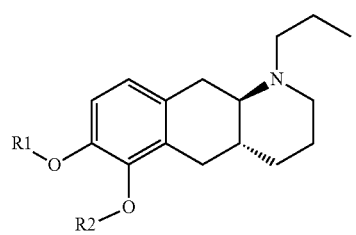

wherein
a) R1 is selected from the group consisting of H, $C_1$-$C_6$ alkyl, methyl substituted with $C_2$-$C_6$ cycloalkyl, benzyl and —C(O)$C_1$-$C_6$ alkyl, and R2 is selected from one of the substituents (i) and (ii) below; or
b) R1 is selected from one of the substituents (i) and (ii) below and R2 is selected from the group consisting of H, $C_1$-$C_6$ alkyl, methyl substituted with $C_2$-$C_6$ cycloalkyl, benzyl and —C(O)$C_1$-$C_6$ alkyl; or
c) R1 and R2 are independently selected from substituent (i) and substituent (ii) below; or
d) R1 and R2 are both represented by substituent (i) below; or
e) R1 and R2 are both represented by substituent (ii) below;

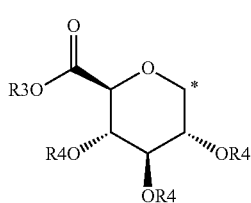

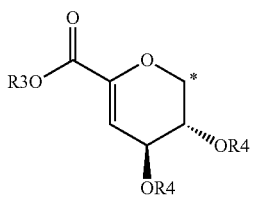

(ii)

wherein * indicates the attachment point; and
wherein the carbon atom at the attachment point on substituent (i) is in the S-configuration; and
wherein R3 is selected from H, $C_1$-$C_6$ alkyl and benzyl; and
wherein R4 is selected from H, —C(O)$C_1$-$C_6$alkyl and —C(O)phenyl;
with the proviso that when both of R3 and R4 in substituent (i) are H, then R1 and R2 cannot both be substituent (i);
and with the proviso that when one of R1 and R2 is substituent (i) wherein both of R3 and R4 in substituent are H, then the other of R1 and R2 cannot be H;
or a pharmaceutically acceptable salt thereof:
with the proviso that the compound of formula (Id) is not one of the following three compounds:
(2S,3R,4S,5S,6S)-2-(((4aR,10aR)-7-acetoxy-1-propyl-1,2,3,4,4a,5,10,10a-octahydro-benzo[g]quinolin-6-yl)oxy)-6-(methoxycarbonyl)tetrahydro-2H-pyran-3,4,5-triyl triacetate,
(2S,3R,4S,5S,6S)-2-(((4aR,10aR)-6-acetoxy-1-propyl-1,2,3,4,4a,5,10,10a-octahydro-benzo[g]quinolin-7-yl)oxy)-6-(methoxycarbonyl)tetrahydro-2H-pyran-3,4,5-triyl triacetate, and
methyl (2S,3S,4S,5R,6S)-6-[[(4aR,10aR)-1-propyl-6-[(2S,3R,4S,5S,6S)-3,4,5-triacetoxy-6-methoxycarbonyl-tetrahydropyran-2-yl]oxy-3,4,4a,5,10,10a-hexahydro-2H-benzo[g]quinolin-7-yl]oxy]-3,4,5-triacetoxy-tetrahydropyran-2-carboxylate.

E3. The compound, or a pharmaceutically acceptable salt thereof according to any embodiments 1-2, wherein
R1 is H and R2 is substituent (i); or
R1 is substituent (i) and R2 is H; or
R1 and R2 are both represented by substituent (i);
R3 is selected from H, $C_1$-$C_6$ alkyl and benzyl;
R4 is selected from H, —C(O)$C_1$-$C_6$alkyl and —C(O) phenyl;
with the proviso that R3 and R4 are not both H.

E4. The compound, or a pharmaceutically acceptable salt thereof according to any of embodiments 1-2, wherein
R1 is H and R2 is substituent (ii); or
R1 is substituent (ii) and R2 is H; or
R1 and R2 are both represented by substituent (ii);
R3 is selected from H, $C_1$-$C_6$ alkyl and benzyl;
R4 is selected from H, —C(O)$C_1$-$C_6$alkyl and —C(O) phenyl.

E5. The compound, or a pharmaceutically acceptable salt thereof according to any of embodiments 1-4, wherein R1 is selected from the group consisting of H, $C_1$-$C_4$ alkyl, methyl substituted with $C_2$-$C_6$ cycloalkyl, benzyl and —C(O)$C_1$-$C_4$ alkyl.

E6. The compound, or a pharmaceutically acceptable salt thereof according to any of embodiments 1-4, wherein R1 is selected from the group consisting of H, $C_1$-$C_3$ alkyl, benzyl.

E7. The compound, or a pharmaceutically acceptable salt thereof according to any of embodiments 1-4, wherein R1 is selected from the group consisting of H, methyl, ethyl, and benzyl.

E8. The compound, or a pharmaceutically acceptable salt thereof according to any of embodiments 1-4, wherein R1 is H.

E9. The compound, or a pharmaceutically acceptable salt thereof according to any of embodiments 1-4, wherein R1 is selected from the group consisting methyl and ethyl.

E10. The compound, or a pharmaceutically acceptable salt thereof according to any of embodiments 1-4, wherein R1 is benzyl.

E11. The compound, or a pharmaceutically acceptable salt thereof according to any of embodiments 1-4, wherein R2 is selected from the group consisting of H, $C_1$-$C_4$ alkyl, methyl substituted with $C_2$-$C_6$ cycloalkyl, benzyl and —C(O)$C_1$-$C_4$ alkyl.

E12. The compound, or a pharmaceutically acceptable salt thereof according to any of embodiments 1-4, wherein R2 is selected from the group consisting of H, $C_1$-$C_3$ alkyl, benzyl.

E13. The compound, or a pharmaceutically acceptable salt thereof according to any of embodiments 1-4, wherein R2 is selected from the group consisting of H, methyl, ethyl, and benzyl.

E14. The compound, or a pharmaceutically acceptable salt thereof according to any of embodiments 1-4, wherein R2 is H.

E15. The compound, or a pharmaceutically acceptable salt thereof according to any of embodiments 1-4, wherein R2 is selected from the group consisting methyl and ethyl.

E16. The compound, or a pharmaceutically acceptable salt thereof according to any of embodiments 1-4, wherein R2 is benzyl.

E17. The compound, or a pharmaceutically acceptable salt thereof according to any of embodiments 1-4, wherein R3 is selected from H, $C_1$-$C_4$ alkyl, and benzyl.

E18. The compound, or a pharmaceutically acceptable salt thereof according to embodiments 5, wherein R3 is selected from H and $C_1$-$C_4$ alkyl.

E19. The compound, or a pharmaceutically acceptable salt thereof according to embodiment 6, wherein R3 is selected from H, methyl, and ethyl.

E20. The compound, or a pharmaceutically acceptable salt thereof according to embodiment 6, wherein R3 is H.

E21. The compound, or a pharmaceutically acceptable salt thereof according to embodiment 6, wherein R3 is selected from methyl and ethyl.

E22. The compound, or a pharmaceutically acceptable salt thereof according to any of embodiment 1 to 7, wherein R4 is selected from H, —C(O)$C_1$-$C_4$alkyl and —C(O)phenyl.

E23. The compound, or a pharmaceutically acceptable salt thereof according to embodiment 8, wherein R4 is selected from H and —C(O)$C_1$-$C_4$alkyl.

E24. The compound, or a pharmaceutically acceptable salt thereof according to embodiment 9, wherein R4 is selected from H, acetyl, propionyl, and pivaloyl.

E25. The compound, or a pharmaceutically acceptable salt thereof according to embodiment 10, wherein R4 is selected from H, acetyl, and pivaloyl.

E26. The compound, or a pharmaceutically acceptable salt thereof according to embodiment 11, wherein R4 is H.

E27. The compound, or a pharmaceutically acceptable salt thereof according to embodiment 11, wherein R4 is selected from acetyl and pivaloyl.

E28. The compound, or a pharmaceutically acceptable salt thereof according to embodiment 11, wherein R1 and R2 are both represented by substituent (i) or R1 and R2 are both represented by substituent (ii).

E29. The compound, or a pharmaceutically acceptable salt thereof according to embodiment 11, wherein R1 and R2 are both represented by substituent (i).

E30. The compound, or a pharmaceutically acceptable salt thereof according to embodiment 11, wherein R1 and R2 are both represented by substituent (ii).

E31. The compound according to embodiment 1, wherein the compound is selected from the group consisting of:

(2S,3R,4S,5S,6S)-2-(((4aR,10aR)-7-(benzyloxy)-1-propyl-1,2,3,4,4a,5,10,10a-octahydro-benzo[g]quinolin-6-yl)oxy)-6-(methoxycarbonyl)tetrahydro-2H-pyran-3,4,5-triyl triacetate;

(2S,3R,4S,5S,6S)-2-(((4aR,10aR)-7-hydroxy-1-propyl-1,2,3,4,4a,5,10,10a-octahydro-benzo[g]quinolin-6-yl)oxy)-6-(methoxycarbonyl)tetrahydro-2H-pyran-3,4,5-triyl triacetate;

(2R,3R,4S)-2-(((4aR,10aR)-7-hydroxy-1-propyl-1,2,3,4,4a,5,10,10a-octahydro-benzo[g]quinolin-6-yl)oxy)-6-(methoxycarbonyl)-3,4-dihydro-2H-pyran-3,4-diyl diacetate;

(2S,3S,4S,5R,6S)-6-(((4aR,10aR)-7-(benzyloxy)-1-propyl-1,2,3,4,4a,5,10,10a-octahydro-benzo[g]quinolin-6-yl)oxy)-3,4,5-trihydroxytetrahydro-2H-pyran-2-carboxylic acid;

(2S,3R,4S,5S,6S)-2-(((4aR,10aR)-7-(benzyloxy)-1-propyl-1,2,3,4,4a,5,10,10a-octahydro-benzo[g]quinolin-6-yl)oxy)-6-((benzyloxy)carbonyl)tetrahydro-2H-pyran-3,4,5-triyl tris(2,2-dimethylpropanoate);

(2S,3S,4S,5R,6S)-6-(((4aR,10aR)-7-hydroxy-1-propyl-1,2,3,4,4a,5,10,10a-octahydrobenzo[g]quinolin-6-yl)oxy)-3,4,5-tris(pivaloyloxy)tetrahydro-2H-pyran-2-carboxylic acid;

(2S,3R,4S,5S,6S)-2-(((4aR,10aR)-7-(benzyloxy)-1-propyl-1,2,3,4,4a,5,10,10a-octahydrobenzo[g]quinolin-6-yl)oxy)-6-((benzyloxy)carbonyl)tetrahydro-2H-pyran-3,4,5-triyl triacetate;

(2S,3S,4S,5R,6S)-3,4,5-triacetoxy-6-(((4aR,10aR)-7-hydroxy-1-propyl-1,2,3,4,4a,5,10,10a-octahydrobenzo[g]quinolin-6-yl)oxy)tetrahydro-2H-pyran-2-carboxylic acid;

(2R,3R,4S)-3,4-dihydroxy-2-(((4aR,10aR)-7-hydroxy-1-propyl-1,2,3,4,4a,5,10,10a-octahydrobenzo[g]quinolin-6-yl)oxy)-3,4-dihydro-2H-pyran-6-carboxylic acid;

(2S,3R,4S,5S,6S)-2-(((4aR,10aR)-7-(benzyloxy)-1-propyl-1,2,3,4,4a,5,10,10a-octahydrobenzo[g]quinolin-6-yl)oxy)-6-(ethoxycarbonyl)tetrahydro-2H-pyran-3,4,5-triyl triacetate;

(2S,3S,4S,5R,6S)-2-(ethoxycarbonyl)-6-(((4aR,10aR)-7-hydroxy-1-propyl-1,2,3,4,4a,5,10,10a-octahydrobenzo[g]quinolin-6-yl)oxy)tetrahydro-2H-pyran-3,4,5-triyl triacetate;

ethyl (2S,3S,4S,5R,6S)-3,4,5-trihydroxy-6-(((4aR,10aR)-7-hydroxy-1-propyl-1,2,3,4,4a,5,10,10a-octahydrobenzo[g]quinolin-6-yl)oxy)tetrahydro-2H-pyran-2-carboxylate;

(2S,3R,4S,5S,6S)-2-(((4aR,10aR)-7-(benzyloxy)-1-propyl-1,2,3,4,4a,5,10,10a-octahydrobenzo[g]quinolin-6-yl)oxy)-6-(ethoxycarbonyl)tetrahydro-2H-pyran-3,4,5-triyl tris(2,2-dimethylpropanoate);

(2S,3S,4S,5R,6S)-2-(ethoxycarbonyl)-6-(((4aR,10aR)-7-hydroxy-1-propyl-1,2,3,4,4a,5,10,10a-octahydrobenzo[g]quinolin-6-yl)oxy)tetrahydro-2H-pyran-3,4,5-triyl tris(2,2-dimethylpropanoate);

(2S,3S,4S,5R,6S)-3,4,5-trihydroxy-6-(((4aR,10aR)-7-methoxy-1-propyl-1,2,3,4,4a,5,10,10a-octahydrobenzo[g]quinolin-6-yl)oxy)tetrahydro-2H-pyran-2-carboxylic acid;

(2S,3S,4S,5R,6S)-2-((benzyloxy)carbonyl)-6-(((4aR,10aR)-7-methoxy-1-propyl-1,2,3,4,4a,5,10,10a-octahydrobenzo[g]quinolin-6-yl)oxy)tetrahydro-2H-pyran-3,4,5-triyl triacetate;

(2S,3S,4S,5R,6S)-3,4,5-triacetoxy-6-(((4aR,10aR)-7-methoxy-1-propyl-1,2,3,4,4a,5,10,10a-octahydrobenzo[g]quinolin-6-yl)oxy)tetrahydro-2H-pyran-2-carboxylic acid;

(2S,3R,4S,5S,6S)-2-(((4aR,10aR)-7-methoxy-1-propyl-1,2,3,4,4a,5,10,10a-octahydrobenzo[g]quinolin-6-yl)oxy)-6-(methoxycarbonyl)tetrahydro-2H-pyran-3,4,5-triyl triacetate;

(2S,3R,4S,5S,6S)-2-(((4aR,10aR)-7-methoxy-1-propyl-1,2,3,4,4a,5,10,10a-octahydrobenzo[g]quinolin-6-yl)oxy)-6-(ethoxycarbonyl)tetrahydro-2H-pyran-3,4,5-triyl triacetate;

(2S,3S,4S,5R,6S)-2-((benzyloxy)carbonyl)-6-(((4aR,10aR)-7-methoxy-1-propyl-1,2,3,4,4a,5,10,10a-octahydrobenzo[g]quinolin-6-yl)oxy)tetrahydro-2H-pyran-3,4,5-triyl tris(2,2-dimethylpropanoate);

(2S,3S,4S,5R,6S)-6-(((4aR,10aR)-7-methoxy-1-propyl-1,2,3,4,4a,5,10,10a-octahydrobenzo[g]quinolin-6-yl)oxy)-3,4,5-tris(pivaloyloxy)tetrahydro-2H-pyran-2-carboxylic acid;

(2S,3S,4S,5R,6S)-2-((methoxy)carbonyl)-6-(((4aR,10aR)-7-methoxy-1-propyl-1,2,3,4,4a,5,10,10a-octahydrobenzo[g]quinolin-6-yl)oxy)tetrahydro-2H-pyran-3,4,5-triyl tris(2,2-dimethylpropanoate);

(2S,3S,4S,5R,6S)-2-((ethoxy)carbonyl)-6-(((4aR,10aR)-7-methoxy-1-propyl-1,2,3,4,4a,5,10,10a-octahydrobenzo[g]quinolin-6-yl)oxy)tetrahydro-2H-pyran-3,4,5-triyl tris(2,2-dimethylpropanoate);

(2S,3S,4S,5R,6S)-6-(((4aR,10aR)-7-(benzyloxy)-1-propyl-1,2,3,4,4a,5,10,10a-octahydrobenzo[g]quinolin-6-yl)oxy)-3,4,5-tris(pivaloyloxy)tetrahydro-2H-pyran-2-carboxylic acid;

(2S,3R,4S,5S,6S)-2-(((4aR,10aR)-7-(benzyloxy)-1-propyl-1,2,3,4,4a,5,10,10a-octahydrobenzo[g]quinolin-6-yl)oxy)-6-(methoxycarbonyl)tetrahydro-2H-pyran-3,4,5-triyl tris(2,2-dimethylpropanoate);

(2S,3S,4S,5R,6S)-2-(methoxycarbonyl)-6-(((4aR,10aR)-7-hydroxy-1-propyl-1,2,3,4,4a,5,10,10a-octahydrobenzo[g]quinolin-6-yl)oxy)tetrahydro-2H-pyran-3,4,5-triyl tris(2,2-dimethylpropanoate); and (2S,3R,4S,5S,6S)-2-(((4aR,10aR)-6-hydroxy-1-propyl-1,2,3,4,4a,5,10,10a-octahydrobenzo[g]quinolin-7-yl)oxy)-6-(methoxycarbonyl)tetrahydro-2H-pyran-3,4,5-triyl triacetate; or a pharmaceutically acceptable salt of any of these compounds.

E32. The compound or pharmaceutically acceptable salt thereof according to any of embodiments 1-23, for use in therapy.

E33. A compound or pharmaceutically acceptable salt thereof according to any of embodiments 1-23, for use as a medicament.

E34. The compound or pharmaceutically acceptable salt for use as a medicament according to embodiment 25, wherein said medicament is an oral medicament such as a tablet or a capsule for oral administration.

E35. A pharmaceutical composition comprising a therapeutically effective amount of the compound or pharmaceutically acceptable salt thereof according to any of embodiments 1-23, and one or more pharmaceutically acceptable excipients.

E36. The pharmaceutical composition according to embodiment 27, wherein said pharmaceutical composition is for oral administration.

E37. The pharmaceutical composition according to any of embodiments 27-28, wherein said pharmaceutical composition is an oral pharmaceutical composition.

E38. The pharmaceutical composition according to any of embodiments 27-29, wherein said pharmaceutical composition is a solid oral dosage form.

E39. The pharmaceutical composition according to any of embodiments 27-30, wherein said pharmaceutical composition is a tablet or a capsule for oral administration.

E40. The pharmaceutical composition according to any of embodiments 27-31, wherein said pharmaceutical composition further comprises another agent which is useful in the treatment of a neurodegenerative disease or disorder such as Parkinson's disease.

E41. The pharmaceutical composition according to any of embodiments 27-31, wherein said pharmaceutical composition further comprises a compound selected from the group consisting of L-DOPA, droxidopa, foliglurax, a MAO-B inhibitor such as selegiline or rasagiline, a COMT inhibitor such as entacapone or tolcapone, an adenosine 2a antagonist such as istradefylline, an antiglutamatergic agent such as amantadine or memantine, an acetylcholinesterase inhibitor such as rivastigmine, donepezil or galantamine, an antipsychotic agent such as quetiapine, clozapine, risperidone, pimavanserin, olanzapine, haloperidol, aripiprazole or brexpiprazole; or an antibody targeting alpha-synuclein, Tau or A-beta protein.

E42. A compound or pharmaceutically acceptable salt thereof according to any of embodiments 1-23, or a compound or a pharmaceutically acceptable salt thereof, wherein said compound is selected from (2S,3R,4S,5S,6S)-2-(((4aR,10aR)-7-acetoxy-1-propyl-1,2,3,4,4a,5,10,10a-octahydrobenzo[g]quinolin-6-yl)oxy)-6-(methoxycarbonyl)tetrahydro-2H-pyran-3,4,5-triyl triacetate, (2S,3R,4S,5S,6S)-2-(((4aR,10aR)-6-acetoxy-1-propyl-1,2,3,4,4a,5,10,10a-octahydrobenzo[g]quinolin-7-yl)oxy)-6-(methoxycarbonyl)tetrahydro-2H-pyran-3,4,5-triyl triacetate, and methyl (2S,3S,4S,5R,6S)-6-[[(4aR,10aR)-1-propyl-6-[(2S,3R,4S,5S,6S)-3,4,5-triacetoxy-6-methoxycarbonyl-tetrahydropyran-2-yl]oxy-3,4,4a,5,10,10a-hexahydro-2H-benzo[g]quinolin-7-yl]oxy]-3,4,5-triacetoxy-tetrahydropyran-2-carboxylate;

for use in the treatment of a neurodegenerative disease or disorder such as Parkinson's Disease, Huntington's disease, Restless leg syndrome or Alzheimer's disease; or a neuropsychiatric disease or disorder such as schizophrenia, attention deficit hyperactivity disorder or drug addiction.

E43. The compound or pharmaceutically acceptable salt thereof according to any of embodiments 1-23, for use in the treatment according to embodiment 34, wherein said neurodegenerative disease or disorder is Parkinson's Disease.

E44. The compound or pharmaceutically acceptable salt thereof according to any of embodiments 1-23, for use in the treatment according to any of embodiments 34-35, wherein said compound is to be used in combination with another agent which is useful in the treatment of a neurodegenerative disease or disorder such as Parkinson's disease.

E45. The compound or pharmaceutically acceptable salt thereof according to any of embodiments 1-23, for use in the treatment according to any of embodiments 34-35, wherein said compound is to be used in combination with a compound selected from the group consisting of L-DOPA, droxidopa, foliglurax, a MAO-B inhibitor such as selegiline or rasagiline, a COMT inhibitor such as entacapone or tolcapone, an adenosine 2a antagonist such as istradefylline, an antiglutamatergic agent such as amantadine or memantine, an acetylcholinesterase inhibitor such as rivastigmine, donepezil or galantamine, an antipsychotic agent such as quetiapine, clozapine, risperidone, pimavanserin, olanzapine, haloperidol, aripiprazole or brexpiprazole; or in combination with an antibody targeting alpha-synuclein, Tau or A-beta protein.

E46. The compound or pharmaceutically acceptable salt thereof according to any of embodiments 1-23, for use in the treatment according to any of embodiments 34-37, wherein said treatment is performed by oral administration of said compound.

E47. The compound or pharmaceutically acceptable salt thereof according to any of embodiments 1-23, for use in the treatment according to any of embodiments 34-38, wherein said compound is comprised in an oral pharmaceutical composition such as a tablet or a capsule for oral administration.

E48. A method for the treatment of a neurodegenerative disease or disorder such as Parkinson's Disease, Huntington's disease, Restless leg syndrome or Alzheimer's disease; or a neuropsychiatric disease or disorder such as schizophrenia, attention deficit hyperactivity disorder or drug addiction; which method comprises the administration of a therapeutically effective amount of a compound or pharmaceutically acceptable salt thereof according to any of embodiments 1-23, to a patient in need thereof.

E49. The method according to embodiment 40, wherein said neurodegenerative disease or disorder is Parkinson's Disease.

E50. The method according to any of embodiments 40-41, wherein said compound or pharmaceutically acceptable salt thereof according to any of embodiments 1-23, is used in combination with another agent which is useful in the treatment of a neurodegenerative disease or disorder such as Parkinson's disease.

E51. The method according to any of embodiments 40-41, wherein said compound or pharmaceutically acceptable salt thereof according to any of embodiments 1-23, is used in combination with a compound selected from the group consisting of L-DOPA, droxidopa, foliglurax, a MAO-B inhibitor such as selegiline or rasagiline, a COMT inhibitor such as entacapone or tolcapone, an adenosine 2a antagonist such as istradefylline, an antiglutamatergic agent such as amantadine or memantine, an acetylcholinesterase inhibitor such as rivastigmine, donepezil or galantamine, an antipsychotic agent such as quetiapine, clozapine, risperidone, pimavanserin, olanzapine, haloperidol, aripiprazole or brexpiprazole; or in combination with an antibody targeting alpha-synuclein, Tau or A-beta protein.

E52. The method according to any of embodiments 40-43, wherein said administration is performed by the oral route.

E53. The method according to any of embodiments 40-44, wherein said compound or pharmaceutically acceptable salt thereof according to any of embodiments 1-23 is comprised in an oral pharmaceutical composition such as a tablet or a capsule for oral administration.

E54. Use of a compound or pharmaceutically acceptable salt thereof according to any of embodiments 1-23, in the manufacture of a medicament for the treatment of a neurodegenerative disease or disorder such as Parkinson's Disease, Huntington's disease, Restless leg syndrome or Alzheimer's disease; or for the treatment of a neuropsychiatric disease or disorder such as schizophrenia, attention deficit hyperactivity disorder or drug addiction.

E55. The use according to embodiment 46, wherein said neurodegenerative disease or disorder is Parkinson's Disease.

E56. The use according to any of embodiments 46-47, wherein said medicament is used in combination with another agent which is useful in the treatment of a neurodegenerative disease or disorder such as Parkinson's disease.

E57. The use according to any of embodiments 46-47, wherein said medicament is used in combination with a compound selected from the group consisting of L-DOPA, droxidopa, foliglurax, a MAO-B inhibitor such as selegiline or rasagiline, a COMT inhibitor such as entacapone or tolcapone, an adenosine 2a antagonist such as istradefylline, an antiglutamatergic agent such as amantadine or memantine, an acetylcholinesterase inhibitor such as rivastigmine, donepezil or galantamine, an antipsychotic agent such as quetiapine, clozapine, risperidone, pimavanserin, olanzapine, haloperidol, aripiprazole or brexpiprazole; or in combination with an antibody targeting alpha-synuclein, Tau or A-beta protein.

E58. The use according to any of embodiments 46-49, wherein said medicament is an oral medicament such as a tablet or a capsule for oral administration.

E59. A compound or pharmaceutically acceptable salt thereof according to any of embodiments 1-13, for use in the treatment of for the treatment of a neurodegenerative disease or disorder such as Parkinson's Disease, Huntington's disease, Restless leg syndrome or Alzheimer's disease; or for the treatment of a neuropsychiatric disease or disorder such as schizophrenia, attention deficit hyperactivity disorder or drug addiction.

E60. The compound or pharmaceutically acceptable salt thereof according to any of embodiments 59, wherein said neurodegenerative disease or disorder is Parkinson's Disease.

E61. The compound according to any of embodiments 59-60, wherein said compound is used in combination with another agent which is useful in the treatment of a neurodegenerative disease or disorder such as Parkinson's disease.

E62. The compound according to any of embodiments 61, wherein said medicament is used in combination with a compound selected from the group consisting of L-DOPA, droxidopa, foliglurax, a MAO-B inhibitor such as selegiline or rasagiline, a COMT inhibitor such as entacapone or tolcapone, an adenosine 2a antagonist such as istradefylline, an antiglutamatergic agent such as amantadine or memantine, an acetylcholinesterase inhibitor such as rivastigmine, donepezil or galantamine, an antipsychotic agent such as quetiapine, clozapine, risperidone, pimavanserin, olanzapine, haloperidol, aripiprazole or brexpiprazole; or in combination with an antibody targeting alpha-synuclein, Tau or A-beta protein.

Items

The following list of items further describe embodiments and aspects of the invention, and are listed as EE1, EE2, and so forth.

EE1. A compound according to formula (Id)

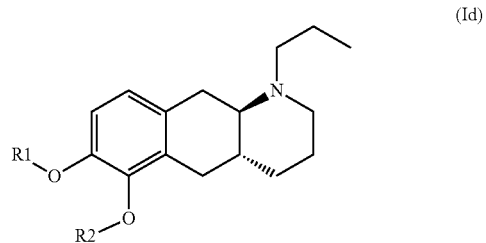

(Id)

wherein a) R1 is selected from the group consisting of H, $C_1$-$C_6$ alkyl, methyl substituted with $C_3$-$C_6$ cycloalkyl, benzyl and —C(O)$C_1$-$C_6$ alkyl, and R2 is selected from one of the substituents (i) and (ii) below; or b) R1 is selected from one of the substituents (i) and (ii) below and R2 is selected from the group consisting of H, $C_1$-$C_6$ alkyl, methyl substituted with $C_3$-$C_6$ cycloalkyl, benzyl and —C(O)$C_1$-$C_6$ alkyl; or c) R1 and R2 are independently selected from substituent (i) and substituent (ii) below; or d) R1 and R2 are both represented by substituent (i) below; or e) R1 and R2 are both represented by substituent (ii) below;

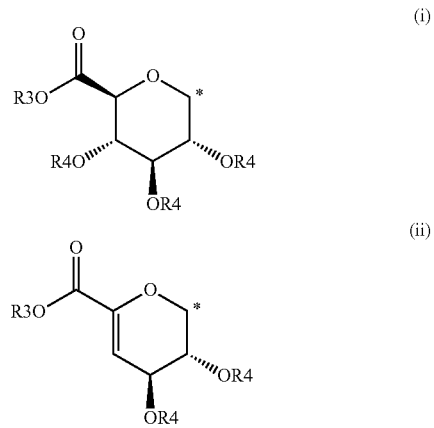

and wherein * indicates the attachment point; and wherein the carbon atom at the attachment point on substituent (i) is in the S-configuration; and wherein R3 is selected from H, $C_1$-$C_6$ alkyl and benzyl; and wherein R4 is selected from H, —C(O)$C_1$-$C_6$alkyl and —C(O)phenyl;

with the proviso that when both of R3 and R4 in substituent (i) are H, then R1 and R2 cannot both be substituent (i);

and with the proviso that when one of R1 and R2 is substituent (i) wherein both of R3 and R4 in substituent are H, then the other of R1 and R2 cannot be H;

or a pharmaceutically acceptable salt thereof.

EE2. A compound according to formula (Id)

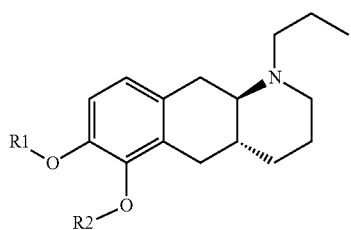

wherein
  a) R1 is selected from the group consisting of H, $C_1$-$C_6$ alkyl, methyl substituted with $C_3$-$C_6$ cycloalkyl, benzyl and —C(O)$C_1$-$C_6$ alkyl, and R2 is selected from one of the substituents (i) and (ii) below; or
  b) R1 is selected from one of the substituents (i) and (ii) below and R2 is selected from the group consisting of H, $C_1$-$C_6$ alkyl, methyl substituted with $C_3$-$C_6$ cycloalkyl, benzyl and —C(O)$C_1$-$C_6$ alkyl; or
  c) R1 and R2 are independently selected from substituent (i) and substituent (ii) below; or
  d) R1 and R2 are both represented by substituent (i) below; or
  e) R1 and R2 are both represented by substituent (ii) below;

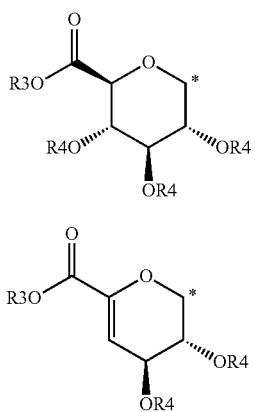

and wherein * indicates the attachment point; and
wherein the carbon atom at the attachment point on substituent (i) is in the S-configuration; and
wherein R3 is selected from H, $C_1$-$C_6$ alkyl and benzyl; and
wherein R4 is selected from H, —C(O)$C_1$-$C_6$alkyl and —C(O)phenyl;
with the proviso that when both of R3 and R4 in substituent (i) are H, then R1 and R2 cannot both be substituent (i);
and with the proviso that when one of R1 and R2 is substituent (i) wherein both of R3 and R4 in substituent are H, then the other of R1 and R2 cannot be H;
or a pharmaceutically acceptable salt thereof;
with the proviso that the compound of formula (Id) is not one of the following three compounds:
(2S,3R,4S,5S,6S)-2-(((4aR,10aR)-7-acetoxy-1-propyl-1,2,3,4,4a,5,10,10a-octahydrobenzo[g]quinolin-6-yl)oxy)-6-(methoxycarbonyl)tetrahydro-2H-pyran-3,4,5-triyl triacetate,
(2S,3R,4S,5S,6S)-2-(((4aR,10aR)-6-acetoxy-1-propyl-1,2,3,4,4a,5,10,10a-octahydrobenzo[g]quinolin-7-yl)oxy)-6-(methoxycarbonyl)tetrahydro-2H-pyran-3,4,5-triyl triacetate, and
methyl (2S,3S,4S,5R,6S)-6-[[(4aR,10aR)-1-propyl-6-[(2S,3R,4S,5S,6S)-3,4,5-triacetoxy-6-methoxycarbonyl-tetrahydropyran-2-yl]oxy-3,4,4a,5,10,10a-hexahydro-2H-benzo[g]quinolin-7-yl]oxy]-3,4,5-triacetoxy-tetrahydropyran-2-carboxylate.

EE3. The compound, or a pharmaceutically acceptable salt thereof according to any one of items EE1-EE2, wherein
  R1 is H and R2 is substituent (i); or
  R1 is substituent (i) and R2 is H; or
  R1 and R2 are both represented by substituent (i); and
  wherein R3 is selected from H, $C_1$-$C_6$ alkyl and benzyl; and
  wherein R4 is selected from H, —C(O)$C_1$-$C_6$alkyl and —C(O)phenyl; and
  with the proviso that R3 and R4 are not both H.

EE4. The compound, or a pharmaceutically acceptable salt thereof according to any one of items EE1-EE2, wherein
  R1 is H and R2 is substituent (ii); or
  R1 is substituent (ii) and R2 is H; or
  R1 and R2 are both represented by substituent (ii); and wherein
  wherein R3 is selected from H, $C_1$-$C_6$ alkyl and benzyl; and
  wherein R4 is selected from H, —C(O)$C_1$-$C_6$alkyl and —C(O)phenyl.

EE5. The compound, or a pharmaceutically acceptable salt thereof according to any one of items EE1-EE4, wherein R1 is selected from the group consisting of H, $C_1$-$C_4$ alkyl, methyl substituted with $C_3$-$C_6$ cycloalkyl, benzyl and —C(O)$C_1$-$C_4$ alkyl.

EE6. The compound, or a pharmaceutically acceptable salt thereof according to any one of items EE1-EE5, wherein R1 is selected from the group consisting of H, $C_1$-$C_3$ alkyl, benzyl.

EE7. The compound, or a pharmaceutically acceptable salt thereof according to any one of items EE1-EE6, wherein R1 is selected from the group consisting of H, methyl, ethyl, and benzyl.

EE8. The compound, or a pharmaceutically acceptable salt thereof according to any one of items EE1-EE7, wherein R1 is H.

EE9. The compound, or a pharmaceutically acceptable salt thereof according to any one of items EE1-EE2, wherein R1 is selected from the group consisting methyl and ethyl.

EE10. The compound, or a pharmaceutically acceptable salt thereof according to any one of items EE1-EE2, wherein R1 is benzyl.

EE11. The compound, or a pharmaceutically acceptable salt thereof according to any one of items EE1-EE3, wherein R1 is (i).

EE12. The compound, or a pharmaceutically acceptable salt thereof according to any one of items EE1-EE2 and EE4, wherein R1 is (ii).

EE13. The compound, or a pharmaceutically acceptable salt thereof according to any one of items EE1-EE12, wherein R2 is selected from the group consisting of H, $C_1$-$C_4$ alkyl, methyl substituted with $C_3$-$C_6$ cycloalkyl, benzyl and —C(O)$C_1$-$C_4$ alkyl.

EE14. The compound, or a pharmaceutically acceptable salt thereof according to any one of items EE1-EE13, wherein R2 is selected from the group consisting of H, $C_1$-$C_3$ alkyl, benzyl.

EE15. The compound, or a pharmaceutically acceptable salt thereof according to any of items EE1-EE14, wherein R2 is selected from the group consisting of H, methyl, ethyl, and benzyl.

EE16. The compound, or a pharmaceutically acceptable salt thereof according to any of items EE1-EE15, wherein R2 is H.

EE17. The compound, or a pharmaceutically acceptable salt thereof according to any of items EE1-EE15, wherein R2 is selected from the group consisting methyl and ethyl.

EE18. The compound, or a pharmaceutically acceptable salt thereof according to any of items EE1-EE15, wherein R2 is benzyl.

EE19. The compound, or a pharmaceutically acceptable salt thereof according to any one of items EE1-EE3 and EE5-EE12, wherein R2 is substituent (i).

EE20. The compound, or a pharmaceutically acceptable salt thereof according to any one of items EE1-EE3 and EE5-EE10, wherein R2 is substituent (i), and R1 is selected from H, methyl or benzyl.

EE21. The compound, or a pharmaceutically acceptable salt thereof according to any one of items EE1-EE3 and EE5-EE8, wherein R2 is substituent (i), and R1 is H.

EE22. The compound, or a pharmaceutically acceptable salt thereof according to any one of items EE1-EE3 and EE5-EE7, wherein R2 is substituent (i), and R1 is methyl.

EE23. The compound, or a pharmaceutically acceptable salt thereof according to any one of items EE1-EE3 and EE5-EE7, wherein R2 is substituent (i), and R1 is benzyl.

EE24. The compound, or a pharmaceutically acceptable salt thereof according to any one of items EE1-EE2 and EE4-EE12, wherein R2 is substituent (ii).

EE25. The compound, or a pharmaceutically acceptable salt thereof according to any one of items EE1-EE2 and EE12, wherein R2 is substituent (ii) and R1 is H.

EE26. The compound, or a pharmaceutically acceptable salt thereof according to any of items EE1-EE25, wherein R3 is selected from H, $C_1$-$C_4$ alkyl, and benzyl.

EE27. The compound, or a pharmaceutically acceptable salt thereof according to any one of items EE1-EE26, wherein R3 is selected from H and $C_1$-$C_4$ alkyl.

EE28. The compound, or a pharmaceutically acceptable salt thereof according to any one of items EE1-EE27, wherein R3 is selected from H, methyl, and ethyl.

EE29. The compound, or a pharmaceutically acceptable salt thereof according to any one of items EE1-EE28, wherein R3 is H.

EE30. The compound, or a pharmaceutically acceptable salt thereof according to any one of items EE1-EE29, wherein R3 is selected from methyl and ethyl.

EE31. The compound, or a pharmaceutically acceptable salt thereof according to any one of items EE1 to EE30, wherein R4 is selected from H, —C(O)$C_1$-$C_4$alkyl and —C(O)phenyl.

EE32. The compound, or a pharmaceutically acceptable salt thereof according to any one of items EE1-EE31, wherein R4 is selected from H and —C(O)$C_1$-$C_4$alkyl.

EE33. The compound, or a pharmaceutically acceptable salt thereof according to any one of items EE1-EE32, wherein R4 is selected from H, acetyl, propionyl, and pivaloyl.

EE34. The compound, or a pharmaceutically acceptable salt thereof according to any one of items EE1-EE33, wherein R4 is selected from H, acetyl, and pivaloyl.

EE35. The compound, or a pharmaceutically acceptable salt thereof according to any one of items EE1-EE34, wherein R4 is H.

EE36. The compound, or a pharmaceutically acceptable salt thereof according to any one of items EE1-EE34, wherein R4 is selected from acetyl and pivaloyl.

EE37. The compound, or a pharmaceutically acceptable salt thereof according to any one of items EE1-EE4, EE27-EE36, wherein R1 and R2 are both represented by substituent (i), or R1 and R2 are both represented by substituent (ii).

EE38. The compound, or a pharmaceutically acceptable salt thereof according to any one of items EE1-EE2, and EE27-EE36, wherein R1 and R2 are both represented by substituent (i).

EE39. The compound, or a pharmaceutically acceptable salt thereof according to according to any one of items EE1-EE2, and EE27-EE36, wherein R1 and R2 are both represented by substituent (ii).

EE40. The compound according to items EE1 and EE2, wherein the compound is selected from the group consisting of:
 (2S,3R,4S,5S,6S)-2-(((4aR,10aR)-7-(benzyloxy)-1-propyl-1,2,3,4,4a,5,10,10a-octahydrobenzo[g]quinolin-6-yl)oxy)-6-(methoxycarbonyl)tetrahydro-2H-pyran-3,4,5-triyl triacetate;
 (2S,3R,4S,5S,6S)-2-(((4aR,10aR)-7-hydroxy-1-propyl-1,2,3,4,4a,5,10,10a-octahydrobenzo[g]quinolin-6-yl)oxy)-6-(methoxycarbonyl)tetrahydro-2H-pyran-3,4,5-triyl triacetate;
 (2R,3R,4S)-2-(((4aR,10aR)-7-hydroxy-1-propyl-1,2,3,4,4a,5,10,10a-octahydrobenzo[g]quinolin-6-yl)oxy)-6-(methoxycarbonyl)-3,4-dihydro-2H-pyran-3,4-diyl diacetate;
 (2S,3S,4S,5R,6S)-6-(((4aR,10aR)-7-(benzyloxy)-1-propyl-1,2,3,4,4a,5,10,10a-octahydrobenzo[g]quinolin-6-yl)oxy)-3,4,5-trihydroxytetrahydro-2H-pyran-2-carboxylic acid;
 (2S,3R,4S,5S,6S)-2-(((4aR,10aR)-7-(benzyloxy)-1-propyl-1,2,3,4,4a,5,10,10a-octahydrobenzo[g]quinolin-6-yl)oxy)-6-((benzyloxy)carbonyl)tetrahydro-2H-pyran-3,4,5-triyl tris(2,2-dimethylpropanoate);
 (2S,3S,4S,5R,6S)-6-(((4aR,10aR)-7-hydroxy-1-propyl-1,2,3,4,4a,5,10,10a-octahydrobenzo[g]quinolin-6-yl)oxy)-3,4,5-tris(pivaloyloxy)tetrahydro-2H-pyran-2-carboxylic acid;
 (2S,3R,4S,5S,6S)-2-(((4aR,10aR)-7-(benzyloxy)-1-propyl-1,2,3,4,4a,5,10,10a-octahydrobenzo[g]quinolin-6-yl)oxy)-6-((benzyloxy)carbonyl)tetrahydro-2H-pyran-3,4,5-triyl triacetate;
 (2S,3S,4S,5R,6S)-3,4,5-triacetoxy-6-(((4aR,10aR)-7-hydroxy-1-propyl-1,2,3,4,4a,5,10,10a-octahydrobenzo[g]quinolin-6-yl)oxy)tetrahydro-2H-pyran-2-carboxylic acid;
 (2R,3R,4S)-3,4-dihydroxy-2-(((4aR,10aR)-7-hydroxy-1-propyl-1,2,3,4,4a,5,10,10a-octahydrobenzo[g]quinolin-6-yl)oxy)-3,4-dihydro-2H-pyran-6-carboxylic acid;
 (2S,3R,4S,5S,6S)-2-(((4aR,10aR)-7-(benzyloxy)-1-propyl-1,2,3,4,4a,5,10,10a-octahydrobenzo[g]quinolin-6-yl)oxy)-6-(ethoxycarbonyl)tetrahydro-2H-pyran-3,4,5-triyl triacetate;
 (2S,3S,4S,5R,6S)-2-(ethoxycarbonyl)-6-(((4aR,10aR)-7-hydroxy-1-propyl-1,2,3,4,4a,5,10,10a-octahydrobenzo[g]quinolin-6-yl)oxy)tetrahydro-2H-pyran-3,4,5-triyl triacetate;
 ethyl (2S,3S,4S,5R,6S)-3,4,5-trihydroxy-6-(((4aR,10aR)-7-hydroxy-1-propyl-1,2,3,4,4a,5,10,10a-octahydrobenzo[g]quinolin-6-yl)oxy)tetrahydro-2H-pyran-2-carboxylate;
 (2S,3R,4S,5S,6S)-2-(((4aR,10aR)-7-(benzyloxy)-1-propyl-1,2,3,4,4a,5,10,10a-octahydrobenzo[g]quinolin-6-yl)

oxy)-6-(ethoxycarbonyl)tetrahydro-2H-pyran-3,4,5-triyl tris(2,2-dimethylpropanoate);

(2S,3S,4S,5R,6S)-2-(ethoxycarbonyl)-6-(((4aR,10aR)-7-hydroxy-1-propyl-1,2,3,4,4a,5,10,10a-octahydrobenzo[g]quinolin-6-yl)oxy)tetrahydro-2H-pyran-3,4,5-triyl tris(2,2-dimethylpropanoate);

(2S,3S,4S,5R,6S)-3,4,5-trihydroxy-6-(((4aR,10aR)-7-methoxy-1-propyl-1,2,3,4,4a,5,10,10a-octahydrobenzo[g]quinolin-6-yl)oxy)tetrahydro-2H-pyran-2-carboxylic acid;

(2S,3S,4S,5R,6S)-2-((benzyloxy)carbonyl)-6-(((4aR,10aR)-7-methoxy-1-propyl-1,2,3,4,4a,5,10,10a-octahydrobenzo[g]quinolin-6-yl)oxy)tetrahydro-2H-pyran-3,4,5-triyl triacetate;

(2S,3S,4S,5R,6S)-3,4,5-triacetoxy-6-(((4aR,10aR)-7-methoxy-1-propyl-1,2,3,4,4a,5,10,10a-octahydrobenzo[g]quinolin-6-yl)oxy)tetrahydro-2H-pyran-2-carboxylic acid;

(2S,3R,4S,5S,6S)-2-(((4aR,10aR)-7-methoxy-1-propyl-1,2,3,4,4a,5,10,10a-octahydrobenzo[g]quinolin-6-yl)oxy)-6-(methoxycarbonyl)tetrahydro-2H-pyran-3,4,5-triyl triacetate;

(2S,3R,4S,5S,6S)-2-(((4aR,10aR)-7-methoxy-1-propyl-1,2,3,4,4a,5,10,10a-octahydrobenzo[g]quinolin-6-yl)oxy)-6-(ethoxycarbonyl)tetrahydro-2H-pyran-3,4,5-triyl triacetate;

(2S,3S,4S,5R,6S)-2-((benzyloxy)carbonyl)-6-(((4aR,10aR)-7-methoxy-1-propyl-1,2,3,4,4a,5,10,10a-octahydrobenzo[g]quinolin-6-yl)oxy)tetrahydro-2H-pyran-3,4,5-triyl tris(2,2-dimethylpropanoate);

(2S,3S,4S,5R,6S)-6-(((4aR,10aR)-7-methoxy-1-propyl-1,2,3,4,4a,5,10,10a-octahydrobenzo[g]quinolin-6-yl)oxy)-3,4,5-tris(pivaloyloxy)tetrahydro-2H-pyran-2-carboxylic acid;

(2S,3S,4S,5R,6S)-2-((methoxy)carbonyl)-6-(((4aR,10aR)-7-methoxy-1-propyl-1,2,3,4,4a,5,10,10a-octahydrobenzo[g]quinolin-6-yl)oxy)tetrahydro-2H-pyran-3,4,5-triyl tris(2,2-dimethylpropanoate);

(2S,3S,4S,5R,6S)-2-((ethoxy)carbonyl)-6-(((4aR,10aR)-7-methoxy-1-propyl-1,2,3,4,4a,5,10,10a-octahydrobenzo[g]quinolin-6-yl)oxy)tetrahydro-2H-pyran-3,4,5-triyl tris(2,2-dimethylpropanoate);

(2S,3S,4S,5R,6S)-6-(((4aR,10aR)-7-(benzyloxy)-1-propyl-1,2,3,4,4a,5,10,10a-octahydrobenzo[g]quinolin-6-yl)oxy)-3,4,5-tris(pivaloyloxy)tetrahydro-2H-pyran-2-carboxylic acid;

(2S,3R,4S,5S,6S)-2-(((4aR,10aR)-7-(benzyloxy)-1-propyl-1,2,3,4,4a,5,10,10a-octahydrobenzo[g]quinolin-6-yl)oxy)-6-(methoxycarbonyl)tetrahydro-2H-pyran-3,4,5-triyl tris(2,2-dimethylpropanoate);

(2S,3S,4S,5R,6S)-2-(methoxycarbonyl)-6-(((4aR,10aR)-7-hydroxy-1-propyl-1,2,3,4,4a,5,10,10a-octahydrobenzo[g]quinolin-6-yl)oxy)tetrahydro-2H-pyran-3,4,5-triyl tris(2,2-dimethylpropanoate); and (2S,3R,4S,5S,6S)-2-(((4aR,10aR)-6-hydroxy-1-propyl-1,2,3,4,4a,5,10,10a-octahydrobenzo[g]quinolin-7-yl)oxy)-6-(methoxycarbonyl)tetrahydro-2H-pyran-3,4,5-triyl triacetate; or a pharmaceutically acceptable salt of any of these compounds.

EE41. The compound according to items EE1 and EE2, wherein the compound is selected from the group consisting of:

Compound (2): (2S,3R,4S,5S,6S)-2-(((4aR,10aR)-7-hydroxy-1-propyl-1,2,3,4,4a,5,10,10a-octahydrobenzo[g]quinolin-6-yl)oxy)-6-(methoxycarbonyl)tetrahydro-2H-pyran-3,4,5-triyl triacetate;

Compound (9): (2R,3R,4S)-3,4-di hydroxy-2-(((4aR,10aR)-7-hydroxy-1-propyl-1,2,3,4,4a,5,10,10a-octahydrobenzo[g]quinolin-6-yl)oxy)-3,4-dihydro-2H-pyran-6-carboxylic acid;

Compound (11): (2S,3S,4S,5R,6S)-2-(ethoxycarbonyl)-6-(((4aR,10aR)-7-hydroxy-1-propyl-1,2,3,4,4a,5,10,10a-octahydrobenzo[g]quinolin-6-yl)oxy)tetrahydro-2H-pyran-3,4,5-triyl triacetate;

Compound (12): ethyl (2S,3S,4S,5R,6S)-3,4,5-trihydroxy-6-(((4aR,10aR)-7-hydroxy-1-propyl-1,2,3,4,4a,5,10,10a-octahydrobenzo[g]quinolin-6-yl)oxy)tetrahydro-2H-pyran-2-carboxylate;

Compound (15): (2S,3S,4S,5R,6S)-3,4,5-tri hydroxy-6-(((4aR,10aR)-7-methoxy-1-propyl-1,2,3,4,4a,5,10,10a-octahydrobenzo[g]quinolin-6-yl)oxy)tetrahydro-2H-pyran-2-carboxylic acid; and Compound (27): (2S,3R,4S,5S,6S)-2-(((4aR,10aR)-6-hydroxy-1-propyl-1,2,3,4,4a,5,10,10a-octahydrobenzo[g]quinolin-7-yl)oxy)-6-(methoxycarbonyl)tetrahydro-2H-pyran-3,4,5-triyl triacetate;

or a pharmaceutically acceptable salt of any of these compounds.

EE42. The compound according to items EE1 and EE2, wherein the compound is selected from the group consisting of:

Compound (2): (2S,3R,4S,5S,6S)-2-(((4aR,10aR)-7-hydroxy-1-propyl-1,2,3,4,4a,5,10,10a-octahydrobenzo[g]quinolin-6-yl)oxy)-6-(methoxycarbonyl)tetrahydro-2H-pyran-3,4,5-triyl triacetate;

Compound (9): (2R,3R,4S)-3,4-di hydroxy-2-(((4aR,10aR)-7-hydroxy-1-propyl-1,2,3,4,4a,5,10,10a-octahydrobenzo[g]quinolin-6-yl)oxy)-3,4-dihydro-2H-pyran-6-carboxylic acid;

Compound (15): (2S,3S,4S,5R,6S)-3,4,5-trihydroxy-6-(((4aR,10aR)-7-methoxy-1-propyl-1,2,3,4,4a,5,10,10a-octahydrobenzo[g]quinolin-6-yl)oxy)tetrahydro-2H-pyran-2-carboxylic acid; and Compound (27): (2S,3R,4S,5S,6S)-2-(((4aR,10aR)-6-hydroxy-1-propyl-1,2,3,4,4a,5,10,10a-octahydrobenzo[g]quinolin-7-yl)oxy)-6-(methoxycarbonyl)tetrahydro-2H-pyran-3,4,5-triyl triacetate;

or a pharmaceutically acceptable salt of any of these compounds.

EE43. A compound with the formula below

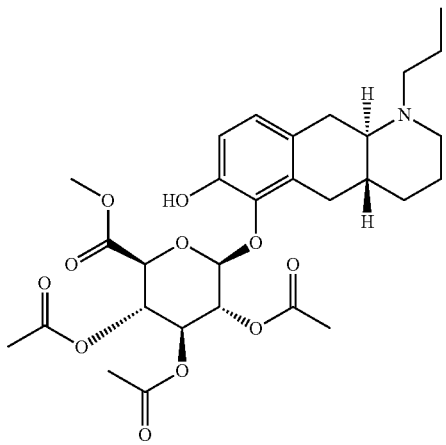 [SMILES: CCCN1CCC[C@@H]2Cc3c(ccc(O)c3O[C@@H]3O[C@H](C(=O)OC)[C@@H](OC(C)=O)[C@H](OC(C)=O)[C@H]3OC(C)=O)C[C@H]21]

or a pharmaceutically acceptable salt thereof.

EE44. A compound with the formula below

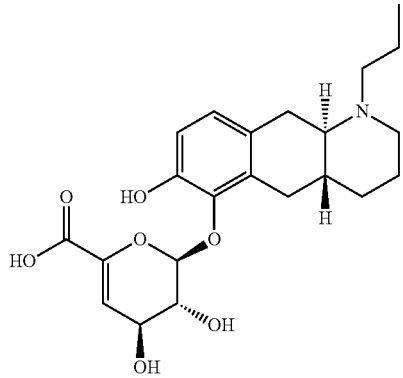 [SMILES: CCCN1CCC[C@@H]2Cc3c(ccc(O)c3O[C@@H]3OC(C(=O)O)=C[C@H](O)[C@H]3O)C[C@H]21]

or a pharmaceutically acceptable salt thereof.

EE45. A compound with the formula below

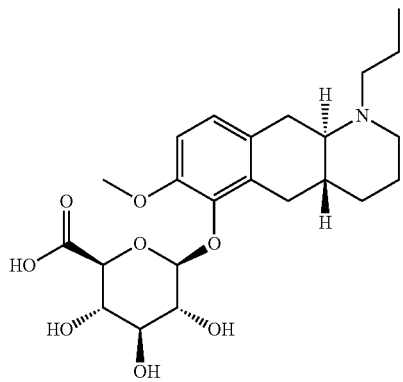 [SMILES: CCCN1CCC[C@@H]2Cc3c(ccc(OC)c3O[C@@H]3O[C@H](C(=O)O)[C@@H](O)[C@H](O)[C@H]3O)C[C@H]21]

or a pharmaceutically acceptable salt thereof.

EE46. A compound with the formula below

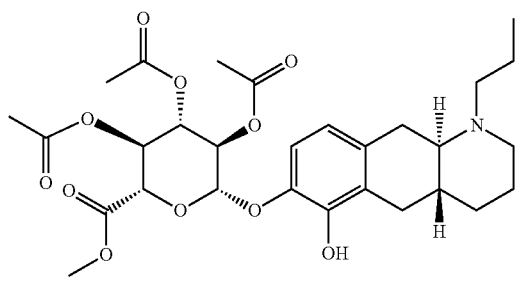 [SMILES: CCCN1CCC[C@@H]2Cc3c(ccc(O[C@@H]4O[C@H](C(=O)OC)[C@@H](OC(C)=O)[C@H](OC(C)=O)[C@H]4OC(C)=O)c3O)C[C@H]21]

or a pharmaceutically acceptable salt thereof.

EE47. A compound with the formula below

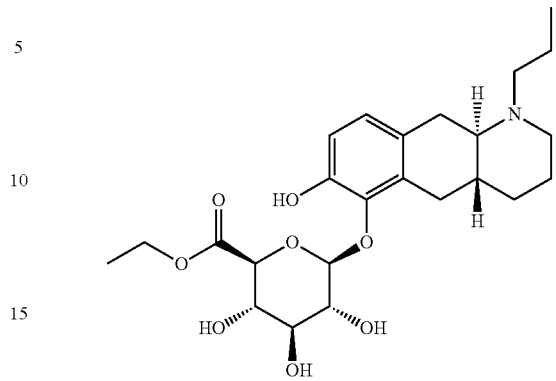

or a pharmaceutically acceptable salt thereof.

EE48. A compound with the formula below

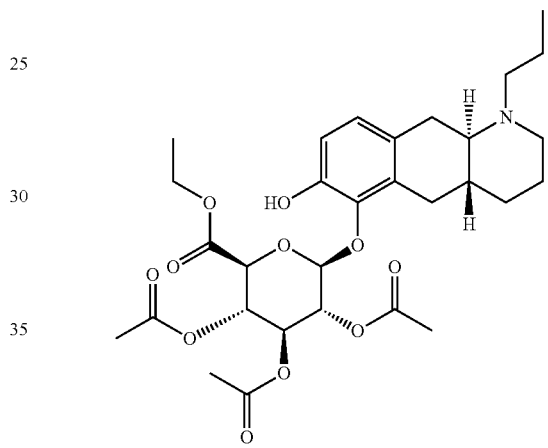

or a pharmaceutically acceptable salt thereof.

EE49. The compound or pharmaceutically acceptable salt thereof according to any of items EE1-EE48 for use in therapy.

EE50. A compound or pharmaceutically acceptable salt thereof according to any of items EE1-EE48, for use as a medicament.

EE51. The compound or pharmaceutically acceptable salt for use as a medicament according to item EE50, wherein said medicament is an oral medicament such as a tablet or a capsule for oral administration.

EE52. A pharmaceutical composition comprising a therapeutically effective amount of the compound or pharmaceutically acceptable salt thereof according to any of items EE1-EE48, and one or more pharmaceutically acceptable excipients.

EE53. The pharmaceutical composition according to item EE52, wherein said pharmaceutical composition is for oral administration.

EE54. The pharmaceutical composition according to any of items EE52-EE53, wherein said pharmaceutical composition is an oral pharmaceutical composition.

EE55. The pharmaceutical composition according to any of items EE52-EE54, wherein said pharmaceutical composition is a solid oral dosage form.

EE56. The pharmaceutical composition according to any of items EE52-EE55, wherein said pharmaceutical composition is a tablet or a capsule for oral administration.

EE57. The pharmaceutical composition according to any of items EE52-EE56, wherein said pharmaceutical composition further comprises another agent which is useful in the treatment of a neurodegenerative disease or disorder such as Parkinson's disease.

EE58. The pharmaceutical composition according to any of items EE52-EE57, wherein said pharmaceutical composition further comprises a compound selected from the group consisting of L-DOPA, droxidopa, foliglurax, a MAO-B inhibitor such as selegiline or rasagiline, a COMT inhibitor such as entacapone or tolcapone, an adenosine 2a antagonist such as istradefylline, an antiglutamatergic agent such as amantadine or memantine an acetylcholinesterase inhibitor such as rivastigmine, donepezil or galantamine, an antipsychotic agent such as quetiapine, clozapine, risperidone, pimavanserin, olanzapine, haloperidol, aripiprazole or brexpiprazole; or an antibody targeting alpha-synuclein, Tau or A-beta protein.

EE59. A compound or pharmaceutically acceptable salt thereof according to any of items EE1-EE48, for use in the treatment of a neurodegenerative disease or disorder such as Parkinson's Disease, Huntington's disease, Restless leg syndrome or Alzheimer's disease; or a neuropsychiatric disease or disorder such as schizophrenia, attention deficit hyperactivity disorder or drug addiction.

EE60. A compound or pharmaceutically acceptable salt thereof according to any of items EE1-EE2, wherein said compound is selected from
(2S,3R,4S,5S,6S)-2-(((4aR,10aR)-7-acetoxy-1-propyl-1,2,3,4,4a,5,10,10a-octahydrobenzo[g]quinolin-6-yl)oxy)-6-(methoxycarbonyl)tetrahydro-2H-pyran-triacetate,
(2S,3R,4S,5S,6S)-2-(((4aR,10aR)-6-acetoxy-1-propyl-1,2,3,4,4a,5,10,10a-octahydrobenzo[g]quinolin-7-yl)oxy)-6-(methoxycarbonyl)tetrahydro-2H-pyran-3,4,5-triyl triacetate, and
methyl (2S,3S,4S,5R,6S)-6-[[(4aR,10aR)-1-propyl-6-[(2S,3R,4S,5S,6S)-3,4,5-triacetoxy-6-methoxycarbonyl-tetrahydropyran-2-yl]oxy-3,4,4a,5,10,10a-hexahydro-2H-benzo[g]quinolin-7-yl]oxy]-3,4,5-triacetoxy-tetrahydropyran-2-carboxylate;
for use in the treatment of a neurodegenerative disease or disorder such as Parkinson's Disease, Huntington's disease, Restless leg syndrome or Alzheimer's disease; or a neuropsychiatric disease or disorder such as schizophrenia, attention deficit hyperactivity disorder or drug addiction.

EE61. The compound or pharmaceutically acceptable salt thereof according to any one of items EE1-EE48, and EE60, for use in treatment of Parkinson's Disease.

EE62. The compound or pharmaceutically acceptable salt thereof according to any one of items EE1-EE48 and EE60 for use in the treatment according to any of items EE59-EE61, wherein said compound is to be used in combination with another agent which is useful in the treatment of a neurodegenerative disease or disorder such as Parkinson's disease.

EE63. The compound or pharmaceutically acceptable salt thereof according to any one of items EE1-EE48 and EE60 for use in the treatment according to any of items EE59-EE62, wherein said compound is to be used in combination with a compound selected from the group consisting of L-DOPA, droxidopa, foliglurax, a MAO-B inhibitor such as selegiline or rasagiline, a COMT inhibitor such as entacapone or tolcapone, an adenosine 2a antagonist such as istradefylline, an antiglutamatergic agent such as amantadine or memantine, an acetylcholinesterase inhibitor such as rivastigmine, donepezil or galantamine, an antipsychotic agent such as quetiapine, clozapine, risperidone, pimavanserin, olanzapine, haloperidol, aripiprazole or brexpiprazole; or in combination with an antibody targeting alpha-synuclein, Tau or A-beta protein.

EE64. The compound or pharmaceutically acceptable salt thereof according to any of items EE1-EE48 and EE60, for use in the treatment according to any of items EE59-EE63 wherein said treatment is performed by oral administration of said compound.

EE65. The compound or pharmaceutically acceptable salt thereof according to any of items EE1-EE48, for use in the treatment according to any of items EE59-EE64, wherein said compound is comprised in an oral pharmaceutical composition such as a tablet or a capsule for oral administration.

EE66. A method for the treatment of a neurodegenerative disease or disorder such as Parkinson's Disease, Huntington's disease, Restless leg syndrome or Alzheimer's disease; or a neuropsychiatric disease or disorder such as schizophrenia, attention deficit hyperactivity disorder or drug addiction; which method comprises the administration of a therapeutically effective amount of a compound or pharmaceutically acceptable salt thereof according to any of items EE1-EE48, to a patient in need thereof.

EE67. The method according to item EE66, wherein said neurodegenerative disease or disorder is Parkinson's Disease.

EE68. The method according to any of items EE66-EE67, wherein said compound or pharmaceutically acceptable salt thereof according to any of items EE1-EE48, is used in combination with another agent which is useful in the treatment of a neurodegenerative disease or disorder such as Parkinson's disease.

EE69. The method according to any of items EE66-EE68, wherein said compound or pharmaceutically acceptable salt thereof according to any of items EE1-EE48, is used in combination with a compound selected from the group consisting of L-DOPA, droxidopa, foliglurax, a MAO-B inhibitor such as selegiline or rasagiline, a COMT inhibitor such as entacapone or tolcapone, an adenosine 2a antagonist such as istradefylline, an antiglutamatergic agent such as amantadine or memantine, an acetylcholinesterase inhibitor such as rivastigmine, donepezil or galantamine, an antipsychotic agent such as quetiapine, clozapine, risperidone, pimavanserin, olanzapine, haloperidol, aripiprazole or brexpiprazole; or in combination with an antibody targeting alpha-synuclein, Tau or A-beta protein.

EE70. The method according to any of items EE66-EE69, wherein said administration is performed by the oral route.

EE71. The method according to any of items EE66-EE70, wherein said compound or pharmaceutically acceptable salt thereof according to any of items EE1-EE48 is comprised in an oral pharmaceutical composition such as a tablet or a capsule for oral administration.

EE72. Use of a compound or pharmaceutically acceptable salt thereof according to any of items EE1-EE48, in the manufacture of a medicament for the treatment of a neurodegenerative disease or disorder such as Parkinson's Disease, Huntington's disease, Restless leg syndrome or Alzheimer's disease; or for the treatment of a neuropsychiatric disease or disorder such as schizophrenia, attention deficit hyperactivity disorder or drug addiction.

EE73. The use according to item EE72, wherein said neurodegenerative disease or disorder is Parkinson's Disease.

EE74. The use according to any of items EE72-EE73, wherein said medicament is used in combination with another agent which is useful in the treatment of a neurodegenerative disease or disorder such as Parkinson's disease.

EE75. The use according to any of items EE72-EE74, wherein said medicament is used in combination with a compound selected from the group consisting of L-DOPA, droxidopa, foliglurax, a MAO-B inhibitor such as selegiline or rasagiline, a COMT inhibitor such as entacapone or tolcapone, an adenosine 2a antagonist such as istradefylline, an antiglutamatergic agent such as amantadine or memantine, an acetylcholinesterase inhibitor such as rivastigmine, donepezil or galantamine, an antipsychotic agent such as quetiapine, clozapine, risperidone, pimavanserin, olanzapine, haloperidol, aripiprazole or brexpiprazole; or in combination with an antibody targeting alpha-synuclein, Tau or A-beta protein.

EE76. The use according to any of items EE72-EE75, wherein said medicament is an oral medicament such as a tablet or a capsule for oral administration.

In the context of the present invention, it is understood that the carbon atom at the attachment point on substituent (i) (depicted in embodiment 1) is at the anomeric position of (i). Similarly, the carbon atom at the attachment point on substituent (ii) (depicted in embodiment 1) is at the anomeric position of (ii).

All references, including publications, patent applications and patents, cited herein are hereby incorporated by reference in their entirety and to the same extent as if each reference were individually and specifically indicated to be incorporated by reference and were set forth in its entirety (to the maximum extent permitted by law).

Headings and sub-headings are used herein for convenience only and should not be construed as limiting the invention in any way.

The description herein of any aspect or aspect of the invention using terms such as "comprising", "having," "including" or "containing" with reference to an element or elements is intended to provide support for a similar aspect or aspect of the invention that "consists of", "consists essentially of" or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

The use of any and all examples, or exemplary language (including "for instance", "for example", "e.g.", "such as" and "as such") in the present specification is intended merely to better illuminate the invention and does not pose a limitation on the scope of invention unless otherwise indicated.

It should be understood that the various aspects, embodiments, implementations and features of the invention mentioned herein may be claimed separately, or in any combination.

The present invention includes all modifications and equivalents of the subject-matter recited in the claims appended hereto, as permitted by applicable law.

Compounds of the Invention

TABLE 2

Exemplified compounds of the invention

| Example | Compound | Structure |
|---|---|---|
| Compound (1) | (2S,3R,4S,5S,6S)-2-(((4aR,10aR)-7-(benzyloxy)-1-propyl-1,2,3,4,4a,5,10,10a-octahydrobenzo[g]quinolin-6-yl)oxy)-6-(methoxycarbonyl)tetrahydro-2H-pyran-3,4,5-triyl triacetate | 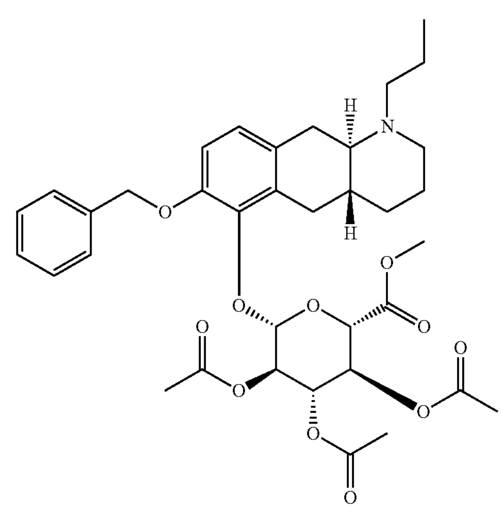 [SMILES: CCCN1CCC[C@@H]2Cc3c(ccc(OCc4ccccc4)c3O[C@@H]3O[C@H](C(=O)OC)[C@@H](OC(C)=O)[C@H](OC(C)=O)[C@H]3OC(C)=O)C[C@H]21] |

TABLE 2-continued

Exemplified compounds of the invention

| Example | Compound | Structure |
|---|---|---|
| Compound (2) | (2S,3R,4S,5S,6S)-2-(((4aR,10aR)-7-hydroxy-1-propyl-1,2,3,4,4a,5,10,10a-octahydrobenzo[g]quinolin-6-yl)oxy)-6-(methoxycarbonyl)tetrahydro-2H-pyran-3,4,5-triyl triacetate | 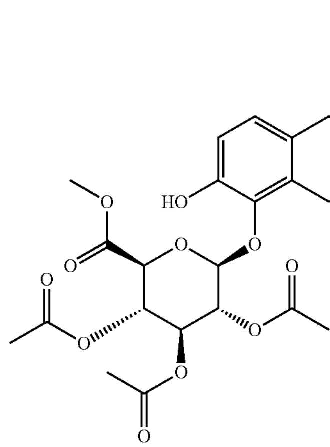 |
| Compound (3) | (2R,3R,4S)-2-(((4aR,10aR)-7-hydroxy-1-propyl-1,2,3,4,4a,5,10,10a-octahydrobenzo[g]quinolin-6-yl)oxy)-6-(methoxycarbonyl)-3,4-dihydro-2H-pyran-3,4-diyl diacetate | 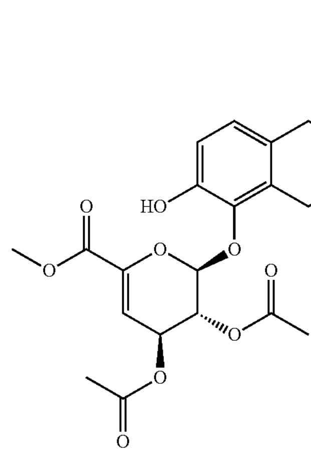 |
| Compound (4) | (2S,3S,4S,5R,6S)-6-(((4aR,10aR)-7-(benzyloxy)-1-propyl-1,2,3,4,4a,5,10,10a-octahydrobenzo[g]quinolin-6-yl)oxy)-3,4,5-trihydroxytetrahydro-2H-pyran-2-carboxylic acid | 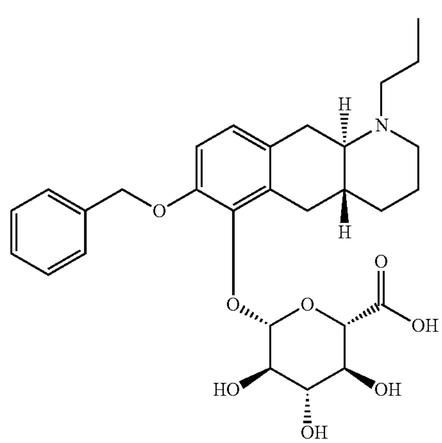 [SMILES: CCCN1CCC[C@@H]2Cc3c(ccc(OCc4ccccc4)c3O[C@@H]3O[C@H](C(=O)O)[C@@H](O)[C@H](O)[C@H]3O)C[C@H]21] |

TABLE 2-continued

Exemplified compounds of the invention

| Example | Compound | Structure |
|---|---|---|
| Compound (5) | (2S,3R,4S,5S,6R)-2-(((4aR,10aR)-7-(benzyloxy)-1-propyl-1,2,3,4,4a,5,10,10a-octahydrobenzo[g]quinolin-6-yl)oxy)-6-((benzyloxy)carbonyl)tetrahydro-2H-pyran-3,4,5-triyl tris(2,2-dimethylpropanoate) | 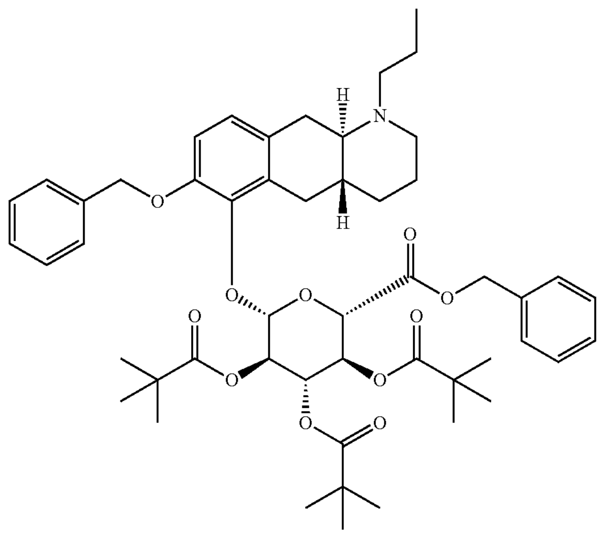 [SMILES: CCCN1CCC[C@@H]2Cc3c(ccc(OCc4ccccc4)c3O[C@@H]3O[C@H](C(=O)OCc4ccccc4)[C@@H](OC(=O)C(C)(C)C)[C@H](OC(=O)C(C)(C)C)[C@H]3OC(=O)C(C)(C)C)C[C@H]21] |
| Compound (6) | (2S,3S,4S,5R,6S)-6-(((4aR,10aR)-7-hydroxy-1-propyl-1,2,3,4,4a,5,10,10a-octahydrobenzo[g]quinolin-6-yl)oxy)-3,4,5-tris(pivaloyloxy)tetrahydro-2H-pyran-2-carboxylic acid | 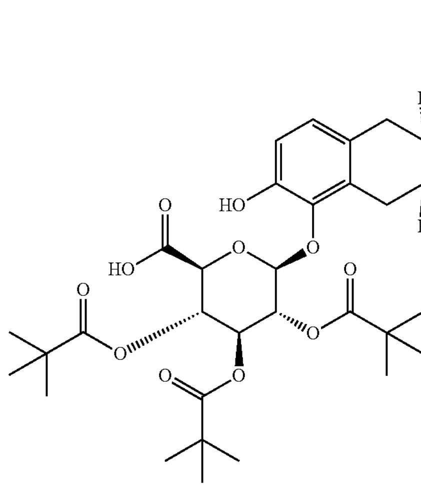 |
| Compound (7) | (2S,3R,4S,5S,6S)-2-(((4aR,10aR)-7-(benzyloxy)-1-propyl-1,2,3,4,4a,5,10,10a-octahydrobenzo[g]quinolin-6-yl)oxy)-6-((benzyloxy)carbonyl)tetrahydro-2H-pyran-3,4,5-triyl triacetate | 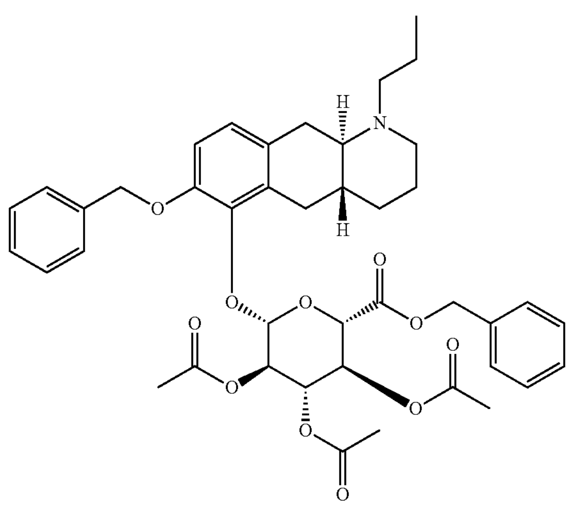 [SMILES: CCCN1CCC[C@@H]2Cc3c(ccc(OCc4ccccc4)c3O[C@@H]3O[C@H](C(=O)OCc4ccccc4)[C@@H](OC(C)=O)[C@H](OC(C)=O)[C@H]3OC(C)=O)C[C@H]21] |

TABLE 2-continued

Exemplified compounds of the invention

| Example | Compound | Structure |
| --- | --- | --- |
| Compound (8) | (2S,3S,4S,5R,6S)-3,4,5-triacetoxy-6-(((4aR,10aR)-7-hydroxy-1-propyl-1,2,3,4,4a,5,10,10a-octahydrobenzo[g]quinolin-6-yl)oxy)tetrahydro-2H-pyran-2-carboxylic acid | 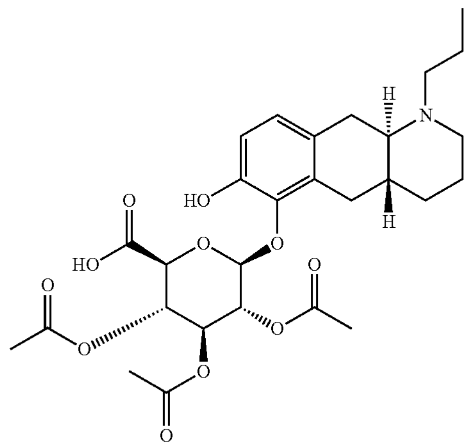 [SMILES: CCCN1CCC[C@@H]2Cc3c(ccc(O)c3O[C@@H]3O[C@H](C(=O)O)[C@@H](OC(C)=O)[C@H](OC(C)=O)[C@H]3OC(C)=O)C[C@H]21] |
| Compound (9) | (2R,3R,4S)-3,4-dihydroxy-2-(((4aR,10aR)-7-hydroxy-1-propyl-1,2,3,4,4a,5,10,10a-octahydrobenzo[g]quinolin-6-yl)oxy)-3,4-dihydro-2H-pyran-6-carboxylic acid | 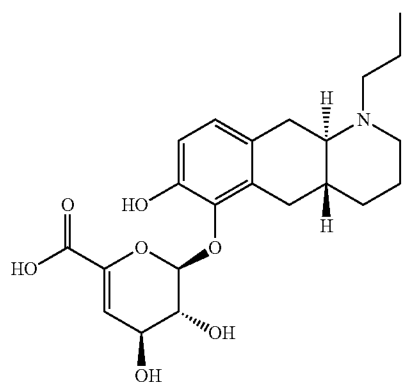 [SMILES: CCCN1CCC[C@@H]2Cc3c(ccc(O)c3O[C@@H]3OC(C(=O)O)=C[C@H](O)[C@H]3O)C[C@H]21] |
| Compound (10) | (2S,3R,4S,5S,6S)-2-(((4aR,10aR)-7-(benzyloxy)-1-propyl-1,2,3,4,4a,5,10,10a-octahydrobenzo[g]quinolin-6-yl)oxy)-6-(ethoxycarbonyl)tetrahydro-2H-pyran-3,4,5-triyl triacetate | 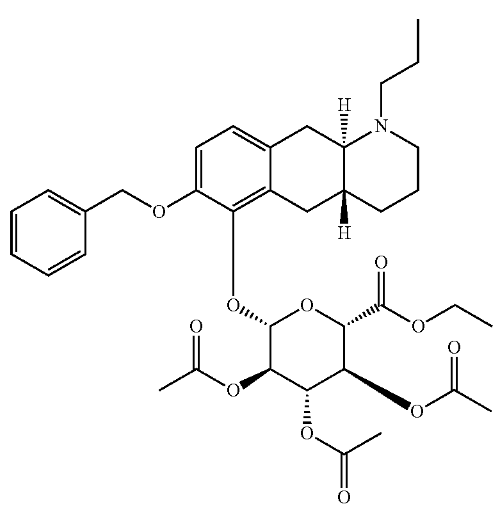 [SMILES: CCCN1CCC[C@@H]2Cc3c(ccc(OCc4ccccc4)c3O[C@@H]3O[C@H](C(=O)OCC)[C@@H](OC(C)=O)[C@H](OC(C)=O)[C@H]3OC(C)=O)C[C@H]21] |

TABLE 2-continued

| Exemplified compounds of the invention | | |
|---|---|---|
| Example | Compound | Structure |
| Compound (11) | (2S,3S,4S,5R,6S)-2-(ethoxycarbonyl)-6-(((4aR,10aR)-7-hydroxy-1-propyl-1,2,3,4,4a,5,10,10a-octahydrobenzo[g]quinolin-6-yl)oxy)tetrahydro-2H-pyran-3,4,5-triyl triacetate | |
| Compound (12) | ethyl (2S,3S,4S,5R,6S)-3,4,5-trihydroxy-6-(((4aR,10aR)-7-hydroxy-1-propyl-1,2,3,4,4a,5,10,10a-octahydrobenzo[g]quinolin-6-yl)oxy)tetrahydro-2H-pyran-2-carboxylate | |
| Compound (13) | (2S,3R,4S,5S,6S)-2-(((4aR,10aR)-7-(benzyloxy)-1-propyl-1,2,3,4,4a,5,10,10a-octahydrobenzo[g]quinolin-6-yl)oxy)-6-(ethoxycarbonyl)tetrahydro-2H-pyran-3,4,5-triyl tris(2,2-dimethylpropanoate) | |

TABLE 2-continued

Exemplified compounds of the invention

| Example | Compound | Structure |
| --- | --- | --- |
| Compound (14) | (2S,3S,4S,5R,6S)-2-(ethoxycarbonyl)-6-(((4aR,10aR)-7-hydroxy-1-propyl-1,2,3,4,4a,5,10,10a-octahydrobenzo[g]quinolin-6-yl)oxy)tetrahydro-2H-pyran-3,4,5-triyl tris(2,2-dimethylpropanoate) | 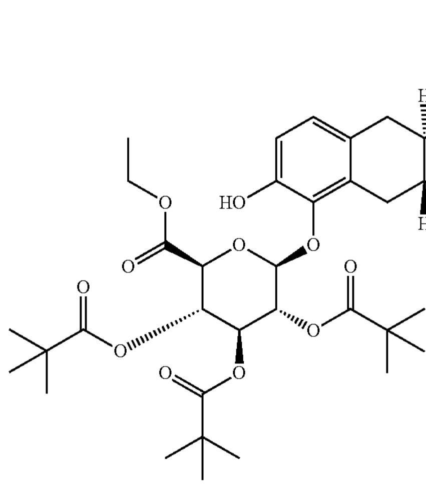 |
| Compound (15) | (2S,3S,4S,5R,6S)-3,4,5-trihydroxy-6-(((4aR,10aR)-7-methoxy-1-propyl-1,2,3,4,4a,5,10,10a-octahydrobenzo[g]quinolin-6-yl)oxy)tetrahydro-2H-pyran-2-carboxylic acid | 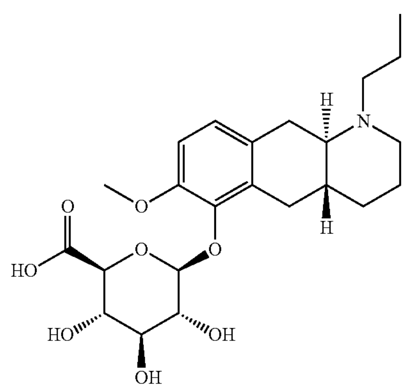 [SMILES: CCCN1CCC[C@@H]2Cc3c(ccc(OC)c3O[C@@H]3O[C@H](C(=O)O)[C@@H](O)[C@H](O)[C@H]3O)C[C@H]21] |
| Compound (16) | (2S,3S,4S,5R,6S)-2-((benzyloxy)carbonyl)-6-(((4aR,10aR)-7-methoxy-1-propyl-1,2,3,4,4a,5,10,10a-octahydrobenzo[g]quinolin-6-yl)oxy)tetrahydro-2H-pyran-3,4,5-triyl triacetate | 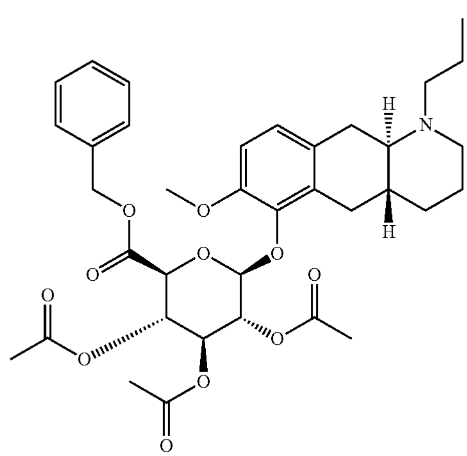 [SMILES: CCCN1CCC[C@@H]2Cc3c(ccc(OC)c3O[C@@H]3O[C@H](C(=O)OCc4ccccc4)[C@@H](OC(C)=O)[C@H](OC(C)=O)[C@H]3OC(C)=O)C[C@H]21] |

TABLE 2-continued

Exemplified compounds of the invention

| Example | Compound | Structure |
| --- | --- | --- |
| Compound (17) | (2S,3S,4S,5R,6S)-3,4,5-triacetoxy-6-(((4aR,10aR)-7-methoxy-1-propyl-1,2,3,4,4a,5,10,10a-octahydrobenzo[g]quinolin-6-yl)oxy)tetrahydro-2H-pyran-2-carboxylic acid | 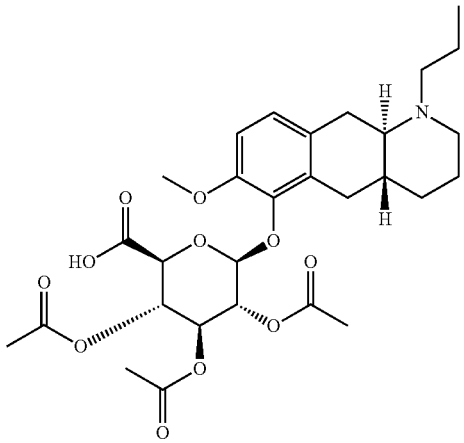 [SMILES: CCCN1CCC[C@@H]2Cc3c(ccc(OC)c3O[C@@H]3O[C@H](C(=O)O)[C@@H](OC(C)=O)[C@H](OC(C)=O)[C@H]3OC(C)=O)C[C@H]21] |
| Compound (18) | (2S,3R,4S,5S,6S)-2-(((4aR,10aR)-7-methoxy-1-propyl-1,2,3,4,4a,5,10,10a-octahydrobenzo[g]quinolin-6-yl)oxy)-6-(methoxycarbonyl)tetrahydro-2H-pyran-3,4,5-triyl triacetate | 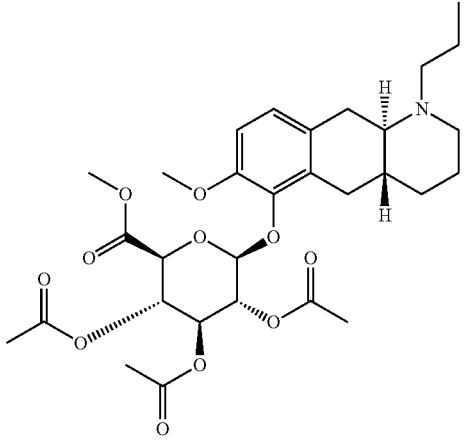 [SMILES: CCCN1CCC[C@@H]2Cc3c(ccc(OC)c3O[C@@H]3O[C@H](C(=O)OC)[C@@H](OC(C)=O)[C@H](OC(C)=O)[C@H]3OC(C)=O)C[C@H]21] |
| Compound (19) | (2S,3R,4S,5S,6S)-2-(((4aR,10aR)-7-methoxy-1-propyl-1,2,3,4,4a,5,10,10a-octahydrobenzo[g]quinolin-6-yl)oxy)-6-(ethoxycarbonyl)tetrahydro-2H-pyran-3,4,5-triyl triacetate | 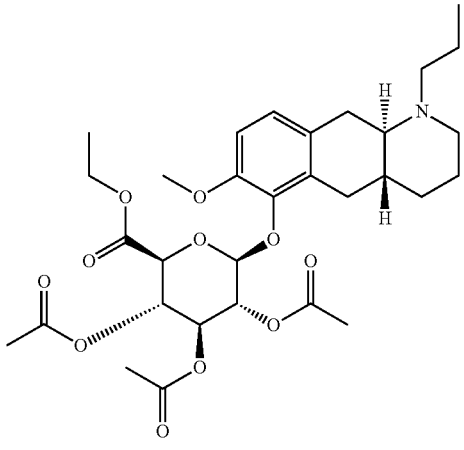 [SMILES: CCCN1CCC[C@@H]2Cc3c(ccc(OC)c3O[C@@H]3O[C@H](C(=O)OCC)[C@@H](OC(C)=O)[C@H](OC(C)=O)[C@H]3OC(C)=O)C[C@H]21] |

TABLE 2-continued

Exemplified compounds of the invention

| Example | Compound | Structure |
|---|---|---|
| Compound (20) | (2S,3S,4S,5R,6S)-2-((benzyloxy)carbonyl)-6-(((4aR,10aR)-7-methoxy-1-propyl-1,2,3,4,4a,5,10,10a-octahydrobenzo[g]quinolin-6-yl)oxy)tetrahydro-2H-pyran-3,4,5-triyl tris(2,2-dimethylpropanoate) | 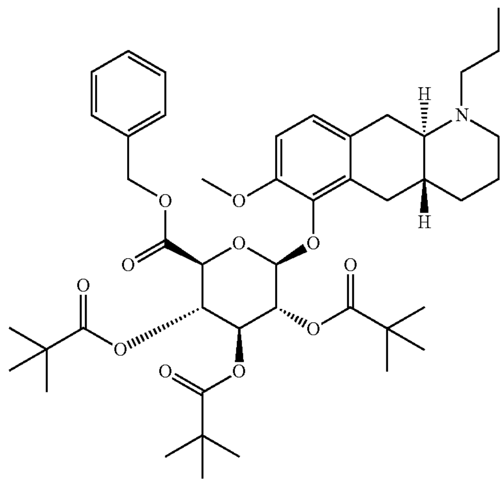 [SMILES: CCCN1CCC[C@@H]2Cc3c(ccc(OC)c3O[C@@H]3O[C@H](C(=O)OCc4ccccc4)[C@@H](OC(=O)C(C)(C)C)[C@H](OC(=O)C(C)(C)C)[C@H]3OC(=O)C(C)(C)C)C[C@H]21] |
| Compound (21) | (2S,3S,4S,5R,6S)-6-(((4aR,10aR)-7-methoxy-1-propyl-1,2,3,4,4a,5,10,10a-octahydrobenzo[g]quinolin-6-yl)oxy)-3,4,5-tris(pivaloyloxy)tetrahydro-2H-pyran-2-carboxylic acid | 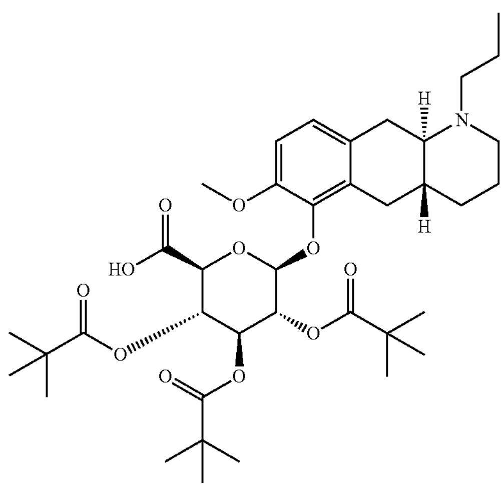 [SMILES: CCCN1CCC[C@@H]2Cc3c(ccc(OC)c3O[C@@H]3O[C@H](C(=O)O)[C@@H](OC(=O)C(C)(C)C)[C@H](OC(=O)C(C)(C)C)[C@H]3OC(=O)C(C)(C)C)C[C@H]21] |
| Compound (22) | (2S,3S,4S,5R,6S)-2-((methoxy)carbonyl)-6-(((4aR,10aR)-7-methoxy-1-propyl-1,2,3,4,4a,5,10,10a-octahydrobenzo[g]quinolin-6-yl)oxy)tetrahyro-2H-pyran-3,4,5-triyl tris(2,2-dimethylpropanoate) | 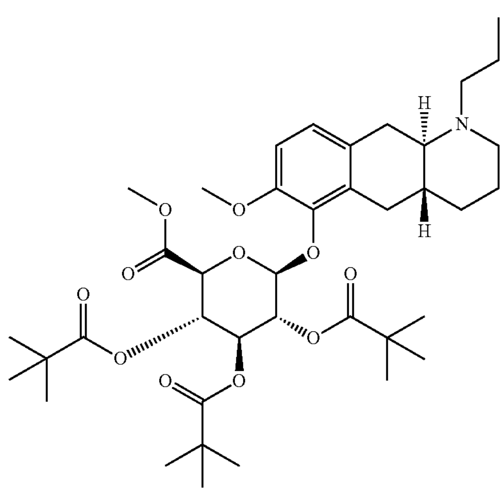 [SMILES: CCCN1CCC[C@@H]2Cc3c(ccc(OC)c3O[C@@H]3O[C@H](C(=O)OC)[C@@H](OC(=O)C(C)(C)C)[C@H](OC(=O)C(C)(C)C)[C@H]3OC(=O)C(C)(C)C)C[C@H]21] |

TABLE 2-continued

Exemplified compounds of the invention

| Example | Compound | Structure |
|---|---|---|
| Compound (23) | (2S,3S,4S,5R,6S)-2-((ethoxy)carbonyl)-6-(((4aR,10aR)-7-methoxy-1-propyl-1,2,3,4,4a,5,10,10a-octahydrobenzo[g]quinolin-6-yl)oxy)tetahydro-2H-pyran-3,4,5-triyl tris(2,2-dimethylpropanoate) | 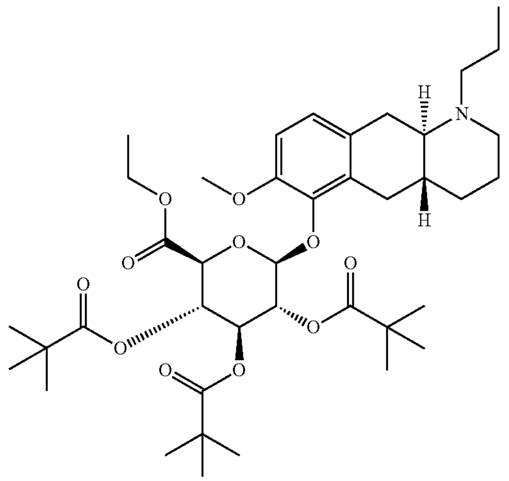 [SMILES: CCCN1CCC[C@@H]2Cc3c(ccc(OC)c3O[C@@H]3O[C@H](C(=O)OCC)[C@@H](OC(=O)C(C)(C)C)[C@H](OC(=O)C(C)(C)C)[C@H]3OC(=O)C(C)(C)C)C[C@H]21] |
| Compound (24) | (2S,3S,4S,5R,6S)-6-(((4aR,10aR)-7-(benzyloxy)-1-propyl-1,2,3,4,4a,5,10,10a-octahydrobenzo[g]quinolin-6-yl)oxy)-3,4,5-tris(pivaloyloxy)tetrahydro-2H-pyran-2-carboxylic acid | 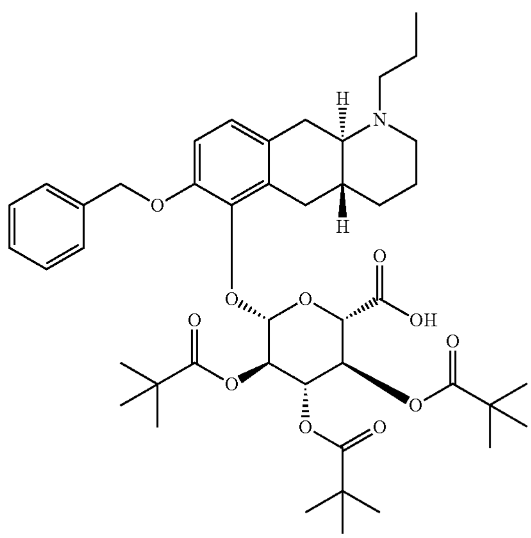 [SMILES: CCCN1CCC[C@@H]2Cc3c(ccc(OCc4ccccc4)c3O[C@@H]3O[C@H](C(=O)O)[C@@H](OC(=O)C(C)(C)C)[C@H](OC(=O)C(C)(C)C)[C@H]3OC(=O)C(C)(C)C)C[C@H]21] |
| Compound (25) | (2S,3R,4S,5S,6S)-2-(((4aR,10aR)-7-(benzyloxy)-1-propyl-1,2,3,4,4a,5,10,10a-octahydrobenzo[g]quinolin-6-yl)oxy)-6-(methoxycarbonyl)tetrahydro-2H-pyran-3,4,5-triyl tris(2,2-dimethylpropanoate) | 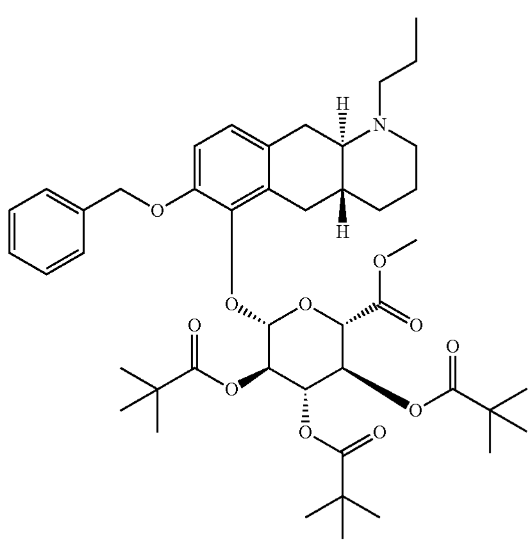 [SMILES: CCCN1CCC[C@@H]2Cc3c(ccc(OCc4ccccc4)c3O[C@@H]3O[C@H](C(=O)OC)[C@@H](OC(=O)C(C)(C)C)[C@H](OC(=O)C(C)(C)C)[C@H]3OC(=O)C(C)(C)C)C[C@H]21] |

TABLE 2-continued

Exemplified compounds of the invention

| Example | Compound | Structure |
| --- | --- | --- |
| Compound (26) | (2S,3S,4S,5R,6S)-2-(methoxycarbonyl)-6-(((4aR,10aR)-7-hydroxy-1-propyl-1,2,3,4,4a,5,10,10a-octahydrobenzo[g]quinolin-6-yl)oxy)tetrahydro-2H-pyran-3,4,5-triyl tris(2,2-dimethylpropanoate) | 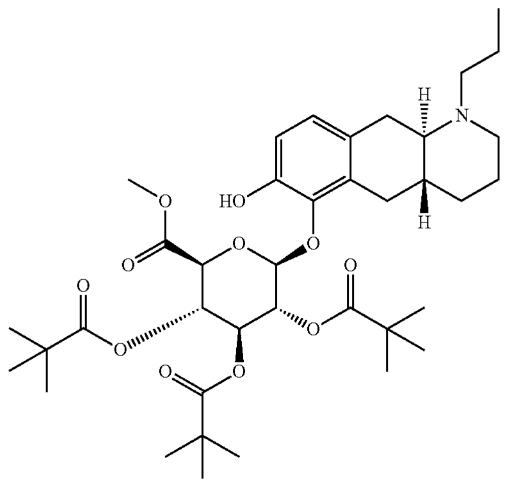 [SMILES: CCCN1CCC[C@@H]2Cc3c(ccc(O)c3O[C@@H]3O[C@H](C(=O)OC)[C@@H](OC(=O)C(C)(C)C)[C@H](OC(=O)C(C)(C)C)[C@H]3OC(=O)C(C)(C)C)C[C@H]21] |
| Compound (27) | (2S,3R,4S,5S,6S)-2-(((4aR,10aR)-6-hydroxy-1-propyl-1,2,3,4,4a,5,10,10a-octahydrobenzo[g]quinolin-7-yl)oxy)-6-(methoxycarbonyl)tetrahydro-2H-pyran-3,4,5-triyl triacetate | 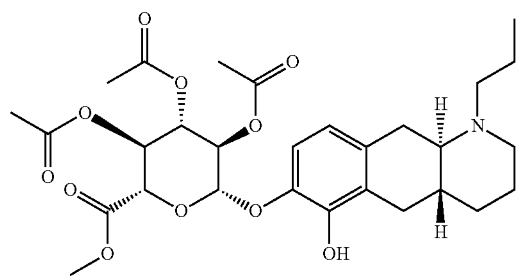 [SMILES: CCCN1CCC[C@@H]2Cc3c(ccc(O[C@@H]4O[C@H](C(=O)OC)[C@@H](OC(C)=O)[C@H](OC(C)=O)[C@H]4OC(C)=O)c3O)C[C@H]21] |

Experimental Section

General Methods

The compounds of formula (Id), or salts thereof may be prepared by methods described below, together with synthetic methods known in the art of organic chemistry, or modifications that are familiar to those of ordinary skill in the art. The starting materials used herein are available commercially or may be prepared by routine methods known in the art, such as those methods described in standard reference books such as "Compendium of Organic Synthetic Methods, Vol. I-XII" (published with Wiley-Interscience). Preferred methods include, but are not limited to, those described below.

The schemes are representative of methods useful in synthesizing the compounds of the present invention. They are not intended to constrain the scope of the invention in any way.

LC-MS Methods

Analytical LC-MS data were obtained using the methods identified below.

Method 25: MS: Ion source: (APPI), Temp 450° C. OR/RNG 20/200 V OR/RNG 5/100 V

Mass: 100-1000 amu

HPLC: Column: dC-18 4.6×30 mm 3 µm Atlantis (Waters)

Column temperature: 40° C., Gradient, reverse phase with ion pairing

Solvent A: 100% $H_2O$ 0.05% TFA

Solvent B: 95% ACN 5% $H_2O$ 0.035% TFA

Flow: 3.3 ml/min, Injection vol: 15 µl

Gradient: 2% B to 100% B in 2.4 min, 2% B 0.4 min, Total run time: 2.8 minutes, UV:254 nm.

ELSD: Glass tube: 21° C., Evaporation chamber: 40° C., pressure: 2.3 bar.

Method 550: LC-MS were run on Waters Aquity UPLC-MS consisting of Waters Aquity including column manager, binary solvent manager, sample organizer, PDA detector (operating at 254 nM), ELS detector, and TQ-MS equipped with APPI-source operating in positive ion mode.

LC-conditions: The column was Acquity UPLC BEH C18 1.7 µm; 2.1×50 mm operating at 60° C. with 1.2 ml/min of a binary gradient consisting of water+0.05% trifluoroacetic acid (A) and acetonitrile/water (95:5)+0.05% trifluoroacetic acid.

Gradient:

| 0.00 min | 10% B |
| 1.00 min | 100% B |
| 1.01 min | 10% B |
| 1.15 min | 10% B |
| Total run time: 1.15 minutes | |

Method 551: LC-MS were run on Waters Aquity UPLC-MS consisting of Waters Aquity including column manager, binary solvent manager, sample organizer, PDA detector (operating at 254 nM), ELS detector, and TO-MS equipped with APPI-source operating in positive ion mode.

LC-conditions: The column was Acquity UPLC HSS T3 1.8 µm; 2.1×50 mm operating at 60° C. with 1.2 ml/min of a binary gradient consisting of water+0.05% trifluoroacetic acid (A) and acetonitrile/water (95:5)+0.05% trifluoroacetic acid.
Gradient:

| | |
|---|---|
| 0.00 min | 2% B |
| 1.00 min | 100% B |
| 1.15 min | 2% B |
| Total run time: 1.15 minutes | |

Method 555: LC-MS were run on Waters Aquity UPLC-MS consisting of Waters Aquity including column manager, binary solvent manager, sample organizer, PDA detector (operating at 254 nM), ELS detector, and TO-MS equipped with APPI-source operating in positive ion mode.

LC-conditions: The column was Acquity UPLC BEH C18 1.7 µm; 2.1×150 mm operating at 60° C. with 0.6 ml/min of a binary gradient consisting of water+0.05% trifluoroacetic acid (A) and acetonitrile/water (95:5)+0.05% trifluoroacetic acid.
Gradient:

| | |
|---|---|
| 0.00 min | 10% B |
| 3.00 min | 100% B |
| 3.60 min | 10% B |
| Total run time: 3.6 minutes | |

Method 111: LC-MS were run on a Shimadzu LCMS-2020 consisting of PDA detector operating at 190-800 nM and MS equipped with ESI source operating in positive mode.

LC-conditions: The column was Phenomenex Kinetex EVO C18 2.6 µm; 2.1×100 mm operating at 25° C. with 0.5 ml/min of a gradient consisting of water+0.1% formic acid (A) and acetonitrile+0.1% formic acid (B).
Gradient:

| | |
|---|---|
| 0.00 min | 2% B |
| 1.00 min | 2% B |
| 10.00 min | 90% B |
| 13.00 min | 90% B |
| 13.10 min | 2% B |
| 18.00 min | 2% B |
| Total run time: 18 minutes | |

Preparative LCMS was performed using the method identified below.

Waters AutoPurification system using combined mass/UV detection.

Column: Sunfire 30×100 mm, 5 µm particles. Operating at 40° C. with 90 ml/min of a binary gradient consisting of water+0.05% trifluoroacetic acid (A) and acetonitrile/water (3:5)+0.05% trifluoroacetic acid.
Gradient:

| | |
|---|---|
| 0.00 min | 98% A |
| 5.00 min | 50% A |
| 5.50 min | 98% A |
| 6.00 min | 98% A |

Method AB01 (Agilent 1200 & 6120):

| | |
|---|---|
| Instrument: | Agilent 1200 & MS 6120 |
| MS Mode: | Positive |
| MS Range: | 100-1000 |
| MS Fragmentor | 70 V |
| Drying Gas Flow | 12 L/min |
| Nebulizer Pressure | 40 psig |
| Drying Gas Temp | 350° C. |
| Capillary Voltage | 3500 V |

LC-conditions: the column was a Luna-C18(2) 2.0×50 mm, 5 µm operated at 40° C. with 0.8 mL/min of a gradient of water+0.037% TFA (A) and MeCN+0.018% TFA (B).
Gradient:

| | |
|---|---|
| 0.00 min | 1% B |
| 0.01-0.40 min | 1% B |
| 0.40-3.40 min | 1-90% B |
| 3.40-3.85 min | 90-100% B |
| 3.85-3.86 min | 100-1% B |
| 3.86-4.50 min | 1% B |
| Total run time: 4.50 minutes | |

Method 0-30AB-HPLC (Agilent XDB):

| | |
|---|---|
| Instrument: | Agilent 1260 & MS 6120 |
| MS Mode: | Positive |
| MS Range: | 100-1000 |
| MS Fragmentor | 70 V |
| Drying Gas Flow | 12 L/min |
| Nebulizer Pressure | 40 psig |
| Drying Gas Temp | 350° C. |
| Capillary Voltage | 2500 V |

0-30AB-HPLC-conditions: the column was an Agilent XDB-C18 4.6×50 mm column (1.8 µm particles) operating at 40° C. with 0.6 mL/min of a binary gradient consisting of water+0.037% trifluoroacetic acid (A) and acetonitrile+0.018% trifluoroacetic acid (B).
Gradient:

| | |
|---|---|
| 0.01-2.00 min | 0-30% B |
| 2.00-4.00 min | 30% B |
| 4.00-4.01 min | 30-0% B |
| Total run time: 4.00 minutes | |

Method 10-90AB (Shimadzu LC-20AD&MS 2010):

| | |
|---|---|
| Method name: | 10-90AB |
| Instrument: | Shimadzu LC-20AD & MS 2020 |
| MS Mode: | Positive |
| MS Range: | 100-1000 |
| CDL Temp | 250° C. |
| Heat block Temp | 28° C. |
| Nebulizing gas flow | 1.5 L/min |

LC-conditions: the column was a Luna-C18(2) 2.0×30 mm, (3 microm particles) operated at 40° C. with 0.8 mL/min (0.01-1.51 min) and 1.2 mL/min (1.52-2.00 min) of a gradient of water+0.037% TFA (A) and MeCN+0.018% TFA (B).
Gradient:

| | |
|---|---|
| 0.01 min | 10% B |
| 0.01-1.15 min | 10-90% B |
| 1.15-1.65 min | 90% B |

-continued

| | |
|---|---|
| 1.65-1.66 min | 90-10% B |
| 1.66-2.00 min | 10% B |
| Total run time: 2.00 minutes | |

Method DELIVER-K-1 (Agilent 1200 & 6110):

| | |
|---|---|
| Instrument: | Agilent 1200 & MS 6110 |
| MS Mode: | Positive |
| MS Range: | 100-1000 |
| MS Fragmentor | 70 V |
| Drying Gas Flow | 12 L/min |
| Nebulizer Pressure | 40 psig |
| Drying Gas Temp | 350° C. |
| Capillary Voltage | 2500 V |

LC-conditions: the column was a Kromasil Eternity-C18 3.0×30 mm, 2.5 μm operated at 40° C. with 0.8 mL/min of a gradient of water+0.037% TFA (A) and MeCN+0.018% TFA (B).
Gradient:

| | |
|---|---|
| 0.01 min | 5% B |
| 0.01-1.60 min | 5-95% B |
| 1.60-2.50 min | 95-100% B |
| 2.50-2.52 min | 100-5% B |
| 2.52-3.00 min | 5% B |
| Total run time: 3.00 minutes | |

Method AB10 (Agilent 1200 & 1956A):

| | |
|---|---|
| Instrument: | Agilent 1200 & MS 1956A |
| MS Mode: | Positive |
| MS Range: | 100-1000 |
| MS Fragmentor | 70 V |
| Drying Gas Flow | 12 L/min |
| Nebulizer Pressure | 55 psig |
| Drying Gas Temp | 350° C. |
| Capillary Voltage | 2500 V |

LC-conditions: the column was a Luna-C18(2) 2.0×50 mm, 5 μm operated at 40° C. with 0.8 mL/min of a gradient of water+0.037% TFA (A) and MeCN+0.018% TFA (B).
Gradient:

| | |
|---|---|
| 0.00 min | 10% B |
| 0.01-0.40 min | 10% B |
| 0.40-3.40 min | 10-100% B |
| 3.40-3.85 min | 100% B |
| 3.85-3.86 min | 100-10% B |
| 3.86-4.50 min | 10% B |
| Total run time: 4.50 minutes | |

Method AB25 (Agilent 1200 & 1956A):

| | |
|---|---|
| Instrument: | Agilent 1200 & MS 1956A |
| MS Mode: | Positive |
| MS Range: | 100-1000 |
| MS Fragmentor | 70 V |
| Drying Gas Flow | 12 L/min |
| Nebulizer Pressure | 55 psig |
| Drying Gas Temp | 350° C. |
| Capillary Voltage | 2500 V |

LC-conditions: the column was a Luna-C18(2) 2.0×50 mm, 5 μm operated at 40° C. with 0.8 mL/min of a gradient of water+0.037% TFA (A) and MeCN+0.018% TFA (B).
Gradient:

| | |
|---|---|
| 0.00 min | 25% B |
| 0.01-0.40 min | 25% B |
| 0.40-3.40 min | 25-100% B |
| 3.40-3.85 min | 100% B |
| 3.85-3.86 min | 100-25% B |
| 3.86-4.50 min | 25% B |
| Total run time: 4.50 minutes | |

Method DELIVER-K (Agilent 1200 & 6110):

| | |
|---|---|
| Instrument: | Agilent 1200 & MS 6110 |
| MS Mode: | Positive |
| MS Range: | 100-1000 |
| MS Fragmentor | 70 V |
| Drying Gas Flow | 12 L/min |
| Nebulizer Pressure | 40 psig |
| Drying Gas Temp | 350° C. |
| Capillary Voltage | 2500 V |

LC-conditions: the column was a Halo-C18 3.0×30 mm mm, 2.7 micrometer operated at 40° C. with 0.8 mL/min of a gradient of water+0.037% TFA (A) and MeCN+0.018% TFA (B).
Gradient:

| | |
|---|---|
| 0.01 min | 5% B |
| 0.01-1.60 min | 5-95% B |
| 1.60-2.50 min | 95-100% B |
| 2.50-2.52 min | 100-5% B |
| 2.52-3.00 min | 5% B |
| Total run time: 3.00 minutes | |

Method AB25-MS1500 (Agilent 1200 & 1956A):

| | |
|---|---|
| Instrument: | Agilent 1200 & MS 1956A |
| MS Mode: | Positive |
| MS Range: | 100-1500 |
| MS Fragmentor | 70 V |
| Drying Gas Flow | 12 L/min |
| Nebulizer Pressure | 55 psig |
| Drying Gas Temp | 350° C. |
| Capillary Voltage | 2500 V |

LC-conditions: the column was a Luna-C18(2) 2.0×50 mm, 5 micrometer operated at 40° C. with 0.8 mL/min of a gradient of water+0.037% TFA (A) and MeCN+0.018% TFA (B).
Gradient:

| | |
|---|---|
| 0.00 min | 25% B |
| 0.01-0.40 min | 25% B |
| 0.40-3.40 min | 25-100% B |
| 3.40-3.85 min | 100% B |
| 3.85-3.86 min | 100-25% B |
| 3.86-4.50 min | 25% B |
| Total run time: 4.50 minutes | |

HighRes MS was run on a Bruker Compact qTOF equipped with electrospray operating in positive or negative mode. Direct infusion was used and calibration was done with sodium formate.

Abbreviations of Chemical Ingredients
Ac: Acetyl
AcCl: Acetyl chloride
AcOH: Acetic acid BF$_3$-OEt$_2$: Boron trifluoride diethyl etherate
BnCl: Benzyl chloride
DBU: 1,8-Diazabicyclo[5.4.0]undec-7-ene
DCM: Dichloromethane
DMF: Dimethylformamide
EtOAc: Ethyl acetate
EtOH: Ethanol
MeI: Methyl iodide
MeOH: Methanol
MeCN: Acetonitrile
MOMCl: Methoxymethyl chloride
MS: Molecular sieves
MTBE: Methyl tert-butyl ether
Pd/C: Palladium on carbon
Piv: Pivaloyl
TFA: Trifluoroacetic acid
THF: Tetrahydrofuran Preparation of Compounds of the Invention—General Methods (4aR,10aR)-1-Propyl-1,2,3,4,4a,5,10,10a-octahydrobenzo[g]quinoline-6,7-diol hydrochloride [Compound (I)] which can for example be prepared as disclosed in WO 2009/026934 was used as a precursor to synthesize of compounds of the invention. WO2019/101917 further describes methods for preparing glucuronidated derivatives of compound (I).

Treatment of compound (I) with excess of a suitable glucuronyl donor such as (2S,3R,4S,5S,6S)-6-(methoxycarbonyl)tetrahydro-2H-pyran-2,3,4,5-tetrayl tetraacetate or (2S,3S,4S,5R,6R)-2-((benzyloxy)carbonyl)-6-(2,2,2-trichloro-1-iminoethoxy)tetrahydro-2H-pyran-3,4,5-triyl tris(2,2-dimethylpropanoate) in the presence of a Lewis acid such as BF$_3$—OEt$_2$ will afford the corresponding bis-glucuronides. Such compounds can be deprotected by saponification. This chemistry is exemplified herein for methyl (2S,3S,4S,5R,6S)-6-[[(4aR,10aR)-1-propyl-6-[(2S,3R,4S,5S,6S)-3,4,5-triacetoxy-6-methoxycarbonyl-tetrahydropyran-2-yl]oxy-3,4,4a,5,10,10a-hexahydro-2H-benzo[g]quinolin-7-yl]oxy]-3,4,5-triacetoxy-tetrahydropyran-2-carboxylate and (2S,2'S,3S,3'S,4S,4'S,5R,5'R,6S,6'S)-6,6'-W4aR,10aR)-1-propyl-1,2,3,4,4a,5,10,10a-octahydrobenzo[g]quinoline-6,7-diyl)bis(oxy))bis(3,4,5-trihydroxytetrahydro-2H-pyran-2-carboxylic acid). For analogues containing benzyl esters, selective deprotection can be achieved by hydrogenolysis.

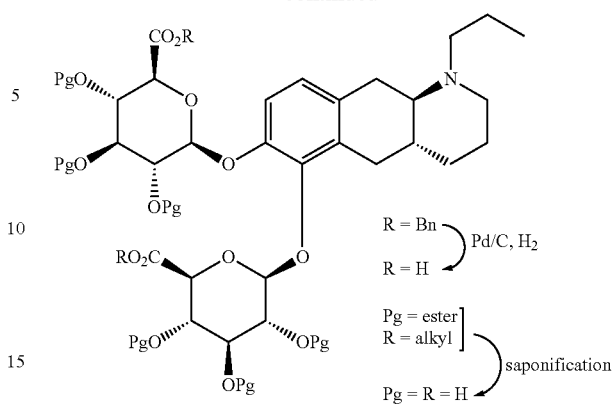

Compounds wherein the catechol 6-hydroxyl group is glucuronidated can be prepared in several ways, for example from (4aR,10aR)-7-(benzyloxy)-1-propyl-1,2,3,4,4a,5,10,10a-octahydrobenzo[g]quinolin-6-ol as outlined below. In brief, glucuronidation of the free catechol hydroxyl group affords prodrugs wherein the catechol 7-hydroxyl group is benzylated. Subsequent saponification affords 7-benzylated compounds with a free glucuronide attached to the 6-position of the catechol (as exemplified by the synthesis of (2S,3S,4S,5R,6S)-6-(((4aR,10aR)-7-(benzyloxy)-1-propyl-1,2,3,4,4a,5,10,10a-octahydrobenzo[g]quinolin-6-yl)oxy)-3,4,5-trihydroxytetrahydro-2H-pyran-2-carboxylic acid). Hydrogenolysis instead of saponification selectively deprotects the catechol 7-hydroxyl group, and if R=benzyl then the carboxyl group of the glucuronide will also be deprotected as exemplified herein for (2S,3R,4S,5S,6S)-2-(((4aR,10aR)-7-hydroxy-1-propyl-1,2,3,4,4a,5,10,10a-octahydrobenzo[g]quinolin-6-yl)oxy)-6-(methoxycarbonyl)tetrahydro-2H-pyran-3,4,5-triyl triacetate. If R' is the only benzyl group after the glucuronidation step then it can be cleaved selectively and subsequent esterification will introduce an acyl group on the catechol 7-hydroxyl group. With the exception of the selective debenzylation step just mentioned, similar chemistry can be applied to (4aR,10aR)-7-methoxy-1-propyl-1,2,3,4,4a,5,10,10a-octahydrobenzo[g]quinolin-6-ol.

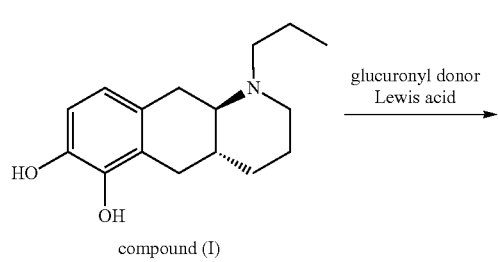

compound (I)

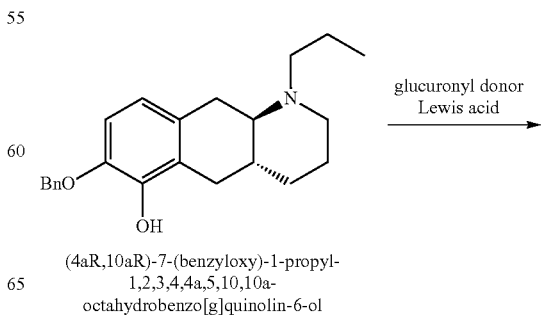

(4aR,10aR)-7-(benzyloxy)-1-propyl-1,2,3,4,4a,5,10,10a-octahydrobenzo[g]quinolin-6-ol

63
-continued
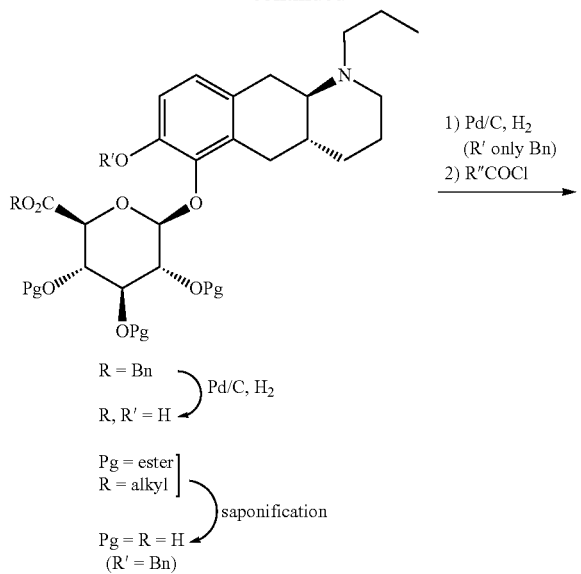
64
-continued
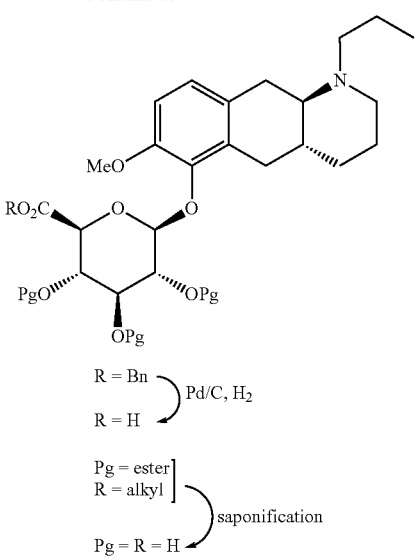
Applying the chemistry discussed above to the regioisomeric O-benzyl/methyl substrates gives the corresponding products as shown below.
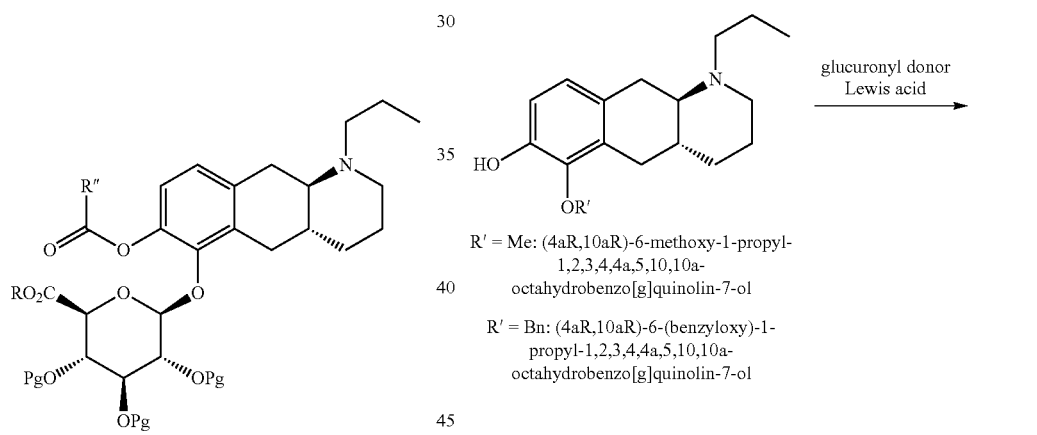
R' = Me: (4aR,10aR)-6-methoxy-1-propyl-1,2,3,4,4a,5,10,10a-octahydrobenzo[g]quinolin-7-ol
R' = Bn: (4aR,10aR)-6-(benzyloxy)-1-propyl-1,2,3,4,4a,5,10,10a-octahydrobenzo[g]quinolin-7-ol
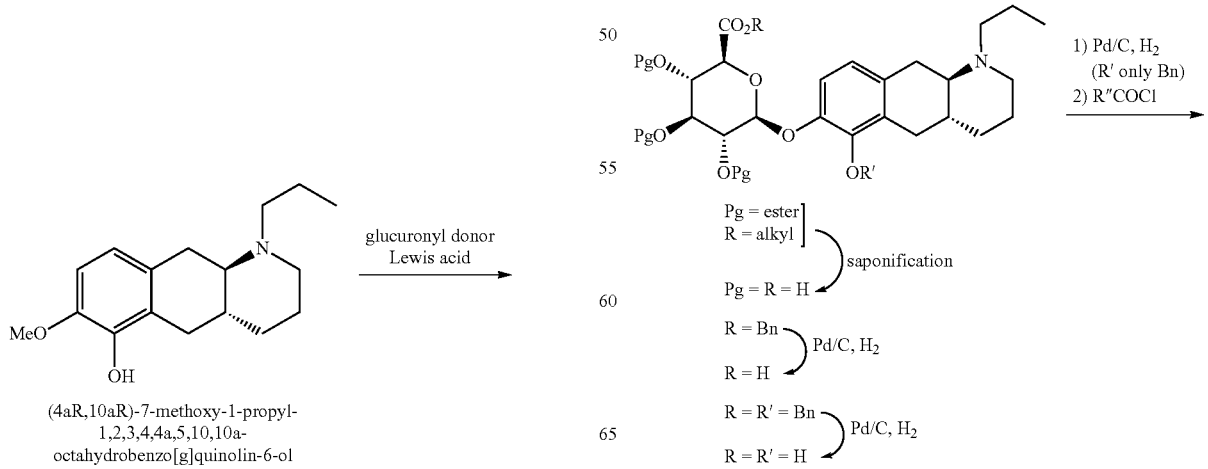
(4aR,10aR)-7-methoxy-1-propyl-1,2,3,4,4a,5,10,10a-octahydrobenzo[g]quinolin-6-ol

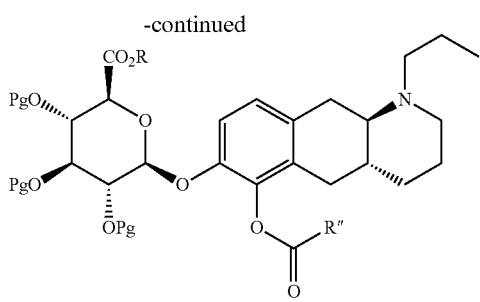

Treatment of glucuronides with a strong base like DBU can lead to formation of the corresponding α,β-unsaturated compounds as exemplified by the synthesis of (2R,3R,4S)-2-W4aR,10aR)-7-hydroxy-1-propyl-1,2,3,4,4a,5,10,10a-octahydrobenzo[g]quinolin-6-yl)oxy)-6-(methoxycarbonyl)-3,4-dihydro-2H-pyran-3,4-diyldiacetate.

Mono-glucuronidation of compound (I) followed by esterification of the catechol 6-hydroxyl group affords up to three different ester prodrug groups (ie., R, Pg, and R'). The synthesis of (2S,3R,4S,5S,6S)-2-(((4aR,10aR)-6-acetoxy-1-propyl-1,2,3,4,4a,5,10,10a-octahydrobenzo[g]quinolin-7-yl)oxy)-6-(methoxycarbonyl)tetrahydro-2H-pyran-3,4,5-triyl triacetate is an example of this chemistry. As before, hydrogenolysis may be applied to selectively cleave glucuronic acid benzyl esters.

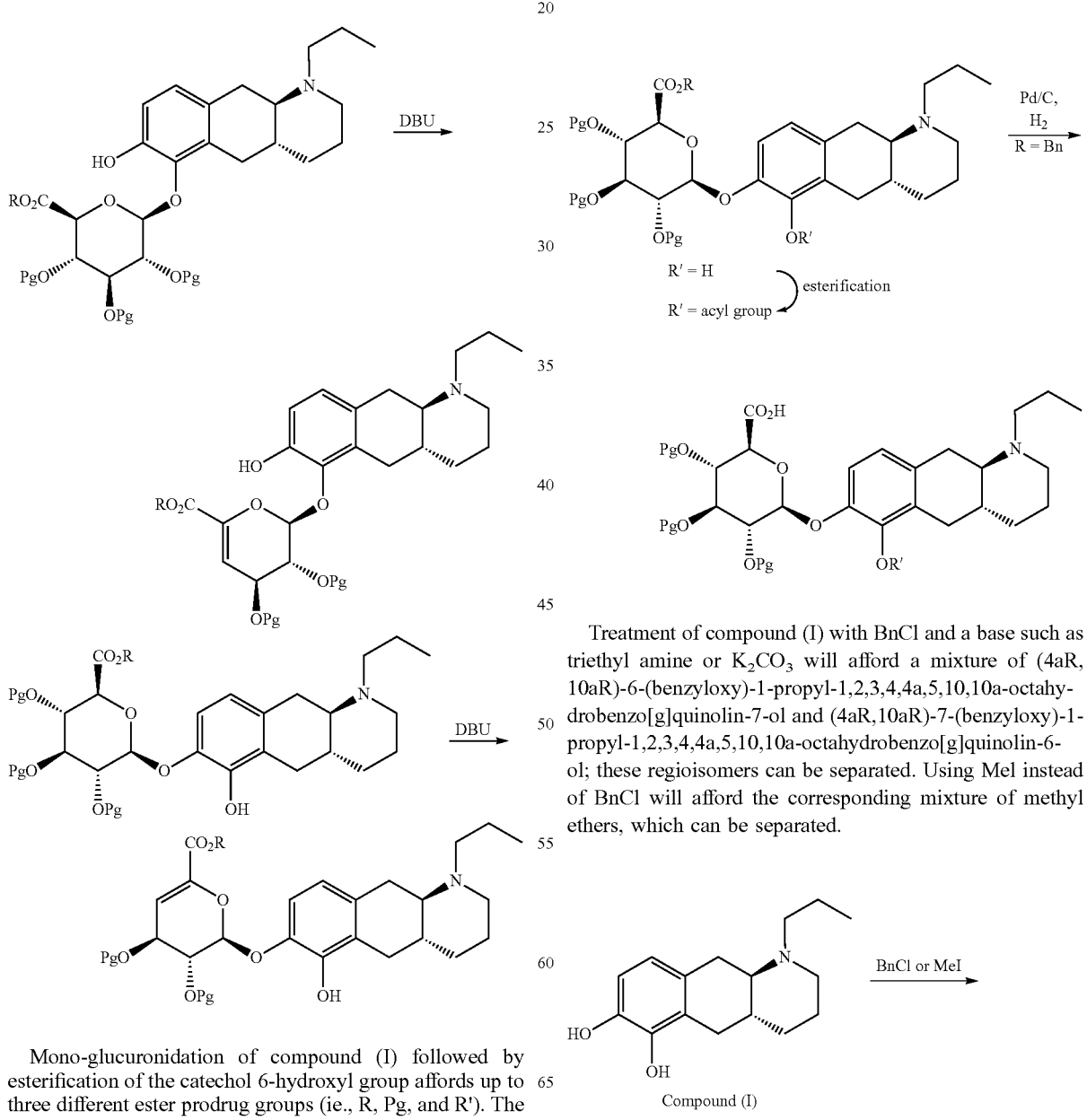

Treatment of compound (I) with BnCl and a base such as triethyl amine or K₂CO₃ will afford a mixture of (4aR,10aR)-6-(benzyloxy)-1-propyl-1,2,3,4,4a,5,10,10a-octahydrobenzo[g]quinolin-7-ol and (4aR,10aR)-7-(benzyloxy)-1-propyl-1,2,3,4,4a,5,10,10a-octahydrobenzo[g]quinolin-6-ol; these regioisomers can be separated. Using MeI instead of BnCl will afford the corresponding mixture of methyl ethers, which can be separated.

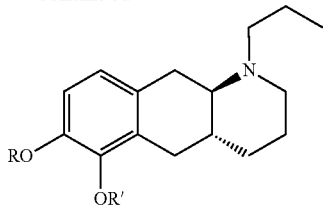

R = H, R' = Bn: (4aR,10aR)-6-(benzyloxy)-1-propyl-1,2,3,4,4a,5,10,10a-octahydrobenzo[g]quinolin-7-ol R = Bn, R' = H: (4aR,10aR)-7-(benzyloxy)-1-propyl-1,2,3,4,4a,5,10,10a-octahydrobenzo[g]quinolin-6-ol R = H, R' = Me: (4aR,10aR)-6-methoxy-1-propyl-1,2,3,4,4a,5,10,10a-octahydrobenzo[g]quinolin-7-ol R = Me, R' = H: (4aR,10aR)-7-methoxy-1-propyl-1,2,3,4,4a,5,10,10a-octahydrobenzo[g]quinolin-6-ol Selective routes to (4aR,10aR)-7-(benzyloxy)-1-propyl-1,2,3,4,4a,5,10,10a-octahydrobenzo[g]quinolin-6-ol and (4aR,10aR)-7-methoxy-1-propyl-1,2,3,4,4a,5,10,10a-octahydrobenzo[g]quinolin-6-ol are provided herein.
Intermediates for Preparation of (Id-ia), (Id-ib) and (Id-iab)

Intermediates: (4aR,10aR)-1-propyl-7-((triisopropylsilyl)oxy)-1,2,3,4,4a,5,10,10a-octahydrobenzo[g]quinolin-6-ol, and (4aR,10aR)-1-propyl-6-((triisopropylsilyl)oxy)-1,2,3,4,4a,5,10,10a-octahydrobenzo[g]quinolin-7-ol

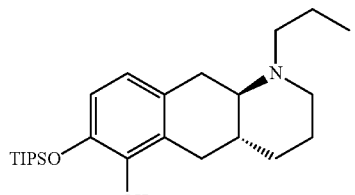

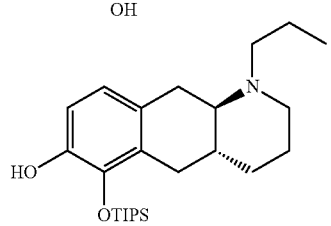

(4aR,10aR)-1-propyl-1,2,3,4,4a,5,10,10a-octahydrobenzo[g]quinoline-6,7-diol, hydrochloride (2.21 g, 7.4 mmol) was suspended in dichloromethane (80 ml) under nitrogen atmosphere at room temperature, N,N-diisopropylethylamine (4.44 g, 6.0 ml, 34.4 mmol) was added followed by triisopropylsilyl chloride (2.73 g, 3.0 ml, 14.2 mmol) and the mixture was stirred at room temperature for 92 hours. 10 mL MeOH was added, and the crude mixture was evaporated, co-evaporated twice with dichloromethane/heptane, re-dissolved in dichloromethane, and evaporated directly on filter aid and purified by column chromatography (eluent: n-heptane/ethyl acetate/triethylamine, 100:0:0-35:60:5) affording 3.14 g as a mixture of (4aR,10aR)-1-propyl-7-((triisopropylsilyl)oxy)-1,2,3,4,4a,5,10,10a-octahydrobenzo[g]quinolin-6-ol and (4aR,10aR)-1-propyl-6-((triisopropylsilyl)oxy)-1,2,3,4,4a,5,10,10a-octahydrobenzo[g]quinolin-7-ol.

NMR (CDCl3) showed >30:1 mixture of silylated isomers

Intermediates: tert-butyl ((4aR,10aR)-1-propyl-7-((triisopropylsilyl)oxy)-1,2,3,4,4a,5,10,10a-octahydrobenzo[g]quinolin-6-yl) carbonate and tert-butyl ((4aR,10aR)-1-propyl-6-((triisopropylsilyl)oxy)-1,2,3,4,4a,5,10,10a-octahydrobenzo[g]quinolin-7-yl) carbonate

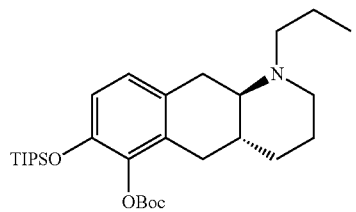

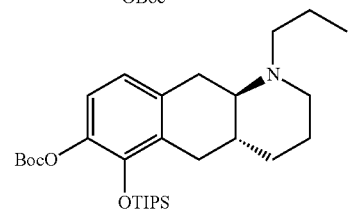

The mixture from the previous step (4aR,10aR)-1-propyl-7-((triisopropylsilyl)oxy)-1,2,3,4,4a,5,10,10a-octahydrobenzo[g]quinolin-6-ol and (4aR,10aR)-1-propyl-6-((triisopropylsilyl)oxy)-1,2,3,4,4a,5,10,10a-octahydrobenzo[g]quinolin-7-ol (2.94 g, 7.0 mmol) was dissolved in dichloromethane (30 ml) under a nitrogen atmosphere and cooled to 0° C. Pyridine (6.00 ml) followed by di-tert-butyl dicarbonate (6.30 g) were added and the reaction mixture was allowed to warm to room temperature over 3-4 hours and then stirred at room temperature overnight. 10 mL MeOH was added and the reaction mixture was evaporated, coevaporated with dichloromethane/n-heptane twice, dissolved in dichloromethane, and evaporated on filter aid.

Purification by column chromatography (eluent: n-heptane/ethyl acetate/triethylamine, 100:0:0-75:20:5) gave a mixture of tert-butyl ((4aR,10aR)-1-propyl-7-((triisopropylsilyl)oxy)-1,2,3,4,4a,5,10,10a-octahydrobenzo[g]quinolin-6-yl) carbonate and tert-butyl ((4aR,10aR)-1-propyl-6-((triisopropylsilyl)oxy)-1,2,3,4,4a,5,10,10a-octahydrobenzo[g]quinolin-7-yl) carbonate (3.6 g).

NMR (CDCl3) after drying showed a mixture of regioisomers.

Intermediates: (4aR,10aR)-6-((tert-butoxycarbonyl)oxy)-1-propyl-1,2,3,4,4a,5,10,10a-octahydrobenzo[g]quinolin-7-yl acetate and (4aR,10aR)-7-((tert-butoxycarbonyl)oxy)-1-propyl-1,2,3,4,4a,5,10,10a-octahydrobenzo[g]quinolin-6-yl acetate.

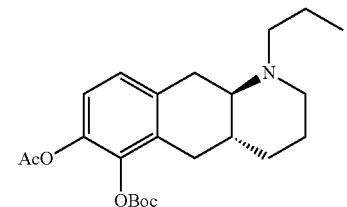

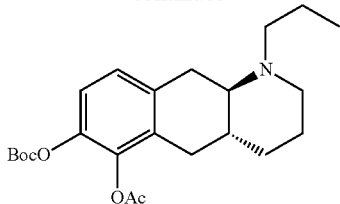

tert-Butyl ((4aR,10aR)-1-propyl-7-((triisopropylsilyl)oxy)-1,2,3,4,4a,5,10,10a-octahydrobenzo[g]quinolin-6-yl) carbonate (3.60 g, 7.0 mmol) (mixture from the previous step) was dissolved in THF (150 ml) under nitrogen atmosphere at 0° C., triethylamine trihydrofluoride (2.97 g, 3.00 ml, 18.4 mmol) was added and the mixture was stirred at 0° C. After 3 hours at 0° C., pyridine (10.0 ml, 124 mmol) and acetic anhydride (4.33 g, 4.00 ml, 42.4 mmol) were added directly to the reaction mixture at 0° C., and the reaction mixture was allowed to warm to room temperature. After 16 hours, 20 mL MeOH was added, and the reaction mixture was evaporated, redissolved in dichloromethane/heptane, and evaporated on filter aid followed by purification by dry column vacuum chromatography affording (4aR,10aR)-6-((tert-butoxycarbonyl)oxy)-1-propyl-1,2,3,4,4a,5,10,10a-octahydrobenzo[g]quinolin-7-yl acetate and (4aR,10aR)-7-((tert-butoxycarbonyl)oxy)-1-propyl-1,2,3,4,4a,5,10,10a-octahydrobenzo[g]quinolin-6-yl acetate.

LCMS (method 550) retention time=0.56 minutes, [M+H]+=404 m/z.

Intermediates I1: (2S,3R,4S,5S,6S)-2-(((4aR,10aR)-7-acetoxy-1-propyl-1,2,3,4,4a,5,10,10a-octahydrobenzo[g]quinolin-6-yl)oxy)-6-(methoxycarbonyl)tetrahydro-2H-pyran-3,4,5-triyl triacetate; and A3: (2S,3R,4S,5S,6S)-2-(((4aR,10aR)-6-acetoxy-1-propyl-1,2,3,4,4a,5,10,10a-octahydrobenzo[g]quinolin-7-yl)oxy)-6-(methoxycarbonyl)tetrahydro-2H-pyran-3,4,5-triyl triacetate

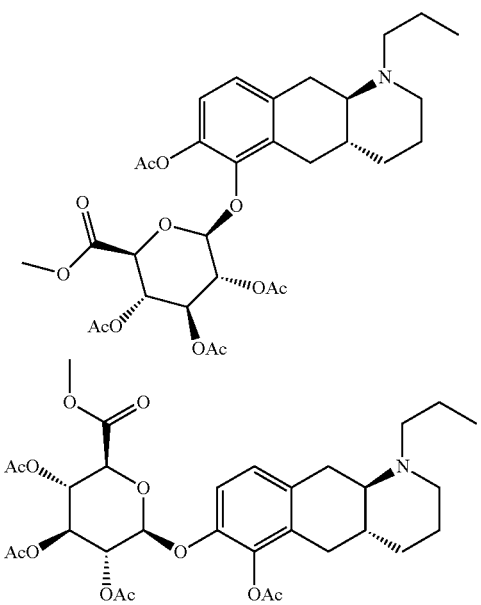

The mixture of (4aR,10aR)-6-((tert-butoxycarbonyl)oxy)-1-propyl-1,2,3,4,4a,5,10,10a-octahydrobenzo[g]quinolin-7-yl acetate and (4aR,10aR)-7-((tert-butoxycarbonyl)oxy)-1-propyl-1,2,3,4,4a,5,10,10a-octahydrobenzo[g]quinolin-6-yl acetate (2.49 g, 6.2 mmol) was dissolved in dichloromethane (60 ml) under nitrogen atmosphere at room temperature, (2S,3R,4S,5S,6S)-6-(Methoxycarbonyl)tetrahydro-2H-pyran-2,3,4,5-tetrayl tetraacetate (7.53 g, 20.0 mmol) was added followed by the addition of boron trifluoride diethyl etherate (6.72 g, 6.0 ml, 47.3 mmol) and the mixture was stirred at room temperature for 5 days. The mixture was diluted with dichloromethane and MeOH and evaporated on filter aid. Purification by dry column vacuum chromatography to give a mixture of (2S,3R,4S,5S,6S)-2-(((4aR,10aR)-7-acetoxy-1-propyl-1,2,3,4,4a,5,10,10a-octahydrobenzo[g]quinolin-6-yl)oxy)-6-(methoxycarbonyl)tetrahydro-2H-pyran-3,4,5-triyl triacetate and (2S,3R,4S,5S,6S)-2-(((4aR,10aR)-6-acetoxy-1-propyl-1,2,3,4,4a,5,10,10a-octahydrobenzo[g]quinolin-7-yl)oxy)-6-(methoxycarbonyl)tetrahydro-2H-pyran-3,4,5-triyl triacetate (4.37 g).

LC-MS (method 555) rt=1.94 minutes, [M+H]+=620 m/z.

Intermediate I2: methyl (2S,3S,4S,5R,6S)-6-[[(4aR,10aR)-1-propyl-6-[(2S,3R,4S,5S,6S)-3,4,5-triacetoxy-6-methoxycarbonyl-tetrahydropyran-2-yl]oxy-3,4,4a,5,10,10a-hexahydro-2H-benzo[g]quinolin-7-yl]oxy]-3,4,5-triacetoxy-tetrahydropyran-2-carboxylate

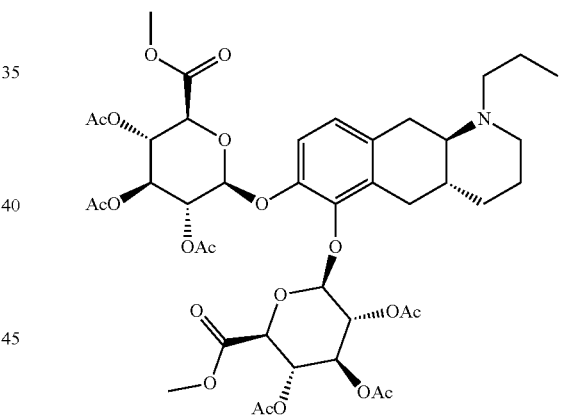

(2S,3S,4S,5R,6R)-2-(methoxycarbonyl)-6-(2,2,2-trichloro-1-iminoethoxy)tetrahydro-2H-pyran-3,4,5-triyl triacetate (1.29 g, 2.7 mmol) and (4aR,10aR)-1-propyl-1,2,3,4,4a,5,10,10a-octahydrobenzo[g]quinoline-6,7-diol, hydrochloride (0.4 g, 1.3 mmol) were dissolved in dichloromethane (4.00 ml), then boron trifluoride diethyl etherate (0.38 g, 0.34 ml, 2.7 mmol) was added under a nitrogen atmosphere and the mixture stirred for 3 days under nitrogen in a 8 mL vial. Additional (2S,3S,4S,5R,6R)-2-(methoxycarbonyl)-6-(2,2,2-trichloro-1-iminoethoxy)tetrahydro-2H-pyran-3,4,5-triyl triacetate (1.29 g, 2.7 mmol) and boron trifluoride diethyl etherate (0.38 g, 0.340 ml, 2.7 mmol) were added and the mixture was stirred for 4 hours, then the mixture was poured into saturated aqueous NaHCO3 (30 mL), then extracted with dichloromethane (2×20 mL) and the combined organic phases were dried (Na2SO4), filtered, and evaporated into dryness in vacuo. The crude foam was suspended in heptane/ethyl acetate (1:1) and stirred overnight. Subsequently, HCl in ether (0.67 ml, 1.3 mmol, 2 molar) was added and the mixture stirred for 1 hour and was evaporated to dryness in vacuo and MTBE (40 mL) was added and the mixture was heated to reflux and allowed to cool to room temperature, then the mixture was filtered and the solid was dried in the vacuum oven for 1 day at 40° C. affording methyl (2S,3S,4S,5R,6S)-6-[[(4aR,10aR)-1-propyl-6-[(2S,3R,4S,5S,6S)-3,4,5-triacetoxy-6-methoxycarbonyl-tetrahydropyran-2-yl]oxy]-3,4,4a,5,10,10a-hexahydro-2H-benzo[g]quinolin-7-yl]oxy]-3,4,5-triacetoxy-tetrahydropyran-2-carboxylate, Hydrochloride (1.09 g).

LC-MS (method 550) retention time=0.63 minutes, [M+H]+=895.7 m/z.

(Id-ib): (2S,3S,4S,5R,6S)-3,4,5-tri hydroxy-6-(((4aR,10aR)-6-hydroxy-1-propyl-1,2,3,4,4a,5,10,10a-octahydrobenzo[g]quinolin-7-yl)oxy)tetrahydro-2H-pyran-2-carboxylic acid, and (Id-ia): (2S,3S,4S,5R,6S)-3,4,5-trihydroxy-6-(((4aR,10aR)-7-hydroxy-1-propyl-1,2,3,4,4a,5,10,10a-octahydrobenzo[g]quinolin-6-yl)oxy)tetrahydro-2H-pyran-2-carboxylic acid

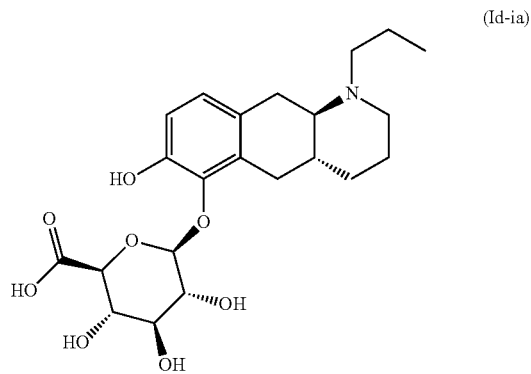

(Id-ia)

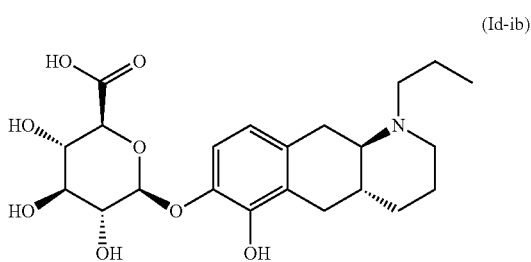

(Id-ib)

A mixture of (2S,3R,4S,5S,6S)-2-(((4aR,10aR)-7-acetoxy-1-propyl-1,2,3,4,4a,5,10,10a-octahydrobenzo[g]quinolin-6-yl)oxy)-6-(methoxycarbonyl)tetrahydro-2H-pyran-3,4,5-triyl triacetate and (2S,3R,4S,5S,6S)-2-(((4aR,10aR)-6-acetoxy-1-propyl-1,2,3,4,4a,5,10,10a-octahydrobenzo[g]quinolin-7-yl)oxy)-6-(methoxycarbonyl)tetrahydro-2H-pyran-3,4,5-triyl triacetate (3.82 g, 6.2 mmol) was dissolved in MeOH (100 ml) and water (20 ml), cooled to 0° C., potassium cyanide (7.295 g, 112 mmol) was added and the suspension was allowed to slowly warm to room temperature for 17.5 hours. The crude mixture was evaporated on filter aid and dried. The crude mixture was purified by silica gel column chromatography (eluent: ethyl acetate/MeOH/water 100:0:0-0:50:50), affording a 5-6:1 ratio of (Id-ib) and (Id-ia). The mixture was separated by preparative LCMS.

Collected Peak 1 fractions containing (Id-ib) were pooled, evaporated, and combined with another batch of 186 mg (Id-ib)-TFA, which had been prepared in a similar manner, using MeOH, evaporated, and dried to give (Id-ib). (Id-ib) was re-suspended in 10 mL EtOH, and 100 mL MTBE was added, and the resulting suspension was stirred at room temperature for 8 hours, the suspension was filtered and the precipitate washed with 2×10 mL MTBE and dried in a vacuum oven overnight to afford (Id-ib) 1.601 g, corresponding to (2S,3S,4S,5R,6S)-3,4,5-trihydroxy-6-(((4aR,10aR)-6-hydroxy-1-propyl-1,2,3,4,4a,5,10,10a-octahydrobenzo[g]quinolin-7-yl)oxy)tetrahydro-2H-pyran-2-carboxylic acid.

Collected Peak 2 fractions containing (Id-ia) were pooled, evaporated, transferred to smaller flask with MeOH, evaporated, redissolved in ca. 12 mL MeOH, and repurified by preparative LCMS, and evaporated to give (Id-ia). Appropriate fractions were pooled, evaporated, transferred with MeOH to a smaller flask, and evaporated and combined with another batch of 40.7 mg (Id-ia), which had been prepared in a similar manner. The combined batch was dissolved in 2.5 mL EtOH, 25 mL MTBE was added, and the suspension was stirred at room temperature. After 8 hours, the suspension was filtered and the precipitate washed with 2×2.5 mL MTBE and dried in the vacuum oven overnight to give 362.2 mg of (Id-ia). (Id-ia) was suspended in ca. 10 mL EtOH, 50 mL MTBE was added, and the suspension was stirred at room temperature and filtered after 19 h and the precipitate was washed with 2×10 mL MTBE, and dried in the vacuum oven at 40° C. to give (2S,3S,4S,5R,6S)-3,4,5-trihydroxy-6-(((4aR,10aR)-7-hydroxy-1-propyl-1,2,3,4,4a,5,10,10a-octahydrobenzo[g]quinolin-6-yl)oxy)tetrahydro-2H-pyran-2-carboxylic acid (Id-ia) (0.279 g).

(Id-ib)

LCMS (method 551) retention time=0.37 minutes.

$^1$H NMR (600 MHz, Methanol-$d_4$) δ 7.02 (d, J=8.4 Hz, 1H), 6.65 (d, J=8.4 Hz, 1H), 4.73 (d, J=7.7 Hz, 1H), 3.89 (d, J=9.7 Hz, 1H), 3.68-3.58 (m, 2H), 3.54 (dd, J=9.3, 7.7 Hz, 1H), 3.49 (t, J=9.1 Hz, 1H), 3.47-3.36 (m, 2H), 3.30 (dt, J=11.2, 5.6 Hz, 1H), 3.21-3.11 (m, 3H), 2.85 (dd, J=15.4, 11.3 Hz, 1H), 2.35 (dd, J=17.6, 11.5 Hz, 1H), 2.12-2.02 (m, 2H), 2.02-1.84 (m, 3H), 1.81-1.71 (m, 1H), 1.49 (qd, J=13.0, 3.7 Hz, 1H), 1.09 (t, J=7.3 Hz, 3H).

(Id-ia)

LCMS (method 551) retention time=0.39 minutes.

1H NMR (600 MHz, Methanol-d4) δ 6.87 (d, J=8.3 Hz, 1H), 6.74 (d, J=8.4 Hz, 1H), 4.62 (d, J=7.9 Hz, 1H), 3.75 (dd, J=17.7, 4.9 Hz, 1H), 3.66-3.62 (m, 2H), 3.61-3.51 (m, 2H), 3.50-3.35 (m, 3H), 3.31-3.22 (m, 1H), 3.14 (qd, J=12.7, 4.0 Hz, 2H), 2.83 (dd, J=15.2, 11.3 Hz, 1H), 2.37 (dd, J=17.7, 11.7 Hz, 1H), 2.12 (d, J=13.4 Hz, 1H), 2.08-2.00 (m, 1H), 1.98-1.83 (m, 3H), 1.81-1.71 (m, 1H), 1.44 (qd, J=13.2, 3.9 Hz, 1H), 1.09 (t, J=7.3 Hz, 3H).

(Id-iab): (2S,2'S,3S,3'S,4S,4'S,5R,5'R,6S,6'S)-6,6'-(((4aR,10aR)-1-propyl-1,2,3,4,4a,5,10,10a-octahydrobenzo[g]quinoline-6,7-diyl)bis(oxy))bis(3,4,5-trihydroxytetrahydro-2H-pyran-2-carboxylic acid)

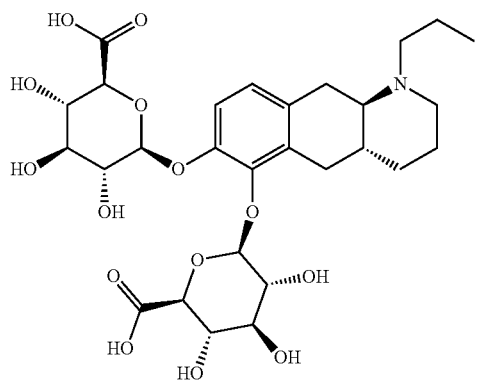

(Id-iab)

Synthesis A:

(1S,4a R,10aR)-1-Propyl-6,7-bis(((2S,3R,4S,5S,6S)-3,4,5-triacetoxy-6-(methoxycarbonyl)tetrahydro-2H-pyran-2-yl)oxy)-1,2,3,4,4a,5,10,10a-octahydrobenzo[g]quinoline (0.25 g, 0.27 mmol) was dissolved in water (1.21 g, 1.21 ml, 67.1 mmol) and MeOH (3.83 g, 4.84 ml, 120 mmol) and aqueous KOH (0.393 g, 0.270 ml, 3.2 mmol, 46%) were added and stirred overnight at room temperature in a sealed vial. A precipitate had formed overnight, which was isolated via filtration. The compound was washed with MeOH (1.5 mL) affording (2S,2'S,3S,3'S,4S,4'S,5R,5'R,6S,6'S)-6,6'-(((4aR,10aR)-1-propyl- 1,2,3,4,4a,5,10,10a-octahydrobenzo[g]quinoline-6,7-diyl)bis(oxy))bis(3,4,5-trihydroxytetrahydro-2H-pyran-2-carboxylic acid), 2Potassium (0.096 g)

LC-MS (method 551) retention time=0.31 minutes, [M+H]+=614.2 m/z.

Synthesis B:

(1S,4a R,10aR)-1-Propyl-6,7-bis(((2S,3R,4S,5S,6S)-3,4,5-triacetoxy-6-(methoxycarbonyl)tetrahydro-2H-pyran-2-yl)oxy)-1,2,3,4,4a,5,10,10a-octahydrobenzo[g]quinoline (0.26 g, 0.29 mmol) was dissolved in water (1.250 g, 1.25 ml, 69.4 mmol) and MeOH (3.96 g, 5 ml, 124 mmol) and KCN (0.34 g, 5.3 mmol) were added and stirred overnight at room temperature in a sealed vial. A precipitate had formed overnight, which was isolated via filtration. The compound was washed with MeOH (1.5 mL) affording (2S,2'S,3S,3'S,4S,4'S,5R,5'R,6S,6'S)-6,6'-(((4aR,10aR)-1-propyl-1,2,3,4,4a,5,10,10a-octahydrobenzo[g]quinoline-6,7-diyl)bis(oxy))bis(3,4,5-trihydroxytetrahydro-2H-pyran-2-carboxylic acid), 2Potassium (0.096 g)

LC-MS (method 551) retention time=0.34 minutes, [M+H]+=614.6 m/z.

1H NMR (600 MHz, DMSO-d6) δ 7.09 (d, J=8.5 Hz, 1H), 6.84 (d, J=8.5 Hz, 1H), 4.91-4.79 (m, 1H), 4.78-4.66 (m, 1H), 3.93 (bs, 22H (OH/water)), 3.42 (d, J=9.8 Hz, 1H), 3.37-3.21 (m, 7H), 3.19 (s, 1H), 3.11 (dd, J=16.2, 4.9 Hz, 1H), 2.90 (d, J=11.0 Hz, 1H), 2.67 (ddd, J=12.9, 10.7, 5.6 Hz, 1H), 2.49 (dd, J=15.9, 10.9 Hz, 1H), 2.39-2.27 (m, 1H), 2.15 (dt, J=17.5, 11.5 Hz, 2H), 2.05 (td, J=10.4, 4.9 Hz, 1H), 1.86 (d, J=11.7 Hz, 1H), 1.67-1.38 (m, 5H), 1.03 (qd, J=12.3, 5.1 Hz, 1H), 0.85 (t, J=7.3 Hz, 3H).

Intermediates of the Compounds of the Invention

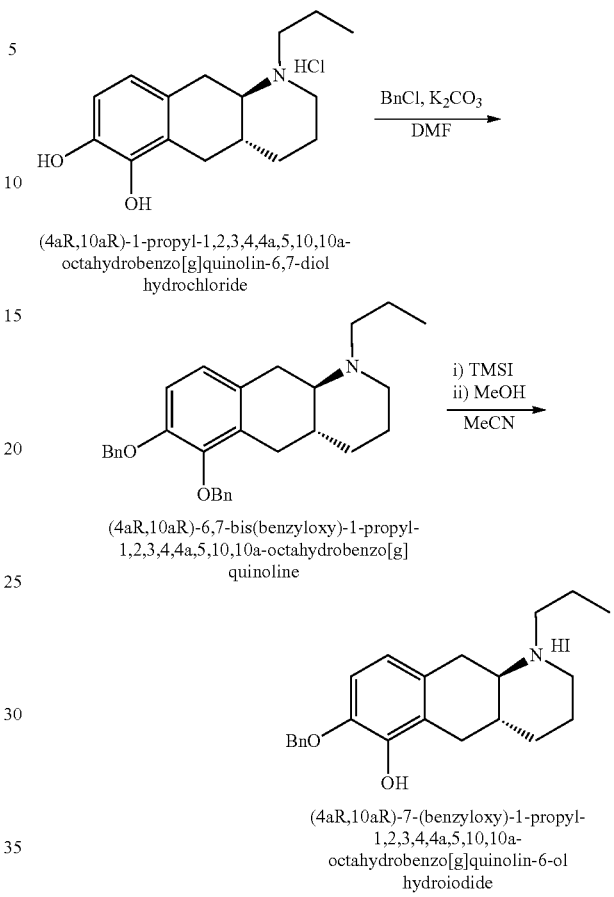

(4aR,10aR)-1-propyl-1,2,3,4,4a,5,10,10a-octahydrobenzo[g]quinolin-6,7-diol hydrochloride (4aR,10aR)-6,7-bis(benzyloxy)-1-propyl-1,2,3,4,4a,5,10,10a-octahydrobenzo[g]quinoline (4aR,10aR)-7-(benzyloxy)-1-propyl-1,2,3,4,4a,5,10,10a-octahydrobenzo[g]quinolin-6-ol hydroiodide A1: (4aR,10aR)-6,7-Bis(benzyloxy)-1-propyl-1,2,3,4,4a,5,10,10a-octahydrobenzo[g]quinoline (4aR,10aR)-1-Propyl-1,2,3,4,4a,5,10,10a-octahydrobenzo[g]quinoline-6,7-diol hydrochloride (10.75 g) and K₂CO₃ (17.5 g) were added to a flask, which was degassed under vacuum and purged with N₂, before DMF (107 mL) and benzyl chloride (8.55 mL) were added and the mixture was stirred at room temperature for 18 hours, then at 100° C. for 5 hours, and at room temperature for 19 hours. K₂CO₃ (7.48 g) and benzyl chloride (6.29 mL) were added and the mixture was stirred at 100° C. for 5 hours. After cooling to room temperature, the mixture was partitioned between water (500 mL) and heptane (250 mL). The aqueous phase was washed with heptane (3×100 mL) and the combined organic phases were washed with brine (100 mL), dried over Na₂SO₄, filtered, and concentrated to afford the title compound (14.6 g).

A2: (4aR,10aR)-7-(Benzyloxy)-1-propyl-1,2,3,4,4a,5,10,10a-octahydrobenzo[g]quinolin-6-ol hydroiodide (4aR,10aR)-6,7-Bis(benzyloxy)-1-propyl-1,2,3,4,4a,5,10,10a-octahydrobenzo[g]quinoline) (11.9 g) was added to a flask, which was evaporated and purged with N₂, before MeCN (180 mL) was added. The mixture was stirred until homogeneous, before trimethylsilyl iodide (10.0 mL) was added and the mixture was stirred under N₂ at room temperature for 2 hours. MeOH (5.5 mL) was added and the mixture was stirred for 1 hour. Isopropyl acetate/heptane (10/150 mL) was added and the mixture was cooled to 0° C. and stirred for 1 hour. The compound was collected, washed with isopropyl acetate/heptane (3/47 mL), and dried to afford the title compound (7.6 g).

$^1$H NMR (600 MHz, CDCl$_3$) δ 10.42 (bs, 1H), 7.43-7.33 (m, 4H), 7.26 (d, J=1.0 Hz, 1H), 6.78 (d, J=8.3 Hz, 1H), 6.58 (d, J=8.3 Hz, 1H), 5.72 (s, 1H), 5.08 (s, 2H), 3.71 (dd, J=11.70, 15.0 Hz, 1H), 3.58 (d, J=11.70, 1H), 3.25-3.11 (m, 4H), 2.94-2.86 (m, 1H), 2.77-2.57 (m, 2H), 2.26 (dd, J=11.70 Hz, 17.0 Hz 1H), 2.19 (d, J=13.80, 1H), 2.01-1.92 (m, 2H), 1.80-1.69 (m, 1H), 1.56-1.53 (m, 1H), 1.39 (qd, J=3.60 Hz, 13.30 Hz, 1H), 1.06 (t, J=7.2 Hz, 3H).

LCMS (method 550), retention time=0.55 minutes, [M+H]+=352.5 m/z.

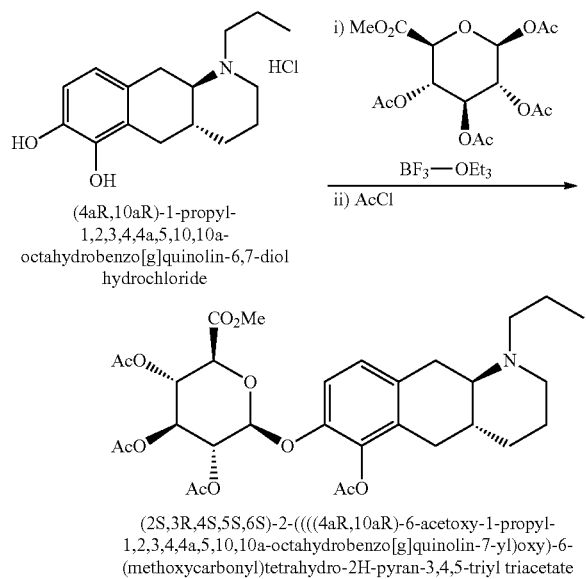

A3: (2S,3R,4S,5S,6S)-2-(((4aR,10aR)-6-Acetoxy-1-propyl-1,2,3,4,4a,5,10,10a-octahydrobenzo[g]quinolin-7-yl)oxy)-6-(methoxycarbonyl)tetrahydro-2H-pyran-3,4,5-triyl triacetate (2S,3R,4S,5S,6S)-6-(Methoxycarbonyl)tetrahydro-2H-pyran-2,3,4,5-tetrayl tetraacetate (9.51 g) and (4aR,10aR)-1-propyl-1,2,3,4,4a,5,10,10a-octahydrobenzo[g]quinoline-6,7-diol hydrochloride (1.10 g) were dissolved in DCM (17 mL) at 0° C. BF$_3$-OEt$_2$ (5.3 mL) was added under N$_2$ at room temperature. The mixture stirred for 3 days before BF$_3$-OEt$_2$ (0.94 mL) was added and the mixture was stirred for 3 days. AcCl (0.59 mL) was added and the mixture was stirred for 2 hours before it was quenched by drop-wise addition into saturated aqueous NaHCO$_3$ (20 mL). The mixture was extracted with DCM (2×15 mL), and the combined organic layers were dried over Na$_2$SO$_4$, filtered, and concentrated. The residue was purified by chromatography on silica gel (n-heptane:EtOAc:MeOH 100:0:0-0:100:0-0:0:100) to afford the compound (3.06 g). This material was dissolved in MeOH (4.3 mL), before water (4.3 mL) was added dropwise at 40-50° C. to precipitate a solid. The mixture was allowed to cool to room temperature, and the compound was collected and dried to afford the title compound (0.62 g).

$^1$H NMR (600 MHz, CDCl$_3$) δ 6.95 (d, J=8.5 Hz, 1H), 6.81 (d, J=8.5 Hz, 1H), 5.34-5.27 (m, 2H), 5.09 (d, J=6.0 Hz, 1H), 4.20-4.15 (m, 1H), 3.74 (s, 3H), 3.14 (dd, J=4.80 Hz, 16.30 Hz, 1H), 3.01-2.97 (m, 1H), 2.79-2.68 (m, 2H), 2.64-2.56 (m, 1H), 2.50-2.43 (m, 1H), 2.30-2.22 (m, 3H), 2.19-2.02 (m, 9H), 1.87 (d, J=10.50 Hz, 1H), 1.72-1.63 (m, 2H), 1.63-1.45 (m, 7H), 1.12-0.99 (m, 1H), 0.89 (t, J=12.7 Hz, 3H).

LCMS (method 555), retention time=1.84 minutes, [M+H]+=621.4 m/z.

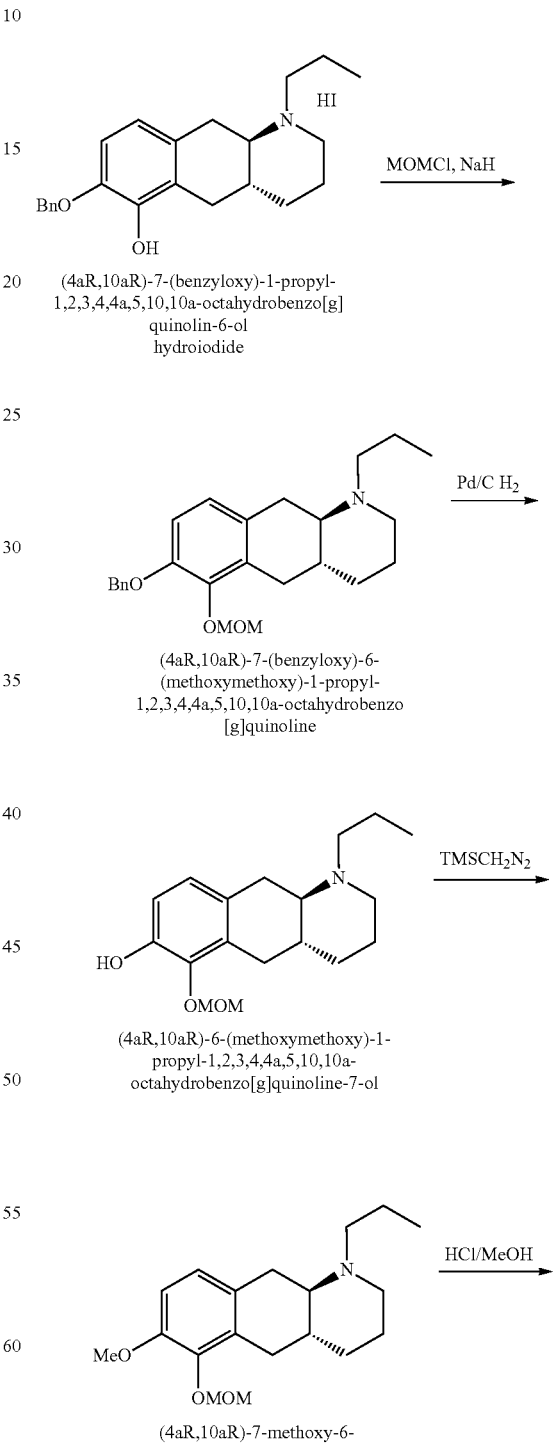

-continued

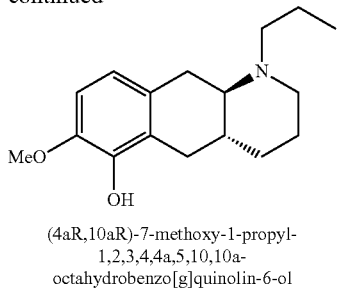

(4aR,10aR)-7-methoxy-1-propyl-
1,2,3,4,4a,5,10,10a-
octahydrobenzo[g]quinolin-6-ol

A4: (4aR,10aR)-7-(Benzyloxy)-6-(methoxymethoxy)-1-propyl-1,2,3,4,4a,5,10,10a-octahydrobenzo[g]quinoline To a mixture of (4aR,10aR)-7-(benzyloxy)-1-propyl-1,2,3,4,4a,5,10,10a-octahydrobenzo[g]quinolin-6-ol hydroiodide (20 g) in DMF (400 mL) was added NaH (4.17 g, 60% dispersion) slowly at 0° C. under $N_2$. The mixture was stirred at 0° C. for 30 min before MOMCl (3.5 mL) was added drop-wise at 0° C. The mixture was stirred at room temperature for 1 hour before it was poured into water (400 mL) and stirred for 20 minutes and then extracted with EtOAc (300 mL×3). The combined organic layers were washed with brine (500 mL), dried over $Na_2SO_4$, filtered, and concentrated to afford the title compound (20 g).

A5: (4aR,10aR)-6-(Methoxymethoxy)-1-propyl-1,2,3,4,4a,5,10,10a-octahydrobenzo[g]quinolin-7-ol To a solution of (4aR,10aR)-7-(benzyloxy)-6-(methoxymethoxy)-1-propyl-1,2,3,4,4a,5,10,10a-octahydrobenzo[g]quinoline (20 g) in MeOH (140 mL) was added Pd/C (10%, 30 g) under $N_2$. The suspension was degassed under vacuum and purged with H2. The mixture was stirred under $H_2$ (50 psi) at room temperature for 12 hours, before the catalyst was filtered off. The filtrate was concentrated to afford the title compound (15.4 g).

A6: (4aR,10aR)-7-methoxy-6-(methoxymethoxy)-1-propyl-1,2,3,4,4a,5,10,10a-octahydrobenzo[g]quinoline To a solution of (4aR,10aR)-6-(methoxymethoxy)-1-propyl-1,2,3,4,4a,5,10,10a-octahydrobenzo[g]quinolin-7-ol (15 g) in MeOH (150 mL) was added drop-wise (trimethylsilyl)diazomethane (2M in ether, 246 mL) at room temperature over 0.5 hours. The mixture was concentrated to afford the title compound (15 g).

A7: (4aR,10aR)-7-methoxy-1-propyl-1,2,3,4,4a,5,10,10a-octahydrobenzo[g]quinolin-6-ol A solution of (4aR,10aR)-7-methoxy-6-(methoxymethoxy)-1-propyl-1,2,3,4,4a,5,10,10a-octahydrobenzo[g]quinoline (15 g) in 4M HCl in MeOH (150 mL) was stirred at room temperature for 1 hour, before it was concentrated. The residue was dissolved in water (100 mL) and the aqueous layer was basified with $NaHCO_3$ to pH 7-8. The aqueous layer was extracted with EtOAc (100 mL and 50 mL). The combined organic layers were washed with brine (100 mL), dried over $Na_2SO_4$, filtered, and concentrated to afford the title compound (7 g).

$^1$H NMR (400 MHz, CDCl$_3$) δ 6.70 (d, J=8.4 Hz, 1H), 6.62 (d, J=8.0 Hz, 1H), 5.71 (br s, 1H), 3.86 (s, 3H), 3.07-3.18 (m, 2H), 3.01 (dd, J=5.2, 17.6 Hz, 1H), 2.72-2.89 (m, 2H), 2.58-2.68 (m, 1H), 2.29-2.44 (m, 2H), 2.24 (dd, J=12.0, 17.6 Hz, 1H), 1.97 (d, J=13.2 Hz, 1H), 1.70-1.92 (m, 3H), 1.54-1.63 (m, 2H), 1.10-1.23 (m, 1H), 0.93 (t, J=7.2 Hz, 3H).

LCMS (method 25), retention time=0.95 minutes, [M+H]$^+$=276.1 m/z.

Exemplified Compounds of the Invention

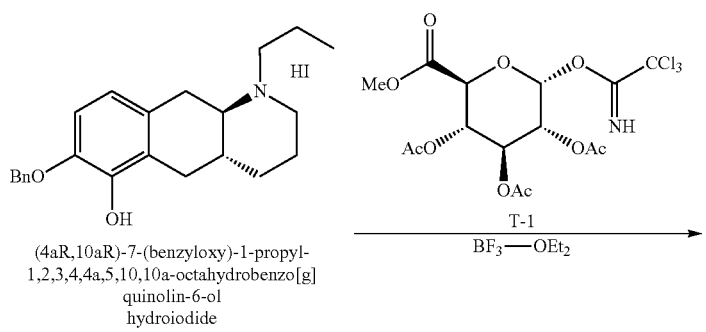

(4aR,10aR)-7-(benzyloxy)-1-propyl-
1,2,3,4,4a,5,10,10a-octahydrobenzo[g]
quinolin-6-ol
hydroiodide T-1
$BF_3$—$OEt_2$

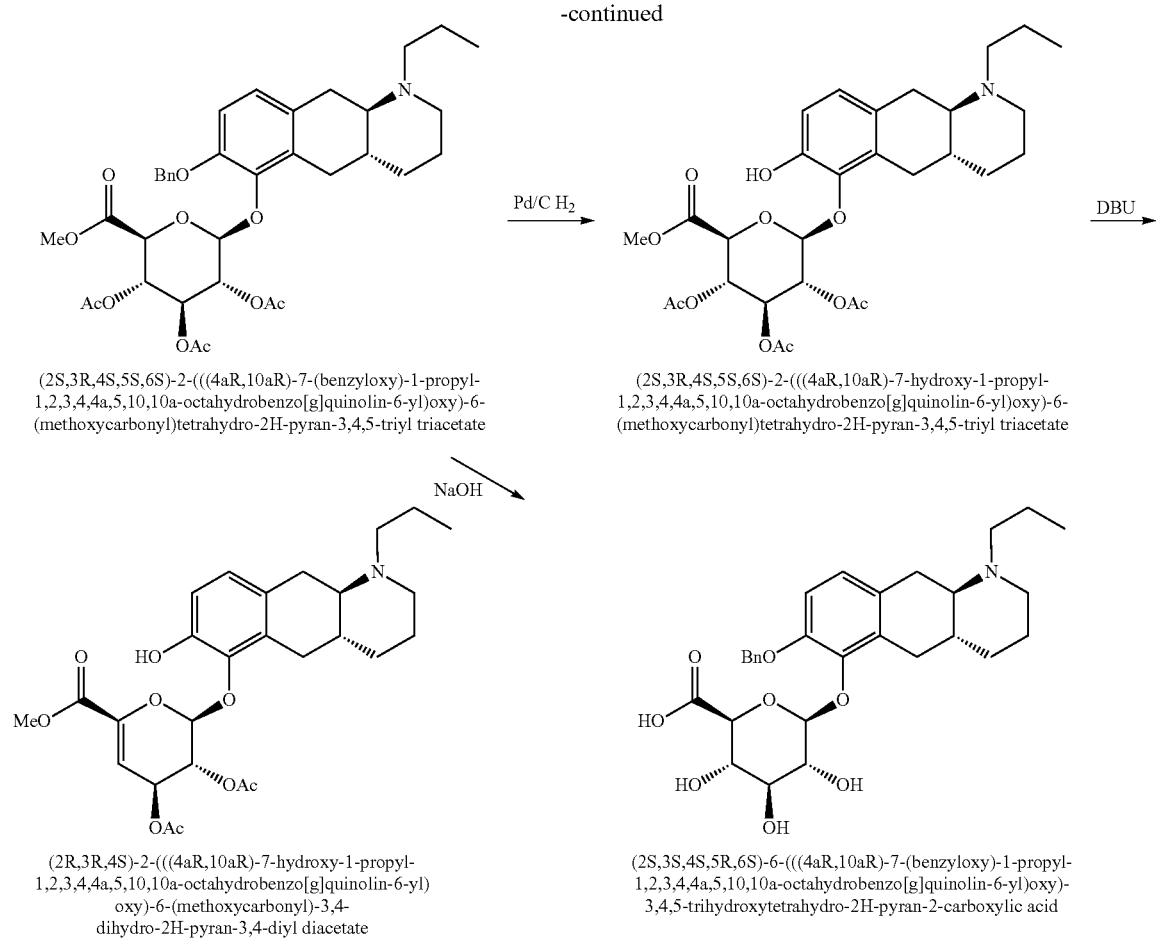

(2S,3R,4S,5S,6S)-2-(((4aR,10aR)-7-(benzyloxy)-1-propyl-1,2,3,4,4a,5,10,10a-octahydrobenzo[g]quinolin-6-yl)oxy)-6-(methoxycarbonyl)tetrahydro-2H-pyran-3,4,5-triyl triacetate (2S,3R,4S,5S,6S)-2-(((4aR,10aR)-7-hydroxy-1-propyl-1,2,3,4,4a,5,10,10a-octahydrobenzo[g]quinolin-6-yl)oxy)-6-(methoxycarbonyl)tetrahydro-2H-pyran-3,4,5-triyl triacetate (2R,3R,4S)-2-(((4aR,10aR)-7-hydroxy-1-propyl-1,2,3,4,4a,5,10,10a-octahydrobenzo[g]quinolin-6-yl)oxy)-6-(methoxycarbonyl)-3,4-dihydro-2H-pyran-3,4-diyl diacetate (2S,3S,4S,5R,6S)-6-(((4aR,10aR)-7-(benzyloxy)-1-propyl-1,2,3,4,4a,5,10,10a-octahydrobenzo[g]quinolin-6-yl)oxy)-3,4,5-trihydroxytetrahydro-2H-pyran-2-carboxylic acid Compound (1): (2S,3R,4S,5S,6S)-2-(((4aR,10aR)-7-(benzyloxy)-1-propyl-1,2,3,4,4a,5,10,10a-octahydrobenzo[g]quinolin-6-yl)oxy)-6-(methoxycarbonyl)tetrahydro-2H-pyran-3,4,5-triyl triacetate To a solution of (4aR,10aR)-7-(benzyloxy)-1-propyl-1,2,3,4,4a,5,10,10a-octahydrobenzo[g]quinolin-6-ol hydroiodide (4 g) and (2S,3S,4S,5R,6R)-2-(methoxycarbonyl)-6-(2,2,2-trichloro-1-iminoethoxy)tetrahydro-2H-pyran-3,4,5-triyl triacetate (T-1; prepared as described in Advances in Chemical Engineering and Science, 2012, 2, 379-383, 7.99 g) in DCM (400 mL) was added $BF_3$-$OEt_2$ (4.12 mL) dropwise at −10° C. The mixture was stirred at −10° C.-room temperature for 12 hours, before it was washed with brine (100 mL), dried over $Na_2SO_4$, filtered, and concentrated. The residue was purified by prep-HPLC using a Agela FL-H600G instrument (Phenomenex Luna C18 250×80 mm, 10 μm particles column operated at room temperature with 150 mL/min of a gradient of water+ 0.225% formic acid (A) and MeCN (B): 0-25 min 22% B to 52% B; 25.1-30 min 95% B; 30.1-35 min 22% B) to afford the title compound (1.8 g).

$^1$H NMR (400 MHz, $CDCl_3$) δ 7.32-7.46 (m, 5H), 6.85 (d, J=8.0 Hz, 1H), 6.80 (d, J=8.4 Hz, 1H), 5.01-5.38 (m, 7H), 3.87 (d, J=9.6 Hz, 1H), 3.69 (s, 3H), 3.51 (s, 2H), 3.13 (d, J=10.0 Hz, 2H), 2.29-2.13 (m, 1H), 2.06 (d, J=4.4 Hz, 1H), 2.04 (s, 3H), 2.03 (s, 3H), 1.87 (bs, 2H), 1.76 (s, 3H), 1.75-1.5 (bs, 5H), 1.13-1.31 (m, 2H), 0.98 (t, J=7.2 Hz, 3H).

QC-LCMS (method AB01), retention time=3.00 minutes, [M+H]$^+$=668.3 m/z.

Compound (2): (2S,3R,4S,5S,6S)-2-(((4aR,10aR)-7-hydroxy-1-propyl-1,2,3,4,4a,5,10,10a-octahydrobenzo[g]quinolin-6-yl)oxy)-6-(methoxycarbonyl)tetrahydro-2H-pyran-3,4,5-triyl triacetate To a solution of (2S,3R,4S,5S,6S)-2-(((4aR,10aR)-7-(benzyloxy)-1-propyl-1,2,3,4,4a,5,10,10a-octahydrobenzo[g]quinolin-6-yl)oxy)-6-(methoxycarbonyl)tetrahydro-2H-pyran-3,4,5-triyl triacetate (1 g) in THF (30 mL) and water (6 mL) was added Pd/C (0.4 g, 50% (w/w)) under $N_2$. The suspension was degassed under vacuum and purged with H2. The mixture was stirred under $H_2$ at room temperature for 12 hours, before the catalyst was filtered off. The filtrate was concentrated to afford the title compound (1 g).

LCMS (method 10-90AB), retention time=0.99 minutes, [M+H]+=578.4 m/z.

Compound (3): (2R,3R,4S)-2-(((4aR,10aR)-7-hydroxy-1-propyl-1,2,3,4,4a,5,10,10a-octahydrobenzo[g]quinolin-6-yl)oxy)-6-(methoxycarbonyl)-3,4-dihydro-2H-pyran-3,4-diyl diacetate DBU (0.52 mL) was added to a solution (2S,3R,4S,5S,6S)-2-(((4aR,10aR)-7-hydroxy-1-propyl-1,2,3,4,4a,5,10,10a-octahydrobenzo[g]quinolin-6-yl)oxy)-6-(methoxycarbonyl)tetra hydro-2H-pyran-3,4,5-triyl triacetate (1 g) in DCM (20 mL), and the mixture was stirred for 12 hours at room temperature. The mixture was washed with brine (20 mL), dried over $Na_2SO_4$, filtered, and concentrated. The residue was purified by prep-HPLC using a GX281 instrument (Phenomenex Luna C18 100×30 mm, 5 µm particles column operated at room temperature with 25 mL/min of a gradient of water+0.225% formic acid (A) and MeCN (B): 0-15 min 1% B to 30% B; 15.1-17 min 100% B; 17.1-20 min 1% B) to afford the title compound (0.2 g).

$^1$H NMR (400 MHz, $CDCl_3$) δ 6.80-6.83 (m, 2H), 6.29 (d, J=4.0 Hz, 1H), 5.51 (d, J=3.6 Hz, 1H), 5.38-5.44 (m, 2H), 3.85 (s, 3H), 3.37 (d, J=9.2 Hz, 1H), 2.97-3.17 (m, 4H), 2.80-2.92 (m, 1H), 2.51-2.71 (m, 3H), 2.26-2.33 (m, 2H), 2.15 (s, 3H), 2.14 (s, 3H), 2.01 (d, J=12.4 Hz, 2H), 1.82 (d, J=14.0 Hz, 1H), 1.60-1.72 (m, J=4.8 Hz, 2H), 1.33-1.15 (m, 1H), 0.99 (t, J=7.2 Hz, 3H).

QC-LCMS (method DELIVER-K-1), retention time=1.49 minutes, [M+H]$^+$=518.2 m/z.

Compound (4): (2S,3S,4S,5R,6S)-6-(((4aR,10aR)-7-(benzyloxy)-1-propyl-1,2,3,4,4a,5,10,10a-octahydrobenzo[g]quinolin-6-yl)oxy)-3,4,5-trihydroxytetrahydro-2H-pyran-2-carboxylic acid NaOH (150 mg) was dissolved in water/MeOH (3/12 mL) at 0° C. and (2S,3R,4S,5S,6S)-2-W4aR,10aR)-7-(benzyloxy)-1-propyl-1,2,3,4,4a,5,10,10a-octahydrobenzo[g]quinolin-6-yl)oxy)-6-(methoxycarbonyl)tetrahydro-2H-pyran-3,4,5-triyl triacetate (0.5 g) was added. The mixture was stirred for 1 hour at 0° C., before it was lyophilized. The residue was purified by prep-HPLC using a Shimadzu LC20AP instrument (Phenomenex Luna C18 250×50 mm, 10 µm particles column operated at room temperature with 80 mL/min of a gradient of water+0.225% formic acid (A) and MeCN (B): 0-20 min 1% B to 30% B; 20.1-25 min 100% B; 25.1-30 min 1% B) to afford the title compound (200 mg).

$^1$H NMR (400 MHz, DMSO-$d_6$) δ 7.50 (d, J=7.2 Hz, 2H), 7.24-7.38 (m, 3H), 6.92 (d, J=8.8 Hz, 1H), 6.82 (d, J=8.4 Hz, 1H), 4.98-5.25 (m, 3H), 4.83 (d, J=7.2 Hz, 1H), 3.51 (d, J=13.6 Hz, 2H), 3.08-3.44 (m, 10H), 2.75-3.03 (m, 3H), 2.10-2.20 (m, 1H), 1.78-1.88 (m, 4H), 1.54-1.70 (m, 2H), 1.25-1.31 (m, 1H), 0.91 (t, J=7.2 Hz, 3H).

QC-LCMS (method AB01), retention time=2.37 minutes, [M+H]$^+$=528.2 m/z.

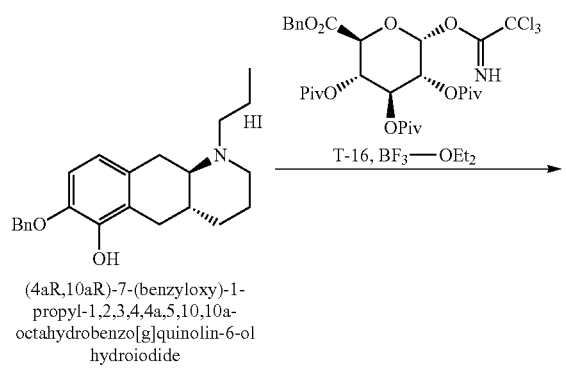

(4aR,10aR)-7-(benzyloxy)-1-propyl-1,2,3,4,4a,5,10,10a-octahydrobenzo[g]quinolin-6-ol hydroiodide

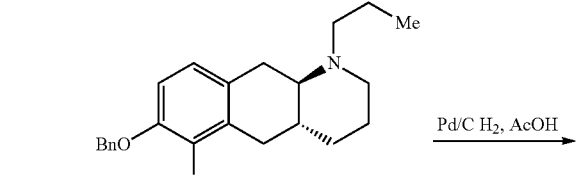

(2S,3R,4S,5S,6S)-2-(((4aR,10aR)-7-(benzyloxy)-1-propyl-1,2,3,4,4a,5,10,10a-octahydrobenzo[g]quinolin-6-yl)oxy)-6-((benzyloxy)carbonyl)tetrahyrdo-2 H-pyran-3,4,5-triyl tris(2,2-dimethylpropanoate)

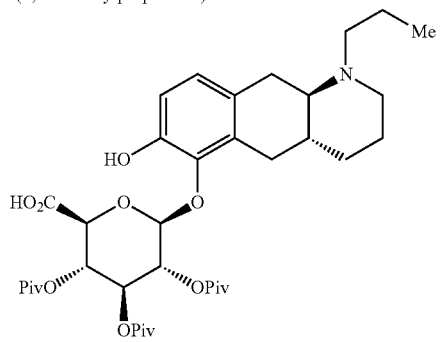

(2S,3S,4S,5R,6S)-6-(((4aR,10aR)-7-hydroxy-1-propyl-1,2,3,4,4a,5,10,10a-octahydrobenzo[g]quinolin-6-yl)oxy)-3,4,5-tris(pivaloyloxy)tetrahydro-2 H-pyran-2-carboxylic acid Compound (5): (2S,3R,4S,5S,6S)-2-(((4aR,10aR)-7-(benzyloxy)-1-propyl-1,2,3,4,4a,5,10,10a-octahydrobenzo[g]quinolin-6-yl)oxy)-6-((benzyloxy)carbonyl)tetrahydro-2H-pyran-3,4,5-triyl tris(2,2-dimethylpropanoate)

To a solution of (4aR,10aR)-7-(benzyloxy)-1-propyl-1,2,3,4,4a,5,10,10a-octahydrobenzo[g]quinolin-6-ol hydroiodide (1.0 g) and (2S,3S,4S,5R,6R)-2-((benzyloxy)carbonyl)-6-(2,2,2-trichloro-1-iminoethoxy)tetrahydro-2H-pyran-3,4,5-triyl tris(2,2-dimethylpropanoate) (T-16; prepared in similar manner as T-1 described in Advances in Chemical Engineering and Science, 2012, 2, 379-383; 3.88 g) in DCM (100 mL) was added $BF_3$-$OEt_2$ (0.7 mL) at −10° C. under $N_2$. The mixture was stirred at room temperature for 1 hour before it was partitioned between saturated aqueous $NaHCO_3$ (100 mL) and DCM (50 mL×2). The combined organic layers were washed with brine (50 mL), dried over $Na_2SO_4$, filtered, and concentrated. The residue was purified by prep-HPLC using a Agela FL-H600G instrument (Phenomenex Luna C18 250×100, 10 µm particles column operated at room temperature with 250 mL/min of a gradient of water+0.225% formic acid (A) and MeCN (B): 0-20 min 55% B to 75% B; 20.1-25 min 100% B; 25.1-30 min 55% B) to afford the title compound (1.20 g). 0.2 g of this material and 0.4 g of the product from a previous batch, prepared under similar conditions were combined and purified by prep-HPLC using a GX281 instrument (Waters Xbridge C18 150×25 mm, 5 µm particles column operated at room temperature with 25 mL/min of a gradient of water+0.225% formic acid (A) and MeCN (B): 0-13 min 45% B to 75% B; 13.1-16 min 100% B; 16.1-19 min 75% B) to afford the title compound (300 mg).

¹H NMR (400 MHz, CDCl₃) δ 7.33-7.44 (m, 10H), 6.78-6.84 (m, 2H), 5.29-5.32 (m, 4H), 5.14-5.18 (d, J=12.4 Hz, 2H), 5.07-5.15 (d, J=12.4 Hz, 2H), 4.98 (d, J=12.0 Hz, 1H), 3.78-3.80 (m, 1H), 3.24-3.30 (m, 2H), 3.10 (d, J=10.8 Hz, 1H), 2.95 (s, 1H), 2.79 (s, 1H), 2.52 (br s, 2H), 2.14-2.21 (m, 1H), 1.86-2.07 (m, 2H), 1.74-1.77 (d, J=12 Hz, 3H), 1.62 (m, 2H), 1.13 (s, 9H), 1.08 (s, 9H), 1.06 (s, 9H), 0.96 (t, J=7.2 Hz, 3H).

QC-LCMS (method DELIVER-K-1), retention time=2.17 minutes, [M+H]⁺=870.4 m/z.

Compound (6): (2S,3S,4S,5R,6S)-6-(((4aR,10aR)-7-hydroxy-1-propyl-1,2,3,4,4a,5,10,10a-octahydrobenzo[g]quinolin-6-yl)oxy)-3,4,5-tris(pivaloyloxy) tetrahydro-2H-pyran-2-carboxylic acid To a mixture of Pd/C (50% (w/w), 4.0 g) in THF (20 mL) and H₂O (4.0 mL) was added (2S,3R,4S,5S,6S)-2-(((4aR,10aR)-7-(benzyloxy)-1-propyl-1,2,3,4,4a,5,10,10a-octahydrobenzo[g]quinolin-6-yl)oxy)-6-((benzyloxy)carbonyl)tetrahydro-2H-pyran-3,4,5-triyl tris(2,2-dimethylpropanoate) (1.00 g) and AcOH (0.066 mL) under N₂. The suspension was degassed under vacuum and purged with H2. The mixture was stirred under H₂ (30 psi) at room temperature for 12 hours, before the catalyst was filtered off. The filtrate was concentrated and purified by prep-HPLC using a Shimadzu LC20AP instrument (Phenomenex Luna C18 250×50 mm, 10 μm particles column operated at room temperature with 80 mL/min of a gradient of water+0.225% formic acid (A) and MeCN (B): 0-20 min 30% B to 60% B; 20.1-25 min 100% B; 25.1-30 min 30% B) to afford the title compound (200 mg).

1H NMR (400 MHz, DMSO) δ 9.44 (br s, 1H), 6.69-6.75 (m, 2H), 5.37 (d, J=18.0 Hz, 2H), 5.07-5.12 (m, 2H), 3.78-3.98 (m, 1H), 3.37-3.43 (m, 4H), 2.99-3.32 (m, 4H), 2.12-2.19 (m, 1H), 1.59-1.84 (m, 6H), 1.28-1.35 (m, 1H), 1.14 (s, 9H), 1.07 (s, 9H), 1.07 (s, 9H), 0.88 (t, J=7.2 Hz, 3H).

LCMS (method 550), retention time=0.78 minutes, [M+H]⁺=690.7 m/z.

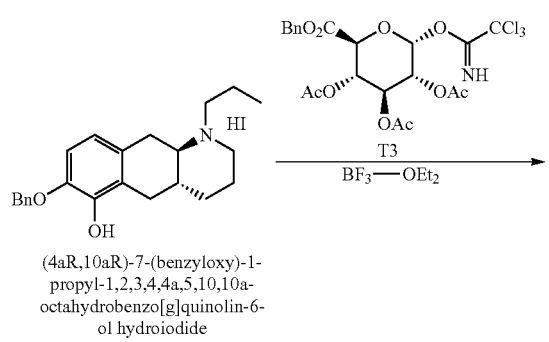

(4aR,10aR)-7-(benzyloxy)-1-propyl-1,2,3,4,4a,5,10,10a-octahydrobenzo[g]quinolin-6-ol hydroiodide

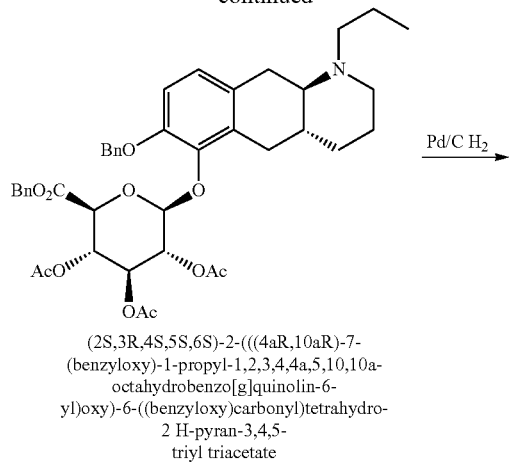

(2S,3R,4S,5S,6S)-2-(((4aR,10aR)-7-(benzyloxy)-1-propyl-1,2,3,4,4a,5,10,10a-octahydrobenzo[g]quinolin-6-yl)oxy)-6-((benzyloxy)carbonyl)tetrahydro-2H-pyran-3,4,5-triyl triacetate

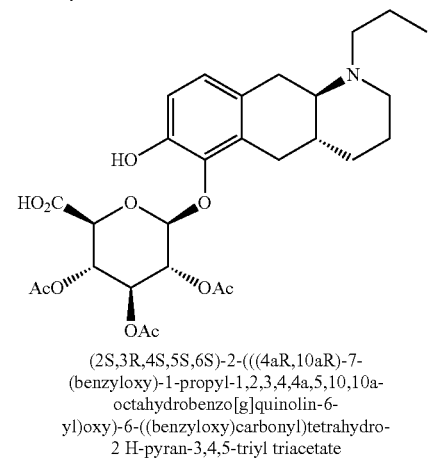

(2S,3R,4S,5S,6S)-2-(((4aR,10aR)-7-(benzyloxy)-1-propyl-1,2,3,4,4a,5,10,10a-octahydrobenzo[g]quinolin-6-yl)oxy)-6-((benzyloxy)carbonyl)tetrahydro-2 H-pyran-3,4,5-triyl triacetate Compound (7): (2S,3R,4S,5S,6S)-2-(((4aR,10aR)-7-(benzyloxy)-1-propyl-1,2,3,4,4a,5,10,10a-octahydrobenzo[g]quinolin-6-yl)oxy)-6-((benzyloxy)carbonyl)tetrahydro-2H-pyran-3,4,5-triyl triacetate To a solution of (4aR,10aR)-7-(benzyloxy)-1-propyl-1,2,3,4,4a,5,10,10a-octahydrobenzo[g]quinolin-6-ol hydroiodide (1.00 g), (2S,3S,4S,5R,6R)-2-((benzyloxy)carbonyl)-6-(2,2,2-trichloro-1-iminoethoxy)tetrahydro-2H-pyran-3,4,5-triyl triacetate (T-3; prepared as described in Bioorg. Med. Chem. 16 (2008) 6312-6318, 2.37 g) and 4 Å MS (1.00 g) in DCM (100 mL) was added BF₃-OEt₂ (0.53 mL) at −40~−20° C. The mixture was stirred at −40° C. for 1 hour and at room temperature for 2 hours. The reaction mixture was poured into saturated aqueous NaHCO₃ (250 mL) and stirred for 20 minutes and then extracted with DCM (100 mL×3). The combined organic layers were washed with brine (100 mL), dried over Na₂SO₄, filtered, and concentrated. The residue was purified by prep-HPLC using a Agela FL-H600G instrument (Phenomenex Luna C18 250× 100 mm, 10 μm particles column operated at room temperature with 250 mL/min of a gradient of water+0.225% formic acid (A) and MeCN (B): 0-30 min 15-45% B; 30.1-35 min 100% B; 35.1-40 min 15% B) to afford the title compound (0.66 g).

¹H NMR (400 MHz, CDCl₃) δ 7.29-7.45 (m, 10H), 6.83-6.88 (m, 1H), 6.76-6.80 (m, 1H), 5.28 (s, 3H), 4.99-5.18 (m, 4H), 3.92 (d, J=8.8 Hz, 1H), 3.32 (d, J=16.0 Hz, 1H), 3.11 (dd, J=4.4, 15.6 Hz, 2H), 2.51-2.89 (m, 4H), 2.34

(br s, 1H), 2.19 (dd, J=12.0, 17.4, Hz, 2H), 2.02 (s, 3H), 1.83 (s, 4H), 1.77 (s, 4H), 1.72 (br s, 2H), 1.56 (br s, 2H), 1.06 (d, J=11.6 Hz, 1H), 0.92 (t, J=7.2 Hz, 3H).

LC-MS (method 10-90AB), retention time=1.02 minutes, [M+H]⁺=744.4 m/z.

Compound (8): (2S,3S,4S,5R,6S)-3,4,5-triacetoxy-6-(((4aR,10aR)-7-hydroxy-1-propyl-1,2,3,4,4a,5,10,10a-octahydrobenzo[g]quinolin-6-yl)oxy)tetrahydro-2H-pyran-2-carboxylic acid To a mixture of Pd/C (1.00 g, 10% Pd) in THF (66 mL) was added (2S,3R,4S,5S,6S)-2-(((4aR,10aR)-7-(benzyloxy)-1-propyl-1,2,3,4,4a,5,10,10a-octahydrobenzo[g]quinolin-6-yl)oxy)-6-((benzyloxy)carbonyl)tetrahydro-2H-pyran-3,4,5-triyl triacetate (0.66 g) under N2. The suspension was degassed under vacuum and purged with H2. The mixture was stirred under H$_2$ (30 psi) at room temperature for 12 hours, before the catalyst was filtered off. The filtrate was concentrated and purified by prep-HPLC using a Shimadzu LC20AP instrument (Agela Durashell C18 250×50 mm, 10 μm particles column operated at room temperature with 80 mL/min of a gradient of water+0.225% formic acid (A) and MeCN (B): 0-20 min 2-35% B; 20.1-25 min 100% B; 25.1-30 min 2% B) to afford the title compound (0.45 g).

¹H NMR (400 MHz, CDCl$_3$) δ 12.40 (br s, 1H), 6.42 (d, J=8.4 Hz, 1H), 6.31 (d, J=8.4 Hz, 1H), 5.99 (d, J=5.0 Hz, 1H), 5.48 (dd, J=7.2, 11.6 Hz, 1H), 5.04 (dd, J=5.2, 11.6 Hz, 1H), 4.73 (d, J=7.2 Hz, 1H), 4.36 (s, 1H), 3.75 (d, J=11.2 Hz, 1H), 3.22-3.44 (m, 2H), 2.86-2.99 (m, 2H), 2.69-2.86 (m, 2H), 2.30-2.53 (m, 3H), 2.23 (d, J=10.8 Hz, 1H), 2.15 (s, 3H), 2.06 (s, 3H), 2.02 (s, 3H), 1.95-1.99 (m, 1H), 1.76-1.94 (m, 4H), 1.09-1.18 (m, 1H), 1.05 (t, J=7.2 Hz, 3H).

QC-LCMS (method AB01), retention time=2.34 minutes, [M+H]⁺=564.2 m/z.

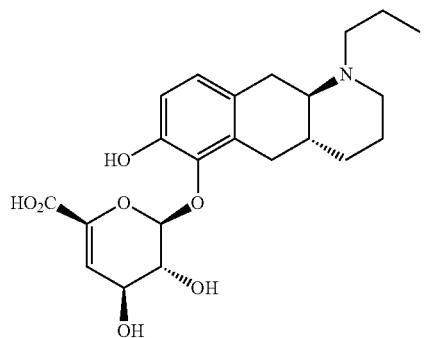

(2S,3R,4S)-3,4-dihydroxy-2-(((4aR,10aR)-7-hydroxy-1-propyl-1,2,3,4,4a,5,10,10a-octahydrobenzo[g]quinolin-6-yl)oxy)-3,4-dihydro-2H-pyran-6-carboxylic acid Compound (9): (2R,3R,4S)-3,4-dihydroxy-2-(((4aR,10aR)-7-hydroxy-1-propyl-1,2,3,4,4a,5,10,10a-octahydrobenzo[g]quinolin-6-yl)oxy)-3,4-dihydro-2H-pyran-6-carboxylic acid To a mixture of K$_2$CO$_3$ (1.12 g) in H$_2$O (4 mL) and MeOH (24 mL) was added (2R,3R,4S)-2-(((4aR,10aR)-7-hydroxy-1-propyl-1,2,3,4,4a,5,10,10a-octahydrobenzo[g]quinolin-6-yl)oxy)-6-(methoxycarbonyl)-3,4-dihydro-2H-pyran-3,4-diyl diacetate (0.7 g) at 0° C. under N$_2$. The mixture was stirred at 0° C. for 2 hours and at room temperature for 2 hours. The mixture was dissolved in H$_2$O (20 mL) and lyophilized. The residue was purified by prep-HPLC using a Shimadzu LC20AP instrument (Phenomenex Luna C18 250×50 mm, 10 μm particles column operated at room temperature with 80 mL/min of a gradient of water+0.225% formic acid (A) and MeCN (B): 0-20 min 1-20% B; 20.1-25 min 100% B; 25.1-30 min 1% B) to afford the title compound (0.39 g).

¹H NMR (400 MHz, D$_2$O) δ 6.77-6.91 (m, 2H), 6.08 (d, J=4.0 Hz, 1H), 5.65 (s, 1H), 4.11-4.28 (m, 2H), 3.55 (d, J=12.0 Hz, 1H), 2.94-3.43 (m, 6H), 2.72-2.84 (m, 1H), 2.14-2.30 (m, 1H), 1.57-2.05 (m, 6H), 1.22-1.41 (m, 1H), 0.95 (t, J=7.2 Hz, 3H).

QC-LCMS (method 0-30AB-HPLC), retention time=4.44 minutes, [M+H]⁺=420.2 m/z.

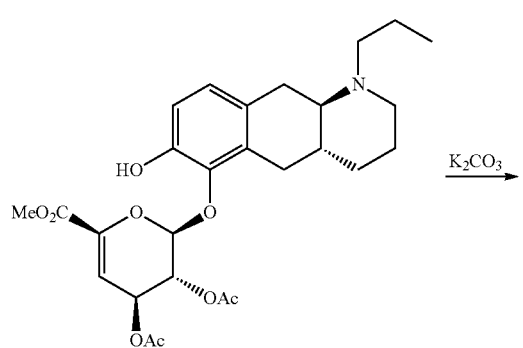

(2R,3R,4S)-2-(((4aR,10aR)-7-hydroxy-1-propyl-1,2,3,4,4a,5,10,10a-octahydrobenzo[g]quinolin-6-yl)oxy)-6-(methoxycarbonyl)-3,4-dihydro-2 H-pyran-3,4-diyl diacetate

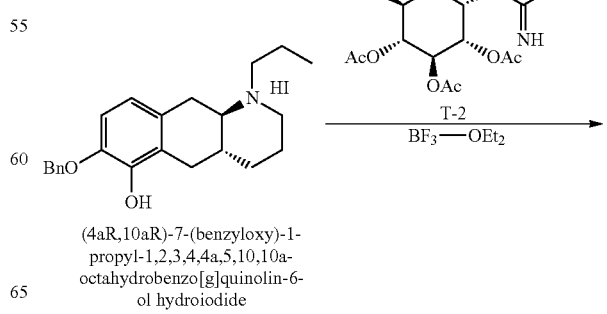

(4aR,10aR)-7-(benzyloxy)-1-propyl-1,2,3,4,4a,5,10,10a-octahydrobenzo[g]quinolin-6-ol hydroiodide

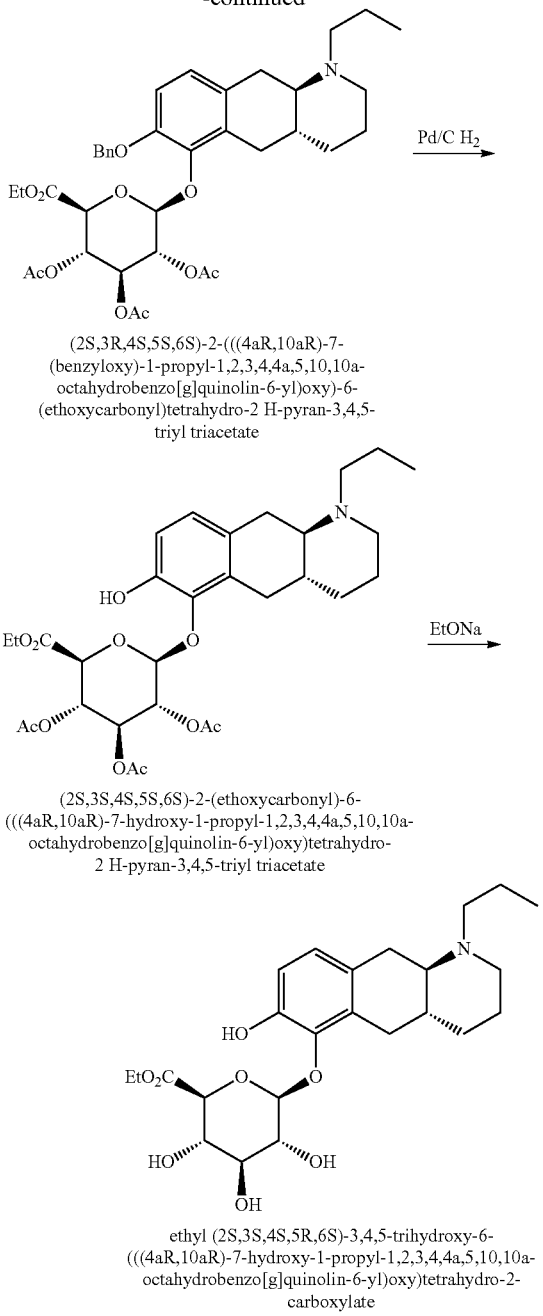

(2S,3R,4S,5S,6S)-2-(((4aR,10aR)-7-(benzyloxy)-1-propyl-1,2,3,4,4a,5,10,10a-octahydrobenzo[g]quinolin-6-yl)oxy)-6-(ethoxycarbonyl)tetrahydro-2H-pyran-3,4,5-triyl triacetate (2S,3S,4S,5S,6S)-2-(ethoxycarbonyl)-6-(((4aR,10aR)-7-hydroxy-1-propyl-1,2,3,4,4a,5,10,10a-octahydrobenzo[g]quinolin-6-yl)oxy)tetrahydro-2H-pyran-3,4,5-triyl triacetate ethyl (2S,3S,4S,5R,6S)-3,4,5-trihydroxy-6-(((4aR,10aR)-7-hydroxy-1-propyl-1,2,3,4,4a,5,10,10a-octahydrobenzo[g]quinolin-6-yl)oxy)tetrahydro-2H-pyran-2-carboxylate Compound (10): (2S,3R,4S,5S,6S)-2-(((4aR,10aR)-7-(benzyloxy)-1-propyl-1,2,3,4,4a,5,10,10a-octahydrobenzo[g]quinolin-6-yl)oxy)-6-(ethoxycarbonyl)tetrahydro-2H-pyran-3,4,5-triyl triacetate To a mixture of (4aR,10aR)-7-(benzyloxy)-1-propyl-1,2,3,4,4a,5,10,10a-octahydrobenzo[g]quinolin-6-ol hydroiodide (2.0 g) and (2S,3S,4S,5R,6R)-2-(ethoxycarbonyl)-6-(2,2,2-trichloro-1-iminoethoxy)tetrahydro-2H-pyran-3,4,5-triyl triacetate (T-2; prepared in similar manner as T-1 described in Advances in Chemical Engineering and Science, 2012, 2, 379-383; 4.77 g) and 4 Å MS (1 g) in DCM (200 mL) was added $BF_3$-$OEt_2$ (1.1 mL) at −20~−10° C. The mixture was stirred at −10° C. for 1 hour and at room temperature for 2 hours. The reaction mixture was poured into saturated aqueous $NaHCO_3$ (200 mL) and stirred for 20 minutes, before it was extracted with DCM (100 mL×3). The combined organic layers were washed with brine (200 mL), dried over $Na_2SO_4$, filtered, and concentrated. The residue was purified by prep-HPLC using a Agela FL-H600G instrument (Phenomenex Luna C18 250×100 mm, 10 μm particles column operated at room temperature with 250 mL/min of a gradient of water+0.225% formic acid (A) and MeCN (B): 0-30 min 15-50% B; 30.1-35 min 100% B; 35.1-40 min 15% B) to afford the title compound (2.38 g).

$^1$H NMR (400 MHz, $CDCl_3$) δ 7.38-7.45 (m, 4H), 7.31-7.37 (m, 1H), 6.85 (d, J=8.0 Hz, 1H), 6.78 (d, J=8.0 Hz, 1H), 5.22-5.30 (m, 4H), 5.07 (q, J=12.0 Hz, 2H), 4.07-4.16 (m, 2H), 3.86 (d, J=9.2 Hz, 1H), 3.37 (dd, J=17.6, 4.6 Hz, 1H), 3.04-3.14 (m, 2H), 2.81 (br s, 1H), 2.70 (br s, 1H), 2.58 (br s, 1H), 2.35 (br s, 1H), 2.16-2.27 (m, 2H), 2.03 (s, 3H), 2.02 (s, 3H), 1.76 (s, 3H), 1.60-1.65 (bs, 6H), 1.22 (t, J=7.5 Hz, 3H), 1.09-1.18 (m, 1H), 0.91 (t, J=7.2 Hz, 3H).

LC-MS (method: 550) retention time=0.68 minutes, $[M+H]^+$=682.6 m/z.

Compound (11): (2S,3S,4S,5R,6S)-2-(ethoxycarbonyl)-6-(((4aR,10aR)-7-hydroxy-1-propyl-1,2,3,4,4a,5,10,10a-octahydrobenzo[g]quinolin-6-yl)oxy)tetrahydro-2H-pyran-3,4,5-triyl triacetate To a mixture of Pd/C (10 g) in THF (200 mL) was added (2S,3R,4S,5S,6S)-2-(((4aR,10aR)-7-(benzyloxy)-1-propyl-1,2,3,4,4a,5,10,10a-octahydrobenzo[g]quinolin-6-yl)oxy)-6-(ethoxycarbonyl)tetrahydro-2H-pyran-3,4,5-triyl triacetate. (2.0 g) under $N_2$. The suspension was degassed under vacuum and purged with H2. The mixture was stirred under $H_2$ (30 psi) at 20° C. for 12 hours, before the catalyst was filtered off. The filtrate was concentrated and combined with another residue prepared in a similar manner. This material was purified by prep-HPLC using a Agela FI-H600G instrument (Phenomenex Luna C18 250×100 mm, 10 μm particles column operated at room temperature with 250 mL/min of a gradient of water+0.225% formic acid (A) and MeCN (B): 0-25 min 10-40% B; 25.1-30 min 100% B; 30.1-35 min 10% B) to afford the title compound (1.0 g).

QC-LC-MS (method AB01), retention time=2.60 minutes, $[M+H]^+$=592.2 m/z.

$^1$H NMR (400 MHz, $CDCl_3$) δ 8.50 (s, 1H), 6.80-6.88 (m, 2H), 5.26-5.37 (m, 3H), 4.79-4.85 (m, 1H), 4.18-4.27 (m, 2H), 4.01-4.05 (m, 1H), 3.53 (br d, J=11.6 Hz, 1H), 2.95-3.24 (m, 6H), 2.74-2.77 (m, 2H), 2.19-2.28 (m, 2H), 2.14 (s, 3H), 2.07 (s, 3H), 2.06 (s, 3H), 2.00 (br s, 1H), 1.88 (d, J=14.4 Hz, 1H), 1.64-1.81 (m, 2H), 1.29 (t, J=7.2 Hz, 3H), 1.26-1.27 (m, 1H), 1.02 (t, J=7.2 Hz, 3H).

Compound (12): ethyl (2S,3S,4S,5R,6S)-3,4,5-trihydroxy-6-(((4aR,10aR)-7-hydroxy-1-propyl-1,2,3,4,4a,5,10,10a-octahydrobenzo[g]quinolin-6-yl)oxy)tetrahydro-2H-pyran-2-carboxylate EtONa (155 mg) was added to solution of (2S,3S,4S,5R,6S)-2-(ethoxycarbonyl)-6-(((4aR,10aR)-7-hydroxy-1-propyl-1,2,3,4,4a,5,10,10a-octahydrobenzo[g]quinolin-6-yl)oxy)tetrahydro-2H-pyran-3,4,5-triyl triacetate (0.68 g) in EtOH (33 mL) at room temperature under $N_2$. The mixture was stirred for 3 hours, before it was purified by prep-HPLC using a GX281 instrument (Phenomenex Luna C18 100×30 mm, 5 μm particles column operated at room temperature with 25 mL/min of a gradient of water+0.225% formic acid (A) and MeCN (B): 0-15 min 1-30% B; 15.1-17 min 100% B; 17.1-20 min 1% B) to afford the title compound (127 mg).

¹H NMR (400 MHz, MeOD) δ 8.54 (s, 1H), 6.85 (d, J=8.4 Hz, 1H), 6.72 (d, J=8.4 Hz, 1H), 5.49 (s, 1H), 4.70 (d, J=8.0 Hz, 1H), 4.23 (q, J=6.8 Hz, 2H), 3.82 (d, J=10.0 Hz, 1H), 3.43-3.63 (m, 6H), 3.36 (d, J=5.2 Hz, 1H), 3.21-3.28 (m, 1H), 2.92-3.11 (m, 3H), 2.74-2.81 (m, 1H), 2.32 (dd, J=17.6, 11.8 Hz, 1H), 1.64-2.02 (m, 7H), 1.36-1.46 (m, 1H), 1.29 (t, J=7.2 Hz, 3H), 1.04 (t, J=7.2 Hz, 3H).

QC-LCMS (method AB01), retention time=2.17 minutes, [M+H]⁺=466.2 m/z.

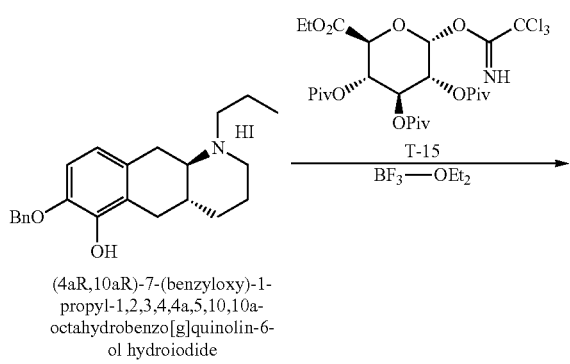

(4aR,10aR)-7-(benzyloxy)-1-propyl-1,2,3,4,4a,5,10,10a-octahydrobenzo[g]quinolin-6-ol hydroiodide

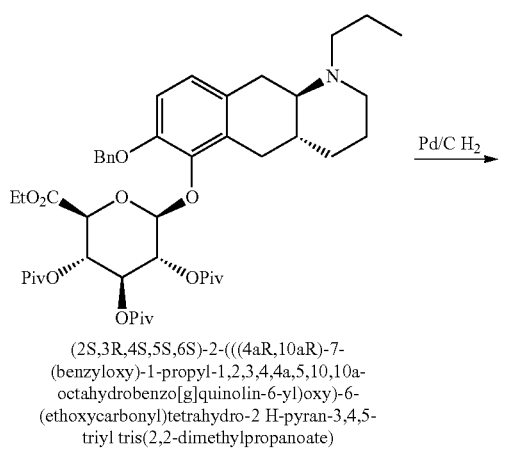

(2S,3R,4S,5S,6S)-2-(((4aR,10aR)-7-(benzyloxy)-1-propyl-1,2,3,4,4a,5,10,10a-octahydrobenzo[g]quinolin-6-yl)oxy)-6-(ethoxycarbonyl)tetrahydro-2 H-pyran-3,4,5-triyl tris(2,2-dimethylpropanoate)

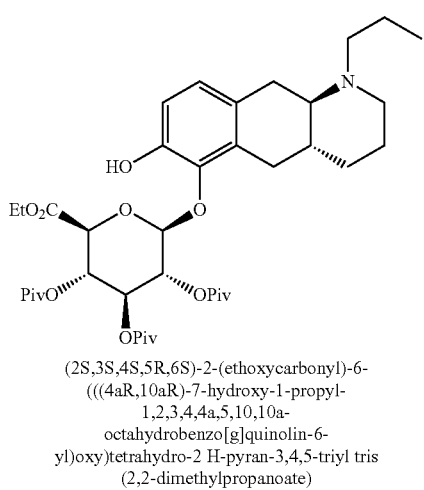

(2S,3S,4S,5R,6S)-2-(ethoxycarbonyl)-6-(((4aR,10aR)-7-hydroxy-1-propyl-1,2,3,4,4a,5,10,10a-octahydrobenzo[g]quinolin-6-yl)oxy)tetrahydro-2 H-pyran-3,4,5-triyl tris(2,2-dimethylpropanoate)

Compound (13): (2S,3R,4S,5S,6S)-2-(((4aR,10aR)-7-(benzyloxy)-1-propyl-1,2,3,4,4a,5,10,10a-octahydrobenzo[g]quinolin-6-yl)oxy)-6-(ethoxycarbonyl)tetrahydro-2H-pyran-3,4,5-triyl tris(2,2-dimethylpropanoate)

To a solution of (4aR,10aR)-7-(benzyloxy)-1-propyl-1,2,3,4,4a,5,10,10a-octahydrobenzo[g]quinolin-6-ol hydroiodide (1.00 g), (2S,3S,4S,5R,6R)-2-(ethoxycarbonyl)-6-(2,2,2-trichloro-1-iminoethoxy)tetrahydro-2H-pyran-3,4,5-triyl tris(2,2-dimethylpropanoate) (T-15; prepared in similar manner as T-1 described in Advances in Chemical Engineering and Science, 2012, 2, 379-383; 2.58 g) and 4 Å MS (1.00 g) in DCM (100 mL) was added BF₃—OEt₂ (0.39 mL) at −20° C. under N₂. The mixture was allowed to warm to room temperature over 3 hours, before it was partitioned between saturated aqueous NaHCO₃ (30 mL) and DCM (20 mL×2). The combined organic layers were washed with brine (20 mL), dried over Na₂SO₄, filtered, and concentrated. The residue was purified by prep-HPLC using an Agela FL-H600G instrument (Phenomenex Luna C18 250× 100 mm, 10 μm particles column operated at room temperature with 250 mL/min of a gradient of water+0.225% formic acid (A) and MeCN (B): 0-25 min 50-80% B; 25.1-30 min 100% B; 30.1-35 min 50% B) to afford the title compound (1.00 g).

¹H NMR (400 MHz, CDCl₃) δ δ 7.37-7.45 (m, 5H), 6.82 (s, 2H), 5.27-5.33 (m, 4H), 5.17 (d, J=12.0 Hz, 1H), 5.09 (d, J=12.4 Hz, 1H), 4.17-4.22 (m, 1H), 4.05-4.10 (m, 1H), 3.72 (d, J=9.2 Hz, 1H), 3.41 (d, J=14.0 Hz, 2H), 3.08-3.12 (m, 3H), 2.68 (s, 2H), 2.21-2.28 (m, 2H), 2.09 (d, J=11.2 Hz, 1H), 1.66-1.87 (m, 5H), 1.25 (t, J=7.2 Hz, 4H), 1.15 (s, 9H), 1.13 (s, 9H), 1.07 (s, 9H), 1.01 (t, J=6.8 Hz, 3H).

LC-MS (method 10-90AB), retention time=1.28 minutes, [M+H]⁺=808.6 m/z

Compound (14): (2S,3S,4S,5R,6S)-2-(ethoxycarbonyl)-6-(((4aR,10aR)-7-hydroxy-1-propyl-1,2,3,4,4a,5,10,10a-octahydrobenzo[g]quinolin-6-yl)oxy)tetrahydro-2H-pyran-3,4,5-triyl tris(2,2-dimethylpropanoate)

To a solution of (2S,3R,4S,5S,6S)-2-(((4aR,10aR)-7-(benzyloxy)-1-propyl-1,2,3,4,4a,5,10,10a-octahydrobenzo[g]quinolin-6-yl)oxy)-6-(ethoxycarbonyl)tetrahydro-2H-pyran-3,4,5-triyl tris(2,2-dimethylpropanoate) (1.00 g) in THF (20 mL) and H₂O (4 mL) was added Pd/C (50%, 2.50 g) and AcOH (0.07 mL) under N₂. The suspension was degassed under vacuum and purged with H2. The mixture was stirred under H₂ (30 psi) at room temperature for 12 hours, before the catalyst was filtered off, and the filtrate was concentrated. The residue was purified by prep-HPLC using a Shimadzu LC20AP instrument (Phenomenex Luna C18 250×50 mm, 10 μm particles column operated at room temperature with 80 mL/min of a gradient of water+0.225% formic acid (A) and MeCN (B): 0-20 min 30-60% B; 20.1-25 min 100% B; 25.1-30 min 30% B) to afford the title compound (0.10 g).

¹H NMR (400 MHz, CDCl₃) δ 6.82-6.89 (m, 2H), 5.44 (d, J=8.8 Hz, 3H), 4.98 (d, J=5.2 Hz, 1H), 4.24-4.28 (m, 1H), 4.16 (d, J=8.0 Hz, 1H), 4.04 (d, J=7.6 Hz, 1H), 3.27 (d, J=10.0 Hz, 1H), 3.13-3.17 (m, 2H), 2.94 (s, 2H), 2.77 (s, 1H), 2.51 (s, 2H), 2.21-2.28 (m, 3H), 1.79-1.98 (m, 4H), 1.64 (s, 2H), 1.30 (t, J=7.2 Hz, 3H), 1.25 (s, 9H), 1.15 (s, 9H), 1.14 (s, 9H), 0.98 (t, J=7.2 Hz, 3H).

QC-LCMS (method AB10), retention time=2.92 minutes, [M+H]⁺=718.4 m/z.

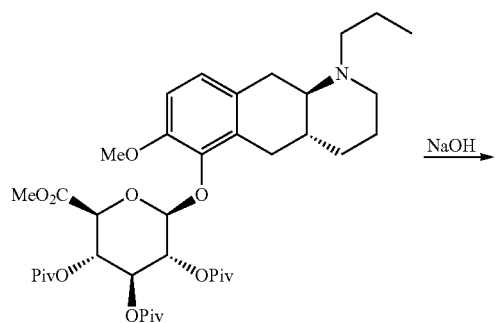

(2S,3S,4S,5R,6S)-6-(((4aR,10aR)-7-methoxy-1-propyl-1,2,3,4,4a,5,10,10a-octahydrobenzo[g]quinolin-6-yl)oxy)-3,4,5-tris(pivaloyloxy)tetrahydro-2H-pyran-2-carboxylic acid

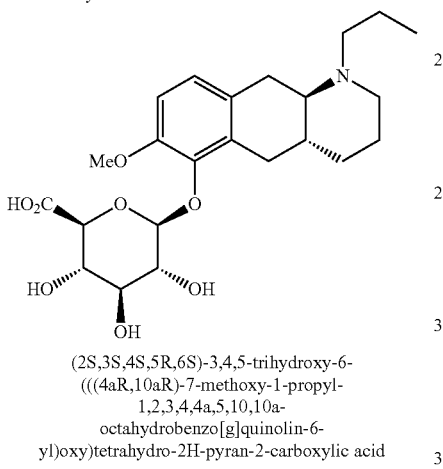

(2S,3S,4S,5R,6S)-3,4,5-trihydroxy-6-(((4aR,10aR)-7-methoxy-1-propyl-1,2,3,4,4a,5,10,10a-octahydrobenzo[g]quinolin-6-yl)oxy)tetrahydro-2H-pyran-2-carboxylic acid Compound (15): (2S,3S,4S,5R,6S)-3,4,5-trihydroxy-6-(((4aR,10aR)-7-methoxy-1-propyl-1,2,3,4,4a,5,10,10a-octahydrobenzo[g]quinolin-6-yl)oxy)tetrahydro-2H-pyran-2-carboxylic acid To a mixture of (2S,3S,4S,5R,6S)-6-(((4aR,10aR)-7-methoxy-1-propyl-1,2,3,4,4a,5,10,10a-octahydrobenzo[g]quinolin-6-yl)oxy)-3,4,5-tris(pivaloyloxy)tetrahydro-2H-pyran-2-carboxylic acid methyl ester (500 mg) in MeOH (6 mL) was added NaOH (568 mg) in $H_2O$ (3 mL). The mixture was stirred at room temperature for 2 days before it was combined with another mixture prepared in a similar manner (600 mg scale) for purification by prep-HPLC using a Shimadzu LC20AP instrument (Phenomenex Luna C18 250×50 mm, 10 μm particles column operated at room temperature with 80 mL/min of a binary of water+0.225% formic acid (A) and MeCN (B): 0-20 min 2-20% B; 20.1-25 min 100% B; 25.1-30 min 2% B) to afford the title compound (390 mg).

$^1$H NMR (400 MHz, $D_2O$) δ 6.98 (d, J=8.4 Hz, 2H), 5.00 (d, J=7.6 Hz, 1H), 3.81 (s, 3H), 3.50-3.59 (m, 5H), 3.35-3.43 (m, 2H), 3.17-3.30 (m, 2H), 3.02-3.13 (m, 2H), 2.73-2.80 (m, 1H), 2.24-2.28 (m, 1H), 1.90-2.05 (m, 2H), 1.60-1.90 (m, 4H), 1.28-1.38 (m, 1H), 0.98 (t, J=7.2 Hz, 3H).

QC-LCMS (method DELIVER-K), retention time=1.18 minutes, [M+H]$^+$=452.2 m/z.

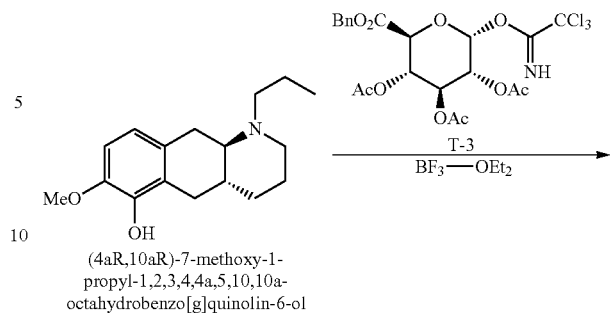

(4aR,10aR)-7-methoxy-1-propyl-1,2,3,4,4a,5,10,10a-octahydrobenzo[g]quinolin-6-ol

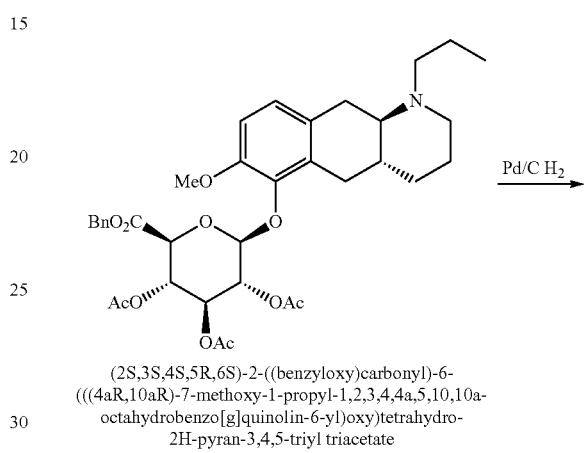

(2S,3S,4S,5R,6S)-2-((benzyloxy)carbonyl)-6-(((4aR,10aR)-7-methoxy-1-propyl-1,2,3,4,4a,5,10,10a-octahydrobenzo[g]quinolin-6-yl)oxy)tetrahydro-2H-pyran-3,4,5-triyl triacetate

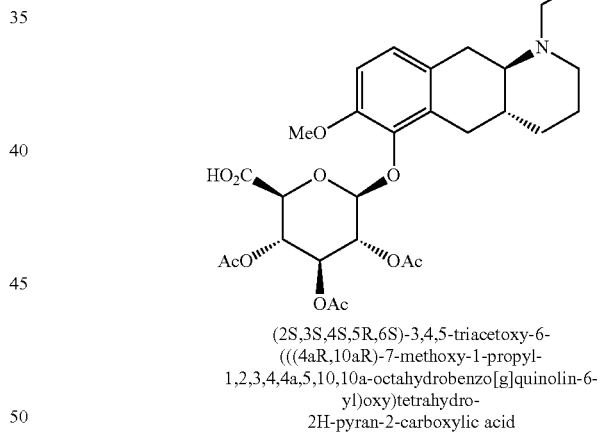

(2S,3S,4S,5R,6S)-3,4,5-triacetoxy-6-(((4aR,10aR)-7-methoxy-1-propyl-1,2,3,4,4a,5,10,10a-octahydrobenzo[g]quinolin-6-yl)oxy)tetrahydro-2H-pyran-2-carboxylic acid Compound (16): (2S,3S,4S,5R,6S)-2-((benzyloxy)carbonyl)-6-(((4aR,10aR)-7-methoxy-1-propyl-1,2,3,4,4a,5,10,10a-octahydrobenzo[g]quinolin-6-yl)oxy)tetrahydro-2H-pyran-3,4,5-triyl triacetate To a stirred solution of (4aR,10aR)-7-methoxy-1-propyl-1,2,3,4,4a,5,10,10a-octahydrobenzo[g]quinolin-6-ol (1.0 g) in DCM (100 mL) was added (2S,3S,4S,5R,6R)-2-((benzyloxy)carbonyl)-6-(2,2,2-trichloro-1-iminoethoxy)tetrahydro-2H-pyran-3,4,5-triyl triacetate (T-3; prepared as described in Bioorg. Med. Chem. 16 (2008) 6312-6318, 4.03 g) and $BF_3$-$OEt_2$ (0.90 mL) at −10° C. under $N_2$. The reaction mixture allowed to warm to room temperature over 3 hours, before it was partitioned between saturated aqueous NaHCO$_3$ (100 mL) and EtOAc (200 mL×2). The combined organic layers were washed with brine (200 mL), dried over Na$_2$SO$_4$, filtered, and concentrated. The residue was purified by prep-HPLC using a Shimadzu LC20AP instrument (Phenomenex Luna C18 250×50 mm, 10 μm particles column operated at room temperature with 80 mL/min of a binary of water+0.225% formic acid (A) and MeCN (B): 0-20 min 20-45% B; 20.1-25 min 100% B; 25.1-30 min 20% B) to afford the title compound (800 mg).

$^1$H NMR (400 MHz, DMSO-d$_6$) δ 7.27-7.40 (m, 5H), 6.81-6.93 (m, 2H), 5.36-5.45 (m, 1H), 5.26 (d, J=7.6 Hz, 1H), 4.98-5.14 (m, 4H), 4.50 (m, 1H), 3.72 (m, 3H), 3.08-3.23 (m, 3H), 2.91 (m, 1H), 2.63-2.74 (m, 1H), 2.23-2.43 (m, 2H), 2.06-2.16 (m, 2H), 2.04 (s, 3H), 1.99 (s, 3H), 1.81 (s, 3H), 1.68 (m, 1H), 1.56-1.64 (m, 1H), 1.37-1.55 (m, 3H), 1.30 (m, 1H), 0.94-1.07 (m, 1H), 0.85 (t, J=7.2 Hz, 3H).

QC-LCMS (method AB10), retention time=2.67 minutes, [M+H]+=668.2 m/z.

Compound (17): (2S,3S,4S,5R,6S)-3,4,5-triacetoxy-6-(((4aR,10aR)-7-methoxy-1-propyl-1,2,3,4,4a,5,10,10a-octahydrobenzo[g]quinolin-6-yl)oxy)tetrahydro-2H-pyran-2-carboxylic acid To a mixture of Pd/C (0.5 g) in THF (20 mL) was added (2S,3S,4S,5R,6S)-2-((benzyloxy)carbonyl)-6-(((4aR,10aR)-7-methoxy-1-propyl-1,2,3,4,4a,5,10,10a-octahydrobenzo[g]quinolin-6-yl)oxy)tetrahydro-2H-pyran-3,4,5-triyl triacetate (0.40 g) under N2. The suspension was degassed under vacuum and purged with H2. The mixture was stirred under H$_2$ (30 psi) at room temperature for 12 hours, before the catalyst was filtered off. The filtrate was concentrated and purified by prep-HPLC using a GX281 instrument (Waters Xbridge C18 150×25 mm, 5 μm particles column operated at room temperature with 25 mL/min of a gradient of water+0.225% formic acid (A) and MeCN (B): 0-13 min 10-45% B; 13.1-16 min 100% B; 16.1-19 min 10% B) to afford the title compound (0.2 g).

$^1$H NMR (400 MHz, DMSO-d$_6$) δ 6.88 (s, 2H), 5.24 (d, J=4.4 Hz, 1H), 5.04 (t, J=9.6 Hz, 1H), 4.98 (d, J=5.6 Hz, 2H), 3.74 (s, 4H), 3.52 (m, 1H), 3.20 (m, 1H), 3.17 (m, 2H), 2.96 (m, 2H), 2.62-2.85 (m, 2H), 2.33-2.34 (m, 1H), 2.10-2.14 (m, 1H), 2.04 (s, 3H), 1.96 (s, 3H), 1.91 (s, 3H), 1.70-1.78 (m, 2H), 1.45-1.55 (m, 3H), 1.20-1.28 (m, 1H), 0.85 (t, J=7.2 Hz, 3H).

QC-LCMS (method AB01), retention time=2.47 minutes, [M+H]$^+$=578.2 m/z.

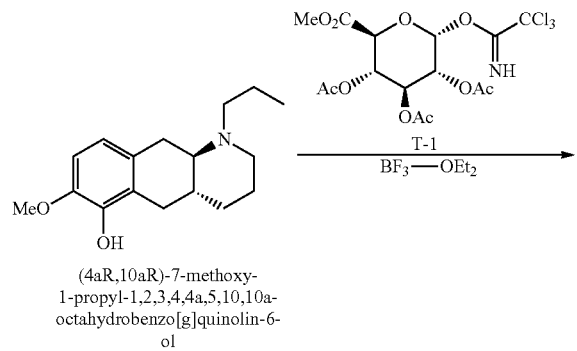

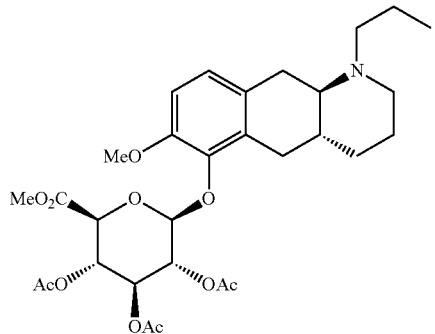

(2S,3R,4S,5S,6S)-2-(((4aR,10aR)-7-methoxy-1-propyl-1,2,3,4,4a,5,10,10a-octahydrobenzo[g]quinolin-6-(methoxycarbonyl)tetrahydro-2 H-pyran-3,4,5-triyl triacetate Compound (18): (2S,3R,4S,5S,6S)-2-(((4aR,10aR)-7-methoxy-1-propyl-1,2,3,4,4a,5,10,10a-octahydrobenzo[g]quinolin-6-yl)oxy)-6-(methoxycarbonyl)tetrahydro-2H-pyran-3,4,5-triyl triacetate To a mixture of (4aR,10aR)-7-methoxy-1-propyl-1,2,3,4,4a,5,10,10a-octahydrobenzo[g]quinolin-6-ol (1.30 g) and (2S,3S,4S,5R,6R)-2-(methoxycarbonyl)-6-(2,2,2-trichloro-1-iminoethoxy)tetrahydro-2H-pyran-3,4,5-triyl triacetate (T-1; prepared as described in Advances in Chemical Engineering and Science, 2012, 2, 379-383, 4.52 g) and 4 Å MS (1.00 g) in DCM (130 mL) was added BF$_3$-Et$_2$O (0.87 mL) at –10-0° C. The mixture was stirred at room temperature for 2 hours, before it was partitioned between saturated aqueous NaHCO$_3$ (200 mL) and DCM (200 mL×3). The combined organic layers were washed with brine (300 mL), dried over Na$_2$SO$_4$, filtered, and concentrated. The residue was purified by prep-HPLC using a Agela FL-H600G instrument (Phenomenex Luna C18 250×80 mm, 10 μm particles column operated at room temperature with 160 mL/min of a gradient of water+0.225% formic acid (A) and MeCN (B): 0-20 min 20-80% B; 20.1-25 min 100% B; 25.1-30 min 20% B) to afford the title compound (1.40 g).

$^1$H NMR: (400 MHz CDCl$_3$) δ 6.87 (d, J=8.4 Hz, 1H), 6.74 (d, J=8.4 Hz, 1H), 5.36 (d, J=9.4 Hz, 1H), 5.22-5.31 (m, 2H), 5.10 (d, J=7.6 Hz, 1H), 3.93 (d, J=10 Hz, 1H), 3.81 (s, 3H), 3.70 (s, 3H), 3.41-3.53 (m, 1H), 3.28 (m, 1H), 3.08-3.18 (m, 1H), 2.99 (m, 2H), 2.80 (m, 1H), 2.54 (m, 4H), 2.16-2.27 (m, 2H), 2.10 (s, 3H), 2.06 (s, 3H), 2.03 (s, 3H), 1.81 (m, J=14.4 Hz, 1H), 1.65 (m, 2H), 1.13-1.27 (m, 1H), 0.97 (t, J=7.2 Hz, 3H).

QC-LCMS: (method DELIVER-K-1), retention time=1.59 minutes, [M+H]$^+$=592.2 m/z.

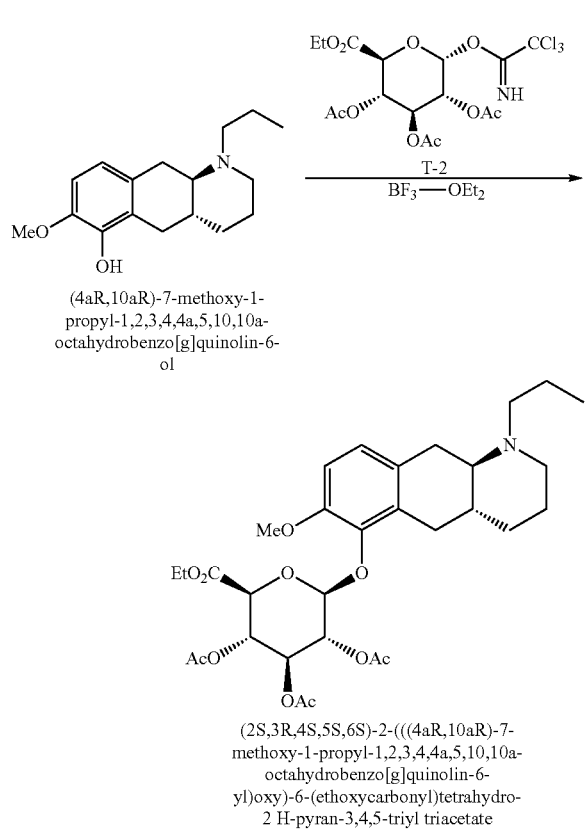

Compound (19): (2S,3R,4S,5S,6S)-2-(((4aR,10aR)-7-methoxy-1-propyl-1,2,3,4,4a,5,10,10a-octahydrobenzo[g]quinolin-6-yl)oxy)-6-(ethoxycarbonyl)tetrahydro-2H-pyran-3,4,5-triyl triacetate To a stirred solution of (4aR,10aR)-7-methoxy-1-propyl-1,2,3,4,4a,5,10,10a-octahydrobenzo[g]quinolin-6-ol (1 g) in DCM (100 mL) was added (2S,3S,4S,5R,6R)-2-(ethoxycarbonyl)-6-(2,2,2-trichloro-1-iminoethoxy)tetrahydro-2H-pyran-3,4,5-triyl triacetate (T-2; prepared in similar manner as T-1 described in Advances in Chemical Engineering and Science, 2012, 2, 379-383; 3.58 g) and BF$_3$-Et$_2$O (0.9 mL) at −10° C. The reaction mixture was stirred at room temperature for 3 hours, before it was partitioned between saturated aqueous NaHCO$_3$ (100 mL) and EtOAc (200 mL×2). The combined organic layers were washed with brine (200 mL), dried over Na$_2$SO$_4$, filtered, and concentrated. The residue was purified by prep-HPLC using a Agela FL-H600G instrument (Phenomenex Luna C18 250× 100 mm, 10 µm particles column operated at room temperature with 250 mL/min of a gradient of water+0.225% formic acid (A) and MeCN (B): 0-30 min 20-35% B; 30.1-35 min 100% B; 35.1-40 min 20% B) to afford the title compound (0.2 g).

$^1$H NMR: (400 MHz DMSO) δ 6.92-6.84 (m, 2H), 5.41 (t, J=9.6 Hz, 1H), 5.23 (d, J=7.6 Hz, 1H), 5.08-5.00 (m, 2H), 4.43 (d, J=10.0 Hz, 1H), 4.11-4.00 (m, 2H), 3.74 (s, 3H), 3.22-3.26 (m, 2H), 3.13 (dd, J=4.8, 15.6 Hz, 1H), 2.91 (d, J=11.2 Hz, 1H), 2.44-2.34 (m, 1H), 2.23-2.34 (m, 2H), 2.18-2.08 (m, 1H), 2.05 (s, 4H), 2.00 (s, 3H), 1.97 (s, 3H), 1.78 (d, J=10.0 Hz, 1H), 1.58-1.70 (m, 1H), 1.27-1.57 (m, 4H), 1.02-1.18 (m, 4H), 0.84 (t, J=7.2 Hz, 3H).

QC-LCMS: (method DELIVER-K-1), retention time=1.62 minutes, [M+H]$^+$=606.2 m/z.

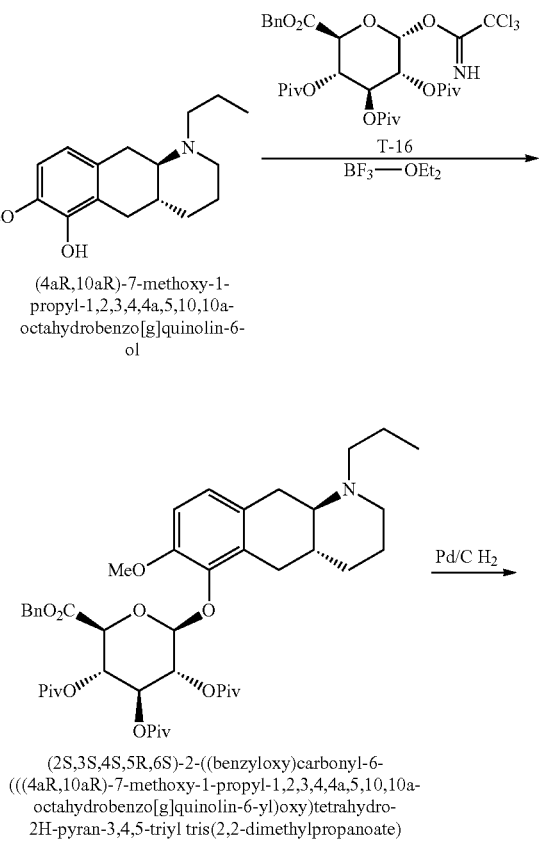

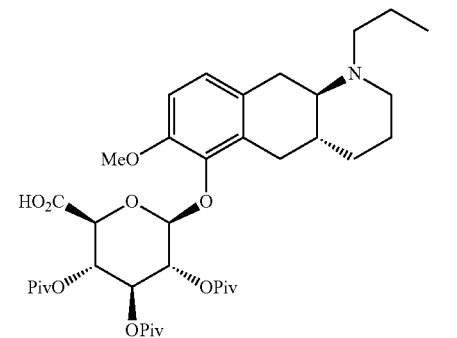

(2S,3S,4S,5S,6S)-6-(((4aR,10aR)-7-methoxy-1-propyl-1,2,3,4,4a,5,10,10a-octahydrobenzo[g]quinolin-6-yl)oxy)-3,4,5-tris(pivaloyloxy)tetrahydro-2H-pyran-2-carboxylic acid Compound (20): (2S,3S,4S,5R,6S)-2-((benzyloxy)carbonyl)-6-(((4aR,10aR)-7-methoxy-1-propyl-1,2,3,4,4a,5,10,10a-octahydrobenzo[g]quinolin-6-yl)oxy)tetrahydro-2H-pyran-3,4,5-triyltris(2,2-dimethylpropanoate)

To a solution of (4aR,10aR)-7-methoxy-1-propyl-1,2,3,4,4a,5,10,10a-octahydrobenzo[g]quinolin-6-ol (1.00 g) and (2S,3S,4S,5R,6R)-2-((benzyloxy)carbonyl)-6-(2,2,2- trichloro-1-iminoethoxy)tetrahydro-2H-pyran-3,4,5-triyl tris(2,2-dimethylpropanoate) (T-16; prepared in similar manner as T-1 described in Advances in Chemical Engineering and Science, 2012, 2, 379-383; 4.95 g) in DCM (100 mL) was added BF$_3$-Et$_2$O (0.9 mL) at −10° C. The mixture was stirred at room temperature for 1 hour, before it was partitioned between saturated aqueous NaHCO$_3$ (100 mL) and DCM (50 mL×2). The combined organic layers were washed with brine (50 mL), dried over Na$_2$SO$_4$, filtered, and concentrated. The residue was purified by prep-HPLC using a Shimadzu LC20AP instrument (Phenomenex Luna C18 250×50 mm, 10 μm particles operated at room temperature with 80 mL/min of a gradient of water+0.225% formic acid (A) and MeCN (B): 0-20 min 50-80% B; 20.1-25 min 100% B; 25.1-30 min 50% B) to afford 1.6 g of the title compound. 0.6 g of this material was purified by prep-HPLC using a GX281 instrument (Waters Xbridge C18 150×25 mm, 5 μm particles column operated at room temperature with 25 mL/min of a gradient of water+0.225% formic acid (A) and MeCN (B): 0-13 min 45-75% B; 13.1-16 min 100% B; 16.1-19 min 45% B) to afford the title compound (0.3 g).

$^1$H NMR: (400 MHz CDCl$_3$) δ 7.23-7.32 (m, 5H), 6.78 (d, J=8.4 Hz, 1H), 6.65 (d, J=8.4 Hz, 1H), 5.38 (t, J=8.8 Hz, 1H), 5.2-5.29 (m, 3H), 5.10 (d, J=12.0 Hz, 1H), 4.92 (d, J=12.0 Hz, 1H), 3.92 (d, J=10.0 Hz, 1H), 3.71 (s, 3H), 3.26 (d, J=13.2 Hz, 2H), 3.02 (d, J=10.4 Hz, 2H), 2.80-2.94 (m, 2H), 2.51 (s, 2H), 2.08-2.16 (m, 2H), 1.95 (br d, J=16.0 Hz, 2H), 1.43-1.70 (m, 4H), 1.18 (s, 9H), 1.13 (s, 9H), 1.06 (s, 9H), 0.90 (t, J=7.2 Hz, 3H).

QC-LCMS: (method AB25), retention time=2.91 minutes, [M+H]$^+$=794.4 m/z.

Compound (21): (2S,3S,4S,5R,6S)-6-(((4aR,10aR)-7-methoxy-1-propyl-1,2,3,4,4a,5,10,10a-octahydrobenzo[g]quinolin-6-yl)oxy)-3,4,5-tris(pivaloyloxy)tetrahydro-2H-pyran-2-carboxylic acid To a solution of (2S,3S,4S,5R,6S)-2-((benzyloxy)carbonyl)-6-(((4aR,10aR)-7-methoxy-1-propyl-1,2,3,4,4a,5,10,10a-octahydrobenzo[g]quinolin-6-yl)oxy)tetrahydro-2H-pyran-3,4,5-triyl tris(2,2-dimethylpropanoate) (1.00 g) in THF (20 mL) and H$_2$O (4 mL) was added Pd/C (50%, 4.00 g) and AcOH (0.07 mL) under N$_2$. The suspension was degassed under vacuum and purged with H2. The mixture was stirred under H$_2$ (30 psi) at room temperature for 12 hours before the catalyst was filtered off. The filtrate was concentrated and purified by prep-HPLC using a Shimadzu LC20AP instrument (Phenomenex Luna C18 250×50 mm, 10 μm particles column operated at room temperature with 80 mL/min of a gradient of water+0.225% formic acid (A) and MeCN (B): 0-20 min 30-60% B; 20.1-25 min 100% B; 25.1-30 min 30% B) to afford the title compound (850 mg).

$^1$H NMR: (400 MHz CDCl$_3$) δ 6.87 (d, J=8.8 Hz, 1H), 6.72 (d, J=8.4 Hz, 1H), 5.44 (t, J=9.2 Hz, 1H), 5.33-5.38 (m, 2H), 5.21 (d, J=7.6 Hz, 1H), 4.82 (s, 1H), 3.79 (s, 3H), 3.64-3.70 (m, 1H), 3.45 (br d, J=11.6 Hz, 1H), 3.29-3.38 (m, 2H), 3.00-3.11 (m, 2H), 2.76-2.87 (m, 2H), 2.25-2.33 (m, 3H), 2.08 (d, J=10.4 Hz, 2H), 1.93 (d, J=14.0 Hz, 1H), 1.59-1.70 (m, 2H), 1.19 (s, 9H), 1.14 (s, 9H), 1.14 (s, 9H), 1.00 (t, J=7.2 Hz, 3H).

QC-LCMS: (method DELIVER-K-1), retention time=1.93 minutes, [M+H]$^+$=704.3 m/z.

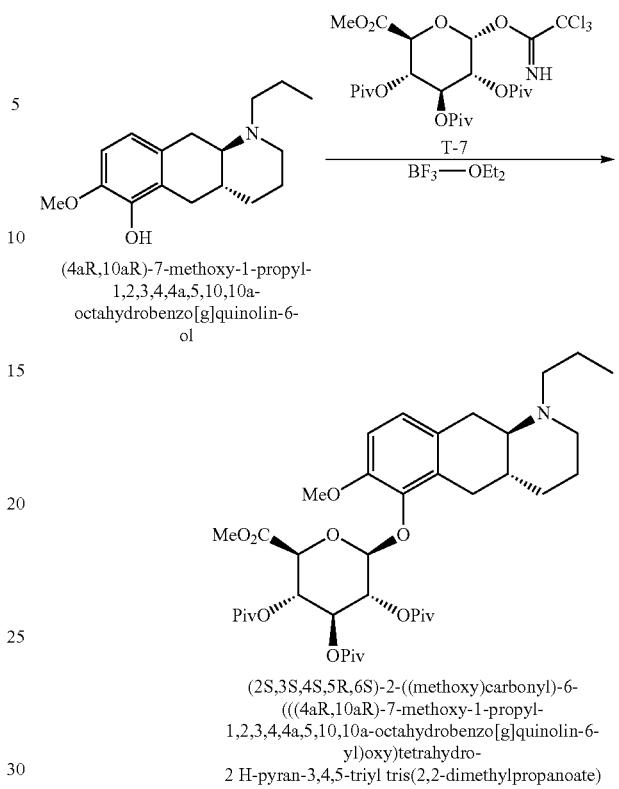

(4aR,10aR)-7-methoxy-1-propyl-1,2,3,4,4a,5,10,10a-octahydrobenzo[g]quinolin-6-ol (2S,3S,4S,5R,6S)-2-((methoxy)carbonyl)-6-(((4aR,10aR)-7-methoxy-1-propyl-1,2,3,4,4a,5,10,10a-octahydrobenzo[g]quinolin-6-yl)oxy)tetrahydro-2H-pyran-3,4,5-triyl tris(2,2-dimethylpropanoate)

Compound (22): (2S,3S,4S,5R,6S)-2-((methoxy)carbonyl)-6-(((4aR,10aR)-7-methoxy-1-propyl-1,2,3,4,4a,5,10,10a-octahydrobenzo[g]quinolin-6-yl)oxy)tetrahydro-2H-pyran-3,4,5-triyl tris(2,2-dimethylpropanoate)

To a stirred solution of (4aR,10aR)-7-methoxy-1-propyl-1,2,3,4,4a,5,10,10a-octahydrobenzo[g]quinolin-6-ol (1 g) in DCM (100 mL) was added (2S,3S,4S,5R,6R)-2-(methoxycarbonyl)-6-(2,2,2-trichloro-1-iminoethoxy)tetrahydro-2H-pyran-3,4,5-triyl tris(2,2-dimethylpropanoate) (T-7; prepared as described in Bioorg. Med. Chem. Lett. 9 (1999) 659-662; 4.39 g) and BF$_3$-Et$_2$O (0.9 mL) at −10° C. The crude mixture was stirred at room temperature for 3 hours. The crude mixture was partitioned between saturated aqueous NaHCO$_3$ (100 mL) and EtOAc (200 mL×2). The combined organic layers were washed with brine (200 mL), dried over Na$_2$SO$_4$, filtered, and concentrated. The residue was purified by prep-HPLC using a Shimadzu LC20AP instrument (Phenomenex Luna C18 250×50 mm, 10 μm particles column operated at RT with 80 mL/min of a gradient of water+0.225% formic acid (A) and MeCN (B): 0-20 min 40-70% B; 20.1-25 min 100% B; 25.1-30 min 40% B) to afford the title compound (0.2 g).

$^1$H NMR: (400 MHz d6-DMSO) δ 6.80-6.92 (m, 2H), 5.42-5.57 (m, 2H), 4.96-5.14 (m, 2H), 4.50 (d, J=10.0 Hz, 1H), 3.74 (s, 3H), 3.55 (s, 3H), 3.24 (d, J=4.8 Hz, 1H), 3.20 (d, J=4.4 Hz, 1H), 3.12 (dd, J=4.4, 16.0 Hz, 1H), 2.92 (d, J=10.8 Hz, 1H), 2.67 (d, J=4.4 Hz, 1H), 2.24-2.46 (m, 2H), 1.97-2.21 (m, 3H), 1.80 (d, J=10.2 Hz, 1H), 1.60-1.69 (m, 1H), 1.27-1.59 (m, 4H), 1.12 (s, 9H), 1.06 (broad s, 18H), 0.84 (t, J=7.2 Hz, 3H).

QC-LCMS: (method AB10), retention time=3.20 minutes, [M+H]$^+$=718.4 m/z.

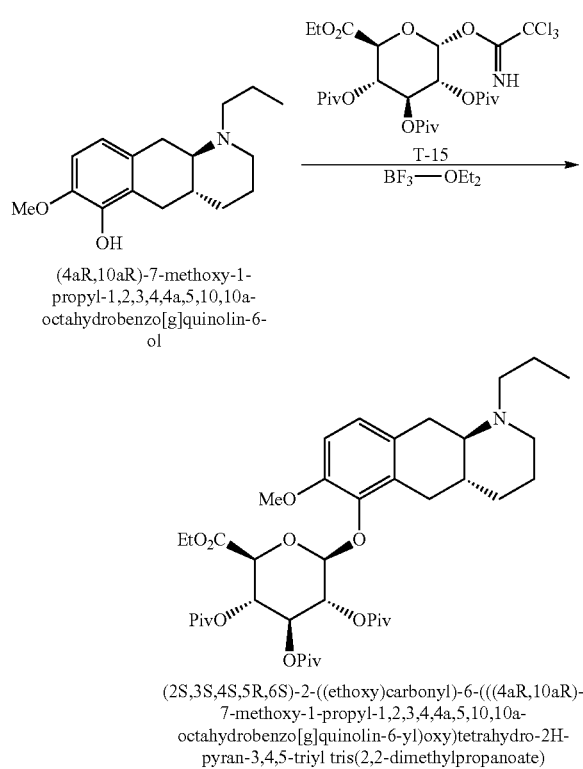

(4aR,10aR)-7-methoxy-1-propyl-1,2,3,4,4a,5,10,10a-octahydrobenzo[g]quinolin-6-ol (2S,3S,4S,5R,6S)-2-((ethoxy)carbonyl)-6-(((4aR,10aR)-7-methoxy-1-propyl-1,2,3,4,4a,5,10,10a-octahydrobenzo[g]quinolin-6-yl)oxy)tetrahydro-2H-pyran-3,4,5-triyl tris(2,2-dimethylpropanoate)

Compound (23): (2S,3S,4S,5R,6S)-2-((ethoxy)carbonyl)-6-(((4aR,10aR)-7-methoxy-1-propyl-1,2,3,4,4a,5,10,10a-octahydrobenzo[g]quinolin-6-yl)oxy)tetrahydro-2H-pyran-3,4,5-triyl tris(2,2-dimethylpropanoate)

To a solution of (4aR,10aR)-7-methoxy-1-propyl-1,2,3,4,4a,5,10,10a-octahydrobenzo[g]quinolin-6-ol (1.00 g) and (2S,3S,4S,5R,6R)-2-(ethoxycarbonyl)-6-(2,2,2-trichloro-1-iminoethoxy)tetrahydro-2H-pyran-3,4,5-triyl tris(2,2-dimethylpropanoate) (T-15; prepared in similar manner as T-1 described in Advances in Chemical Engineering and Science, 2012, 2, 379-383; 4.49 g) in DCM (100 mL) was added BF$_3$-Et$_2$O (0.9 mL) at −10° C. The mixture was stirred at room temperature for 1 hour, before it was partitioned between saturated aqueous NaHCO$_3$ (100 mL) and DCM (50 mL×2). The combined organic layers were washed with brine (50 mL), dried over Na$_2$SO$_4$, filtered, and concentrated. The residue was purified by prep-HPLC using an Agela FL-H600G instrument (Phenomenex Luna C18 250× 100 mm, 10 μm particles column operated at room temperature with 250 mL/min of a gradient of water+0.225% formic acid (A) and MeCN (B): 0-20 min 50-70% B; 20.1-25 min 100% B; 25.1-30 min 50% B) to afford 1.2 g of the title compound. 0.5 g of this material was purified by prep-HPLC using a GX281 instrument (Waters Xbridge C18 150×25 mm, 5 μm particles column operated at room temperature with 25 mL/min of a gradient of water+0.225% formic acid (A) and MeCN (B): 0-13 min 40-75% B; 13.1-16 min 100% B; 16.1-19 min 40% B) to afford the title compound (250 mg).

1H NMR: (400 MHz CDCl3) δ 6.79 (d, J=8.4 Hz, 1H), 6.67 (d, J=8.4 Hz, 1H), 5.37 (t, J=9.2 Hz, 1H), 5.20-5.27 (m, 3H), 4.08-4.16 (m, 1H), 3.96-4.03 (m, 1H), 3.86 (d, J=9.6 Hz, 1H), 3.72 (s, 3H), 3.34-3.39 (m, 1H), 3.24 (d, J=10.8 Hz, 1H), 3.06 (d, J=4.4 Hz, 2H), 2.90-2.95 (m, 1H), 2.78 (br s, 1H), 2.52 (d, J=10.0 Hz, 2H), 2.13-2.20 (m, 1H), 1.97-2.08 (m, 3H), 1.75 (br d, J=14.0 Hz, 1H), 1.54-1.69 (m, 2H), 1.17 (t, J=7.2 Hz, 4H), 1.12 (s, 9H), 1.06 (s, 9H), 1.05 (s, 9H), 0.90 (t, J=7.2 Hz, 3H).

QC-LCMS: (method DELIVER-K-1), retention time=2.02 minutes, [M+H]$^+$=732.4 m/z, 98.5% purity.

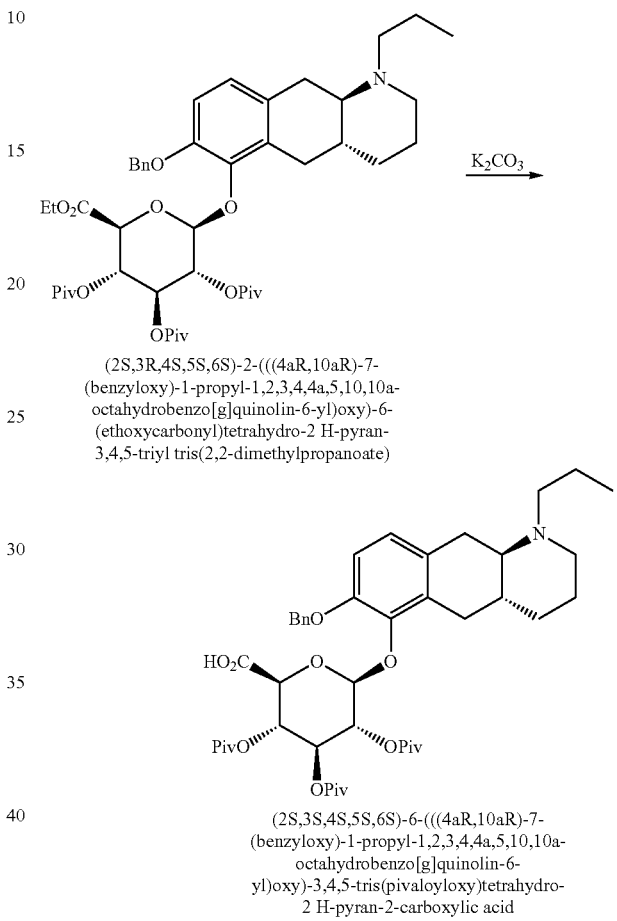

(2S,3R,4S,5S,6S)-2-(((4aR,10aR)-7-(benzyloxy)-1-propyl-1,2,3,4,4a,5,10,10a-octahydrobenzo[g]quinolin-6-yl)oxy)-6-(ethoxycarbonyl)tetrahydro-2H-pyran-3,4,5-triyl tris(2,2-dimethylpropanoate)

(2S,3S,4S,5S,6S)-6-(((4aR,10aR)-7-(benzyloxy)-1-propyl-1,2,3,4,4a,5,10,10a-octahydrobenzo[g]quinolin-6-yl)oxy)-3,4,5-tris(pivaloyloxy)tetrahydro-2H-pyran-2-carboxylic acid Compound (24): (2S,3S,4S,5R,6S)-6-(((4aR,10aR)-7-(benzyloxy)-1-propyl-1,2,3,4,4a,5,10,10a-octahydrobenzo[g]quinolin-6-yl)oxy)-3,4,5-tris(pivaloyloxy)tetrahydro-2H-pyran-2-carboxylic acid To a solution of (2S,3R,4S,5S,6S)-2-(((4aR,10aR)-7-(benzyloxy)-1-propyl-1,2,3,4,4a,5,10,10a-octahydrobenzo[g]quinolin-6-yl)oxy)-6-(ethoxycarbonyl)tetrahydro-2H-pyran-3,4,5-triyl tris(2,2-dimethylpropanoate) (compound 13) (1.00 g) in MeOH (20 mL) was added 20% aqueous K$_2$CO$_3$ (5 mL). The mixture was stirred at room temperature for 2 hours, before it was purified by prep-HPLC using a Shimadzu LC20AP instrument (Phenomenex Luna C18 250×50 mm, 10 μm particles column operated at RT with 80 mL/min of a gradient of water+0.225% formic acid (A) and MeCN (B): 0-20 min 30-65% B; 20.1-25 min 100% B; 25.1-30 min 30% B) to afford the title compound (0.50 g).

$^1$H NMR: (400 MHz CDCl$_3$) δ 7.27-7.45 (m, 5H), 6.83 (d, J=8.8 Hz, 1H), 6.74 (d, J=8.4 Hz, 1H), 5.23-5.33 (m, 3H), 5.06-5.05 (m, 3H), 3.47-3.63 (m, 1H), 3.20-3.43 (m, 4H), 2.92-2.97 (m, 1H), 2.60-2.87 (m, 4H), 2.12-2.25 (m, 2H), 1.86-2.01 (m, 2H), 1.81 (br d, J=14.0 Hz, 1H), 1.36-1.60 (m, 2H), 1.12-1.22 (m, 1H), 1.09 (s, 9H) 1.06 (s, 9H), 0.96 (s, 9H), 0.95 (t, J=7.2 Hz, 3H).

QC-LC-MS: (method: AB25), retention time=2.79 minutes, [M+H]$^+$=780.3 m/z.

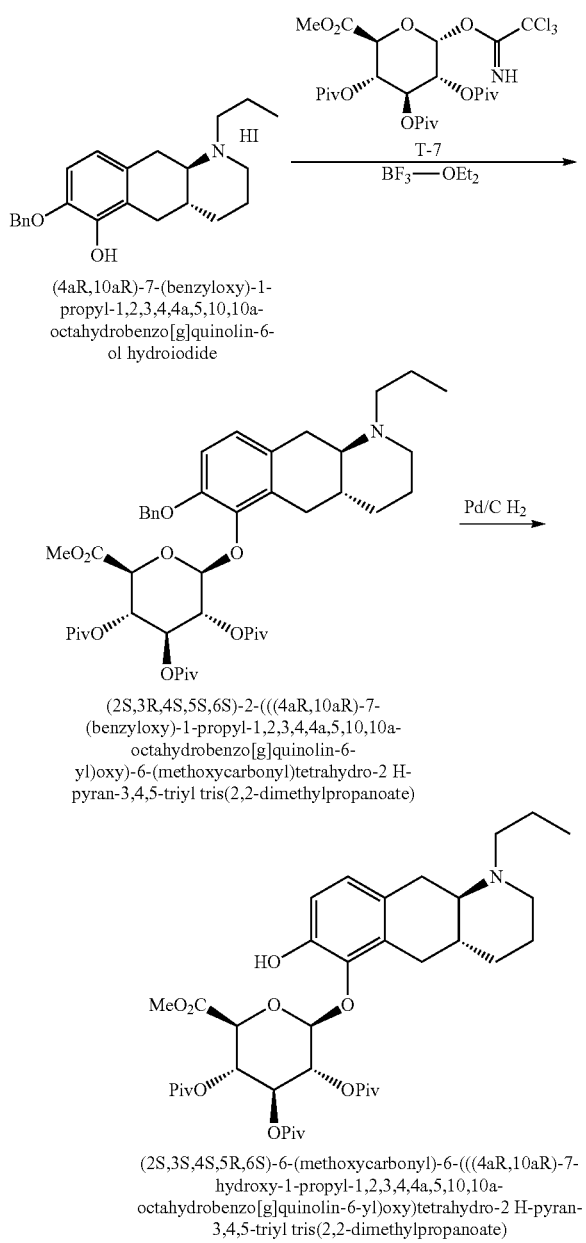

(4aR,10aR)-7-(benzyloxy)-1-propyl-1,2,3,4,4a,5,10,10a-octahydrobenzo[g]quinolin-6-ol hydroiodide (2S,3R,4S,5S,6S)-2-(((4aR,10aR)-7-(benzyloxy)-1-propyl-1,2,3,4,4a,5,10,10a-octahydrobenzo[g]quinolin-6-yl)oxy)-6-(methoxycarbonyl)tetrahydro-2 H-pyran-3,4,5-triyl tris(2,2-dimethylpropanoate)

(2S,3S,4S,5R,6S)-6-(methoxycarbonyl)-6-(((4aR,10aR)-7-hydroxy-1-propyl-1,2,3,4,4a,5,10,10a-octahydrobenzo[g]quinolin-6-yl)oxy)tetrahydro-2 H-pyran-3,4,5-triyl tris(2,2-dimethylpropanoate)

Compound (25): (2S,3R,4S,5S,6S)-2-(((4aR,10aR)-7-(benzyloxy)-1-propyl-1,2,3,4,4a,5,10,10a-octahydrobenzo[g]quinolin-6-yl)oxy)-6-(methoxycarbonyl)tetrahydro-2H-pyran-3,4,5-triyl tris(2,2-dimethylpropanoate)

To a stirred mixture of (4aR,10aR)-7-(benzyloxy)-1-propyl-1,2,3,4,4a,5,10,10a-octahydrobenzo[g]quinolin-6-ol hydroiodide (2 g), 4 Å MS (2 g) and (2S,3S,4S,5R,6R)-2-(methoxycarbonyl)-6-(2,2,2-trichloro-1-iminoethoxy)tetrahydro-2H-pyran-3,4,5-triyl tris(2,2-dimethylpropanoate) (T-7; prepared as described in Bioorg. Med. Chem. Lett. 9 (1999) 659-662; 5.16 g) in DCM (200 mL) was added BF$_3$-Et$_2$O (1.05 mL) drop-wise at −10° C. The mixture was stirred at room temperature for 2 hours, before it was partitioned between saturated aqueous NaHCO$_3$ (200 mL) and DCM (100 mL×2). The combined organic layers were dried over Na$_2$SO$_4$, filtered, and concentrated. The residue was purified by prep-HPLC using a Shimadzu LC20AP instrument (Phenomenex Luna C18 250×50 mm, 10 μm particles column operated at room temperature with 80 mL/min of a gradient of water+0.225% formic acid (A) and MeCN (B): 0-20 min 45-75% B; 20.1-25 min 100% B; 25.1-30 min 45% B) to afford the title compound (1.25 g).

$^1$H NMR: (400 MHz CDCl$_3$) δ 7.34-7.48 (m, 5H), 6.83 (s, 2H), 5.09-5.32 (m, 6H), 3.64-3.75 (m, 4H), 3.22-3.31 (m, 3H), 3.01-3.31 (m, 3H), 2.73-2.97 (m, 2H), 2.12-2.43 (m, 3H), 1.41-1.98 (m, 4H), 1.19-1.34 (m, 1H), 1.13-1.15 (m, 18H), 1.08 (s, 9H), 1.03 (t, J=7.2 Hz, 3H).

QC-LC-MS: (method DELIVER-K-1), retention time=2.09 minutes, [M+H]$^+$=794.4 m/z.

Compound (26): (2S,3S,4S,5R,6S)-2-(methoxycarbonyl)-6-(((4aR,10aR)-7-hydroxy-1-propyl-1,2,3,4,4a,5,10,10a-octahydrobenzo[g]quinolin-6-yl)oxy)tetrahydro-2H-pyran-3,4,5-triyl tris(2,2-dimethylpropanoate)

To a mixture of Pd/C (4 g, 50%) in THF (20 mL) was added (2S,3R,4S,5S,6S)-2-(((4aR,10aR)-7-(benzyloxy)-1-propyl-1,2,3,4,4a,5,10,10a-octahydrobenzo[g]quinolin-6-yl)oxy)-6-(methoxycarbonyl)tetrahydro-2H-pyran-3,4,5-triyl tris(2,2-dimethylpropanoate) (1 g) under N2. The suspension was degassed under vacuum and purged with H2. The mixture was stirred under H$_2$ (30 psi) at room temperature for 12 hours, before the catalyst was filtered off. The filtrate was concentrated and purified by prep-HPLC using GX281 instrument (Phenomenex Luna C18 100×30 mm, 5 μm particles column operated at room temperature with 25 mL/min of a gradient of water+0.225% formic acid (A) and MeCN (B): 0-15 min 30-60% B; 15.1-17 min 100% B; 17.1-20 min 30% B) to afford the title compound (200 mg).

$^1$H NMR: (400 MHz d6-DMSO) δ 9.27 (s, 1H), 6.65-6.78 (m, 2H), 5.47-5.58 (m, 2H), 5.14 (dd, J=9.6, 8.0 Hz, 1H), 5.04 (t, J=9.6 Hz, 1H), 4.55 (d, J=10.0 Hz, 1H), 3.57 (s, 3H), 3.24 (dd, J=4.8, 17.6 Hz, 2H), 3.15 (d, J=10.4 Hz, 2H), 2.90 (s, 1H), 2.67 (s, 2H), 2.12 (dd, J=11.6, 17.2 Hz, 1H), 1.44-1.89 (m, 6H), 1.17-1.30 (m, 2H), 1.14 (s, 9H), 1.07 (m, 18H), 0.89 (t, J=7.2 Hz, 3H).

QC-LC-MS: (method AB01), retention time=3.33 minutes, [M+H]$^+$=704.3 m/z.

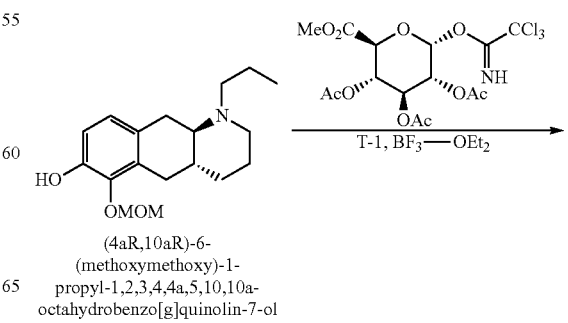

(4aR,10aR)-6-(methoxymethoxy)-1-propyl-1,2,3,4,4a,5,10,10a-octahydrobenzo[g]quinolin-7-ol -continued

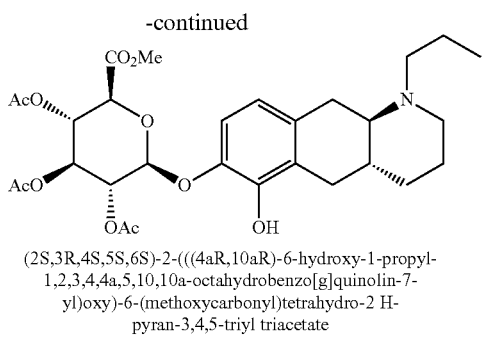

(2S,3R,4S,5S,6S)-2-(((4aR,10aR)-6-hydroxy-1-propyl-1,2,3,4,4a,5,10,10a-octahydrobenzo[g]quinolin-7-yl)oxy)-6-(methoxycarbonyl)tetrahydro-2 H-pyran-3,4,5-triyl triacetate Compound (27): (2S,3R,4S,5S,6S)-2-(((4aR,10aR)-6-hydroxy-1-propyl-1,2,3,4,4a,5,10,10a-octahydrobenzo[g]quinolin-7-yl)oxy)-6-(methoxycarbonyl)tetrahydro-2H-pyran-3,4,5-triyl triacetate To a solution of (4aR,10aR)-6-(methoxymethoxy)-1-propyl-1,2,3,4,4a,5,10,10a-octahydrobenzo[g]quinolin-7-ol (1.0 g), (2S,3S,4S,5R,6R)-2-(methoxycarbonyl)-6-(2,2,2-trichloro-1-iminoethoxy)tetrahydro-2H-pyran-3,4,5-triyl triacetate (T-1; prepared as described in Advances in Chemical Engineering and Science, 2012, 2, 379-383, 3.13 g) and 4 Å MS (1.0 g) in DCM (100 mL) was added $BF_3$-$Et_2O$ (0.81 mL) drop-wise at −10-0° C. The mixture was stirred at room temperature for 2 hours, before it was partitioned between saturated aqueous $NaHCO_3$ (200 mL) and DCM (200 mL×3). The combined organic layers were washed with brine (300 mL), dried over $Na_2SO_4$, filtered, and concentrated. The residue was purified by prep-HPLC using a Agela FI-H600G instrument (Phenomenex Luna C18 250*100 mm, 10 μm particles column operated at room temperature with 250 mL/min of a gradient of water+ 0.225% formic acid (A) and MeCN (B): 0-25 min 50-80% B; 25.1-30 min 100% B; 30.1-35 min 50% B) to afford the title compound (0.2 g).

$^1$H NMR: 400 MHz $CDCl_3$: δ 6.77 (d, J=8.4 Hz, 1H), 6.60 (d, J=8.4 Hz, 1H), 5.24-5.38 (m, 3H), 4.96 (d, J=7.2 Hz, 1H), 4.14 (d, J=9.2 Hz, 1H), 3.77 (s, 3H), 3.33 (d, J=10.4 Hz, 1H), 2.94-3.18 (m, 4H), 2.85-2.87 (m, 1H), 2.59 (s, 2H), 2.19-2.27 (m, 3H), 2.12 (s, 3H), 2.06 (d, J=3.2 Hz, 6H), 2.02 (s, 1H), 1.81 (d, J=12.4 Hz, 1H), 1.61-1.71 (m, 3H), 1.23-1.26 (m, 1H), 0.98 (t, J=7.2 Hz, 3H).

QC-LCMS: (method DELIVER-K), retention time=1.54 minutes, [M+H]$^+$=578.2 m/z.

In Vitro and In Vivo Characterization of Compounds of the Invention

Example 1: Conversion of Compounds of the Invention in Human Plasma and Hepatocytes Example 1a: Conversion of Compounds of the Invention in Human Plasma Frozen human plasma was thawed and then centrifuged at 3200×g for 5 min to remove debris. The pH value of the supernatant was then measured and adjusted to 7.4±0.1 by adding 1% phosphoric acid or 1 N sodium hydroxide. 2 μL of dosing solution (50 μM for test compounds and 100 μM for positive control (propantheline bromide)) was mixed with 98 μL of blank plasma to achieve 1 μM test compound and 2 μM positive control of final concentration. The mixture was incubated, and samples were withdrawn from the incubations at the pre-determined time points of 0, 0.5, 1, 2, 4 and 6 hr (in duplicate) at 37° C. in water bath. At each corresponding time point 10 μL inhibitor and 20 μL ascorbic acid and 2 μL formic acid (20%) are added, and then added 400 μL of "stop solution" (200 ng/mL tolbutamide plus 200 ng/mL labetalol in 50% ACN/MeOH) to precipitate protein. The substance was mixed thoroughly and thereafter Centrifugated at 4,000 rpm for 20 minutes. Then an aliquot of supernatant (50 μL) was transferred from each well to a sample plate and mixed with 100 μL ultrapure water. The plate was shaked at 800 rpm for about 10 minutes before submitting to LC-MS/MS analysis.

Example 1b: Conversion of Compounds of the Invention in Human Hepatocytes

Incubations were conducted in 96-well plates at 1 μM compound concentration in duplicate. The hepatocyte cell concentration was 0.5×106 cells/mL used for final incubation at 37° C. in an incubator of 5% $CO_2$ 95% relative humidity. The medium control samples were included at 0 and 60 minutes in the absence of cells. The total organic concentration was 1% (DMSO 0.1%) in the final incubation. The controls, (7-ethoxycoumarin and 7-hydroxycoumarin) was incubated parallel at 3 μM. 2 μL of dosing solution (50 μM for test compounds and 100 μM for positive control) was mixed with 98 μL of 100 mM PBS to achieve 1 μM test compound and 2 μM positive control of final concentration. The mixture was incubated, and samples were withdrawn from the incubations at pre-determined time points of 0, 0.5, 1, 2, 4 and 6 hr (in duplicate) at 37° C. in water bath. To each sample, 10 μL inhibitor and 20 μL ascorbic acid and 2 μL formic acid (20%) were added followed by 400 μL of stop solution (200 ng/mL tolbutamide plus 200 ng/mL labetalol in 50% ACN/MeOH). The substance was mixed thoroughly and thereafter centrifuged at 4,000 rpm for 20 minutes. An aliquot of supernatant (50 μL) from each well were transferred to a sample plate and mixed with 100 μL ultrapure water. The plate was shaked at 800 rpm for about 10 minutes before submitting to LC-MS/MS analysis.

Instrumentation Used for Analysis of Plasma and Hepatocyte Incubation Samples

Mass spectrometer (LC-MS/MS) Shimadzu LC 20-AD Shimadzu UHPLC API 4000. Analytical column ACQUITY UPLC® BEH Phenyl 1.7 μm 2.1×50 mm. Mobile phase A: 0.1% Formic Acid in Water. Mobile phase B: 0.1% Formic Acid in Acetonitrile. Gradient run from 95/5% to 5/95 in 2.0 min. Flow rate 0.7 mL/min. MRM monitoring (multiple reaction monitoring) of test item and the added analytical standards (Labetalol or Tolbutamide).

Example 1c: Conversion of the Compounds (Id-ia), (Id-ib) and (Id-iab) in Rat and Human Hepatocytes The compounds were incubated separately at 1 μg/mL with hepatocytes from human or rat suspended in DMEM (Dulbecco's Modified Eagle Medium) with HEPES (4-(2-hydroxyethyl)-1-piperazineethanesulfonic acid) at pH 7.4. The cell concentration at incubation was 1×10$^6$ viable cells/mL. The incubations were performed in glass tubes at 37° C. with a total incubation volume of 3.5 mL and with duplicate incubations for each test item. The 3.5 mL of hepatocyte suspension was equilibrated for 10 minutes in a water bath set to 37° C. where after the incubations were initiated by adding 3.5 μL of a stock solution of the test item in DMSO (Dimethyl sulfoxide) and gently inverting the tubes. The final solvent concentration in the incubations was 0.1% DMSO. Samples of 600 μL were withdrawn from the incubations at the pre-determined time points of 0.25, 5, 15, 30 and 60 minutes after ensuring homogeneity of hepatocyte suspensions. The withdrawn volume was added to 1 mL Nunc cryo tubes on wet ice containing 60 μL of ice cold ascorbic acid (100 mg/mL) and 30 μL of ice cold 100 mM saccharic acid 1,4-lactone in 0.5 M citric acid. The tubes were mixed and 35 μL of a solution of ice cold 20% formic acid was added. The tubes were mixed thoroughly and stored at −80° C. awaiting analysis. Analysis method and Instrumentation used for analysis of (I) from dosing (Id-ia), (Id-ib), and (Id-iab), were the one described in Examples 3 in the section "Instrumentation used for analysis of compound (I) from dosing of compounds (Ic), (Id-ia), (Id-ib), (Id-iab), compound (2), compound (9), compound (15), compound (27), A2 and A7."

Analysis method and Instrumentation used for analysis of (I) from dosing (Id-iab) consisted of mixing equal aliquots of the samples and precipitation solution (acetonitrile (MeCN) with 10% methanol (MeOH) and 1% formic acid), followed by centrifugation at 4° C. at 16000 g for 10 minutes. Supernatants were collected and analysed by LC-MS/MS. Mass spectrometer: Waters Acquity—Waters Xevo TQ-MS. Analytical column: Acquity UPLC HSS T3, 100× 2.1 mm, 1.8 μm. Mobile phase A: 0.2% formic acid in water. Mobile phase B: 0.2% formic acid in acetonitrile. Gradient run from 95/5% to 60/40 in 5 minutes. Flow rate 0.3 mL/min. MRM monitoring of (I) in the study samples and in the analytical standards.

Example 1d: Conversion of the Compounds (Id-Ia) and (Id-Ib) in Fresh Rat and Human Blood Conversion of (Id-ia) and (Id-ib) in human blood (average of 3 donors) and rat blood (average of 45 donors) to (I) was shown in fresh blood at 37° C. spiked with 1 μg/mL of (Id-ia), (Id-ib), and (Id-iab) separately, (I) was measured at 0, 5, 15, 30 and 60 minutes in isolated plasma. Analysis method and Instrumentation as described in Examples 3 in the section "Instrumentation used for analysis of compound (I) from dosing of compounds (Ic), (Id-ia), (Id-ib), (Id-iab), compound (2), compound (9), compound (15), compound (27), A2 and A7".

Example 2: 5-HT2B Agonist Activity and Binding Assay

5-HT2B Agonist Activity Assay

Evaluation of the agonist activity of compounds (I), (Ia), (Ib), (Ic), (Ia-iab), compound (2), compound (9), compound (15), compound (27), A2, A3, and A7 at the human 5-HT2B receptor was performed by Eurofins/Cerep (France) measuring the compound effects on inositol monophosphate (IP1) production using the HTRF detection method. Briefly, the human 5-HT2B receptor was expressed in transfected CHO cells. The cells were suspended in a buffer containing 10 mM Hepes/NaOH (pH 7.4), 4.2 mM KCl, 146 mM NaCl, 1 mM $CaCl_2$, 0.5 mM MgCl2, 5.5 mM glucose and 50 mM LiCl, then distributed in microplates at a density of 4100 cells/well and incubated for 30 minutes at 37° C. in the presence of buffer (basal control), test compound or reference agonist. For stimulated control measurement, separate assay wells contained 1 μM 5-HT. Following incubation, the cells were lysed and the fluorescence acceptor (fluorophen D2-labeled IP1) and fluorescence donor (anti-IP1 antibody labeled with europium cryptate) were added. After 60 minutes at room temperature, the fluorescence transfer was measured at lambda(Ex) 337 nm and lambda(Em) 620 and 665 nm using a microplate reader (Rubystar, BMG). The IP1 concentration was determined by dividing the signal measured at 665 nm by that measured at 620 nm (ratio). The results were expressed as a percent of the control response to 1 μM 5-HT. The standard reference agonist was 5-HT, which was tested in each experiment at several concentrations to generate a concentration-response curve from which its EC50 value is calculated as described above for dopamine functional assays.

5-HT2B Binding Assay

Evaluation of the affinity of said compounds for the human 5-HT2B receptor was determined in a radioligand binding assay at Eurofins/Cerep (France). Membrane homogenates prepared from CHO cells expressing the human 5HT2B receptor were incubated for 60 min at room temperature with 0.2 nM [125I](±)DOI (1-(4-iodo-2,5-dimethoxyphenyl)propan-2-amine) in the absence or presence of the test compound in a buffer containing 50 mM Tris-HCl (pH 7.4), 5 mM $MgCl_2$, 10 μM pargyline and 0.1% ascorbic acid. Nonspecific binding is determined in the presence of 1 μM (±)DOI. Following incubation, the samples were filtered rapidly under vacuum through glass fiber filters (GF/B, Packard) presoaked with 0.3% polyethyleneimine (PEI) and rinsed several times with ice-cold 50 mM Tris-HCl using a 96-sample cell harvester (Unifilter, Packard). The filters were dried and counted for radioactivity in a scintillation counter (Topcount, Packard) using a scintillation cocktail (Microscint 0, Packard). The results are expressed as a percent inhibition of the control radioligand specific binding. The standard reference compound was (±)DOI, which was tested in each experiment at several concentrations to obtain a competition curve from which its $IC_{50}$ is calculated.

TABLE 3

In vitro activities for the compounds of the invention obtained according to Examples 2 and 3

|  | Compound | 5-HT2B $EC_{50}$ (nM)/Emax |
|---|---|---|
| Parent compound | (I) | 2900 nM/50% |
| Prodrugs in the state of the art | (Ia) | >6000 nM, 58% @ 30 uM |
|  | (Ib) | 3.8 nM/79% |
|  | (Ic) | −5% @ 10 μM |
| Compounds (Id-ia, Id-ib and Id-iab) | (Id-ia) | −25% @ 10 μM* |
|  | (Id-ib) | −39% @ 10 μM* |
|  | (Id-iab) | 17% @ 10 μM* |
| Compounds of the invention | Compound (2) | 10% @ 10 μM |
|  | Compound (9) | 9% @ 10 μM |
|  | Compound (15) | 0% @ 10 μM |
|  | Compound (27) | 2% @ 10 μM |
|  | A2 | 30% @ 10 μM |
|  | A3 | 3% @ 10 μM |
|  | A7 | 27% @ 10 μM |

*indicate binding affinity (% inhibition of control, specific binding at concentration indicated)
nd: not determined Example 3: PK Experiments in Rats For all the experiments, blood samples of approximately 0.68 mL were drawn from the tail or sublingual vein and put into $K_3$EDTA tubes that had been pre-cooled and prepared with stabilizing solution consisting of 80 μL ascorbic acid and 40 μL 100 mM D-saccharic acid 1,4 lactone in water. The tubes were inverted gently 6-8 times to ensure thorough mixing and then placed in wet ice. The collecting tube was placed in wet ice for up to 30 minutes until centrifugation. Once removed from the wet ice the centrifugation was initiated immediately. Immediately after end of centrifugation the samples were returned to wet ice. Three sub-samples of 130 μL plasma were transferred to each of three appropriately labelled cryo tubes containing 6.5 μL pre-cooled formic acid (20%) (the tubes were pre-spiked and stored refrigerated prior to use). The tube lid was immediately replaced, and the plasma solution was thoroughly mixed by inverting gently 6-8 times. The samples were stored frozen at nominally −70° C. within 60 minutes after sampling. Centrifugation conditions at 3000 G for 10 minutes at 4° C. Plasma was placed on water-ice following collection. Final storage at approximately −70° C.

Plasma samples were analyzed by solid phase extraction or direct protein precipitation followed by UPLC-MS/MS. MS detection using electrospray in the positive ion mode with monitoring of specific mass-to-charge transitions for compound (I) using internal standards for correcting the response. The concentration-time data was analyzed, using standard software using appropriate noncompartmental techniques to obtain estimates of the derived PK parameters.

Instrumentation Used for Analysis of Compound (I) from Dosing Compound (Ia):

Mass spectrometer (LC-MS/MS) Waters Acquity-Sciex API 5000. Analytical column Waters BEH UPLC Phenyl 100×2.1 mm column, 1.7 μm particle size. Mobile phase A: 20 mM ammonium formate (aq)+0.5% formic acid. Mobile phase B: Acetonitrile. Gradient run from 95/5% to 2/98 in 6.1 minutes. Flow rate 0.5 mL/min. MRM monitoring (multiple reaction monitoring) of test item and the added analytical standards Dosing and blood sampling: Han Wistar rats were supplied by Charles River Laboratories, Sulzfeld, Germany. An artificial, automatically controlled, light and dark cycle of 12 hours was maintained. The rats received a standard laboratory diet from Brogaarden (Altromin 1324 pellets). The rats had unrestricted access to the diet. During the study (a 4-week toxicity study) the rats received once daily doses of (Ia) orally by gavage. From rats given 300 μg/kg (Ia), blood samples) from 3 male satellite animals were collected on the following time points at Day 29: 0.5, 1, 2, 4, 6, 8, 12 and 24 hours after dosing.

Instrumentation Used for Analysis of Compound (I) from Dosing of Compound (Ib):

Mass spectrometer (LC-MS/MS) Waters Acquity-Sciex API 5000. Analytical column Waters BEH UPLC Phenyl 100×2.1 mm column, 1.7 μm particle size. Mobile phase A: 20 mM ammonium formate (aq)+0.5% formic acid. Mobile phase B: Acetonitrile. Gradient run from 95/5% to 2/98 in 6.1 minutes. Flow rate 0.5 mL/min. MRM monitoring of test item and the added analytical standards.

Dosing and blood sampling: Han Wistar rats were supplied by Charles River Laboratories, UK. An artificial, automatically controlled, light and dark cycle of 12 hours was maintained. The rats received a standard laboratory diet (Teklad 2014C Diet.). The rats had unrestricted access to the diet. During the study (a 26-week toxicity study) the rats received once daily doses of (Ib) orally by gavage. From rats given 300 μg/kg (Ib), blood samples from 3 male satellite animals were collected on the following time points at day 182: 0.5, 1, 2, 4, 8 and 24 hours after dosing.

Instrumentation Used for Analysis of Compound (I) from Dosing of Compounds (Ic), (Id-ia), (Id-ib), (Id-iab), Compound (2), Compound (9), Compound (15), Compound (27), A2 and A7:

Mass spectrometer (LC-MS/MS) Waters Acquity—Waters Xevo TO-S. Analytical column Acquity BEH C18 100×2.1 mm, 1.7 μm. Mobile phase A: 20 mM $NH_4$-Formate+0.2% formic acid. Mobile phase B: Acetonitrile+ 0.2% formic acid. Gradient run from 95/5% to 5/95% in 11.0 minutes. Flow rate 0.3 mL/min. MRM monitoring of test item and the added analytical standards.

Dosing and blood sampling for compounds (Id-ia) and (Id-ib): Han Wistar rats were supplied by Charles River Laboratories, Wiga GmbH, Germany. An artificial, automatically controlled, light and dark cycle of 12 hours was maintained. The rats received a standard laboratory diet from Brogaarden (Altromin 1324 pellets). The rats had unrestricted access to the diet. Male Han Wistar rats were dosed a single oral gavage administration of (Id-ia) and (Id-ib), respectively, orally by gavage. Rats were given 633 μg/kg (Id-ia) or (Id-ib), blood samples from 3 male animals were collected on the following time points at Day 1: 0.5, 1, 2, 4, 6, 8, and 24 hours after dosing.

Dosing and blood sampling for compounds (Ic), (Id-iab), compound (2), compound (9), compound (15), compound (27), A2 and A7: Han Wistar rats were supplied by Envigo, UK. An artificial, automatically controlled, light and dark cycle of 12 hours was maintained. The rats received a standard laboratory diet Teklad 2014C. The rats had unrestricted access to the diet. Male Han Wistar rats were dosed a single oral gavage administration of (Ic), (Id-iab), compound (9), compound (2), compound (27), A7, A2 or compound (15) respectively, orally by gavage. Rats were given 793 μg/kg (Id-iab), 494 μg/kg (Ic), 664 μg/kg compound (2), 483 μg/kg compound (9), 665 μg/kg compound (27), 519 μg/kg compound (15), 359 μg/kg A7 and 551 μg/kg A2. Blood samples from 3 male animals were collected on the following time points at Day 1: 0.25, 0.5, 1, 2, 4, 8, and 24 hours after dosing Instrumentation Used for Analysis Apomorphine from Dosing Apomorphine:

Mass spectrometer (UPCLC-MS/MS) Waters Acquity I-Class-Waters Xevo TO-S. Analytical column Acquity HSS T3 C18 50×2.1 mm, 1.8 μm. Mobile phase A: 10 mM $NH_4$—Formate 0.2% formic acid:Acetonitril (95:5). Mobile phase B: 10 mM $NH_4$—Formate 0.2% formic acid:Acetonitril (5:95). Gradient run from 95/5% to 5/95% in 2.40 minutes. Flow rate 0.3 mL/min. MRM detection of test items and the added analytical standards Dosing and blood sampling: Han Wistar rats were supplied by Charles River Laboratories, Wiga GmbH, Germany. An artificial, automatically controlled, light and dark cycle of 12 hours was maintained. The rats received a standard laboratory diet from Brogaarden (Altromin 1324 pellets). The rats had unrestricted access to the diet. Male Han Wistar rats were administered a single dose of apomorphine subcutaneously. From rats administered 3000 μg/kg apomorphine blood samples from 3 male animals were collected on the following time points at Day 1: 0.25, 0.5, 1, 2, 4 and 6 hours SC administration.

TABLE 4

PK parameters for (4aR,10aR)-1-Propyl-1,2,3,4,4a,5,10,10a-octahydro-benzo[g]quinoline-6,7-diol (compound (I)) after oral dosing of 0.300 mg/kg (Ia), 0.300 mg/kg (Ib), 0.633 mg/kg of (Id-ia) 0.633 mg/kg of (Id-ib), 793 µg/kg (Id-iab), 494 µg/kg (Ic) 483 µg/kg compound (9), 664 µg/kg compound (2), 665 µg/kg compound (27), 519 µg/kg compound (15), 359 µg/kg A7 and 551 µg/kg A2 to Wistar rats according to Example 3

|  | compound | $T_{max}$ (h) | $C_{max}$ (pg/mL) | $AUC_{0-24}$ (pg * h/mL) | $t_{1/2}$ (h) | Exposure at 24 h (pg/mL) |
|---|---|---|---|---|---|---|
| Prodrugs in the state of the art | (Ia) | 1.0 | 3160 | 13600 | 4.09 | 48 ± 26 |
|  | (Ib) | 1.0 | 4990 | 31000 | N/A | 147 ± 28 |
|  | (Ic) | 1.0 | 14 | 104 | N/A | N/A |
| Compounds (Id-ia), Id-ib) and (Id-iab) | (Id-ia) | 4.0 | 1350 | 15500 | 6.8 | 208 ± 89 |
|  | (Id-ib) | 4.0 | 2150 | 21100 | 7.1 | 270 ± 112 |
|  | (Id-iab) | 4.0 | 964 | 18900 | N/A | 800 ± 244 |
| Compounds of the invention | Compound (2) | 8 | 178 | 2530 | nd | 55 ± 13.7 |
|  | Compound (9) | 4 | 942 | 11200 | nd | 181 ± 56.2 |
|  | Compound (15) | 8 | 548 | 6400 | nd | 111 ± 18.1 |
|  | compound (27) | 0.08 | 272 | 4660 | nd | 142 ± 66.3 |
|  | A7 | 8 | 77 | 1380 | nd | 39 ± 10 |
|  | A2 | 24 | 380 | 5590 | nd | 380 ± 230 |

Example 4: PK/PD of Compound (Id-ia)/Compound (I) in Rat Hyperactivity Assay Animals In total, 206 male CD rats (Charles River, Germany) weighing 200-250 grams (165-190 grams upon arrival) were used in the study. Animals were housed at a standard temperature (22±1° C.) and in a light-controlled environment (lights on from 7 am to 8 pm) with ad libitum access to food and water. The experiment described below was performed in accordance with the standard operating procedures of Charles River Discovery Research Services Finland Ltd. and in accordance with the national Animal Experiment Board of Finland (Elainkoelautakunta, ELLA) authority on animal testing.

Locomotor Activity Testing, Open Field

The test device is a square Plexiglass-arena (measuring 40×40×40 cm), in which the movement paths of the rats are recorded by an activity monitor (Med. Associates Inc.). Before the test period is initiated, rats are habituated to their test cage for 60 minutes. Upon completion of habituation, animals were treated with either compound or vehicle and placed back into the open field apparatus. The main test parameter measured is ambulatory distance (recorded in 5 minute segments). Overall time of measurement after receiving initial treatment was 360 minutes. Total follow up period in the study was 420 minutes, including 60 minutes of habituation.

Blood samples were taken and processed and analyzed as described under PK experiments in rats in Example 3.

Results

Oral administration of compound (Id-ia) was assessed in the rat locomotor activity assay, and this functional readout was then correlated to plasma concentrations of compound (I). Apomorphine and pramipexole were also concomitantly tested in this assay as comparators (i.e. known standard-of-care (SoC) in the Parkinson's Disease field), and plasma concentration was analyzed for apomorphine.

As shown in FIG. 3, compound (Id-ia) (10 to 300 µg/kg, p.o.) increases locomotor activity with an effect starting approximatively 2 hours' post-administration (around the 180-minute time point) and lasting until the end of recording (at the 415-minute time point). In contrary, the hyperactivity induced by apomorphine (3 mg/kg, s.c.) is immediate but short-lasting as the effect is gone 1.5 hours. post administration (at the 150-minute time point). Pramipexole (0.3 mg/kg, s.c.) also induces an increase in activity, but its effect appears about 1 hour post administration and is gone 2.5 hours later (at the 270-minute time point). The total distance travelled as seen in FIG. 4 demonstrates a significantly increased activity for both compound (Id-ia) and the two comparators tested, and this effect is the one that is to be expected from dopamine agonists.

In parallel with the locomotor activity assessment, plasma samples were taken from satellite animals at 6 different time points (0.5, 1, 2, 3, 4 & 6 hour's post-dose for animals treated with compound (Id-ia)). Pharmacokinetic analysis demonstrates that the behavioral effects of compound (Id-ia) (100 µg/kg, p.o.) correlate with the plasma concentrations of compound (I) (see FIG. 5), demonstrating that the behavioral effect of compound (Id-ia) is driven by Compound (I) rather than by Compound (Id-ia) itself. The corresponding exposure analysis of apomorphine (at 0.25, 0.5, 1, 2, 4, & 6 hour's post-dose) resulted in a correlation between plasma concentrations of apomorphine and hyperactive behavior (see FIG. 6).

The invention claimed is:

1. A compound according to formula (Id)

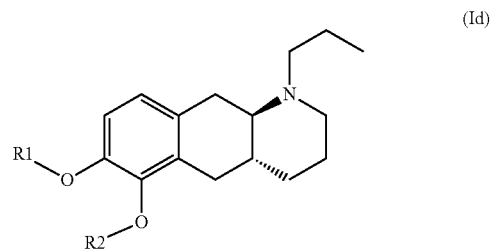

(Id)

wherein
a) R1 is selected from the group consisting of H, $C_1$-$C_6$ alkyl, methyl substituted with $C_3$-$C_6$ cycloalkyl, benzyl and —C(O)$C_1$-$C_6$ alkyl, and R2 is selected from the group consisting of the substituents (i) and (ii) below; or
b) R1 is selected from the group consisting of the substituents (i) and (ii) below and R2 is selected from the group consisting of H, $C_1$-$C_6$ alkyl, methyl substituted with $C_3$-$C_6$ cycloalkyl, benzyl and —C(O)$C_1$-$C_6$ alkyl; or
c) R1 and R2 are independently selected from the group consisting of substituent (i) and substituent (ii) below; or
d) R1 and R2 are both substituent (i) below; or
e) R1 and R2 are both substituent (ii) below;

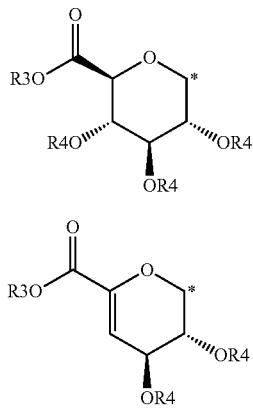

(i)

(ii)

wherein * indicates the attachment point; and
wherein the carbon atom at the attachment point on substituent (i) is in the S-configuration; and
wherein R3 is selected from the group consisting of H, $C_1$-$C_6$ alkyl and benzyl; and
wherein R4 is selected from the group consisting of H, —C(O)$C_1$-$C_6$ alkyl and —C(O)phenyl;
or a pharmaceutically acceptable salt thereof;
with the proviso that when both of R3 and R4 in substituent (i) are H, then R1 and R2 cannot both be substituent (i);
and with the proviso that when one of R1 and R2 is substituent (i) wherein both of R3 and R4 in substituent are H, then the other of R1 and R2 cannot be H.

2. A compound according to formula (Id)

(Id)

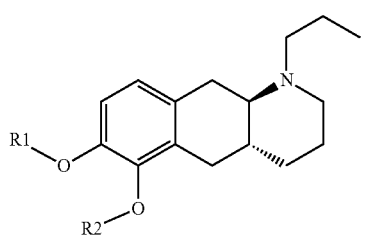

wherein
a) R1 is selected from the group consisting of H, $C_1$-$C_6$ alkyl, methyl substituted with $C_3$-$C_6$ cycloalkyl, benzyl and —C(O)$C_1$-$C_6$ alkyl, and R2 is selected from the group consisting of the substituents (i) and (ii) below; or b) R1 is selected from the group consisting of the substituents (i) and (ii) below and R2 is selected from the group consisting of H, $C_1$-$C_6$ alkyl, methyl substituted with $C_3$-$C_6$ cycloalkyl, benzyl and —C(O)$C_1$-$C_6$ alkyl; or
c) R1 and R2 are independently selected from the group consisting of substituent (i) and substituent (ii) below; or
d) R1 and R2 are both substituent (i) below; or
e) R1 and R2 are both substituent (ii) below;

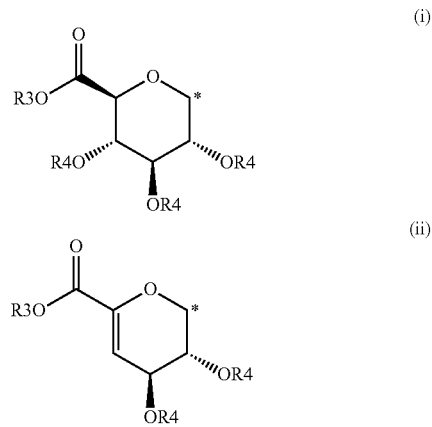

(i)

(ii)

wherein * indicates the attachment point; and
wherein the carbon atom at the attachment point on substituent (i) is in the S-configuration; and
wherein R3 is selected from the group consisting of H, $C_1$-$C_6$ alkyl and benzyl; and
wherein R4 is selected from the group consisting of H, —C(O)$C_1$-$C_6$ alkyl and —C(O)phenyl;
or a pharmaceutically acceptable salt thereof;
with the proviso that when both of R3 and R4 in substituent (i) are H, then R1 and R2 cannot both be substituent (i);
with the proviso that when one of R1 and R2 is substituent (i) wherein both of R3 and R4 in substituent are H, then the other of R1 and R2 cannot be H;
and with the proviso that the compound of formula (Id) is not one of the following compounds (2S,3R,4S,5S,6S)-2-(((4aR,10aR)-7-acetoxy-1-propyl-1,2,3,4,4a,5,10,10a-octahydrobenzo[g]quinolin-6-yl)oxy)-6-(methoxycarbonyl)tetrahydro-2H-pyran-3,4,5-triyl triacetate,
(2S,3R,4S,5S,6S)-2-(((4aR,10aR)-6-acetoxy-1-propyl-1,2,3,4,4a,5,10,10a-octahydrobenzo[g]quinolin-7-yl)oxy)-6-(methoxycarbonyl)tetrahydro-2H-pyran-3,4,5-triyl triacetate, and
methyl (2S,3S,4S,5R,6S)-6-[[(4aR,10aR)-1-propyl-6-[(2S,3R,4S,5S,6S)-3,4,5-triacetoxy-6-methoxycarbonyl-tetrahydropyran-2-yl]oxy-3,4,4a,5,10,10a-hexahydro-2H-benzo[g]quinolin-7-yl]oxy]-3,4,5-triacetoxy-tetrahydropyran-2-carboxylate.

3. The compound, or a pharmaceutically acceptable salt thereof according to claim 1, wherein
R1 is H and R2 is substituent (i); or
R1 is substituent (i) and R2 is H; or
R1 and R2 are both represented by substituent (i); and
wherein R3 is selected from the group consisting of H, $C_1$-$C_6$ alkyl and benzyl; and wherein R4 is selected from the group consisting of H, —C(O)C$_1$-C$_6$alkyl and —C(O)phenyl;
with the proviso that R3 and R4 are not both H.

4. The compound, or a pharmaceutically acceptable salt thereof according to claim 1, wherein
R1 is H and R2 is substituent (ii); or
R1 is substituent (ii) and R2 is H; or
R1 and R2 are both represented by substituent (ii); and
wherein R3 is selected from the group consisting of H, C$_1$-C$_6$ alkyl and benzyl; and
wherein R4 is selected from the group consisting of H, —C(O)C$_1$-C$_6$ alkyl and —C(O)phenyl.

5. The compound, or a pharmaceutically acceptable salt thereof according to claim 1, wherein R1 is selected from the group consisting of H, C$_1$-C$_4$ alkyl, methyl substituted with C$_3$-C$_6$ cycloalkyl, benzyl and —C(O)C$_1$-C$_4$ alkyl.

6. The compound, or a pharmaceutically acceptable salt thereof according to claim 1, wherein R1 is selected from the group consisting of H, C$_1$-C$_3$ alkyl, and benzyl.

7. The compound, or a pharmaceutically acceptable salt thereof according to claim 1, wherein R2 is selected from the group consisting of H, C$_1$-C$_4$ alkyl, methyl substituted with C$_3$-C$_6$ cycloalkyl, benzyl and —C(O)C$_1$-C$_4$ alkyl.

8. The compound, or a pharmaceutically acceptable salt thereof according to claim 1, wherein R2 is selected from the group consisting of H, C$_1$-C$_3$ alkyl, and benzyl.

9. The compound, or a pharmaceutically acceptable salt thereof according to claim 1, wherein R3 is selected from the group consisting of H, C$_1$-C$_4$ alkyl, and benzyl.

10. The compound, or a pharmaceutically acceptable salt thereof according to claim 1, wherein R4 is selected from the group consisting of H, —C(O)C$_1$-C$_4$ alkyl and —C(O)phenyl.

11. The compound, or a pharmaceutically acceptable salt thereof according to claim 1, wherein R4 is selected from the group consisting of H and —C(O)C$_1$-C$_4$ alkyl.

12. The compound, or a pharmaceutically acceptable salt thereof according to claim 1, wherein R1 and R2 are both represented by substituent (i) or R1 and R2 are both represented by substituent (ii).

13. The compound according to claim 1, wherein the compound is selected from the group consisting of:
- (2S,3R,4S,5S,6S)-2-(((4aR,10aR)-7-(benzyloxy)-1-propyl-1,2,3,4,4a,5,10,10a-octahydrobenzo[g]quinolin-6-yl)oxy)-6-(methoxycarbonyl)tetrahydro-2H-pyran-3,4,5-triyl triacetate;
- (2S,3R,4S,5S,6S)-2-(((4aR,10aR)-7-hydroxy-1-propyl-1,2,3,4,4a,5,10,10a-octahydrobenzo[g]quinolin-6-yl)oxy)-6-(methoxycarbonyl)tetrahydro-2H-pyran-3,4,5-triyl triacetate;
- (2R,3R,4S)-2-(((4aR,10aR)-7-hydroxy-1-propyl-1,2,3,4,4a,5,10,10a-octahydrobenzo[g]quinolin-6-yl)oxy)-6-(methoxycarbonyl)-3,4-dihydro-2H-pyran-3,4-diyl diacetate;
- (2S,3S,4S,5R,6S)-6-(((4aR,10aR)-7-(benzyloxy)-1-propyl-1,2,3,4,4a,5,10,10a-octahydrobenzo[g]quinolin-6-yl)oxy)-3,4,5-trihydroxytetrahydro-2H-pyran-2-carboxylic acid;
- (2S,3R,4S,5S,6S)-2-(((4aR,10aR)-7-(benzyloxy)-1-propyl-1,2,3,4,4a,5,10,10a-octahydrobenzo[g]quinolin-6-yl)oxy)-6-((benzyloxy)carbonyl)tetrahydro-2H-pyran-3,4,5-triyl tris(2,2-dimethylpropanoate);
- (2S,3S,4S,5R,6S)-6-(((4aR,10aR)-7-hydroxy-1-propyl-1,2,3,4,4a,5,10,10a-octahydrobenzo[g]quinolin-6-yl)oxy)-3,4,5-tris(pivaloyloxy)tetrahydro-2H-pyran-2-carboxylic acid;
- (2S,3R,4S,5S,6S)-2-(((4aR,10aR)-7-(benzyloxy)-1-propyl-1,2,3,4,4a,5,10,10a-octahydrobenzo[g]quinolin-6-yl)oxy)-6-((benzyloxy)carbonyl)tetrahydro-2H-pyran-3,4,5-triyl triacetate;
- (2S,3S,4S,5R,6S)-3,4,5-triacetoxy-6-(((4aR,10aR)-7-hydroxy-1-propyl-1,2,3,4,4a,5,10,10a-octahydrobenzo[g]quinolin-6-yl oxy)tetrahydro-2H-pyran-2-carboxylic acid;
- (2R,3R,4S)-3,4-dihydroxy-2-(((4aR,10aR)-7-hydroxy-1-propyl-1,2,3,4,4a,5,10,10a-octahydrobenzo[g]quinolin-6-yl)oxy)-3,4-dihydro-2H-pyran-6-carboxylic acid;
- (2S,3R,4S,5S,6S)-2-(((4aR,10aR)-7-(benzyloxy)-1-propyl-1,2,3,4,4a,5,10,10a-octahydrobenzo[g]quinolin-6-yl)oxy)-6-(ethoxycarbonyl) tetrahydro-2H-pyran-3,4,5-triyl triacetate;
- (2S,3S,4S,5R,6S)-2-(ethoxycarbonyl)-6-(((4aR,10aR)-7-hydroxy-1-propyl-1,2,3,4,4a,5,10,10a-octahydrobenzo[g]quinolin-6-yl)oxy)tetrahydro-2H-pyran-3,4,5-triyl triacetate;
- ethyl (2S,3S,4S,5R,6S)-3,4,5-trihydroxy-6-(((4aR,10aR)-7-hydroxy-1-propyl-1,2,3,4,4a,5,10,10a-octahydrobenzo[g]quinolin-6-yl)oxy)tetrahydro-2H-pyran-2-carboxylate;
- (2S,3R,4S,5S,6S)-2-(((4aR,10aR)-7-(benzyloxy)-1-propyl-1,2,3,4,4a,5,10,10a-octahydrobenzo[g]quinolin-6-yl)oxy)-6-(ethoxycarbonyl)tetrahydro-2H-pyran-3,4,5-triyl tris (2,2-dimethylpropanoate);
- (2S,3S,4S,5R,6S)-2-(ethoxycarbonyl)-6-(((4aR,10aR)-7-hydroxy-1-propyl-1,2,3,4,4a,5,10,10a-octahydrobenzo[g]quinolin-6-yl)oxy)tetrahydro-2H-pyran-3,4,5-triyl tris (2,2-dimethylpropanoate);
- (2S,3S,4S,5R,6S)-3,4,5-trihydroxy-6-(((4aR,10aR)-7-methoxy-1-propyl-1,2,3,4,4a,5,10,10a-octahydrobenzo[g]quinolin-6-yl)oxy)tetrahydro-2H-pyran-2-carboxylic acid;
- (2S,3S,4S,5R,6S)-2-((benzyloxy) carbonyl)-6-(((4aR,10aR)-7-methoxy-1-propyl-1,2,3,4,4a,5,10,10a-octahydrobenzo[g]quinolin-6-yl)oxy)tetrahydro-2H-pyran-3,4,5-triyl triacetate;
- (2S,3S,4S,5R,6S)-3,4,5-triacetoxy-6-(((4aR,10aR)-7-methoxy-1-propyl-1,2,3,4,4a,5,10,10a-octahydrobenzo[g]quinolin-6-yl)oxy)tetrahydro-2H-pyran-2-carboxylic acid;
- (2S,3R,4S,5S,6S)-2-(((4aR,10aR)-7-methoxy-1-propyl-1,2,3,4,4a,5,10,10a-octahydrobenzo[g]quinolin-6-yl)oxy)-6-(methoxycarbonyl)tetrahydro-2H-pyran-3,4,5-triyl triacetate;
- (2S,3R,4S,5S,6S)-2-(((4aR,10aR)-7-methoxy-1-propyl-1,2,3,4,4a,5,10,10a-octahydrobenzo[g]quinolin-6-yl)oxy)-6-(ethoxycarbonyl)tetrahydro-2H-pyran-3,4,5-triyl triacetate;
- (2S,3S,4S,5R,6S)-2-((benzyloxy) carbonyl)-6-(((4aR,10aR)-7-methoxy-1-propyl-1,2,3,4,4a,5,10,10a-octahydrobenzo[g]quinolin-6-yl)oxy)tetrahydro-2H-pyran-3,4,5-triyl tris (2,2-dimethylpropanoate);
- (2S,3S,4S,5R,6S)-6-(((4aR,10aR)-7-methoxy-1-propyl-1,2,3,4,4a,5,10,10a-octahydrobenzo[g]quinolin-6-yl)oxy)-3,4,5-tris(pivaloyloxy)tetrahydro-2H-pyran-2-carboxylic acid;
- (2S,3S,4S,5R,6S)-2-((methoxy) carbonyl)-6-(((4aR,10aR)-7-methoxy-1-propyl-1,2,3,4,4a,5,10,10a-octahydrobenzo[g]quinolin-6-yl)oxy)tetrahydro-2H-pyran-3,4,5-triyl tris (2,2-dimethylpropanoate);
- (2S,3S,4S,5R,6S)-2-((ethoxy) carbonyl)-6-(((4aR,10aR)-7-methoxy-1-propyl-1,2,3,4,4a,5,10,10a-octahydrobenzo[g]quinolin-6-yl)oxy)tetrahydro-2H-pyran-3,4,5-triyl tris (2,2-dimethylpropanoate);

(2S,3S,4S,5R,6S)-6-(((4aR,10aR)-7-(benzyloxy)-1-propyl-1,2,3,4,4a,5,10,10a-octahydrobenzo[g]quinolin-6-yl)oxy)-3,4,5-tris(pivaloyloxy)tetrahydro-2H-pyran-2-carboxylic acid;

(2S,3R,4S,5S,6S)-2-(((4aR,10aR)-7-(benzyloxy)-1-propyl-1,2,3,4,4a,5,10,10a-octahydrobenzo[g]quinolin-6-yl)oxy)-6-(methoxycarbonyl) tetrahydro-2H-pyran-3,4,5-triyl tris(2,2-dimethylpropanoate);

(2S,3S,4S,5R,6S)-2-(methoxycarbonyl)-6-(((4aR,10aR)-7-hydroxy-1-propyl-1,2,3,4,4a,5,10,10a-octahydrobenzo[g]quinolin-6-yl)oxy)tetrahydro-2H-pyran-3,4,5-triyl tris (2,2-dimethylpropanoate); and (2S,3R,4S,5S,6S)-2-(((4aR,10aR)-6-hydroxy-1-propyl-1,2,3,4,4a,5,10,10a-octahydrobenzo[g]quinolin-7-yl)oxy)-6-(methoxycarbonyl)tetrahydro-2H-pyran-3,4,5-triyl triacetate;

or a pharmaceutically acceptable salt of any of these compounds.

14. The compound, or a pharmaceutically acceptable salt thereof according to claim 1, wherein R2 is represented by substituent (i).

15. The compound, or a pharmaceutically acceptable salt thereof according to claim 1, wherein R2 is represented by substituent (ii).

16. The compound of claim 2 with the formula below

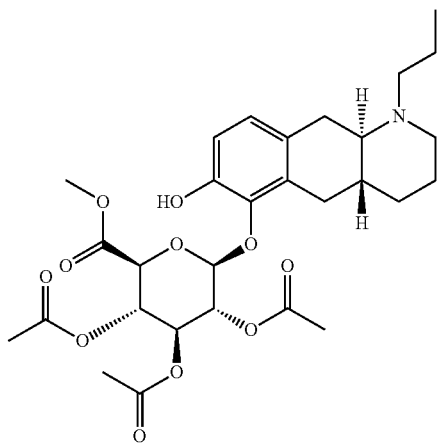 [SMILES: CCCN1CCC[C@@H]2Cc3c(ccc(O)c3O[C@@H]3O[C@H](C(=O)OC)[C@@H](OC(C)=O)[C@H](OC(C)=O)[C@H]3OC(C)=O)C[C@H]21]

or a pharmaceutically acceptable salt thereof.

17. The compound of claim 2 with the formula below

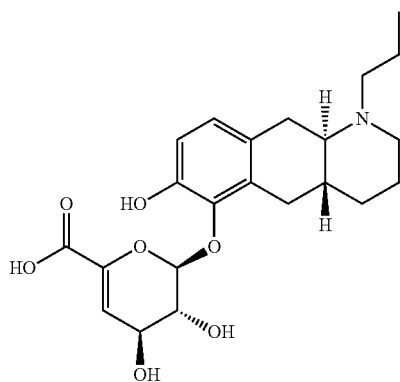 [SMILES: CCCN1CCC[C@@H]2Cc3c(ccc(O)c3O[C@@H]3OC(C(=O)O)=C[C@H](O)[C@H]3O)C[C@H]21]

or a pharmaceutically acceptable salt thereof.

18. The compound of claim 2 with the formula below

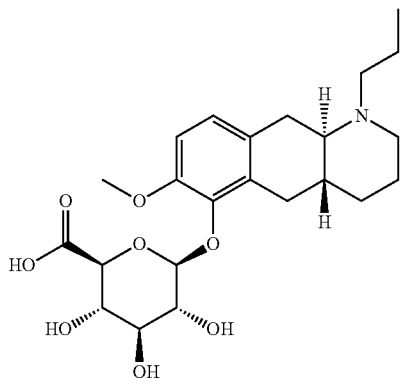 [SMILES: CCCN1CCC[C@@H]2Cc3c(ccc(OC)c3O[C@@H]3O[C@H](C(=O)O)[C@@H](O)[C@H](O)[C@H]3O)C[C@H]21]

or a pharmaceutically acceptable salt thereof.

19. The compound of claim 2 with the formula below

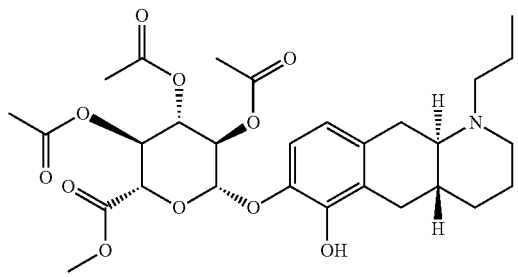 [SMILES: CCCN1CCC[C@@H]2Cc3c(ccc(O[C@@H]4O[C@H](C(=O)OC)[C@@H](OC(C)=O)[C@H](OC(C)=O)[C@H]4OC(C)=O)c3O)C[C@H]21]

or a pharmaceutically acceptable salt thereof.

20. The compound of claim 2 with the formula below

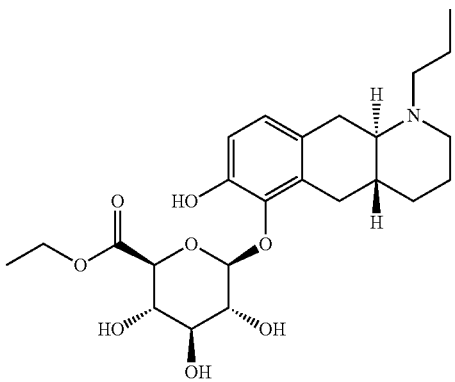 [SMILES: CCCN1CCC[C@@H]2Cc3c(ccc(O)c3O[C@@H]3O[C@H](C(=O)OCC)[C@@H](O)[C@H](O)[C@H]3O)C[C@H]21]

or a pharmaceutically acceptable salt thereof.

21. The compound of claim 2 with the formula below

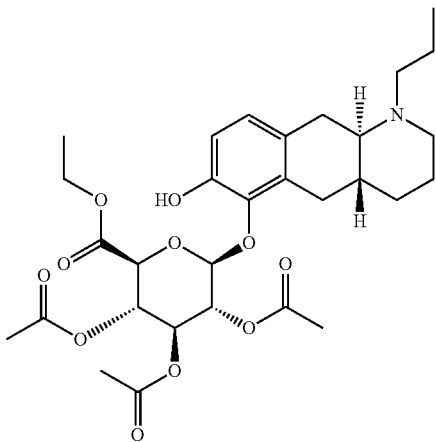 [SMILES: CCCN1CCC[C@@H]2Cc3c(ccc(O)c3O[C@@H]3O[C@H](C(=O)OCC)[C@@H](OC(C)=O)[C@H](OC(C)=O)[C@H]3OC(C)=O)C[C@H]21]

or a pharmaceutically acceptable salt thereof.

22. A pharmaceutical composition comprising a compound or pharmaceutically acceptable salt thereof according to claim 1, and one or more pharmaceutically acceptable carriers or diluents.

23. The pharmaceutical composition according to claim 22, wherein the compound or pharmaceutically acceptable salt thereof is selected from the group consisting of:

(2S,3R,4S,5S,6S)-2-(((4aR,10aR)-7-(benzyloxy)-1-propyl-1,2,3,4,4a,5,10,10a-octahydrobenzo[g]quinolin-6-yl)oxy)-6-(methoxycarbonyl) tetrahydro-2H-pyran-3,4,5-triyl triacetate;

(2S,3R,4S,5S,6S)-2-(((4aR,10aR)-7-hydroxy-1-propyl-1,2,3,4,4a,5,10,10a-octahydrobenzo[g]quinolin-6-yl)oxy)-6-(methoxycarbonyl)tetrahydro-2H-pyran-3,4,5-triyl triacetate;

(2R,3R,4S)-2-(((4aR,10aR)-7-hydroxy-1-propyl-1,2,3,4,4a,5,10,10a-octahydrobenzo[g]quinolin-6-yl) oxy)-6-(methoxycarbonyl)-3,4-dihydro-2H-pyran-3,4-diyl diacetate;

(2S,3S,4S,5R,6S)-6-(((4aR,10aR)-7-(benzyloxy)-1-propyl-1,2,3,4,4a,5,10,10a-octahydrobenzo[g]quinolin-6-yl)oxy)-3,4,5-trihydroxytetrahydro-2H-pyran-2-carboxylic acid;

(2S,3R,4S,5S,6S)-2-(((4aR,10aR)-7-(benzyloxy)-1-propyl-1,2,3,4,4a,5,10,10a-octahydrobenzo[g]quinolin-6-yl)oxy)-6-((benzyloxy)carbonyl)tetrahydro-2H-pyran-3,4,5-triyl tris(2,2-dimethylpropanoate);

(2S,3S,4S,5R,6S)-6-(((4aR,10aR)-7-hydroxy-1-propyl-1,2,3,4,4a,5,10,10a-octahydrobenzo[g]quinolin-6-yl) oxy)-3,4,5-tris(pivaloyloxy)tetrahydro-2H-pyran-2-carboxylic acid;

(2S,3R,4S,5S,6S)-2-(((4aR,10aR)-7-(benzyloxy)-1-propyl-1,2,3,4,4a,5,10,10a-octahydrobenzo[g]quinolin-6-yl)oxy)-6-((benzyloxy)carbonyl)tetrahydro-2H-pyran-3,4,5-triyl triacetate;

(2S,3S,4S,5R,6S)-3,4,5-triacetoxy-6-(((4aR,10aR)-7-hydroxy-1-propyl-1,2,3,4,4a,5,10,10a-octahydrobenzo[g]quinolin-6-yl)oxy)tetrahydro-2H-pyran-2-carboxylic acid;

(2R,3R,4S)-3,4-dihydroxy-2-(((4aR,10aR)-7-hydroxy-1-propyl-1,2,3,4,4a,5,10,10a-octahydrobenzo[g]quinolin-6-yl)oxy)-3,4-dihydro-2H-pyran-6-carboxylic acid;

(2S,3R,4S,5S,6S)-2-(((4aR,10aR)-7-(benzyloxy)-1-propyl-1,2,3,4,4a,5,10,10a-octahydrobenzo[g]quinolin-6-yl)oxy)-6-(ethoxycarbonyl)tetrahydro-2H-pyran-3,4,5-triyl triacetate;

(2S,3S,4S,5R,6S)-2-(ethoxycarbonyl)-6-(((4aR,10aR)-7-hydroxy-1-propyl-1,2,3,4,4a,5,10,10a-octahydrobenzo[g]quinolin-6-yl)oxy)tetrahydro-2H-pyran-3,4,5-triyl triacetate;

ethyl (2S,3S,4S,5R,6S)-3,4,5-trihydroxy-6-(((4aR,10aR)-7-hydroxy-1-propyl-1,2,3,4,4a,5,10,10a-octahydrobenzo[g]quinolin-6-yl)oxy)tetrahydro-2H-pyran-2-carboxylate;

(2S,3R,4S,5S,6S)-2-(((4aR,10aR)-7-(benzyloxy)-1-propyl-1,2,3,4,4a,5,10,10a-octahydrobenzo[g]quinolin-6-yl)oxy)-6-(ethoxycarbonyl) tetrahydro-2H-pyran-3,4,5-triyl tris (2,2-dimethylpropanoate);

(2S,3S,4S,5R,6S)-2-(ethoxycarbonyl)-6-(((4aR,10aR)-7-hydroxy-1-propyl-1,2,3,4,4a,5,10,10a-octahydrobenzo[g]quinolin-6-yl)oxy)tetrahydro-2H-pyran-3,4,5-triyl tris (2,2-dimethylpropanoate);

(2S,3S,4S,5R,6S)-3,4,5-trihydroxy-6-(((4aR,10aR)-7-methoxy-1-propyl-1,2,3,4,4a,5,10,10a-octahydrobenzo[g]quinolin-6-yl)oxy)tetrahydro-2H-pyran-2-carboxylic acid;

(2S,3S,4S,5R,6S)-2-((benzyloxy) carbonyl)-6-(((4aR,10aR)-7-methoxy-1-propyl-1,2,3,4,4a,5,10,10a-octahydrobenzo[g]quinolin-6-yl) oxy)tetrahydro-2H-pyran-3,4,5-triyl triacetate;

(2S,3S,4S,5R,6S)-3,4,5-triacetoxy-6-(((4aR,10aR)-7-methoxy-1-propyl-1,2,3,4,4a,5,10,10a-octahydrobenzo[g]quinolin-6-yl)oxy)tetrahydro-2H-pyran-2-carboxylic acid;

(2S,3R,4S,5S,6S)-2-(((4aR,10aR)-7-methoxy-1-propyl-1,2,3,4,4a,5,10,10a-octahydrobenzo[g]quinolin-6-yl)oxy)-6-(methoxycarbonyl)tetrahydro-2H-pyran-3,4,5-triyl triacetate;

(2S,3R,4S,5S,6S)-2-(((4aR,10aR)-7-methoxy-1-propyl-1,2,3,4,4a,5,10,10a-octahydrobenzo[g]quinolin-6-yl)oxy)-6-(ethoxycarbonyl)tetrahydro-2H-pyran-3,4,5-triyl triacetate;

(2S,3S,4S,5R,6S)-2-((benzyloxy)carbonyl)-6-(((4aR,10aR)-7-methoxy-1-propyl-1,2,3,4,4a,5,10,10a-octahydrobenzo[g]quinolin-6-yl)oxy)tetrahydro-2H-pyran-3,4,5-triyl tris(2,2-dimethylpropanoate);

(2S,3S,4S,5R,6S)-6-(((4aR,10aR)-7-methoxy-1-propyl-1,2,3,4,4a,5,10,10a-octahydrobenzo[g]quinolin-6-yl)oxy)-3,4,5-tris(pivaloyloxy)tetrahydro-2H-pyran-2-carboxylic acid;

(2S,3S,4S,5R,6S)-2-((methoxy) carbonyl)-6-(((4aR,10aR)-7-methoxy-1-propyl-1,2,3,4,4a,5,10,10a-octahydrobenzo[g]quinolin-6-yl)oxy)tetrahydro-2H-pyran-3,4,5-triyl tris(2,2-dimethylpropanoate);

(2S,3S,4S,5R,6S)-2-((ethoxy)carbonyl)-6-(((4aR,10aR)-7-methoxy-1-propyl-1,2,3,4,4a,5,10,10a-octahydrobenzo[g]quinolin-6-yl)oxy)tetrahydro-2H-pyran-3,4,5-triyl tris (2,2-dimethylpropanoate);

(2S,3S,4S,5R,6S)-6-(((4aR,10aR)-7-(benzyloxy)-1-propyl-1,2,3,4,4a,5,10,10a-octahydrobenzo[g]quinolin-6-yl)oxy)-3,4,5-tris(pivaloyloxy)tetrahydro-2H-pyran-2-carboxylic acid;

(2S,3R,4S,5S,6S)-2-(((4aR,10aR)-7-(benzyloxy)-1-propyl-1,2,3,4,4a,5,10,10a-octahydrobenzo[g]quinolin-6-yl)oxy)-6-(methoxycarbonyl)tetrahydro-2H-pyran-3,4,5-triyl tris(2,2-dimethylpropanoate);

(2S,3S,4S,5R,6S)-2-(methoxycarbonyl)-6-(((4aR,10aR)-7-hydroxy-1-propyl-1,2,3,4,4a,5,10,10a-octahydrobenzo[g]quinolin-6-yl)oxy)tetrahydro-2H-pyran-3,4,5-triyl tris (2,2-dimethylpropanoate); and (2S,3R,4S,5S,6S)-2-(((4aR,10aR)-6-hydroxy-1-propyl-1,2,3,4,4a,5,10,10a-octahydrobenzo[g]quinolin-7-yl)oxy)-6-(methoxycarbonyl)tetrahydro-2H-pyran-3,4,5-triyl triacetate;
and pharmaceutically acceptable salts of any of these compounds.

24. A pharmaceutical composition comprising a compound selected from the group consisting of
(2S,3R,4S,5S,6S)-2-(((4aR,10aR)-7-acetoxy-1-propyl-1,2,3,4,4a,5,10,10a-octahydrobenzo[g]quinolin-6-yl)oxy)-6-(methoxycarbonyl)tetrahydro-2H-pyran-3,4,5-triyl triacetate,
(2S,3R,4S,5S,6S)-2-(((4aR,10aR)-6-acetoxy-1-propyl-1,2,3,4,4a,5,10,10a-octahydrobenzo[g]quinolin-7-yl)oxy)-6-(methoxycarbonyl)tetrahydro-2H-pyran-3,4,5-triyl triacetate, and
methyl (2S,3S,4S,5R,6S)-6-[[(4aR,10aR)-1-propyl-6-[(2S,3R,4S,5S,6S)-3,4,5-triacetoxy-6-methoxycarbonyl-tetrahydropyran-2-yl] oxy-3,4,4a,5,10,10a-hexahydro-2H-benzo[g]quinolin-7-yl] oxy]-3,4,5-triacetoxy-tetrahydropyran-2-carboxylate,
or pharmaceutically acceptable salt thereof;
and one or more pharmaceutically acceptable excipients.

25. A method for the treatment of a neurodegenerative disease or disorder selected from the group consisting of Parkinson's Disease, Huntington's disease, Restless leg syndrome and Alzheimer's disease; or a neuropsychiatric disease or disorder selected from the group consisting of schizophrenia, attention deficit hyperactivity disorder and drug addiction; which method comprises the administration of a therapeutically effective amount of a compound or pharmaceutically acceptable salt thereof according to claim 1, or which method comprises the administration of a therapeutically effective amount of a compound or a pharmaceutically acceptable salt thereof, wherein said compound is selected from the group consisting of:
(2S,3R,4S,5S,6S)-2-(((4aR,10aR)-7-acetoxy-1-propyl-1,2,3,4,4a,5,10,10a-octahydrobenzo[g]quinolin-6-yl)oxy)-6-(methoxycarbonyl)tetrahydro-2H-pyran-3,4,5-triyl triacetate,
(2S,3R,4S,5S,6S)-2-(((4aR,10aR)-6-acetoxy-1-propyl-1,2,3,4,4a,5,10,10a-octahydrobenzo[g]quinolin-7-yl)oxy)-6-(methoxycarbonyl)tetrahydro-2H-pyran-3,4,5-triyl triacetate, and
methyl (2S,3S,4S,5R,6S)-6-[[(4aR,10aR)-1-propyl-6-[(2S,3R,4S,5S,6S)-3,4,5-triacetoxy-6-methoxycarbonyl-tetrahydropyran-2-yl]oxy-3,4,4a,5,10,10a-hexahydro-2H-benzo[g]quinolin-7-yl]oxy]-3,4,5-triacetoxy-tetrahydropyran-2-carboxylate;
to a patient in need thereof.

26. A method for the treatment of a neurodegenerative disease or disorder selected from the group consisting of Parkinson's Disease, Huntington's disease, Restless leg syndrome and Alzheimer's disease; or a neuropsychiatric disease or disorder selected from the group consisting of schizophrenia, attention deficit hyperactivity disorder and drug addiction; which method comprises the administration of a therapeutically effective amount of a compound or pharmaceutically acceptable salt thereof according to claim 1, to a patient in need thereof.

27. The method of claim 26, wherein the compound or pharmaceutically acceptable salt thereof is selected from the group consisting of:
(2S,3R,4S,5S,6S)-2-(((4aR,10aR)-7-(benzyloxy)-1-propyl-1,2,3,4,4a,5,10,10a-octahydrobenzo[g]quinolin-6-yl)oxy)-6-(methoxycarbonyl)tetrahydro-2H-pyran-3,4,5-triyl triacetate;
(2S,3R,4S,5S,6S)-2-(((4aR,10aR)-7-hydroxy-1-propyl-1,2,3,4,4a,5,10,10a-octahydrobenzo[g]quinolin-6-yl)oxy)-6-(methoxycarbonyl)tetrahydro-2H-pyran-3,4,5-triyl triacetate;
(2R,3R,4S)-2-(((4aR,10aR)-7-hydroxy-1-propyl-1,2,3,4,4a,5,10,10a-octahydrobenzo[g]quinolin-6-yl)oxy)-6-(methoxycarbonyl)-3,4-dihydro-2H-pyran-3,4-diyl diacetate;
(2S,3S,4S,5R,6S)-6-(((4aR,10aR)-7-(benzyloxy)-1-propyl-1,2,3,4,4a,5,10,10a-octahydrobenzo[g]quinolin-6-yl)oxy)-3,4,5-trihydroxytetrahydro-2H-pyran-2-carboxylic acid;
(2S,3R,4S,5S,6S)-2-(((4aR,10aR)-7-(benzyloxy)-1-propyl-1,2,3,4,4a,5,10,10a-octahydrobenzo[g]quinolin-6-yl)oxy)-6-((benzyloxy)carbonyl)tetrahydro-2H-pyran-3,4,5-triyl tris(2,2-dimethylpropanoate);
(2S,3S,4S,5R,6S)-6-(((4aR,10aR)-7-hydroxy-1-propyl-1,2,3,4,4a,5,10,10a-octahydrobenzo[g]quinolin-6-yl)oxy)-3,4,5-tris(pivaloyloxy)tetrahydro-2H-pyran-2-carboxylic acid;
(2S,3R,4S,5S,6S)-2-(((4aR,10aR)-7-(benzyloxy)-1-propyl-1,2,3,4,4a,5,10,10a-octahydrobenzo[g]quinolin-6-yl)oxy)-6-((benzyloxy)carbonyl)tetrahydro-2H-pyran-3,4,5-triyl triacetate;
(2S,3S,4S,5R,6S)-3,4,5-triacetoxy-6-(((4aR,10aR)-7-hydroxy-1-propyl-1,2,3,4,4a,5,10,10a-octahydrobenzo[g]quinolin-6-yl)oxy)tetrahydro-2H-pyran-2-carboxylic acid;
(2R,3R,4S)-3,4-dihydroxy-2-(((4aR,10aR)-7-hydroxy-1-propyl-1,2,3,4,4a,5,10,10a-octahydrobenzo[g]quinolin-6-yl)oxy)-3,4-dihydro-2H-pyran-6-carboxylic acid;
(2S,3R,4S,5S,6S)-2-(((4aR,10aR)-7-(benzyloxy)-1-propyl-1,2,3,4,4a,5,10,10a-octahydrobenzo[g]quinolin-6-yl)oxy)-6-(ethoxycarbonyl)tetrahydro-2H-pyran-3,4,5-triyl triacetate;
(2S,3S,4S,5R,6S)-2-(ethoxycarbonyl)-6-(((4aR,10aR)-7-hydroxy-1-propyl-1,2,3,4,4a,5,10,10a-octahydrobenzo[g]quinolin-6-yl)oxy)tetrahydro-2H-pyran-3,4,5-triyl triacetate;
ethyl (2S,3S,4S,5R,6S)-3,4,5-trihydroxy-6-(((4aR,10aR)-7-hydroxy-1-propyl-1,2,3,4,4a,5,10,10a-octahydrobenzo[g]quinolin-6-yl)oxy)tetrahydro-2H-pyran-2-carboxylate;
(2S,3R,4S,5S,6S)-2-(((4aR,10aR)-7-(benzyloxy)-1-propyl-1,2,3,4,4a,5,10,10a-octahydrobenzo[g]quinolin-6-yl)oxy)-6-(ethoxycarbonyl) tetrahydro-2H-pyran-3,4,5-triyl tris(2,2-dimethylpropanoate);
(2S,3S,4S,5R,6S)-2-(ethoxycarbonyl)-6-(((4aR,10aR)-7-hydroxy-1-propyl-1,2,3,4,4a,5,10,10a-octahydrobenzo[g]quinolin-6-yl)oxy)tetrahydro-2H-pyran-3,4,5-triyl tris (2,2-dimethylpropanoate);
(2S,3S,4S,5R,6S)-3,4,5-trihydroxy-6-(((4aR,10aR)-7-methoxy-1-propyl-1,2,3,4,4a,5,10,10a-octahydrobenzo[g]quinolin-6-yl)oxy)tetrahydro-2H-pyran-2-carboxylic acid;
(2S,3S,4S,5R,6S)-2-((benzyloxy)carbonyl)-6-(((4aR,10aR)-7-methoxy-1-propyl-1,2,3,4,4a,5,10,10a-octahydrobenzo[g]quinolin-6-yl)oxy)tetrahydro-2H-pyran-3,4,5-triyl triacetate;
(2S,3S,4S,5R,6S)-3,4,5-triacetoxy-6-(((4aR,10aR)-7-methoxy-1-propyl-1,2,3,4,4a,5,10,10a-octahydrobenzo[g]quinolin-6-yl)oxy)tetrahydro-2H-pyran-2-carboxylic acid;
(2S,3R,4S,5S,6S)-2-(((4aR,10aR)-7-methoxy-1-propyl-1,2,3,4,4a,5,10,10a-octahydrobenzo[g]quinolin-6-yl)oxy)-6-(methoxycarbonyl)tetrahydro-2H-pyran-3,4,5-triyl triacetate;

(2S,3R,4S,5S,6S)-2-(((4aR,10aR)-7-methoxy-1-propyl-1,2,3,4,4a,5,10,10a-octahydrobenzo[g]quinolin-6-yl)oxy)-6-(ethoxycarbonyl)tetrahydro-2H-pyran-3,4,5-triyl triacetate;

(2S,3S,4S,5R,6S)-2-((benzyloxy)carbonyl)-6-(((4aR,10aR)-7-methoxy-1-propyl-1,2,3,4,4a,5,10,10a-octahydrobenzo[g]quinolin-6-yl)oxy)tetrahydro-2H-pyran-3,4,5-triyl tris(2,2-dimethylpropanoate);

(2S,3S,4S,5R,6S)-6-(((4aR,10aR)-7-methoxy-1-propyl-1,2,3,4,4a,5,10,10a-octahydrobenzo[g]quinolin-6-yl)oxy)-3,4,5-tris(pivaloyloxy)tetrahydro-2H-pyran-2-carboxylic acid;

(2S,3S,4S,5R,6S)-2-((methoxy)carbonyl)-6-(((4aR,10aR)-7-methoxy-1-propyl-1,2,3,4,4a,5,10,10a-octahydrobenzo[g]quinolin-6-yl)oxy)tetrahydro-2H-pyran-3,4,5-triyl tris(2,2-dimethylpropanoate);

(2S,3S,4S,5R,6S)-2-((ethoxy)carbonyl)-6-(((4aR,10aR)-7-methoxy-1-propyl-1,2,3,4,4a,5,10,10a-octahydrobenzo[g]quinolin-6-yl)oxy) tetrahydro-2H-pyran-3,4,5-triyl tris(2,2-dimethylpropanoate);

(2S,3S,4S,5R,6S)-6-(((4aR,10aR)-7-(benzyloxy)-1-propyl-1,2,3,4,4a,5,10,10a-octahydrobenzo[g]quinolin-6-yl)oxy)-3,4,5-tris(pivaloyloxy)tetrahydro-2H-pyran-2-carboxylic acid;

(2S,3R,4S,5S,6S)-2-(((4aR,10aR)-7-(benzyloxy)-1-propyl-1,2,3,4,4a,5,10,10a-octahydrobenzo[g]quinolin-6-yl)oxy)-6-(methoxycarbonyl)tetrahydro-2H-pyran-3,4,5-triyl tris(2,2-dimethylpropanoate);

(2S,3S,4S,5R,6S)-2-(methoxycarbonyl)-6-(((4aR,10aR)-7-hydroxy-1-propyl-1,2,3,4,4a,5,10,10a-octahydrobenzo[g]quinolin-6-yl)oxy)tetrahydro-2H-pyran-3,4,5-triyl tris(2,2-dimethylpropanoate); and (2S,3R,4S,5S,6S)-2-(((4aR,10aR)-6-hydroxy-1-propyl-1,2,3,4,4a,5,10,10a-octahydrobenzo[g]quinolin-7-yl)oxy)-6-(methoxycarbonyl)tetrahydro-2H-pyran-3,4,5-triyl triacetate;

and pharmaceutically acceptable salts of any of these compounds.

\* \* \* \* \*

UNITED STATES PATENT AND TRADEMARK OFFICE
CERTIFICATE OF CORRECTION

Page 1 of 1

PATENT NO. : 12,384,765 B2
APPLICATION NO. : 17/606319
DATED : August 12, 2025
INVENTOR(S) : Morten Jørgensen et al.

It is certified that error appears in the above-identified patent and that said Letters Patent is hereby corrected as shown below:

In the Claims

In Claim 13, at Column 114, Lines 5-8, the text: "(2S,3S,4S,5R,6S)-3,4,5-triacetoxy-6-(((4aR,10aR)-7-hydroxy-1-propyl-1,2,3,4,4a,5,10,10a-octahydrobenzo[g]quinolin-6-yl oxy)tetrahydro-2H-pyran-2-carboxylic acid" should be replaced with:
-- (2S,3S,4S,5R,6S)-3,4,5-triacetoxy-6-(((4aR,10aR)-7-hydroxy-1-propyl-1,2,3,4,4a,5,10,10a-octahydrobenzo[g]quinolin-6-yl)oxy)tetrahydro-2H-pyran-2-carboxylic acid --.

Signed and Sealed this
Seventh Day of October, 2025

John A. Squires
*Director of the United States Patent and Trademark Office*